(12) United States Patent
Sauerberg et al.

(10) Patent No.: US 7,943,613 B2
(45) Date of Patent: May 17, 2011

(54) COMPOUNDS, THEIR PREPARATION AND USE

(75) Inventors: Per Sauerberg, Farum (DK); Pavel Pihera, Prague (CZ); Zdenek Polivka, Prague (CZ); Miroslav Havranek, Prague (CZ); Ingrid Pettersson, Frederiksberg (DK); John Patrick Mogensen, Herlev (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 52 days.

(21) Appl. No.: 12/097,564

(22) PCT Filed: Dec. 21, 2006

(86) PCT No.: PCT/EP2006/070096
§ 371 (c)(1),
(2), (4) Date: Oct. 23, 2008

(87) PCT Pub. No.: WO2007/071766
PCT Pub. Date: Jun. 28, 2007

(65) Prior Publication Data
US 2009/0093484 A1    Apr. 9, 2009

(30) Foreign Application Priority Data

Dec. 22, 2005  (EP) .................................. 05112758
Jun. 19, 2006  (EP) .................................. 06115631

(51) Int. Cl.
C07D 295/155 (2006.01)
A61K 31/5375 (2006.01)

(52) U.S. Cl. .................................. 514/239.5; 544/171
(58) Field of Classification Search ............... 514/239.5; 544/171
See application file for complete search history.

(56) References Cited

U.S. PATENT DOCUMENTS

| | | | |
|---|---|---|---|
| 4,148,915 A | 4/1979 | Thuillier et al. |
| 4,920,132 A | 4/1990 | Huang et al. |
| 5,324,743 A | 6/1994 | Dillard et al. |
| 5,773,469 A | 6/1998 | Kanojia et al. |
| 5,919,793 A | 7/1999 | Brown et al. |
| 6,448,293 B1 | 9/2002 | Andrews et al. |
| 6,525,094 B1 | 2/2003 | Zhang et al. |
| 6,555,577 B1 | 4/2003 | Mogensen et al. |
| 6,569,901 B2 | 5/2003 | Mogensen et al. |
| 6,630,504 B2 | 10/2003 | Andrews et al. |
| 6,867,218 B2 | 3/2005 | Mogensen et al. |
| 6,869,967 B2 | 3/2005 | Jeppesen et al. |
| 6,869,975 B2 | 3/2005 | Abe et al. |
| 6,875,780 B2 | 4/2005 | Auerbach et al. |
| 6,972,294 B1 | 12/2005 | Murray et al. |
| 7,067,530 B2 | 6/2006 | Jeppesen et al. |
| 7,091,245 B2 | 8/2006 | Jeppesen et al. |
| 7,129,268 B2 | 10/2006 | Jeppesen et al. |
| 7,202,213 B2 | 4/2007 | Mogensen et al. |
| 7,220,877 B2 | 5/2007 | Sauerberg et al. |
| 7,709,528 B2 | 5/2010 | Jeppesen et al. |
| 2004/0024034 A1 | 2/2004 | Brooks et al. |
| 2005/0080115 A1 | 4/2005 | Jeppesen et al. |
| 2008/0114036 A1 | 5/2008 | Havranek et al. |
| 2009/0012171 A1 | 1/2009 | Polivka |
| 2009/0048257 A1 | 2/2009 | Sauerberg |
| 2009/0192162 A1 | 7/2009 | Ebdrup |
| 2010/0197950 A1 | 8/2010 | Rasmussen et al. |
| 2010/0210653 A1 | 8/2010 | Havranek et al. |

FOREIGN PATENT DOCUMENTS

| | | |
|---|---|---|
| JP | 2003/171275 | 6/2003 |
| WO | 97/27847 | 8/1997 |
| WO | 97/27857 | 8/1997 |
| WO | 97/28115 | 8/1997 |
| WO | 97/28137 | 8/1997 |
| WO | 97/28149 | 8/1997 |
| WO | 97/43241 | 11/1997 |
| WO | 97/48674 | 12/1997 |
| WO | 98/27974 | 7/1998 |
| WO | 99/04815 | 2/1999 |
| WO | WO 99/20275 | 4/1999 |
| WO | 00/63153 | 10/2000 |
| WO | 01/00603 | 1/2001 |
| WO | 01/25181 | 4/2001 |
| WO | WO 01/25226 | 4/2001 |
| WO | WO 01/34137 | 5/2001 |
| WO | WO 01/34200 | 5/2001 |
| WO | 01/55085 | 8/2001 |
| WO | 01/55086 | 8/2001 |
| WO | WO 01/60807 | 8/2001 |
| WO | WO 01/66098 | 9/2001 |
| WO | 01/79150 | 10/2001 |
| WO | 01/79197 | 10/2001 |
| WO | 02/14291 | 2/2002 |
| WO | WO 02/28434 | 4/2002 |
| WO | 02/46154 | 6/2002 |

(Continued)

OTHER PUBLICATIONS

Landreth et al. Neurobiology of Aging, 2001, 22, 937-944.*
Peters et al. Biochimica et Biophysica Acta 2009, 1796, 230-241.*
Golub et al., Science, vol. 286, Oct. 15, 1999, pp. 531-537.*
Epple et al. Bioorganic & Medicinal Chemistry Letters 2006, 16, 4376-4380.*
Gross et al. Best Practice & Research Clinical Endocrinology & Metabolism 2007, 21, 687-710.*
Colagiuri et al. American Journal of Public Health, Sep. 2006, vol. 96, No. 9, pp. 1562-1569.*
Park Diabetes Research and Clinical Practice 66S (2004), S33-S35.*
Curtis et al. The Journal of the American Board of Family Practice, vol. 18, pp. 37-43, (2005).*
Hussain et al. Diabetes Research and Clinical Practice 2007, 76, 317-326.*
Giron, D. J. Therm. Anal. Cal. 2001, 64, pp. 37-60.*
Giron, D. J. Therm. Anal. Cal. 2002, 68, pp. 335-357.*

(Continued)

*Primary Examiner* — Joseph Kosack
*Assistant Examiner* — Matthew P Coughlin
(74) *Attorney, Agent, or Firm* — Robert S. Dailey

(57) ABSTRACT

Novel compounds of the general formula (I), the use of these compounds as pharmaceutical compositions, pharmaceutical compositions comprising the compounds and methods of treatment employing these compounds and compositions. The present compounds are activators of PPARδ and should be useful for treating conditions mediated by the same.

24 Claims, No Drawings

FOREIGN PATENT DOCUMENTS

| | | |
|---|---|---|
| WO | WO 02/50048 | 6/2002 |
| WO | WO 02/053547 | 7/2002 |
| WO | 02/059098 | 8/2002 |
| WO | WO 02/062774 | 8/2002 |
| WO | WO 02/070011 | 9/2002 |
| WO | 02/076957 | 10/2002 |
| WO | 02/079162 | 10/2002 |
| WO | 02/080899 | 10/2002 |
| WO | 02/098840 | 12/2002 |
| WO | 02/100812 | 12/2002 |
| WO | WO 03/002081 | 1/2003 |
| WO | 03/011814 | 2/2003 |
| WO | 03/016265 | 2/2003 |
| WO | 03/016291 | 2/2003 |
| WO | WO 03/011807 | 2/2003 |
| WO | WO 03/024395 | 3/2003 |
| WO | 03/033453 | 4/2003 |
| WO | 03/033493 | 4/2003 |
| WO | 03/035603 | 5/2003 |
| WO | 03/072100 | 9/2003 |
| WO | 03/074050 | 9/2003 |
| WO | WO 03/074051 | 9/2003 |
| WO | WO 03/074052 | 9/2003 |
| WO | WO 03/074495 | 9/2003 |
| WO | 03/084916 | 10/2003 |
| WO | 03/097607 | 11/2003 |
| WO | WO 2004/000315 | 12/2003 |
| WO | WO 2004/000762 | 12/2003 |
| WO | 2004/005253 | 1/2004 |
| WO | WO 2004/007439 | 1/2004 |
| WO | 2004/022533 | 3/2004 |
| WO | WO 2004/037775 | 5/2004 |
| WO | WO 2004/037776 | 5/2004 |
| WO | WO 2004/060871 | 7/2004 |
| WO | WO 2004/063165 | 7/2004 |
| WO | WO 2004/063166 | 7/2004 |
| WO | WO 2004/073606 | 9/2004 |
| WO | WO 2004/080943 | 9/2004 |
| WO | WO 2004/080947 | 9/2004 |
| WO | WO 2004/092117 | 10/2004 |
| WO | WO 2004/093879 | 11/2004 |
| WO | WO 2004/099170 | 11/2004 |
| WO | WO 2005/054176 | 6/2005 |
| WO | WO 2005/097098 | 10/2005 |
| WO | WO 2005/097762 | 10/2005 |
| WO | WO 2005/097763 | 10/2005 |
| WO | 2005/105725 | 11/2005 |
| WO | 2005/105736 | 11/2005 |
| WO | WO 2005/105735 | 11/2005 |
| WO | WO 2005105735 A1 * | 11/2005 |
| WO | 2007/003581 | 1/2007 |
| WO | 2007/101864 | 9/2007 |
| WO | 2007/141295 | 12/2007 |

OTHER PUBLICATIONS

B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Berger, Joel et al., "Novel Peroxisome Proliferator-activated Receptor (PPAR) gamma and PPAR delta Ligands Produce Distinct Biological Effect" Journal of Biological Chemistry, vol. 274, No. 10, Issue of March 5, pp. 6718-6725, 1999.
Leibowitz, Mark D. et al., "Activation of PPAR delta alters lipidmetabolism in db/db mice" FEBS Letters 473 (2000) pp. 333-336.
Muoio, Deborah M. "Fatty Acid Homestasis and Induction of Lipid Regulatory Genes in Skeletal Muscles of Peroxisome Proliferator-activated Receptor (PPAR) Knock-out Mice" Journal of Biological Chemistry, vol. 277, No. 29, Issue of July 19, pp. 26089-26097, 2002.
Oliver, William R. Jr. et al., "A Selective peroxisome proliferator-activated receptor delta agonist promotes reverse cheolesterol transport" Proceedings of the National Academy of Sciences, vol. 98, No. 9 pp. 5306-5311, Apr. 24, 2001.
PCT International Search Report for Application No. PCT/EP2006/070096 dated Jul. 26, 2007.
Vippagunta, S.R. et al., Adv. Drug Delivery Rev. 48 (2001) 3-26.
Caira, M.R., Topics in Current Chem. 198 (1998) 163-208.
Guillory, J.K., "Generation of Polymorphs, Hydrates, Solvates, and Amorphous Solids" in Polymorphism in Pharmaceutical Solids (Brittain, H.G., ed., 1999) 183-226.
Byrn, S.R. et al., Solid-State Chemistry of Drugs, 2nd edition (1999) 233-248 (Chapter 11).
U.S. Appl. No. 11/917,811, Notice of Allowance, dated Feb. 18, 2011.
U.S. Appl. No. 12/282,244, Notice of Allowance, dated Feb. 22, 2011.
M. Havranek et al., "E/Z Isomerization of 3,3-disubstituted allylic thioethers" Tetrahedron Lett., vol. 48, pp. 6970-6973 (2007).
P. Sauerberg et al., "Identification and Synthesis of a Novel Selective Partial PPAR-delta Agonist with Full Efficacy on Lipid Metabolism In Vitro and In Vivo" J. Med. Chem., vol. 50, pp. 1495-1503 (2007).
M. Tiikkainen et al., "Effects of Rosiglitazone and Metformin on Liver Fat Content . . . " Diabetes, vol. 53, pp. 2169-2176 (2004).
T. Wilson et al., "The PPARs: From Orphan Receptors to Drug Discovery" J. Med. Chem., vol. 43(4), pp. 527-550 (2000).
S. Kersten et al., "Roles of PPARs in health and disease" Nature, vol. 405, pp. 421-424 (2000).
F. Kaplan et al., "PPARs, Insulin Resistance and Type 2 Diabetes" J. Cardiovasc. Risk, vol. 8(4), pp. 211-217 (2001).
J. Berger et al., "Physiological and Therapeutic Roles of Peroxisome Proliferator-Activated Receptors" Diabetes Technology & Therapeutics, vol. 4(2), pp. 163-174 (2002).
J. Fruchart, "PPAR and Cardiovascular Risk: Overview" J. Cardiovasc. Risk, vol. 8(4), pp. 185-186 (2001).
B. Jones, "Peroxisome Proliferative-Activated Receptor (PPAR) Modulators: Diabetes and Beyond" Med. Res. Rev., vol. 21(6), pp. 540-552 (2001).
J. Vamecq et al., "Medical Significance of Peroxisome Proliferator-Activated Receptors" The Lancet, vol. 354, pp. 141-148 (1999).
I. Torra et al., "Peroxisome proliferator-activated receptors: from transcriptional control to clinical practice" Curr. Opin. Lipidol., vol. 12, pp. 245-254 (2001).
A. Michalik et al., "Peroxisome proliferator-activated receptors: three isotypes for a multitude of functions" Curr. Opin. Biotechnology, vol. 10, pp. 564-570 (1999).
A. Miller et al., "Novel peroxisome proliferator-activated receptor ligands for type 2 diabetes and the metabolic syndrome" Expert Opin. Investig. Drugs, vol. 12(9), pp. 1489-1500 (2003).
W. Wahli, "Peroxisome Proliferator-Activated Receptors (PPARs): from metabolic control to epidermal wound healing" Swiss Med. Weekly, vol. 132, pp. 83-91 (2002).
L. Everett, "The role of hepatic peroxisome proliferator-activated receptors (PPARs) in health and disease" Liver, vol. 20, pp. 191-199 (2000).
A. Mital, "PPARs: Nuclear Receptors for Antidiabetics" CRIPS, vol. 3(1), pp. 5-8 (2002).
K. Liu et al., "Identification of a Series of PPAR gamme/delta Dual Agonists via Solid-Phase Parallel Synthesis" Bioorg. Med. Chem. Lett., vol. 11, pp. 2959-2962 (2001).
Pending Claims for U.S. Appl. No. 11/579,716, dated Nov. 3, 2006.
Pending Claims for U.S. Appl. No. 12/689,014, dated Jan. 18, 2010.
Pending Claims for U.S. Appl. No. 11/917,811, dated May 28, 2010.
Notice of Allowance for U.S. Appl. No. 11/917,811, dated Aug. 6, 2010.
Chilonczyk et al., "Hypolipidaemic and antiplatelet agents", 2001, Expert Opin. Ther. Patents, 11 (8), pp. 1301-1327.
Lee, C.H. et al., "PPAR-delta regulates glucose metabolism and insulin sensitivity", Proceedings of the National Academy of Sciences of the USA, 2006, vol. 103, No. 9, pp. 3444-3449.
Schiffrin et al., "Peroxisome Proliferator-Activated Receptors: Vascular and Cardiac Effects in Hypertension", Hypertension, 2003, 42; pp. 664-668.
Holst et al., "Nutritional regulation and role of peroxisome proliferator-activated receptor delta in fatty acid catabolism in skeletal muscle" Biochim. Biophys. Acta, vol. 1633, pp. 43-50 (2003).
Luquet et al., "Peroxisome proliferator-activated receptor delta controls muscle development and oxydative capability" FASEB J., vol. 17(13), pp. 209-226 (2003).

Wang et al., "Peroxisome-proliferator-activated receptor delta activates fat metabolism to prevent obesity" Cell, vol. 113, pp. 159-170 (2003).

Dressel et al., "The Peroxisome Proliferator-Activated Receptor beta/delta Agonist . . . " Mol. Endocrin., vol. 17(12), pp. 2477-2493 (2003).

Lee et al., "Transcriptional Repression of Atherogenic Inflammation: Modulation by PPAR-delta" Science, vol. 32, pp. 453-457 (2003).

Tanaka et al., "Activation of peroxisome proliferator-activated receptor delta induces fatty acid beta-oxidation in skeletal muscle and attenuates metabolic syndrome" PNAS, vol. 100(26), pp. 15924-15929 (2003).

Pending Claims of U.S. Appl. No. 11/579,716, dated Nov. 17, 2010.
Pending Claims of U.S. Appl. No. 11/579,717, dated Nov. 15, 2010.
Pending Claims of U.S. Appl. No. 12/282,244, dated Jan. 28, 2011.
Pending Claims of U.S. Appl. No. 12/689,014, dated Feb. 11, 2011.
Pending Claims of U.S. Appl. No. 12/771,530, dated Nov. 15, 2011.
Notice of Allowance for U.S. Appl. No. 11/917,811, dated Jan. 5, 2011.

* cited by examiner

COMPOUNDS, THEIR PREPARATION AND USE

CROSS-REFERENCE TO RELATED APPLICATIONS

This application is the United States national stage application, pursuant to 35 U.S.C. 371, of PCT/EP2006/070096, filed Dec. 21, 2006, which claims benefit of priority to European Patent Application No. 05112758.7, filed Dec. 22, 2005, and European Patent Application No. 06115631.1, filed Jun. 19, 2006.

FIELD OF THE INVENTION

The present invention relates to novel compounds, to the use of these compounds as pharmaceutical compositions, to pharmaceutical compositions comprising the compounds and to a method of treatment employing these compounds and compositions. The compounds are activators of peroxisome proliferator-activated receptors (PPAR)-δ.

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content.

PPARδ activation was initially reported not to be involved in modulation of glucose or triglyceride levels. (Berger et al., j. Biol. Chem., 1999, Vol 274, pp. 6718-6725). Later it has been shown that PPARδ activation leads to increased levels of HDL cholesterol in db/db mice (Leibowitz et al. FEBS letters 2000, 473, 333-336). Further, a PPARδ agonist when dosed to insulin-resistant middle-aged obese rhesus monkeys caused a dramitic dose-dependent rise in serum HDL cholesterol while lowering the levels of small dense LDL, fasting triglycerides and fasting insulin (Oliver et al. PNAS 2001, 98, 5306-5311). The same paper also showed that PPARδ activation increased the reverse cholesterol transporter ATP-binding cassette A1 and induced apolipoprotein A1-specific cholesterol efflux. The involvement of PPARδ in fatty acid oxidation in muscles was further substantiated in PPARα knock-out mice. Muoio et al. (J. Biol. Chem. 2002, 277, 26089-26097) showed that the high levels of PPARδ in skeletal muscle can compensate for deficiency in PPARα. In addition to the effects on cholesterol homeostasis, PPARδ treatment was observed to lower plasma glucose and insulin and improve insulin sensitivity in diabetic ob/ob mice and high fat diet induced insulin resistant mice (PNAS 2003, 100, 15924-15929). Taken together these observations suggest that PPARδ activation is useful in the treatment and prevention of Type 2 diabetes and cardiovascular diseases and conditions including atherosclerosis, hypertriglyceridemia, and mixed dyslipidaemia (WO 01/00603).

A number of PPARδ compounds have been reported to be useful in the treatment of hyperglycemia, hyperlipidemia and hypercholesterolemia (WO 02/59098, WO 01/603, WO 01/25181, WO 02/14291, WO 01/79197, WO 99/4815, WO 97/28149, WO 98/27974, WO 97/28115 WO 97/27857, WO 97/28137, WO 97/27847 WO 2004093879, WO 2004092117, WO 2004080947, WO 2004080943, WO 2004073606, WO 2004063166, WO 2004063165, WO 2003072100, WO 2004060871, WO 2004005253, WO 2003097607, WO 2003035603, WO 2004000315, WO 2004000762, WO 2003074495, WO 2002070011, WO 2003084916, US 20040209936, WO 2003074050, WO 2003074051, WO 2003074052, JP 2003171275, WO 2003033493, WO 2003016291, WO 2002076957, WO 2002046154, WO 2002014291, WO 2001079197, WO 2003024395, WO 2002059098, WO 2002062774, WO 2002050048, WO 2002028434, WO 2001000603, WO 2001060807, WO 9728149, WO 2001034200, WO 9904815, WO 200125226, WO 2005097098, WO 2005097762, and WO 2005097763.

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia. This indicate that research for compounds displaying various degree of PPARδ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

Definitions

All references described herein are incorporated in there entirety by reference.

"Substituted" signifies that one or more hydrogen atoms are replaced by the designated substituent. Only pharmaceutically stable compounds are intended to be covered.

When examples of definitions are provided, the definition is not meant to be limited to the specific examples.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When O or S is listed as a substituent, oxo and sulfo, respectively, it is intended that a carbon atom be replaced by either the O or S. For example if alkyl were substituted by O, then an ether would be formed. Preferably heteroatom-heteroatom bonds such as 0-0, O—S, O—N, S—S, and S—N are not formed.

The term "$C_{1-6}$-alkyl" as used herein, alone or in combination, represent a linear or branched, saturated hydrocarbon chain having the indicated number of carbon atoms. Representative examples include, but are not limited to methyl, ethyl, n-propyl, isopropyl, butyl, isobutyl, sec-butyl, tert-butyl, pentyl, isopentyl, hexyl, isohexyl and the like.

The term "$C_{1-6}$-alkylcarbonyl" as used herein, represents a "$C_{1-6}$-alkyl" group as defined above having the indicated number of carbon atoms linked through a carbonyl group. Representative examples include, but are not limited to, methylcarbonyl, ethylcarbonyl, n-propylcarbonyl, isopropylcarbonyl, butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl and the like.

The term "$C_{1-6}$-alkylsulfonyl" as used herein refers to a monovalent substituent comprising a "$C_{1-6}$-alkyl" group as defined above linked through a sulfonyl group. Representative examples include, but are not limited to, methylsulfonyl, ethylsulfonyl, n-propylsulfonyl, iso-propylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl and the like.

The term "$C_{1-6}$-alkylamido" as used herein, refers to an acyl group linked through an amino group; Representative examples include, but are not limited to acetylamino, propionylamino, butyrylamino, isobutyrylamino, pivaloylamino, valerylamino and the like.

The term "$C_{3-6}$-cycloalkyl" as used herein, alone or in combination, represent a saturated monocyclic hydrocarbon group having the indicated number of carbon atoms. Representative examples include, but are not limited to cyclopropyl, cyclobutyl, cyclopentyl, cyclohexyl and the like.

The term "$C_{2-6}$-alkenyl" as used herein, represent an olefinically unsaturated branched or straight hydrocarbon group having from 2 to the specified number of carbon atoms and at least one double bond. Representative examples include, but are not limited to, vinyl, 1-propenyl, 2-propenyl, allyl, isopropenyl, 1,3-butadienyl, 1-butenyl, hexenyl, pentenyl and the like.

The term "$C_{2-6}$-alkynyl" as used herein, represent an unsaturated branched or straight hydrocarbon group having from 2 to the specified number of carbon atoms and at least one triple bond. Representative examples include, but are not limited to, 1-propynyl, 2-propynyl, 1-butynyl, 2-butynyl, 1-pentynyl, 2-pentynyl and the like.

The term "$C_{4-6}$-alkenynyl" as used herein, represent an unsaturated branched or straight hydrocarbon group having from 4 to the specified number of carbon atoms and both at least one double bond and at least one triple bond. Representative examples include, but are not limited to, 1-penten-4-ynyl, 3-penten-1-ynyl, 1,3-hexadiene-5-ynyl and the like.

The term "$C_{1-6}$-alkoxy" as used herein, alone or in combination, refers to a straight or branched configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentyloxy, isohexyloxy and the like.

The term "$C_{3-6}$-cycloalkoxy" as used herein, alone or in combination, represent a saturated monocyclic hydrocarbon group having the indicated number of carbon atoms linked through an ether oxygen having its free valence bond from the ether oxygen. Examples of cycloalkoxy groups are cyclopropyloxy, cyclobutyloxy, cyclopentyloxy, cyclohexyloxy and the like.

The term "$C_{1-6}$-alkylthio" as used herein, alone or in combination, refers to a straight or branched monovalent substituent comprising a "$C_{1-6}$-alkyl" group as defined above linked through a divalent sulfur atom having its free valence bond from the sulfur atom and having 1 to 6 carbon atoms. Representative examples include, but are not limited to, methylthio, ethylthio, propylthio, butylthio, pentylthio and the like.

The term "$C_{3-6}$-cycloalkylthio" as used herein, alone or in combination, represent a saturated monocyclic hydrocarbon group having the indicated number of carbon atoms linked through a divalent sulfur atom having its free valence bond from the sulfur atom. Representative examples include, but are not limited to are cyclopropylthio, cyclobutylthio, cyclopentylthio, cyclohexylthio and the like.

The term "$C_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "$C_{3-6}$-cycloalkylsulfinyl" as used herein refers to a monovalent substituent comprising a $C_{3-6}$-cycloalkyl group linked through a sulfinyl group (—S(=O)—); such as e.g. cyclopropylsulfinyl, cyclobutylsulfinyl, cyclopentylsulfinyl, cyclohexylsulfinyl and the like.

The term "$C_{1-6}$-alkylamino" as used herein, alone or in combination, refers to a straight or branched monovalent substituent comprising a "$C_{1-6}$-alkyl" group as defined above linked through amino having a free valence bond from the nitrogen atom. Representative examples include, but are not limited to, methylamino, ethylamino, propylamino, butylamino, pentylamino and the like.

The term "$C_{1-6}$-alkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl and the like.

The term "$C_{3-6}$-cycloalkylamino" as used herein, alone or in combination, represent a saturated monocyclic hydrocarbon group having the indicated number of carbon atoms linked through amino having a free valence bond from the nitrogen atom. Representative examples include, but are not limited to, cyclopropylamino, cyclobutylamino, cyclopentylamino, cyclohexylamino and the like.

The term "$C_{1-6}$-alkoxyC$_{1-6}$-alkyl" as used herein, alone or in combination, refers to a "$C_{1-6}$-alkyl" group as defined above whereto is attached a "$C_{1-6}$-alkoxy" group as defined above. Representative examples include, but are not limited to, methoxymethyl, ethoxymethyl, methoxyethyl, ethoxyethyl and the like.

The term "aryl" as used herein is intended to include monocyclic, bicyclic or polycyclic carbocyclic aromatic rings. Representative examples are phenyl, naphthyl (e.g. naphth-1-yl, naphth-2-yl), anthryl (e.g. anthr-1-yl, anthr-9-yl), phenanthryl (e.g. phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g. biphenyl-2-yl, biphenyl-3-yl, biphenyl-4-yl), phenylnaphthyl (e.g. 1-phenylnaphth-2-yl, 2-phenylnaphth-1-yl), and the like. Aryl is also intended to include partially saturated bicyclic or polycyclic carbocyclic rings with at least one unsaturated moiety (e.g. a benzo moiety). Representative examples are, indanyl (e.g. indan-1-yl, indan-5-yl), indenyl (e.g. inden-1-yl, inden-5-yl), 1,2,3,4-tetrahydronaphthyl (e.g. 1,2,3,4-tetrahydronaphth-1-yl, 1,2,3,4-tetrahydronaphth-2- yl, 1,2,3,4-tetrahydronaphth-6-yl), 1,2-dihydronaphthyl (e.g. 1,2-dihydronaphth-1-yl, 1,2-dihydronaphth-4-yl, 1,2-dihydronaphth-6-yl), fluorenyl (e.g. fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g. benzonorborn-3-yl, benzonorborn-6-yl), 1,4-ethano-1,2,3,4-tetrahydronapthyl (e.g. 1,4-ethano-1,2,3,4-tetrahydronapth-2-yl, 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro[piperidine-4,2'-indane]-1-yl, spiro[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,2'-indane]-1-yl, spiro[piperidine-4,1'-indene]-1-yl, and the like. Other examples of "aryl" are phenyl, naphthyl, anthracenyl, phenanthrenyl, azulenyl, fluorenyl, indenyl and pentalenyl.

The term "arylene" as used herein refers to divalent aromatic monocyclic or a divalent aromatic fused bi- or tricyclic hydrocarbon group. Representative examples include, but are not limited to, phenylene, naphthylene and the like.

The term "arylcarbonyl" as used herein refers to the radical aryl-C(=O)—. Representative examples are benzoyl, naphthylcarbonyl, 4-phenylbenzoyl, anthrylcarbonyl, phenanthrylcarbonyl, azulenylcarbonyl and the like.

The term "heteroarylcarbonyl" as used herein refers to the radical heteroaryl-C(=O)—. Representative examples are pyridinylcarbonyl (e.g. pyridin-2-ylcarbonyl, pyridin-4-ylcarbonyl), quinolinylcarbonyl (e.g. 2-(quinolin-2-yl)carbonyl, 1-(quinolin-2-yl)carbonyl), imidazolylcarbonyl (e.g. imidazol-2-ylcarbonyl, imidazol-5-ylcarbonyl), and the like.

The term "arylsulfonyl" as used herein refers to an "aryl" group as defined above linked through a sulfonyl group. Representative examples include, but are not limited to, phenylsulfonyl, naphthylsulfonyl, anthracenylsulfonyl, phenanthrenylsulfonyl, azulenylsulfonyl, and the like.

The term "arylamido" as used herein refers to an arylcarbonyl group linked through an amino group. Representative examples include, but are not limited to phenylcarbonylamino, naphthylcarbonylamino, anthracenylcarbonylamino, phenanthrenylcarbonylamino, azulenylcarbonylamino and the like.

The term "halogen" means fluorine, chlorine, bromine or iodine.

The term "perhalomethyl" means trifluoromethyl, trichloromethyl, tribromomethyl or triiodomethyl.

The term "perhalomethoxy" means trifluoromethoxy, trichloromethoxy, tribromomethoxy or triiodomethoxy.

The term "$C_{1-6}$-dialkylamino" as used herein refers to an amino group wherein the two hydrogen atoms independently are substituted with a straight or branched, saturated hydrocarbon chain having the indicated number of carbon atoms. Representative examples include, but are not limited to, N,N-dimethylamino, N-ethyl-N-methylamino, N,N-diethylamino, N,N-dipropylamino (e.g. N,N-(prop-1-yl)$_2$amino, N,N-(prop-2-yl)$_2$amino, N,N-(prop-3-yl)$_2$-amino), N-(but-1-yl)-N-methylamino, N,N-(pent-1-yl)$_2$amino, and the like.

The term "acyl" as used herein refers to a monovalent substituent comprising a "$C_{1-6}$-alkyl" group as defined above linked through a carbonyl group. Representative examples include, but are not limited to, acetyl, propionyl, butyryl, isobutyryl, pivaloyl, valeryl and the like.

The term "heteroaryl" as used herein, alone or in combination, refers to a monovalent substituent comprising a 5-7 membered monocyclic aromatic system or a 8-10 membered bicyclic aromatic system containing one or more heteroatoms selected from nitrogen, oxygen and sulphur. Examples of "heteroaryl" are pyrrolyl (e.g. pyrrol-1-yl, pyrrol-2-yl, pyrrol-3-yl), furanyl (e.g. furan-2-yl, furan-3-yl), thienyl (e.g. thien-2-yl, thien-3-yl), oxazolyl (e.g. oxazol-2-yl, oxazol-4-yl, oxazol-5-yl), thiazolyl (e.g. thiazol-2-yl, thiazol-4-yl, thiazol-5-yl), imidazolyl (e.g. imidazol-2-yl, imidazol-4-yl, imidazol-5-yl), pyrazolyl (e.g. pyrazol-1-yl, pyrazol-3-yl, pyrazol-5-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), 1,2,3-triazolyl (e.g. 1,2,3-triazol-1-yl, 1,2,3-triazol-4-yl, 1,2,3-triazol-5-yl), 1,2,4-triazolyl (e.g. 1,2,4-triazol-1-yl, 1,2,4-triazol-3-yl, 1,2,4-triazol-5-yl), 1,2,3-oxadiazolyl (e.g. 1,2,3-oxadiazol-4-yl, 1,2,3-oxadiazol-5-yl), 1,2,4-oxadiazolyl (e.g. 1,2,4-oxadiazol-3-yl, 1,2,4-oxadiazol-5-yl), 1,2,5-oxadiazolyl (e.g. 1,2,5-oxadiazol-3-yl, 1,2,5-oxadiazol-4-yl), 1,3,4-oxadiazolyl (e.g. 1,3,4-oxadiazol-2-yl, 1,3,4-oxadiazol-5-yl), 1,2,3-thiadiazolyl (e.g. 1,2,3-thiadiazol-4-yl, 1,2,3-thiadiazol-5-yl), 1,2,4-thiadiazolyl (e.g. 1,2,4-thiadiazol-3-yl, 1,2,4-thiadiazol-5-yl), 1,2,5-thiadiazolyl (e.g. 1,2,5-thiadiazol-3-yl, 1,2,5-thiadiazol-4-yl), 1,3,4-thiadiazolyl (e.g. 1,3,4-thiadiazol-2-yl, 1,3,4-thiadiazol-5-yl), tetrazolyl (e.g. tetrazol-1-yl, tetrazol-5-yl), pyranyl (e.g. pyran-2-yl), pyridinyl (e.g. pyridine-2-yl, pyridine-3-yl, pyridine-4-yl), pyridazinyl (e.g. pyridazin-2-yl, pyridazin-3-yl), pyrimidinyl (e.g. pyrimidin-2-yl, pyrimidin-4-yl, pyrimidin-5-yl), pyrazinyl, 1,2,3-triazinyl, 1,2,4-triazinyl, 1,3,5-triazinyl, thiadiazinyl, azepinyl, azecinyl, indolyl (e.g. indol-1-yl, indol-2-yl, indol-3-yl, indol-5-yl), isoindolyl, benzofuranyl (e.g. benzo[b]furan-2-yl, benzo[b]furan-3-yl, benzo[b]furan-5-yl, benzo[c]furan-2-yl, benzo[c]furan-3-yl, benzo[c]furan-5-yl), benzothienyl (e.g. benzo[b]thien-2-yl, benzo[b]thien-3-yl, benzo[b]thien-5-yl, benzo[c]thien-2-yl, benzo[c]thien-3-yl, benzo-[c]thien-5-yl), indazolyl (e.g. indazol-1-yl, indazol-3-yl, indazol-5-yl), indolizinyl (e.g. indolizin-1-yl, indolizin-3-yl), benzopyranyl (e.g. benzo[b]pyran-3-yl, benzo[b]pyran-6-yl, benzo[c]-pyran-1-yl, benzo[c]pyran-7-yl), benzimidazolyl (e.g. benzimidazol-1-yl, benzimidazol-2-yl, benzimidazol-5-yl), benzothiazolyl (e.g. benzothiazol-2-yl, benzothiazol-5-yl), benzisothiazolyl, benzoxazolyl, benzisoxazolyl, benzoxazinyl, benzotriazolyl, naphthyridinyl (e.g. 1,8-naphthyridin-2-yl, 1,7-naphthyridin-2-yl, 1,6-naphthyridin-2-yl), phthalazinyl (e.g. phthalazin-1-yl, phthalazin-5-yl), pteridinyl, purinyl (e.g. purin-2-yl, purin-6-yl, purin-7-yl, purin-8-yl, purin-9-yl), quinazolinyl (e.g. quinazolin-2-yl, quinazolin-4-yl, quinazolin-6-yl), cinnolinyl, quinoliny (e.g. quinolin-2-yl, quinolin-3-yl, quinolin-4-yl, quinolin-6-yl), isoquinolinyl (e.g. isoquinolin-1-yl, isoquinolin-3-yl, isoquinolin-4-yl), quinoxalinyl (e.g. quinoxalin-2-yl, quinoxalin-5-yl), pyrrolopyridinyl (e.g. pyrrolo[2,3-b]pyridinyl, pyrrolo[2,3-c]pyridinyl, pyrrolo[3,2-c]pyridinyl), furopyridinyl (e.g. furo[2,3-b]pyridinyl, furo[2,3-c]pyridinyl, furo[3,2-c]pyridinyl), thienopyridinyl (e.g. thieno[2,3-b]pyridinyl, thieno[2,3-c]pyridinyl, thieno[3,2-c]pyridinyl), imidazopyridinyl (e.g. imidazo[4,5-b]pyridinyl, imidazo[4,5-c]pyridinyl, imidazo[1,5-a]pyridinyl, imidazo[1,2-a]pyridinyl), imidazopyrimidinyl (e.g. imidazo[1,2-a]pyrimidinyl, imidazo[3,4-a]pyrimidinyl), pyrazolopyridinyl (e.g. pyrazolo[3,4-b]pyridinyl, pyrazolo[3,4-c]pyridinyl, pyrazolo[1,5-a]pyridinyl), pyrazolopyrimidinyl (e.g. pyrazolo[1,5-a]pyrimidinyl, pyrazolo[3,4-d]pyrimidinyl), thiazolopyridinyl (e.g. thiazolo[3,2-d]pyridinyl), thiazolopyrimidinyl (e.g. thiazolo[5,4-d]pyrimidinyl), imdazothiazolyl (e.g. imidazo[2,1-b]thiazolyl), triazolopyridinyl (e.g. triazolo[4,5-b]pyridinyl), triazolopyrimidinyl (e.g. 8-azapurinyl), carbazolyl (e.g. carbazol-2-yl, carbazol-3-yl, carbazol-9-yl), phenoxazinyl (e.g. phenoxazin-10-yl), phenazinyl (e.g. phenazin-5-yl), acridinyl (e.g. acridin-9-yl, acridin-10-yl), phenolthiazinyl (e.g. phenothiazin-10-yl), carbolinyl (e.g. pyrido[3,4-b]indol-1-yl, pyrido[3,4-b]indol-3-yl), phenanthrolinyl (e.g. phenanthrolin-5-yl), pyrrolinyl, pyrazolinyl, imidazolinyl (e.g. 4,5-dihydroimidazol-2-yl, 4,5-dihydroimidazol-1-yl), indolinyl (e.g. 2,3-dihydroindol-1-yl, 2,3-dihydroindol-5-yl), dihydrobenzofuranyl (e.g. 2,3-dihydrobenzo[b]furan-2-yl, 2,3-dihydrobenzo[b]furan-4-yl), dihydrobenzothienyl (e.g. 2,3-dihydrobenzo[b]thien-2-yl, 2,3-dihydrobenzo[b]thien-5-yl), 4,5,6,7-tetrahydrobenzo[b]furan-5-yl), dihydrobenzopyranyl (e.g. 3,4-dihydrobenzo[b]pyran-3-yl, 3,4-dihydrobenzo[b]pyran-6-yl, 3,4-dihydrobenzo[c]pyran-1-yl, dihydrobenzo[c]pyran-7-yl), oxazolinyl (e.g. 4,5-dihydrooxazol-2-yl, 4,5-dihydrooxazol-4-yl, 4,5-dihydrooxazol-5-yl), isoxazolinyl, oxazepinyl, tetrahydroindazolyl (e.g. 4,5,6,7-tetrahydroindazol-1-yl, 4,5,6,7-tetrahydroindazol-3-yl, 4,5,6,7-tetrahydroindazol-4-yl, 4,5,6,7-tetrahydroindazol-6-yl), tetrahydrobenzimidazolyl (e.g. 4,5,6,7-tetrahydrobenzimidazol-1-yl, 4,5,6,7-tetrahydrobenzimidazol-5-yl), tetrahydroimidazo[4,5-c]pyridyl (e.g. 4,5,6,7-tetrahydroimidazo[4,5-c]pyrid-1-yl, 4,5,6,7-tetrahydroimidazo[4,5-c]pyrid-5-yl, 4,5,6,7-tetrahydroimidazo[4,5-c]pyrid-6-yl), tetrahydroquinolinyl (e.g. 1,2,3,4-tetrahydroquinolinyl, 5,6,7,8-tetrahydroquinolinyl), tetrahydroisoquinolinyl (e.g. 1,2,3,4-tetrahydroisoquinolinyl, 5,6,7,8-tetrahydroisoquinolinyl), tetrahydroquinoxalinyl (e.g. 1,2,3,4-tetrahydroquinoxalinyl, 5,6,7,8-tetrahydroquinoxalinyl), spiro[isoquinoline-3,1'-cyclohexan]-1-yl, spiro[piperidine-4,1'-benzo[c]thiophen]-1-yl, spiro[piperidine-4,1'-benzo[c]furan]-1-yl, spiro[piperidine-4,3'-benzo[b]furan]-1-yl, spiro[piperidine-4,3'-coumarin]-1-yl.

Other examples of "heteroaryl" are furyl, thienyl, pyrrolyl, imidazolyl, pyrazolyl, triazolyl, pyridyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinnyl, indolyl, benzimidazolyl, benzofuranyl, benzothienyl, benzoxazolyl, tetrazolyl, carbazolyl pteridinyl and purinyl.

The term "heteroarylene" as used herein, alone or in combination, refers to divalent 5-7 membered monocyclic aromatic system or a 8-10 membered bicyclic aromatic system containing one or more heteroatoms selected from nitrogen, oxygen and sulfur, e.g. furylene, thienylene, pyrrolylene, imidazolylene, pyrazolylene, triazolylene, pyridylene, pyrazinylene, pyrimidinylene, pyridazinylene, isothiazolylene, isoxazolylene, oxazolylene, oxadiazolylene, thiadiazolylene, quinolylene, isoquinolylene, quinazolinylene, quinoxalinnylene, indolylene, benzimidazolylene, benzofuranylene, benzothienylene, pteridinylene and purinylene and the like.

The term "heteroaryloxy" as used herein, alone or in combination, refers to a heteroaryl as defined herein linked to an oxygen atom having its free valence bond from the oxygen atom e.g. pyrrolyloxy, imidazolyloxy, pyrazolyloxy, triazolyloxy, pyrazinyloxy, pyrimidinyloxy, pyridazinyloxy, isothiazolyloxy, isoxazolyloxy, oxazolyloxy, oxadiazolyloxy, thiadiazolyloxy, quinolinyloxy, isoquinolinyloxy, quinazolinyloxy, quinoxalinyloxy, indoltloxy, benzimidazolyloxy, benzofuranyloxy, pteridinyloxy and purinyloxy and the like.

The term "aralkyl" as used herein refers to a straight or branched saturated carbon chain containing from 1 to 6 carbons substituted with an aromatic carbohydride. Representative examples include, but are not limited to, benzyl, phenethyl, 3-phenylpropyl, 1-naphthylmethyl, 2-(1-naphthyl)ethyl and the like.

The term "aryloxy" as used herein refers to phenoxy, 1-naphthyloxy, 2-naphthyloxy and the like.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroarylalkyl as defined herein linked to an oxygen atom having its free valence bond from the oxygen atom. Representative examples include, but are not limited to, (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy. Representative examples include, but are not limited to, phenylthio, (4-methylphenyl)-thio, (2-chlorophenyl)thio and the like.

The term "Heterocyclyl" or "heterocycle" signifies a mono-, bi-, or tricyclic ring consisting of carbon atoms and from one to three heteroatom, wherein the heteroatom is selected from oxygen, nitrogen, and sulphur. If sulphur is present, then it can be S, S(O), or S(O)$_2$. If nitrogen is present, then it can be N, NH, substituted N, or N-oxide. The heterocycle is a saturated or partially saturated ring. From 0-2 CH$_2$ groups of the heterocycle can be replaced by C(O). The heterocycle can be attached via a carbon or nitrogen atom, unless linking the nitrogen atom would lead to a quaternary nitrogen. If the heterocycle is bicyclic, then one or both of the rings may have a heteroatom(s) present. If the heterocycle is tricyclic, then one, two, or all three of the rings may have a heteroatom(s) present. Examples of "heterocycle" are aziridinyl (e.g. aziridin-1-yl), azetidinyl (e.g. azetidin-1-yl, azetidin-3-yl), oxetanyl, pyrrolidinyl (e.g. pyrrolidin-1-yl, pyrrolidin-2-yl, pyrrolidin-3-yl), imidazolidinyl (e.g. imidazolidin-1-yl, imidazolidin-2-yl, imidazolidin-4-yl), oxazolidinyl (e.g. oxazolidin-2-yl, oxazolidin-3-yl, oxazolidin-4-yl), thiazolidinyl (e.g. thiazolidin-2-yl, thiazolidin-3-yl, thiazolidin-4-yl), isothiazolidinyl, piperidinyl (e.g. piperidin-1-yl, piperidin-2-yl, piperidin-3-yl, piperidin-4-yl), homopiperidinyl (e.g. homopiperidin-1-yl, homopiperidin-2-yl, homopiperidin-3-yl, homopiperidin-4-yl), piperazinyl (e.g. piperazin-1-yl, piperazin-2-yl), morpholinyl (e.g. morpholin-2-yl, morpholin-3-yl, morpholin-4-yl), thiomorpholinyl (e.g. thiomorpholin-2-yl, thiomorpholin-3-yl, thiomorpholin-4-yl), 1-oxo-thiomorpholinyl, 1,1-dioxothiomorpholinyl, tetrahydrofuranyl (e.g. tetrahydrofuran-2-yl, tetrahydrofuran-3-yl), tetrahydrothienyl, tetrahydro-1,1-dioxothienyl, tetrahydropyranyl (e.g. 2-tetrahydropyranyl), tetrahydrothiopyranyl (e.g. 2-tetrahydrothiopyranyl), 1,4-dioxanyl, 1,3-dioxanyl, octahydroindolyl (e.g. octahydroindol-1-yl, octahydroindol-2-yl, octahydroindol-3-yl, octahydroindol-5-yl), decahydroquinolinyl (e.g. decahydroquinolin-1-yl, decahydroquinolin-2-yl, decahydroquinolin-3-yl, decahydroquinolin-4-yl, decahydroquinolin-6-yl), decahydroquinoxalinyl (e.g. decahydroquinoxalin-1-yl, decahydroquinoxalin- 2-yl, decahydroquinoxalin-6-yl), 3-azabicyclo[3.2.2]nonyl, 2-azabicyclo[2.2.1]heptyl, 3-azabicyclo[3,1,0]hexyl, 2,5-diazabicyclo[2.2.1]heptyl, atropinyl, tropinyl, quinuclidinyl, 1,4-diazabicyclo[2.2.2]octanyl, 1,4-dioxaspiro[4.5]decanyl (e.g. 1,4-dioxaspiro[4.5]decan-2-yl, 1,4-dioxaspiro[4.5]decan-7-yl), 1,4-dioxa-8-azaspiro[4.5]decanyl (e.g. 1,4-dioxa-8-azaspiro[4.5]decan-2-yl, 1,4-dioxa-8-azaspiro[4.5]decan-8-yl), 8-azaspiro[4.5]decanyl (e.g. 8-azaspiro[4.5]decan-1-yl, 8-azaspiro[4.5]decan-8-yl), 2-azaspiro[5.5]undecanyl (e.g. 2-azaspiro[5.5]undecan-2-yl), 2,8-diazaspiro[4.5]decanyl (e.g. 2,8-diazaspiro[4.5]decan-2-yl, 2,8-diazaspiro[4.5]decan-8-yl), 2,8-diazaspiro[5.5]undecanyl (e.g. 2,8-diazaspiro[5.5]undecan-2-yl), 1,3,8-triazaspiro[4.5]decanyl (e.g. 1,3,8-triazaspiro[4.5]decan-1-yl, 1,3,8-triazaspiro[4.5]decan-3-yl, and 1,3,8-triazaspiro[4.5]decan-8-yl). Other examples of "heterocycle" are pyrrolidinyl, pyrrolinyl, tetrahydrofuranyl, dihydrofuranyl, tetrahydrothiophenyl, dihydrothiophenyl, imidzolidnyl, imidazolinyl, pyrazolidinyl, pyrazolinyl, oxazolidinyl, oxazoline, isoxazolidinyl, isoxazoline, thioxazolidinyl, thioxazoline, isothioxazolidinyl, isothioxazoline, triazolidinyl, triazolinyl, tetrazolidinyl, tetrazolinyl, tetrahydropyranyl, dihydropyranyl, pyran, piperidinyl, piperazinyl, homopiperazinyl, morpholino, thiomorpholino, and 1,1-dioxothiomorpholino.

The term "five to eight member ring" as used herein refers to a saturated or unsaturated, substituted or unsubstituted hydrocarbon chain or hydrocarbon-heteroatom chain having from 3 to 6 atoms wherein the carbon atom in Ar, to which they are attached, and the adjacent carbon atom form a five to eight member ring.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

The term "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, e.g., arresting or slowing its development; and/or (c) relieving the disease-state, e.g., causing regression of the disease state itself or some symptom of the disease state.

The term "pharmaceutically acceptable" is defined as being suitable for administration to humans without adverse events.

The term "therapeutically effective amount" is intended to include an amount of a compound of the present invention that is effective when administered alone or in combination to activate glucokinase.

DESCRIPTION OF THE INVENTION

The present invention relates to compounds of the general formula (I):

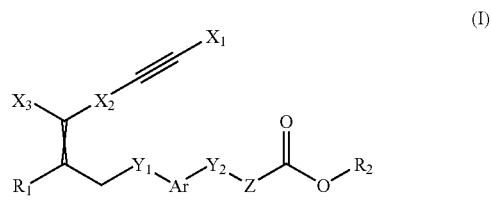

wherein is a double bond, with either E or Z substitution;
$X_1$ is heterocyclyl, aryl or heteroaryl each of which is optionally substituted with one or more substituents selected from
  halogen, hydroxy, cyano, amino, oxo or carboxy; or
  $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of hydroxy or halogen; or
wherein $X_1$ is heterocyclyl-$C_{1-6}$-alkyl, aralkyl or heteroaralkyl each of which is optionally substituted with one or more substituents selected from
  halogen, hydroxy, cyano, amino, oxo or carboxy; or
  $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, heterocyclyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of hydroxy, carboxy or halogen; or
$X_1$ is $C_{1-6}$-alkyl, $C_{3-6}$-cycloalkyl, $C_{2-6}$-alkenyl, carbamoyl or $C_{3-6}$-cycloalkyl-$C_{1-6}$-alkyl each of which is optionally substituted with one or more substituents selected from
  halogen, hydroxy, cyano, amino or carboxy; or
  $C_{1-6}$-alkyl, $C_{3-6}$-cycloalkyl, $C_{2-6}$-alkenyl, $C_{2-6}$-alkynyl, $C_{3-6}$-cycloalkyl-$C_{1-6}$-alkyl, aryl, aralkyl, heteroaryl, heteroaralkyl, heterocyclyl, $C_{1-6}$-alkoxy, $C_{3-6}$-cycloalkoxy, $C_{3-6}$-cycloalkyl-$C_{1-6}$-alkoxy, aryloxy, heteroaryloxy, aralkoxy, heteroaralkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, heteroaryl-$C_{1-6}$-alkylthio, $C_{1-6}$-alkylcarbonyl, $C_{3-6}$-cycloalkylcarbonyl, $C_{3-6}$-cycloalkyl-$C_{1-6}$-alkyl-carbonyl, arylcarbonyl, heteroarylcarbonyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkoxycarbonyl, $C_{3-6}$-cycloalkoxycarbonyl, $C_{3-6}$-cycloalkyl-$C_{1-6}$-alkoxycarbonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, $C_{3-6}$-cycloalkylamido, $C_{3-6}$-cycloalkyl-$C_{1-6}$-alkylamido, arylamido, $C_{1-6}$-alkylaminocarbonyl, $C_{3-6}$-cycloalkylaminocarbonyl, $C_{3-6}$-cycloalkyl-$C_{1-6}$-alkylaminocarbonyl, di-($C_{1-6}$-alkyl)aminocarbonyl, di-($C_{3-6}$-cycloalkyl-$C_{1-6}$-alkyl)aminocarbonyl, $C_{1-6}$-alkylamino, $C_{1-6}$-dialkylamino, $C_{3-6}$-cycloalkylamino, $C_{3-6}$-cycloalkyl-$C_{1-6}$-alkylamino, di-($C_{1-6}$-alkyl)amino, di-($C_{3-6}$-cycloalkyl)amino or di-($C_{3-6}$-cycloalkyl-$C_{1-6}$-alkyl)amino each of which is optionally substituted with one or more of halogen, $C_{1-6}$-alkyl, cyano, hydroxy, hydroxy-$C_{1-6}$-alkyl, acetyl or oxo;

$X_2$ is arylene or heteroarylene each of which is optionally substituted with one or more substituents selected from halogen, hydroxy, cyano, amino or carboxy; or $C_{1-6}$-alkyl, $C_{3-6}$-cycloalkyl, $C_{2-6}$-alkenyl, $C_{2-6}$-alkynyl, $C_{1-6}$-alkoxy, $C_{3-6}$-cycloalkoxy, $C_{1-6}$-alkylthio, $C_{3-6}$-cycloalkylthio, $C_{1-6}$-alkylamino, $C_{1-6}$-dialkylamino or $C_{3-6}$-cycloalkylamino each of which is optionally substituted with one or more halogens; and $X_3$ is aryl or heteroaryl each of which is optionally substituted with one or more substituents selected from halogen, perhalomethyl, hydroxy, cyano, amino or carboxy; or $C_{1-6}$-alkyl, $C_{3-6}$-cycloalkyl, $C_{2-6}$-alkenyl, $C_{1-6}$-alkoxy, $C_{3-6}$-cycloalkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, aryl, heteroaryl or $C_{3-6}$-cycloalkylamino each of which is optionally substituted with one or more $C_{1-6}$-alkyl or halogens; and Ar is arylene which is optionally substituted with one or more substituents selected from halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or two of the substituents when placed in adjacent positions together with the atoms to which they are attached may form a five to eight member ring; and $Y_1$ is O or S; and $Y_2$ is O, S or $CH_2$; and Z is —$(CH_2)_n$— wherein n is 1, 2 or 3; and $R_1$ is hydrogen, halogen or a substituent selected from $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; and $R_2$ is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl; or a pharmaceutically acceptable salt thereof, or a pharmaceutically acceptable solvate thereof, or any tautomeric forms, stereoisomers, mixture of stereoisomers including a racemic mixture, or polymorphs.

In another embodiment, the present invention relates to compounds of the general formula (I) wherein $X_1$ is heterocyclyl, aryl or heteroaryl each of which is optionally substituted with one or more substituents selected from halogen, hydroxy, cyano, amino, oxo or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of hydroxy or halogen; or wherein $X_1$ is heterocyclyl-$C_{1-6}$-alkyl, aralkyl or heteroaralkyl each of which is optionally substituted with one or more substituents selected from halogen, hydroxy, cyano, amino, oxo or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, heterocyclyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of hydroxy, carboxy or halogen; or $X_1$ is $C_{1-6}$-alkyl, $C_{3-6}$-cycloalkyl, $C_{2-6}$-alkenyl, carbamoyl or $C_{3-6}$-cycloalkyl-$C_{1-6}$-alkyl each of which is optionally substituted with one or more substituents selected from halogen, hydroxy, cyano, amino or carboxy; or $C_{1-6}$-alkyl, $C_{3-6}$-cycloalkyl, $C_{2-6}$-alkenyl, $C_{2-6}$-alkynyl, $C_{3-6}$-cycloalkyl-$C_{1-6}$-alkyl, $C_{1-6}$-alkoxy, $C_{3-6}$-cycloalkoxy, $C_{3-6}$-cycloalkyl-$C_{1-6}$-alkoxy, aryloxy, heteroaryloxy, aralkoxy, heteroaralkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, heteroaryl-$C_{1-6}$-alkylthio, $C_{1-6}$-alkylcarbonyl, $C_{3-6}$-cycloalkylcarbonyl, $C_{3-6}$-cycloalkyl-$C_{1-6}$-alkyl-carbonyl, arylcarbonyl, heteroarylcarbonyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkoxycarbonyl, $C_{3-6}$-cycloalkoxycarbonyl, $C_{3-6}$-cycloalkyl-$C_{1-6}$-alkoxycarbonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, $C_{3-6}$-cycloalkylamido, $C_{3-6}$-cycloalkyl-$C_{1-6}$-alkylamido, arylamido, $C_{1-6}$-alkylaminocarbonyl, $C_{3-6}$-cycloalkylaminocarbonyl, $C_{3-6}$-cycloalkyl-$C_{1-6}$-alkylaminocarbonyl, di-($C_{1-6}$-alkyl)-aminocarbonyl, di-($C_{3-6}$-cycloalkyl-$C_{1-6}$-alkyl)aminocarbonyl, $C_{1-6}$-alkylamino, $C_{1-6}$-dialkylamino, $C_{3-6}$-cycloalkylamino, $C_{3-6}$-cycloalkyl-$C_{1-6}$-alkylamino, di-($C_{1-6}$-alkyl)amino, di-($C_{3-6}$-cycloalkyl)amino or di-($C_{3-6}$-cycloalkyl-$C_{1-6}$-alkyl)amino each of which is optionally substituted with one or more of halogen, $C_{1-6}$-alkyl, cyano, hydroxy, hydroxy-$C_{1-6}$-alkyl, acetyl or oxo.

In another embodiment, the present invention relates to compounds of the general formula (I), wherein $X_1$ is aryl or heteroaryl each of which is optionally substituted with one or more substituents selected from halogen, hydroxy, cyano, amino, oxo or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of hydroxy or halogen; or $X_1$ is $C_{1-6}$-alkyl, $C_{3-6}$-cycloalkyl, $C_{2-6}$-alkenyl, carbamoyl or $C_{3-6}$-cycloalkyl-$C_{1-6}$-alkyl each of which is optionally substituted with one or more substituents selected from halogen, hydroxy, cyano, amino or carboxy; or $C_{1-6}$-alkyl, $C_{3-6}$-cycloalkyl, $C_{2-6}$-alkenyl, $C_{2-6}$-alkynyl, $C_{3-6}$-cycloalkyl-$C_{1-6}$-alkyl, aryl, aralkyl, heteroaryl, heteroaralkyl, heterocyclyl, $C_{1-6}$-alkoxy, $C_{3-6}$-cycloalkoxy, $C_{3-6}$-cycloalkyl-$C_{1-6}$-alkoxy, aryloxy, heteroaryloxy, aralkoxy, heteroaralkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, heteroaryl-$C_{1-6}$-alkylthio, $C_{1-6}$-alkylcarbonyl, $C_{3-6}$-cycloalkylcarbonyl, $C_{3-6}$-cycloalkyl-$C_{1-6}$-alkyl-carbonyl, arylcarbonyl, heteroarylcarbonyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkoxycarbonyl, $C_{3-6}$-cycloalkoxycarbonyl, $C_{3-6}$-cycloalkyl-$C_{1-6}$-alkoxycarbonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, $C_{3-6}$-cycloalkylamido, $C_{3-6}$-cycloalkyl-$C_{1-6}$-alkylamido, arylamido, $C_{1-6}$-alkylaminocarbonyl, $C_{3-6}$-cycloalkylaminocarbonyl, $C_{3-6}$-cycloalkyl-$C_{1-6}$-alkylaminocarbonyl, di-($C_{1-6}$-alkyl)aminocarbonyl, di-($C_{3-6}$-cycloalkyl-$C_{1-6}$-alkyl)aminocarbonyl, $C_{1-6}$-alkylamino, $C_{1-6}$-dialkylamino, $C_{3-6}$-cycloalkylamino, $C_{3-6}$-cycloalkyl-$C_{1-6}$-alkylamino, di-($C_{1-6}$-alkyl)amino, di-($C_{3-6}$-cycloalkyl)amino or di-($C_{3-6}$-cycloalkyl-$C_{1-6}$-alkyl)amino each of which is optionally substituted with one or more of halogen, $C_{1-6}$-alkyl, cyano, hydroxy, hydroxy-$C_{1-6}$-alkyl, acetyl or oxo.

In another embodiment, the present invention is concerned with compounds of formula (I) wherein $X_1$ is heterocyclyl optionally substituted with one or more substituents selected from
halogen, hydroxy, oxo or carboxy; or
$C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkyl, amino, each of which is optionally substituted with one or more halogens.

In another embodiment, the present invention is concerned with compounds of formula (I) wherein $X_1$ is heterocyclyl, which is optionally substituted with one or more substituents selected from
halogen, hydroxy or oxo; or
$C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heterocyclyl, which is optionally substituted with one or more substituents selected from
halogen, hydroxy or oxo; or
$C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is heterocyclyl, which is optionally substituted with one or more substituents selected from
halogen or hydroxy; or
$C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is aryl optionally substituted with one or more substituents selected from
halogen, hydroxy, oxo or carboxy; or
$C_{1-6}$-alkyl, $C_{3-6}$-cycloalkyl, aryl, aralkyl, heteroaryl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of hydroxy or halogen.

In another embodiment, the present invention is concerned with compounds of formula (I) wherein $X_1$ is aryl optionally substituted with one or more substituents selected from
halogen or oxo; or
$C_{1-6}$-alkyl, aryl, $C_{1-6}$-alkoxy or $C_{1-6}$-alkylsulfonyl each of which is optionally substituted with one or more of hydroxy or halogen.

In another embodiment, the present invention is concerned with compounds of formula (I) wherein $X_1$ is aryl optionally substituted with one or more substituents selected from
halogen; or
$C_{1-6}$-alkyl optionally substituted with hydroxy.

In another embodiment, the present invention is concerned with compounds of formula (I) wherein $X_1$ is aryl substituted with $C_{1-6}$-alkyl.

In another embodiment, the present invention is concerned with compounds of formula (I) wherein $X_1$ is aryl.

In another embodiment, the present invention is concerned with compounds of formula (I) wherein $X_1$ is phenyl optionally substituted with one or more substituents selected from
halogen or oxo; or
$C_{1-6}$-alkyl, aryl, $C_{1-6}$-alkoxy or $C_{1-6}$-alkylsulfonyl each of which is optionally substituted with one or more of hydroxy or halogen.

In another embodiment, the present invention is concerned with compounds of formula (I) wherein $X_1$ is phenyl optionally substituted with one or more substituents selected from
halogen; or
$C_{1-6}$-alkyl optionally substituted with hydroxy or halogen.

In another embodiment, the present invention is concerned with compounds of formula (I) wherein $X_1$ is phenyl optionally substituted with trifluoromethyl.

In another embodiment, the present invention is concerned with compounds of formula (I) wherein $X_1$ is phenyl optionally substituted with one or more halogens.

In another embodiment, the present invention is concerned with compounds of formula (I) wherein $X_1$ is phenyl optionally substituted with one or more of methyl or ethyl, each of which is substituted with hydroxy.

In another embodiment, the present invention is concerned with compounds of formula (I) wherein $X_1$ is phenyl substituted with one or more of methyl or ethyl.

In another embodiment, the present invention is concerned with compounds of formula (I) wherein $X_1$ is phenyl.

In another embodiment, the present invention is concerned with compounds of formula (I) wherein $X_1$ is heteroaryl optionally substituted with one or more substituents selected from
halogen, hydroxy, oxo or carboxy; or
$C_{1-6}$-alkyl, $C_{3-6}$-cycloalkyl, aryl, aralkyl, heteroaryl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of hydroxy or halogen.

In another embodiment, the present invention is concerned with compounds of formula (I) wherein $X_1$ is heteroaryl optionally substituted with one or more substituents selected from
- halogen or oxo; or
- $C_{1-6}$-alkyl, aryl, $C_{1-6}$-alkoxy or $C_{1-6}$-alkylsulfonyl each of which is optionally substituted with one or more of hydroxy or halogen.

In another embodiment, the present invention is concerned with compounds of formula (I) wherein $X_1$ is heteroaryl optionally substituted with one or more substituents selected from
- halogen or oxo; or
- $C_{1-6}$-alkyl or $C_{1-6}$-alkoxy each of which is optionally substituted with one or more of hydroxy or halogen.

In another embodiment, the present invention is concerned with compounds of formula (I) wherein $X_1$ is heteroaryl.

In another embodiment, the present invention is concerned with compounds of formula (I) wherein $X_1$ is pyridyl optionally substituted with one or more of $C_{1-6}$-alkyl.

In another embodiment, the present invention is concerned with compounds of formula (I) wherein $X_1$ is pyridyl.

In another embodiment, the present invention is concerned with compounds of formula (I) wherein $X_1$ is benzothienyl optionally substituted with one or more of oxo and $C_{1-6}$-alkyl.

In another embodiment, the present invention is concerned with compounds of formula (I) wherein $X_1$ is thienyl optionally substituted with one or more of $C_{1-6}$-alkyl.

In another embodiment, the present invention is concerned with compounds of formula (I) wherein $X_1$ is heterocyclyl-$C_{1-6}$-alkyl optionally substituted with one or more substituents selected from
- halogen, hydroxy, oxo or carboxy; or
- $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkyl, amino, each of which is optionally substituted with one or more halogens.

In another embodiment, the present invention is concerned with compounds of formula (I) wherein $X_1$ is heterocyclyl-$C_{1-6}$-alkyl optionally substituted with one or more substituents selected from
- halogen, hydroxy or oxo; or
- $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heterocyclyl-$C_{1-6}$-alkyl optionally substituted with one or more substituents selected from
- halogen, hydroxy or oxo; or
- $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is heterocyclyl-$C_{1-6}$-alkyl optionally substituted with one or more substituents selected from
- halogen or hydroxy; or
- $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is aralkyl optionally substituted with one or more substituents selected from
- halogen, hydroxy, oxo or carboxy; or
- $C_{1-6}$-alkyl, $C_{3-6}$-cycloalkyl, aryl, aralkyl, heteroaryl, heteroaralkyl, heterocyclyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkyl, amino, each of which is optionally substituted with one or more of carboxy or halogen.

In another embodiment, the present invention is concerned with compounds of formula (I) wherein $X_1$ is aralkyl optionally substituted with one or more substituents selected from
- halogen, hydroxy or oxo; or
- $C_{1-6}$-alkyl, $C_{3-6}$-cycloalkyl, aryl, aralkyl, heteroaryl, heteroaralkyl, heterocyclyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more of carboxy or halogen.

In another embodiment, the present invention is concerned with compounds of formula (I) wherein $X_1$ is aralkyl optionally substituted with one or more substituents selected from
- halogen, hydroxy or oxo; or
- $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is aralkyl optionally substituted with one or more substituents selected from
- halogen or hydroxy; or
- $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is aralkyl optionally substituted with heterocyclyl, which is optionally substituted with one or more of carboxy or halogen.

In another embodiment, the present invention is concerned with compounds of formula (I) wherein $X_1$ is aralkyl optionally substituted with piperidinyl optionally substituted with carboxy.

In another embodiment, the present invention is concerned with compounds of formula (I) wherein $X_1$ is heteroaralkyl optionally substituted with one or more substituents selected from
- halogen, hydroxy, oxo or carboxy; or
- $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkyl, amino, each of which is optionally substituted with one or more halogens.

In another embodiment, the present invention is concerned with compounds of formula (I) wherein $X_1$ is heteroaralkyl optionally substituted with one or more substituents selected from halogen, hydroxy or oxo; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heteroaralkyl optionally substituted with one or more substituents selected from halogen, hydroxy or oxo; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is heteroaralkyl optionally substituted with one or more substituents selected from halogen or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is $C_{1-6}$-alkyl optionally substituted with one or more substituents selected from halogen, hydroxy, cyano, amino or carboxy; or $C_{1-6}$-alkyl, $C_{3-6}$-cycloalkyl, $C_{2-6}$-alkenyl, $C_{2-6}$-alkynyl, $C_{3-6}$-cycloalkyl-$C_{1-6}$-alkyl, aryl, aralkyl, heteroaryl, heteroaralkyl, heterocyclyl, $C_{1-6}$-alkoxy, $C_{3-6}$-cycloalkoxy, $C_{3-6}$-cycloalkyl-$C_{1-6}$-alkoxy, aryloxy, heteroaryloxy, aralkoxy, heteroaralkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, heteroaryl-$C_{1-6}$-alkylthio, $C_{1-6}$-alkylcarbonyl, $C_{3-6}$-cycloalkylcarbonyl, $C_{3-6}$-cycloalkyl-$C_{1-6}$-alkyl-carbonyl, arylcarbonyl, heteroarylcarbonyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkoxycarbonyl, $C_{3-6}$-cycloalkoxycarbonyl, $C_{3-6}$-cycloalkyl-$C_{1-6}$-alkoxycarbonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, $C_{3-6}$-cycloalkylamido, $C_{3-6}$-cycloalkyl-$C_{1-6}$-alkylamido, arylamido, $C_{1-6}$-alkylaminocarbonyl, $C_{3-6}$-cycloalkylaminocarbonyl, $C_{3-6}$-cycloalkyl-$C_{1-6}$-alkylaminocarbonyl, di-($C_{1-6}$-alkyl)aminocarbonyl, di-($C_{3-6}$-cycloalkyl-$C_{1-6}$-alkyl)aminocarbonyl, $C_{1-6}$-alkylamino, $C_{1-6}$-dialkylamino, $C_{3-6}$-cycloalkylamino, $C_{3-6}$-cycloalkyl-$C_{1-6}$-alkylamino, di-($C_{1-6}$-alkyl)amino, di-($C_{3-6}$-cycloalkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl, acetyl or oxo.

In another embodiment, the present invention is concerned with compounds of formula (I) wherein $X_1$ is $C_{1-6}$-alkyl optionally substituted with one or more substituents selected from halogen, hydroxy, cyano, amino or carboxy; or $C_{1-6}$-alkyl, $C_{3-6}$-cycloalkyl, $C_{2-6}$-alkenyl, $C_{2-6}$-alkynyl, $C_{3-6}$-cycloalkyl-$C_{1-6}$-alkyl, $C_{1-6}$-alkoxy, $C_{3-6}$-cycloalkoxy, $C_{3-6}$-cycloalkyl-$C_{1-6}$-alkoxy, aryloxy, heteroaryloxy, aralkoxy, heteroaralkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, heteroaryl-$C_{1-6}$-alkylthio, $C_{1-6}$-alkylcarbonyl, $C_{3-6}$-cycloalkylcarbonyl, $C_{3-6}$-cycloalkyl-$C_{1-6}$-alkyl-carbonyl, arylcarbonyl, heteroarylcarbonyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkoxycarbonyl, $C_{3-6}$-cycloalkoxycarbonyl, $C_{3-6}$-cycloalkyl-$C_{1-6}$-alkoxycarbonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, $C_{3-6}$-cycloalkylamido, $C_{3-6}$-cycloalkyl-$C_{1-6}$-alkylamido, arylamido, $C_{1-6}$-alkylaminocarbonyl, $C_{3-6}$-cycloalkylaminocarbonyl, $C_{3-6}$-cycloalkyl-$C_{1-6}$-alkylaminocarbonyl, di-($C_{1-6}$-alkyl)aminocarbonyl, di-($C_{3-6}$-cycloalkyl-$C_{1-6}$-alkyl)aminocarbonyl, $C_{1-6}$-alkylamino, $C_{1-6}$-dialkylamino, $C_{3-6}$-cycloalkylamino, $C_{3-6}$-cycloalkyl-$C_{1-6}$-alkylamino, di-($C_{1-6}$-alkyl)amino, di-($C_{3-6}$-cycloalkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl, acetyl or oxo.

In another embodiment, the present invention is concerned with compounds of formula (I) wherein $X_1$ is $C_{1-6}$-alkyl optionally substituted with one or more substituents selected from halogen or hydroxy; or $C_{1-6}$-alkyl, aryl, aralkyl, heteroaryl, heteroaralkyl, heterocyclyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{1-6}$-alkyl optionally substituted with one or more substituents selected from halogen or hydroxy; or $C_{1-6}$-alkyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{1-6}$-alkyl optionally substituted with one or more substituents selected from halogen or hydroxy; or $C_{1-6}$-alkyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{1-6}$-alkyl optionally substituted with one or more substituents selected from $C_{1-6}$-alkyl, aryl, heterocyclyl, $C_{1-6}$-alkylsulfonyl, $C_{1-6}$-alkylthio, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl optionally substituted with one or more substituents selected from halogen or hydroxy; or $C_{1-6}$-alkyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{1-6}$-alkyl optionally substituted with one or more substituents selected from aryl, aralkyl, heteroaryl, heteroaralkyl, heterocyclyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{1-6}$-alkyl optionally substituted with one or more substituents selected from aryl, heteroaryl, heterocyclyl, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, $C_{3-6}$-cycloalkylamino, or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{1-6}$-alkyl optionally substituted with one or more substituents selected from $C_{1-6}$-alkyl, $C_{1-6}$-alkylsulfonyl, $C_{1-6}$-alkylthio, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl optionally substituted with one or more of $C_{1-6}$-alkyl.

In another embodiment, the present invention is concerned with compounds of formula (I) wherein $X_1$ is $C_{1-6}$-alkyl optionally substituted with aryl, aralkyl, heteroaryl, heteroaralkyl, heterocyclyl, each of which is optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl substituted with aryl optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl substituted with aralkyl optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl substituted with heteroaryl optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl substituted with heteroaralkyl optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl substituted with heterocyclyl, optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl optionally substituted with heteroaryl.

In another embodiment, the present invention is concerned with compounds of formula (I) wherein $X_1$ is $C_{1-6}$-alkyl substituted with pyrazolyl.

In another embodiment, the present invention is concerned with compounds of formula (I) wherein $X_1$ is $C_{1-6}$-alkyl substituted with pyridyl.

In another embodiment, the present invention is concerned with compounds of formula (I) wherein $X_1$ is $C_{1-6}$-alkyl substituted with thienyl.

In another embodiment, the present invention is concerned with compounds of formula (I) wherein $X_1$ is $C_{1-6}$-alkyl optionally substituted with one or more of heterocyclyl optionally substituted with one or more $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl optionally substituted with one or more of morpholinyl, piperazinyl, piperidinyl or pyrrolidinyl, each of which is optionally substituted with one or more of $C_{1-6}$-alkyl, hydroxy or hydroxy-$C_{1-6}$-alkyl.

In another embodiment, the present invention is concerned with compounds of formula (I) wherein $X_1$ is $C_{1-6}$-alkyl optionally substituted with one or more of morpholino, piperazino, piperidino or pyrrolidino.

In another embodiment, the present invention is concerned with compounds of formula (I) wherein $X_1$ is $C_{1-6}$-alkyl substituted with morpholino.

In another embodiment, the present invention is concerned with compounds of formula (I) wherein $X_1$ is $C_{1-6}$-alkyl optionally substituted with one or more of $C_{1-6}$-alkylsulfonyl.

In another embodiment, the present invention is concerned with compounds of formula (I) wherein $X_1$ is $C_{1-6}$-alkyl optionally substituted with one or more of $C_{1-6}$-alkylthio.

In another embodiment, the present invention is concerned with compounds of formula (I) wherein $X_1$ is $C_{1-6}$-alkyl optionally substituted with $C_{1-6}$-alkylamino.

In another embodiment, the present invention is concerned with compounds of formula (I) wherein $X_1$ is $C_{1-6}$-alkyl optionally substituted with $C_{1-6}$-dialkylamino.

In another embodiment, the present invention is concerned with compounds of formula (I) wherein $X_1$ is $C_{1-6}$-alkyl optionally substituted with di-($C_{1-6}$-alkyl)amino.

In another embodiment, the present invention is concerned with compounds of formula (I) wherein $X_1$ is $C_{1-6}$-alkyl optionally substituted with di-($C_{3-6}$-cycloalkyl-$C_{1-6}$-alkyl)amino.

In another embodiment, the present invention is concerned with compounds of formula (I) wherein $X_1$ is $C_{3-6}$-cycloalkyl optionally substituted with one or more substituents selected from
  halogen or hydroxy; or
  $C_{1-6}$-alkyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{3-6}$-cycloalkyl optionally substituted with one or more substituents selected from $C_{1-6}$-alkyl, $C_{1-6}$-alkylsulfonyl, $C_{1-6}$-alkylthio, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{2-6}$-alkenyl optionally substituted with one or more substituents selected from
  halogen or hydroxy; or
  $C_{1-6}$-alkyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{2-6}$-alkenyl optionally substituted with one or more substituents selected from $C_{1-6}$-alkyl, $C_{1-6}$-alkylsulfonyl, $C_{1-6}$-alkylthio, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is carbamoyl optionally substituted with one or more substituents selected from
  halogen or hydroxy; or
  $C_{1-6}$-alkyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is carbamoyl optionally substituted with one or more substituents selected from $C_{1-6}$-alkyl, $C_{1-6}$-alkylsulfonyl, $C_{1-6}$-alkylthio, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, hydroxy or hydroxy-$C_{1-6}$-alkyl.

In another embodiment, the present invention is concerned with compounds of formula (I) wherein $X_1$ is $C_{3-6}$-cycloalkyl-$C_{1-6}$-alkyl optionally substituted with one or more substituents selected from
  halogen or hydroxy; or
  $C_{1-6}$-alkyl, $C_{1-6}$-alkoxy, $C_{1-6}$-alkylthio, $C_{3-6}$-cycloalkylthio, $C_{3-6}$-cycloalkyl-$C_{1-6}$-alkylthio, arylthio, heteroarylthio, aryl-$C_{1-6}$-alkylthio, $C_{1-6}$-alkylcarbonyl, arylcarbonyl, $C_{1-6}$-alkylsulfonyl, arylsulfonyl, amino-$C_{1-6}$-alkyl, $C_{1-6}$-alkylamino-$C_{1-6}$-alkyl, di-($C_{1-6}$-alkyl)amino-$C_{1-6}$-alkyl, $C_{1-6}$-alkylamido, arylamido, $C_{1-6}$-alkylaminocarbonyl, di-($C_{1-6}$-alkyl)aminocarbonyl, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, cyano, hydroxy, hydroxy-$C_{1-6}$-alkyl or oxo.

In another embodiment, the present invention is concerned with compounds of formula (I) wherein $X_1$ is $C_{3-6}$-cycloalkyl-$C_{1-6}$-alkyl optionally substituted with one or more substituents selected from $C_{1-6}$-alkyl, $C_{1-6}$-alkylsulfonyl, $C_{1-6}$-alkylthio, $C_{1-6}$-alkylamino, $C_{1-6}$-dialkylamino, $C_{3-6}$-cycloalkylamino, di-($C_{1-6}$-alkyl)amino or di-($C_{3-6}$-cycloalkyl-$C_{1-6}$-alkyl)amino, each of which is optionally substituted with one or more of halogen, $C_{1-6}$-alkyl, hydroxy or hydroxy-$C_{1-6}$-alkyl.

In another embodiment, the present invention is concerned with compounds of formula (I) wherein $X_2$ is arylene optionally substituted with one or more substituents selected from
  halogen or
  $C_{1-6}$-alkyl optionally substituted with one or more halogens.

In another embodiment, the present invention is concerned with compounds of formula (I) wherein $X_2$ is arylene optionally substituted with one or more halogens.

In another embodiment, the present invention is concerned with compounds of formula (I) wherein $X_2$ is phenylene optionally substituted with one or more substituents selected from
  halogen or
  $C_{1-6}$-alkyl optionally substituted with one or more halogens.

In another embodiment, the present invention is concerned with compounds of formula (I) wherein $X_2$ is phenylene optionally substituted with one or more halogens.

In another embodiment, the present invention is concerned with compounds of formula (I) wherein $X_2$ is phenylene optionally substituted with one or more of $C_{1-6}$-alkyl.

In another embodiment, the present invention is concerned with compounds of formula (I) wherein $X_2$ is phenylene.

In another embodiment, the present invention is concerned with compounds of formula (I) wherein $X_2$ is heteroarylene optionally substituted with one or more substituents selected from
halogen or
$C_{1-6}$-alkyl optionally substituted with one or more halogens.

In another embodiment, the present invention is concerned with compounds of formula (I) wherein $X_2$ is heteroarylene optionally substituted with one or more halogens.

In another embodiment, the present invention is concerned with compounds of formula (I) wherein $X_2$ is heteroarylene.

In another embodiment, the present invention is concerned with compounds of formula (I) wherein $X_3$ is aryl or heteroaryl each of which is substituted with one or more substituents selected from
halogen, perhalomethyl, or
$C_{1-6}$-alkyl, $C_{3-6}$-cycloalkyl, $C_{1-6}$-alkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, aryl or heteroaryl, each of which is optionally substituted with one or more $C_{1-6}$-alkyl or halogens.

In another embodiment, the present invention is concerned with compounds of formula (I) wherein $X_3$ is aryl or heteroaryl each of which is substituted with one or more substituents selected from
halogen, perhalomethyl, or
$C_{1-6}$-alkyl, $C_{3-6}$-cycloalkyl, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, aryl or heteroaryl, each of which is optionally substituted with one or more $C_{1-6}$-alkyl.

In another embodiment, the present invention is concerned with compounds of formula (I) wherein $X_3$ is aryl or heteroaryl each of which is substituted with halogen, hydroxy or amino; or $C_{1-6}$-alkoxy, $C_{3-6}$-cycloalkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl or heteroaryl each of which is substituted with halogen, hydroxy or amino.

In another embodiment, the present invention is concerned with compounds of formula (I) wherein $X_3$ is aryl or heteroaryl each of which is substituted with one or more halogens.

In another embodiment, the present invention is concerned with compounds of formula (I) wherein $X_3$ is aryl or heteroaryl each of which is substituted with halogen.

In another embodiment, the present invention is concerned with compounds of formula (I) wherein $X_3$ is aryl or heteroaryl each of which is substituted with $C_{1-6}$-alkoxy, $C_{3-6}$-cycloalkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl or heteroaryl each of which is substituted with $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino, each of which is optionally substituted with one or more $C_{1-6}$-alkyl or halogens.

In another embodiment, the present invention is concerned with compounds of formula (I) wherein $X_3$ is aryl or heteroaryl each of which is substituted with $C_{1-6}$-alkylthio, perhalomethylthio, $C_{1-6}$-alkylsulfinyl, $C_{1-6}$-alkylsulfonyl, $C_{1-6}$-alkylsulfamoyl, each of which is optionally substituted with one or more $C_{1-6}$-alkyl or halogens.

In another embodiment, the present invention is concerned with compounds of formula (I) wherein $X_3$ is aryl or heteroaryl each of which is substituted with $C_{3-6}$-cycloalkoxy, $C_{3-6}$-cycloalkylthio, $C_{3-6}$-cycloalkylsulfinyl, $C_{3-6}$-cycloalkylsulfonyl, $C_{3-6}$-cycloalkyl-$C_{1-6}$-alkylsulfonyl, arylsulfonyl, heteroarylsulfonyl or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl or heteroaryl each of which is substituted with $C_{3-6}$-cycloalkoxy, $C_{3-6}$-cycloalkylthio, $C_{3-6}$-cycloalkylsulfinyl, $C_{3-6}$-cycloalkylsulfonyl or arylsulfonyl, each of which is optionally substituted with one or more $C_{1-6}$-alkyl or halogens.

In another embodiment, the present invention is concerned with compounds of formula (I) wherein $X_3$ is aryl or heteroaryl each of which is substituted with perhalomethyl, cyano or carboxy; or $C_{1-6}$-alkyl, $C_{2-6}$-alkenyl, $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino each of which is optionally substituted with one or more $C_{1-6}$-alkyl or halogens.

In another embodiment, the present invention is concerned with compounds of formula (I) wherein $X_3$ is aryl or heteroaryl each of which is substituted with perhalomethyl, cyano or carboxy.

In another embodiment, the present invention is concerned with compounds of formula (I) wherein $X_3$ is aryl or heteroaryl each of which is substituted with $C_{1-6}$-alkyl, $C_{2-6}$-alkenyl, $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino each of which is optionally substituted with one or more $C_{1-6}$-alkyl or halogens.

In another embodiment, the present invention is concerned with compounds of formula (I) wherein $X_3$ is aryl or heteroaryl each of which is substituted with $C_{1-6}$-alkyl or $C_{2-6}$-alkenyl, each of which is optionally substituted with one or more $C_{1-6}$-alkyl or halogens.

In another embodiment, the present invention is concerned with compounds of formula (I) wherein $X_3$ is aryl or heteroaryl each of which is substituted with $C_{3-6}$-cycloalkyl, $C_{3-6}$-cycloalkoxy, $C_{3-6}$-cycloalkylthio, $C_{3-6}$-cycloalkylsulfinyl, $C_{3-6}$-cycloalkylsulfonyl, $C_{3-6}$-cycloalkyl-$C_{1-6}$-alkylsulfonyl, arylsulfonyl, heteroarylsulfonyl, aryl, heteroaryl or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl or heteroaryl each of which is substituted with $C_{3-6}$-cycloalkyl, aryl or heteroaryl each of which is optionally substituted with one or more $C_{1-6}$-alkyl or halogens;

In another embodiment, the present invention is concerned with compounds of formula (I) wherein $X_3$ is aryl or heteroaryl.

In another embodiment, the present invention is concerned with compounds of formula (I) wherein $X_3$ is aryl optionally substituted with one or more substituents selected from
halogen, perhalomethyl, or
$C_{1-6}$-alkyl, $C_{3-6}$-cycloalkyl, $C_{1-6}$-alkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, aryl or heteroaryl, each of which is optionally substituted with one or more $C_{1-6}$-alkyl or halogens.

In another embodiment, the present invention is concerned with compounds of formula (I) wherein $X_3$ is aryl optionally substituted with one or more substituents selected from
halogen, perhalomethyl, or
$C_{1-6}$-alkyl, $C_{3-6}$-cycloalkyl, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, aryl or heteroaryl, each of which is optionally substituted with one or more $C_{1-6}$-alkyl.

In another embodiment, the present invention is concerned with compounds of formula (I) wherein $X_3$ is aryl substituted with halogen, hydroxy or amino; or $C_{1-6}$-alkoxy, $C_{3-6}$-cycloalkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl substituted with halogen, hydroxy or amino.

In another embodiment, the present invention is concerned with compounds of formula (I) wherein $X_3$ is aryl substituted with one or more halogens.

In another embodiment, the present invention is concerned with compounds of formula (I) wherein $X_3$ is aryl substituted with halogen.

In another embodiment, the present invention is concerned with compounds of formula (I) wherein $X_3$ is aryl substituted with $C_{1-6}$-alkoxy, $C_{3-6}$-cycloalkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl substituted with $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino, each of which is optionally substituted with one or more $C_{1-6}$-alkyl or halogens.

In another embodiment, the present invention is concerned with compounds of formula (I) wherein $X_3$ is aryl substituted with $C_{1-6}$-alkylthio, perhalomethylthio, $C_{1-6}$-alkylsulfinyl, $C_{1-6}$-alkylsulfonyl, $C_{1-6}$-alkylsulfamoyl, each of which is optionally substituted with one or more $C_{1-6}$-alkyl or halogens.

In another embodiment, the present invention is concerned with compounds of formula (I) wherein $X_3$ is aryl substituted with $C_{3-6}$-cycloalkoxy, $C_{3-6}$-cycloalkylthio, $C_{3-6}$-cycloalkylsulfinyl, $C_{3-6}$-cycloalkylsulfonyl, $C_{3-6}$-cycloalkyl-$C_{1-6}$-alkylsulfonyl, arylsulfonyl, hetero-arylsulfonyl or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl substituted with $C_{3-6}$-cycloalkoxy, $C_{3-6}$-cycloalkylthio, $C_{3-6}$-cycloalkylsulfinyl, $C_{3-6}$-cycloalkylsulfonyl or arylsulfonyl, each of which is optionally substituted with one or more $C_{1-6}$-alkyl or halogens.

In another embodiment, the present invention is concerned with compounds of formula (I) wherein $X_3$ is aryl substituted with perhalomethyl, cyano or carboxy; or $C_{1-6}$-alkyl, $C_{2-6}$-alkenyl, $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino each of which is optionally substituted with one or more $C_{1-6}$-alkyl or halogens.

In another embodiment, the present invention is concerned with compounds of formula (I) wherein $X_3$ is aryl substituted with perhalomethyl, cyano or carboxy.

In another embodiment, the present invention is concerned with compounds of formula (I) wherein $X_3$ is aryl substituted with $C_{1-6}$-alkyl, $C_{2-6}$-alkenyl, $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino each of which is optionally substituted with one or more $C_{1-6}$-alkyl or halogens.

In another embodiment, the present invention is concerned with compounds of formula (I) wherein $X_3$ is aryl substituted with $C_{1-6}$-alkyl or $C_{2-6}$-alkenyl, each of which is optionally substituted with one or more $C_{1-6}$-alkyl or halogens.

In another embodiment, the present invention is concerned with compounds of formula (I) wherein $X_3$ is aryl substituted with $C_{3-6}$-cycloalkyl, $C_{3-6}$-cycloalkoxy, $C_{3-6}$-cycloalkylthio, $C_{3-6}$-cycloalkylsulfinyl, $C_{3-6}$-cycloalkylsulfonyl, $C_{3-6}$-cycloalkyl-$C_{1-6}$-alkylsulfonyl, arylsulfonyl, heteroarylsulfonyl, aryl, heteroaryl or $C_{3-6}$-cycloalkylamino each of which is optionally substituted with one or more $C_{1-6}$-alkyl or halogens.

In another embodiment, the present invention is concerned with compounds of formula (I) wherein $X_3$ is aryl substituted with $C_{3-6}$-cycloalkyl, aryl or heteroaryl each of which is optionally substituted with one or more $C_{1-6}$-alkyl or halogens;

In another embodiment, the present invention is concerned with compounds of formula (I) wherein $X_3$ is aryl.

In another embodiment, the present invention is concerned with compounds of formula (I) wherein $X_3$ is phenyl optionally substituted with one or more substituents selected from
halogen, perhalomethyl, or
$C_{1-6}$-alkyl, $C_{3-6}$-cycloalkyl, $C_{1-6}$-alkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, aryl or heteroaryl, each of which is optionally substituted with one or more $C_{1-6}$-alkyl or halogens.

In another embodiment, the present invention is concerned with compounds of formula (I) wherein $X_3$ is phenyl substituted with one or more halogens.

In another embodiment, the present invention is concerned with compounds of formula (I) wherein $X_3$ is phenyl substituted halogen.

In another embodiment, the present invention is concerned with compounds of formula (I) wherein $X_3$ is phenyl optionally substituted with one or more of perhalomethyl.

In another embodiment, the present invention is concerned with compounds of formula (I) wherein $X_3$ is phenyl substituted trifluoromethyl.

In another embodiment, the present invention is concerned with compounds of formula (I) wherein $X_3$ is phenyl substituted with $C_{1-6}$-alkyl, which is optionally substituted with one or more $C_{1-6}$-alkyl.

In another embodiment, the present invention is concerned with compounds of formula (I) wherein $X_3$ is phenyl substituted with $C_{3-6}$-cycloalkyl.

In another embodiment, the present invention is concerned with compounds of formula (I) wherein $X_3$ is phenyl substituted with $C_{1-6}$-alkylthio.

In another embodiment, the present invention is concerned with compounds of formula (I) wherein $X_3$ is phenyl substituted with $C_{3-6}$-cycloalkylthio.

In another embodiment, the present invention is concerned with compounds of formula (I) wherein $X_3$ is phenyl substituted with perhalomethylthio.

In another embodiment, the present invention is concerned with compounds of formula (I) wherein $X_3$ is phenyl substituted with $C_{1-6}$-alkylsulfinyl.

In another embodiment, the present invention is concerned with compounds of formula (I) wherein $X_3$ is phenyl substituted with $C_{3-6}$-cycloalkylsulfinyl.

In another embodiment, the present invention is concerned with compounds of formula (I) wherein $X_3$ is phenyl substituted with methyl.

In another embodiment, the present invention is concerned with compounds of formula (I) wherein $X_3$ is phenyl optionally substituted with one or more of thienyl, which is optionally substituted with one or more $C_{1-6}$-alkyl.

In another embodiment, the present invention is concerned with compounds of formula (I) wherein $X_3$ is phenyl.

In another embodiment, the present invention is concerned with compounds of formula (I) wherein $X_3$ is heteroaryl optionally substituted with one or more substituents selected from
halogen, perhalomethyl, or
$C_{1-6}$-alkyl, $C_{3-6}$-cycloalkyl, $C_{1-6}$-alkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, aryl or heteroaryl, each of which is optionally substituted with one or more of $C_{1-6}$-alkyl or halogen.

In another embodiment, the present invention is concerned with compounds of formula (I) wherein $X_3$ is heteroaryl optionally substituted with one or more substituents selected from
halogen, perhalomethyl, or
$C_{1-6}$-alkyl, $C_{3-6}$-cycloalkyl, $C_{1-6}$-alkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{1-6}$-alkylamino, $C_{1-6}$-dialkylamino, aryl or heteroaryl, each of which is optionally substituted with one or more of $C_{1-6}$-alkyl or halogen.

In another embodiment, the present invention is concerned with compounds of formula (I) wherein $X_3$ is heteroaryl optionally substituted with one or more substituents selected from
halogen, or
$C_{1-6}$-alkyl, $C_{1-6}$-alkoxy, $C_{1-6}$-alkylthio, $C_{1-6}$-alkylamino, $C_{1-6}$-dialkylamino, aryl or heteroaryl, each of which is optionally substituted with one or more of $C_{1-6}$-alkyl or halogen.

In another embodiment, the present invention is concerned with compounds of formula (I) wherein $X_3$ is heteroaryl optionally substituted with one or more substituents selected from
halogen, or
$C_{1-6}$-alkyl or aryl, each of which is optionally substituted with one or more of $C_{1-6}$-alkyl or halogen.

In another embodiment, the present invention is concerned with compounds of formula (I) wherein $X_3$ is heteroaryl substituted with halogen, hydroxy or amino; or $C_{1-6}$-alkoxy, $C_{3-6}$-cycloalkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, or $C_{3-6}$-cycloalkylamino each of which is optionally substituted with one or more $C_{1-6}$-alkyl or halogens.

In another embodiment, the present invention is concerned with compounds of formula (I) wherein $X_3$ is heteroaryl substituted with halogen, hydroxy or amino.

In another embodiment, the present invention is concerned with compounds of formula (I) wherein $X_3$ is heteroaryl substituted with one or more halogens.

In another embodiment, the present invention is concerned with compounds of formula (I) wherein $X_3$ is heteroaryl substituted with halogen.

In another embodiment, the present invention is concerned with compounds of formula (I) wherein $X_3$ is heteroaryl substituted with $C_{1-6}$-alkoxy, $C_{3-6}$-cycloalkoxy, $C_{1-6}$-alkylthio, $C_{3-6}$-cycloalkylthio, perhalomethylthio, $C_{1-6}$-alkylsulfinyl, $C_{3-6}$-cycloalkylsulfinyl, $C_{1-6}$-alkylsulfonyl, $C_{3-6}$-cycloalkylsulfonyl, $C_{3-6}$-cycloalkyl-$C_{1-6}$-alkylsulfonyl, arylsulfonyl, heteroarylsulfonyl, $C_{1-6}$-alkylsulfamoyl, di-($C_{1-6}$-alkyl)sulfamoyl, $C_{1-6}$-alkylamino, $C_{1-6}$-dialkylamino, or $C_{3-6}$-cycloalkylamino each of which is optionally substituted with one or more $C_{1-6}$-alkyl or halogens.

In another embodiment, the present invention is concerned with compounds of formula (I) wherein $X_3$ is heteroaryl substituted with $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino, each of which is optionally substituted with one or more $C_{1-6}$-alkyl or halogens.

In another embodiment, the present invention is concerned with compounds of formula (I) wherein $X_3$ is heteroaryl substituted with $C_{1-6}$-alkylthio, perhalomethylthio, $C_{1-6}$-alkylsulfinyl, $C_{1-6}$-alkylsulfonyl, $C_{1-6}$-alkylsulfamoyl, each of which is optionally substituted with one or more $C_{1-6}$-alkyl or halogens.

In another embodiment, the present invention is concerned with compounds of formula (I) wherein $X_3$ is heteroaryl substituted with $C_{3-6}$-cycloalkoxy, $C_{3-6}$-cycloalkylthio, $C_{3-6}$-cycloalkylsulfinyl, $C_{3-6}$-cycloalkylsulfonyl, $C_{3-6}$-cycloalkyl-$C_{1-6}$-alkylsulfonyl, arylsulfonyl, heteroarylsulfonyl or $C_{3-6}$-cycloalkylamino each of which is optionally substituted with one or more $C_{1-6}$-alkyl or halogens.

In another embodiment, the present invention is concerned with compounds of formula (I) wherein $X_3$ is heteroaryl substituted with $C_{3-6}$-cycloalkoxy, $C_{3-6}$-cycloalkylthio, $C_{3-6}$-cycloalkylsulfinyl, $C_{3-6}$-cycloalkylsulfonyl or arylsulfonyl, each of which is optionally substituted with one or more $C_{1-6}$-alkyl or halogens.

In another embodiment, the present invention is concerned with compounds of formula (I) wherein $X_3$ is heteroaryl substituted with perhalomethyl, cyano or carboxy; or $C_{1-6}$-alkyl, $C_{2-6}$-alkenyl, $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino each of which is optionally substituted with one or more $C_{1-6}$-alkyl or halogens.

In another embodiment, the present invention is concerned with compounds of formula (I) wherein $X_3$ is heteroaryl substituted with perhalomethyl, cyano or carboxy.

In another embodiment, the present invention is concerned with compounds of formula (I) wherein $X_3$ is heteroaryl substituted with $C_{1-6}$-alkyl, $C_{2-6}$-alkenyl, $C_{1-6}$-alkoxy, $C_{1-6}$-alkylthio, perhalomethylthio, $C_{1-6}$-alkylsulfinyl, $C_{1-6}$-alkylsulfonyl, $C_{1-6}$-alkylsulfamoyl, di-($C_{1-6}$-alkyl)sulfamoyl, $C_{1-6}$-alkylamino or $C_{1-6}$-dialkylamino each of which is optionally substituted with one or more $C_{1-6}$-alkyl or halogens.

In another embodiment, the present invention is concerned with compounds of formula (I) wherein $X_3$ is heteroaryl substituted with $C_{1-6}$-alkyl or $C_{2-6}$-alkenyl, each of which is optionally substituted with one or more $C_{1-6}$-alkyl or halogens.

In another embodiment, the present invention is concerned with compounds of formula (I) wherein $X_3$ is heteroaryl substituted with $C_{3-6}$-cycloalkyl, $C_{3-6}$-cycloalkoxy, $C_{3-6}$-cycloalkylthio, $C_{3-6}$-cycloalkylsulfinyl, $C_{3-6}$-cycloalkylsulfonyl, $C_{3-6}$-cycloalkyl-$C_{1-6}$-alkylsulfonyl, arylsulfonyl, heteroarylsulfonyl, aryl, heteroaryl or $C_{3-6}$-cycloalkylamino each of which is optionally substituted with one or more $C_{1-6}$-alkyl or halogens.

In another embodiment, the present invention is concerned with compounds of formula (I) wherein $X_3$ is heteroaryl substituted with $C_{3-6}$-cycloalkyl, aryl or heteroaryl each of which is optionally substituted with one or more $C_{1-6}$-alkyl or halogens;

In another embodiment, the present invention is concerned with compounds of formula (I) wherein $X_3$ is heteroaryl.

In another embodiment, the present invention is concerned with compounds of formula (I) wherein $X_3$ is benzofuran optionally substituted with one or more of $C_{1-6}$-alkyl.

In another embodiment, the present invention is concerned with compounds of formula (I) wherein $X_3$ is benzothiophene optionally substituted with one or more of $C_{1-6}$-alkyl.

In another embodiment, the present invention is concerned with compounds of formula (I) wherein $X_3$ is pyridine optionally substituted with one or more of aryl.

In another embodiment, the present invention is concerned with compounds of formula (I) wherein $X_3$ is thienyl optionally substituted with one or more substituents selected from halogen or $C_{1-6}$-alkyl.

In another embodiment, the present invention is concerned with compounds of formula (I) wherein Ar is arylene which is optionally substituted with one or more substituents selected from
  halogen; or
  $C_{1-6}$-alkyl, $C_{1-6}$-alkoxy, aryloxy or aralkoxy each of which is optionally substituted with one or more halogens; or
  two of the substituents when placed in adjacent positions together with the atoms to which they are attached form a five membered carbon cycle.

In another embodiment, the present invention is concerned with compounds of formula (I) wherein Ar is phenylene which is optionally substituted with one or more substituents selected from
  halogen; or
  $C_{1-6}$-alkyl, $C_{1-6}$-alkoxy, aryloxy or aralkoxy each of which is optionally substituted with one or more halogens; or
  two of the substituents when placed in adjacent positions together with the atoms to which they are attached form a five membered carbon cycle.

In another embodiment, the present invention is concerned with compounds of formula (I) wherein Ar is phenylene where two of the substituents placed in adjacent positions together with the atoms to which they are attached form a five membered carbon cycle.

In another embodiment, the present invention is concerned with compounds of formula (I) wherein Ar is benzofuranyl.

In another embodiment, the present invention is concerned with compounds of formula (I) wherein Ar is phenylene which is optionally substituted with one or more substituents selected from halogen or $C_{1-6}$-alkyl.

In another embodiment, the present invention is concerned with compounds of formula (I) wherein Ar is phenylene which is optionally substituted with halogen.

In another embodiment, the present invention is concerned with compounds of formula (I) wherein Ar is phenylene which is optionally substituted with one or more of $C_{1-6}$-alkyl optionally substituted with one or more halogens.

In another embodiment, the present invention is concerned with compounds of formula (I) wherein Ar is phenylene which is optionally substituted with one or more of $C_{1-6}$-alkoxy optionally substituted with one or more halogens.

In another embodiment, the present invention is concerned with compounds of formula (I) wherein Ar is phenylene which is optionally substituted with one or more of aryloxy optionally substituted with one or more halogens.

In another embodiment, the present invention is concerned with compounds of formula (I) wherein Ar is phenylene which is optionally substituted with one or more of aralkoxy optionally substituted with one or more halogens.

In another embodiment, the present invention is concerned with compounds of formula (I) wherein Ar is phenylene which is optionally substituted with methyl.

In another embodiment, the present invention is concerned with compounds of formula (I) wherein Ar is phenylene.

In another embodiment, the present invention is concerned with compounds of formula (I) wherein $Y_1$ is S.

In another embodiment, the present invention is concerned with compounds of formula (I) wherein $Y_1$ is O.

In another embodiment, the present invention is concerned with compounds of formula (I) wherein $Y_2$ is O.

In another embodiment, the present invention is concerned with compounds of formula (I) wherein $Y_2$ is S.

In another embodiment, the present invention is concerned with compounds of formula (I) wherein $Y_2$ is $CH_2$.

In another embodiment, the present invention is concerned with compounds of formula (I) wherein n is 1.

In another embodiment, the present invention is concerned with compounds of formula (I) wherein n is 2.

In another embodiment, the present invention is concerned with compounds of formula (I) wherein $R_1$ is hydrogen or a substituent selected from $C_{1-6}$-alkyl, aralkyl, $C_{1-6}$-alkoxy, aryloxy, aralkoxy each of which is optionally substituted with one or more halogens.

In another embodiment, the present invention is concerned with compounds of formula (I) wherein $R_1$ is hydrogen or a substituent selected from $C_{1-6}$-alkyl, $C_{1-6}$-alkoxy each of which is optionally substituted with one or more halogens.

In another embodiment, the present invention is concerned with compounds of formula (I) wherein $R_1$ is hydrogen.

In another embodiment, the present invention is concerned with compounds of formula (I) wherein $R_1$ is methyl or ethyl.

In another embodiment, the present invention is concerned with compounds of formula (I) wherein $R_1$ is methoxy or ethoxy.

In another embodiment, the present invention is concerned with compounds of formula (I) wherein $R_2$ is hydrogen or $C_{1-6}$-alkyl.

In another embodiment, the present invention is concerned with compounds of formula (I) wherein $R_2$ is hydrogen.

In another embodiment, the present invention is concerned with compounds of formula (I) wherein $R_2$ is methyl or ethyl.

In another embodiment, the present invention is concerned with compounds of formula I wherein alkyl is methyl or ethyl.

In another embodiment, the present invention is concerned with compounds of formula I wherein alkenyl is vinyl or 1-propenyl.

In another embodiment, the present invention is concerned with compounds of formula I wherein alkynyl is 1-propynyl.

In another embodiment, the present invention is concerned with compounds of formula I wherein alkenynyl is 1-pentene-4-yne.

In another embodiment, the present invention is concerned with compounds of formula I wherein alkoxy is methoxy, ethoxy, isopropoxy or cyclopropoxy.

In another embodiment, the present invention is concerned with compounds of formula I wherein aryl is phenyl.

In another embodiment, the present invention is concerned with compounds of formula I wherein arylene is phenylene.

In another embodiment, the present invention is concerned with compounds of formula I wherein halogen is bromine, fluorine or chlorine.

In another embodiment, the present invention is concerned with compounds of formula I wherein perhalomethyl is trifluoromethyl.

In another embodiment, the present invention is concerned with compounds of formula I wherein perhalomethoxy is trifluoromethoxy, In another embodiment, the present invention is concerned with compounds of formula I wherein heteroaryl is furyl or thienyl.

In another embodiment, the present invention is concerned with compounds of formula I wherein heteroaryl is pyrazolyl, pyrrolyl or pyridyl.

In another embodiment, the present invention is concerned with compounds of formula I wherein heteroaryl is benzofuryl or benzothienyl.

In another embodiment, the present invention is concerned with compounds of formula I wherein heterocyclyl is pyrrolidinyl, piperidinyl, piperazinyl or morpholinyl.

In another embodiment, the present invention is concerned with compounds of formula I wherein heteroarylene is thienylene.

In another embodiment, the present invention is concerned with compounds of formula I wherein aralkyl is benzyl.

In another embodiment, the present invention is concerned with compounds of formula I wherein aryloxy is phenoxy.

In another embodiment, the present invention is concerned with compounds of formula I wherein aralkoxy is benzyloxy.

In another embodiment, the present invention is concerned with compounds of formula I which are PPARδ agonists.

In another embodiment, the present invention is concerned with compounds of formula I which are selective PPARδ agonists.

Examples of compounds of the invention are:
(E)-[2-Methyl-4-[3-phenyl-3-[4-(phenylethynyl)phenyl]allylsulfanyl]phenoxy]acetic acid;
(E)-[2-Methyl-4-[3-[4-[3-(morpholin-4-yl)propynyl]phenyl]-3-phenylallyloxy]phenoxy]acetic acid;
(Z)-[2-Methyl-4-[3-(4-methylphenyl)-3-[4-[3-(morpholin-4-yl)propynyl]phenyl]allyloxy]-phenoxy]acetic acid;
(E)-[2-Methyl-4-[3-[4-[3-(pyrazol-1-yl)prop-1-ynyl]phenyl]-3-(4-trifluoromethyl phenyl)-allyloxy]-phenoxy]acetic acid;
(E)-[2-Methyl-4-[3-[4-(pyridin-2-ylethynyl)phenyl]-3-(4-trifluoromethylphenyl)allyloxy]-phenoxy]acetic acid;
(Z)-[4-[3-(4-Chlorophenyl)-3-[4-(4-methylphenylethynyl)phenyl]allyloxy]-2-methylphenoxy]-acetic acid;
(E)-[4-[3-(4-Chlorophenyl)-3-[4-(3,3-dimethylbutynyl)phenyl]allyloxy]-2-methylphenoxy]acetic acid;
(E)-[4-[3-(4-Chlorophenyl)-3-[4-[3-(dimethylamino)propynyl]phenyl]allyloxy]-2-methylphenoxy]acetic acid;
(E)-[4-[3-(4-Chlorophenyl)-3-[4-(pyridin-2-ylethynyl)phenyl]allyloxy]-2-methylphenoxy]acetic acid;
(E)-[4-[3-(4-Fluorophenyl)-3-[4-[3-(morpholin-4-yl)propynyl]phenyl]allyloxy]-2-methylphenoxy]acetic acid;
(E)-[4-[3-(4-Fluorophenyl)-3-[4-[3-(methylsulfanyl)propynyl]phenyl]allyloxy]-2-methylphenoxy]acetic acid;
(E)-[4-[3-(4-Fluorophenyl)-3-[4-[(pyridin-2-yl)ethynyl]phenyl]allyloxy]-2-methylphenoxy]acetic acid
(E)-[4-[3-[4-[3-(Dimethylamino)propynyl]phenyl]-3-(4-fluorophenyl)allyloxy]-2-methylphenoxy]acetic acid;
(E)-[4-[3-(4-Fluorophenyl)-3-[4-[3-(pyrazol-1-yl)propynyl]phenyl]allyloxy]-2-methylphenoxy]acetic acid;
(E)-[4-[3-(4-Chlorophenyl)-3-[4-[3-(pyrrolidin-1-yl)propynyl]phenyl]allyloxy]-2-methylphenoxy]acetic acid;
(E)-[4-[3-(4-Chlorophenyl)-3-[4-[3-(pyrazol-1-yl)propynyl]phenyl]allyloxy]-2-methylphenoxy]acetic acid;
(E)-[2-Methyl-4-[3-[4-(5-methylthiophen-2-yl)phenyl]-3-[4-[3-(morpholin-4-yl)propynyl]-phenyl]allyloxy]phenoxy]acetic acid;
(Z)-[2-Methyl-4-[3-(4-methylphenyl)-3-[4-(pyridin-2-ylethynyl)phenyl]allyloxy]phenoxy]acetic acid;
(Z)-[2-Methyl-4-[3-(4-methylphenyl)-3-[4-(3-pyrazol-1-yl-propynyl)phenyl]allyloxy]phenoxy]-acetic acid;
E)-[2-Methyl-4-[3-[4-[3-(morpholin-4-yl)propynyl]phenyl]-3-(4-trifluoromethylphenyl)allyloxy]-phenoxy]acetic acid;
(E)-[4-[3-[4-[3-(4-Hydroxypiperidin-1-yl)propynyl]phenyl]-3-(4-trifluoromethylphenyl)allyloxy]-2-methylphenoxy]acetic acid;
(E)-[2-Methyl-4-[3-[4-[3-(N,N-dimethylamino)propynyl]phenyl]-3-(4-trifluoromethyl phenyl)-allyloxy]phenoxy]acetic acid;
(E)-[2-Methyl-4-[3-[4-[(5-methylthiophen-2-yl)ethynyl]phenyl]-3-(4-trifluoromethylphenyl)-allyloxy]phenoxy]acetic acid;
(E)-[2-Methyl-4-[3-[4-(5-methylthiophen-2-yl)phenyl]-3-[4-[3-(pyrrolidin-1-yl)propynyl]phenyl]-allyloxy]phenoxy]acetic acid;
(E)-[2-Methyl-4-[3-(2-methylbenzo[b]furan-5-yl)-3-[4-(3-(pyrrolidin-1-yl)propynyl)phenyl]-allyloxy]phenoxy]acetic acid;
(E)-[2-Methyl-4-[3-(2-methylbenzo[b]furan-5-yl)-3-[4-(3-(morpholin-4-yl)propynyl)phenyl]-allyloxy]phenoxy]acetic acid;

(E)-[2-Methyl-4-[3-(2-methylbenzo[b]furan-5-yl)-3-[4-(3-(dimethylamino)propynyl)phenyl]-allyloxy]phenoxy]acetic acid;
(E)-[4-[3-[4-[3-[N-(2-Hydroxyethyl)-N-methylamino]propynyl]phenyl]-3-(2-methylbenzo[b]-furan-5-yl)allyloxy]-2-methylphenoxy]acetic acid;
(E)-[2-Methyl-4-[3-[4-[3-(pyrrolidin-1-yl)propynyl]phenyl]-3-(4-trifluoromethylphenyl)allyloxy]-phenoxy]acetic acid;
(Z)-[4-[3-(4-tert-Butylphenyl)-3-[4-[3-(morpholin-4-yl)propynyl]phenyl]allyloxy]-2-methylphenoxy]acetic acid;
(Z)-[4-[3-(4-tert-Butylphenyl)-3-[4-(2-methyl-1,1-dioxobenzo[b]thiophen-5-ylethynyl)phenyl]-allyloxy]-2-methylphenoxy]acetic acid;
(E)-[2-Methyl-4-[3-[4-[3-(morpholin-4-yl)propynyl]phenyl]-3-(6-phenylpyridin-3-yl)allyloxy]-phenoxy]acetic acid;
(E)-[4-[3-(4-Chlorophenyl)-3-[4-[3-(N-cyclopropylamino)propynyl]phenyl]allyloxy]-2-methylphenoxy]acetic acid;
(E)-[2-Methyl-4-[3-[4-[3-(pyrazol-1-yl)propynyl]phenyl]-3-(3-trifluoromethyl phenyl)allyloxy]-phenoxy]acetic acid;
(E)-[2-Methyl-4-[3-[4-[3-(morpholin-4-yl)propynyl]phenyl]-3-(3-trifluoromethylphenyl)allyloxy]phenoxy]acetic acid;
(E)-[4-[3-[4-[3-(4-Hydroxypiperidin-1-yl)propynyl]phenyl]-3-(3-trifluoromethylphenyl)allyloxy]-2-methylphenoxy]acetic acid;
(E)-[4-[3-[4-[3-(N,N-Dimethylamino)propynyl]phenyl]-3-(3-trifluoromethylphenyl)allyloxy]-2-methylphenoxy]acetic acid;
(Z)-[4-[3-(4-Cyclopropylphenyl)-3-[4-[3-(morpholin-4-yl)propynyl]phenyl]allyloxy]-2-methylphenoxy]acetic acid;
(Z)-[4-[3-(4-Cyclopropylphenyl)-3-[4-[3-(N,N-dimethylamino)propynyl]phenyl]allyloxy]-2-methylphenoxy]acetic acid;
(E)-[2-Methyl-4-[3-(4-methylsulfanylphenyl)-3-[4-[3-(morpholin-4-yl)propynyl]phenyl]-allyloxy]phenoxy]acetic acid;
(E)-[2-Methyl-4-[3-(4-methylsulfinylphenyl)-3-[4-[3-(morpholin-4-yl)propynyl]phenyl]allyloxy]-phenoxy]acetic acid;
(E)-[2-Methyl-4-[3-[4-[(5-methylthiophen-2-yl)ethynyl]phenyl]-3-(3-trifluoromethylphenyl)-allyloxy]phenoxy]acetic acid;
(Z)-[4-[3-(4-tert-Butyl phenyl)-3-[4-[3-(N,N-dimethylamino)propynyl]phenyl]allyloxy]-2-methylphenoxy]acetic acid;
(E)-[4-[3-(4-Chlorophenyl)-3-[4-[3-(4-methylpiperazin-1-yl)propynyl]phenyl]allyloxy]-2-methylphenoxy]acetic acid;
(E)-[4-[3-(4-Chlorophenyl)-3-[4-[3-[N-(2-hydroxyethyl)-N-methylamino]propynyl]phenyl]-allyloxy]-2-methylphenoxy]acetic acid;
(E)-[4-[3-(4-Chlorophenyl)-3-[4-[3-(morpholin-4-yl)propynyl]phenyl]allyloxy]-2-methylphenoxy]acetic acid;
(E)-[4-[3-(4-Chlorophenyl)-3-[4-[3-(4-hydroxypiperidin-1-yl)propynyl]phenyl]allyloxy]-2-methylphenoxy]acetic acid;
(E)-[2-Methyl-4-[3-(4-methylsulfanylphenyl)-3-[4-[3-(pyrazol-1-yl)propynyl]phenyl]allyloxy]-phenoxy]acetic acid;
(E)-[4-[3-(4-Chlorophenyl)-3-[4-[3-[4-(hydroxymethyl)piperidin-1-yl]propynyl]phenyl]allyloxy]-2-methylphenoxy]acetic acid;
(Z)-[4-[3-(4-tert-Butylphenyl)-3-[4-[3-(4-hydroxypiperidin-1-yl)propynyl]phenyl]allyloxy]-2-methylphenoxy]acetic acid;
(Z)-[4-[3-(4-tert-Butyl phenyl)-3-[4-[3-[N-(2-hydroxyethyl)-N-methylamino]propynyl]phenyl]-allyloxy]-2-methylphenoxy]acetic acid;
(Z)-[4-[3-(4-tert-Butylphenyl)-3-[4-[3-(pyrazol-1-yl)propynyl]phenyl]allyloxy]-2-methylphenoxy]acetic acid;
(E)-[4-[3-(4-Cyclopropylsulfanylphenyl)-3-[4-[3-(morpholin-4-yl)propynyl]phenyl]allyloxy]-2-methylphenoxy]acetic acid;
(E)-[4-[3-(4-Cyclopropylsulfanylphenyl)-3-[4-[3-(N,N-dimethylamino)propynyl]phenyl]allyloxy]-2-methylphenoxy]acetic acid;
(E)-[4-[3-(4-Cyclopropylsulfinylphenyl)-3-[4-[3-(morpholin-4-yl)propynyl]phenyl]allyloxy]-2-methylphenoxy]acetic acid;
(E)-[2-Methyl-4-[[3-[4-[3-(morpholin-4-yl)propynyl]phenyl]-3-[4-(trifluoromethylsulfanyl)-phenyl]allyloxy]phenoxy]acetic acid;
(E)-[4-[3-[4-[3-(4-Hydroxypiperidin-1-yl)propynyl]phenyl]-3-[4-(trifluoromethylsulfanyl)-phenyl]allyloxy]-2-methylphenoxy]acetic acid;
(E)-[4-[3-[4-(Methylsulfinyl)phenyl]-3-[4-[3-(pyrazol-1-yl)propynyl]phenyl]allyloxy]-2-methylphenoxy]acetic acid;
(E)-[4-[3-[4-[3-(4-Hydroxypiperidin-1-yl)propynyl]phenyl]-3-[4-(methylsulfanyl)phenyl]-allyloxy]-2-methylphenoxy]acetic acid;
(Z)-[4-[3-(4-tert-Butyl phenyl)-3-[4-[4-(hydroxymethyl)phenylethynyl]phenyl]allyloxy]-2-methylphenoxy]acetic acid;
(E)-[4-[3-(4-Bromophenyl)-3-[4-[3-(morpholin-4-yl)propynyl]phenyl]allyloxy]-2-methylphenoxy]acetic acid;
(E)-[4-[3-(4-Bromophenyl)-3-[4-[3-(4-hydroxypiperidin-1-yl)propynyl]phenyl]allyloxy]-2-methylphenoxy]acetic acid;
(E)-[4-[3-(4-Chlorophenyl)-3-[4-[3-(morpholin-4-yl)propynyl]phenyl]allyloxy]-2-methyl phenyl]-propionic acid;
{4-[(Z)-3-(4-Fluoro-phenyl)-3-(4-phenylethynyl-phenyl)-allyloxy]-2-methyl-phenoxy}-acetic acid;
(4-{(E)-3-[4-(3-Dimethylamino-prop-1-ynyl)-phenyl]-3-phenyl-allyloxy}-2-methyl-phenoxy)-acetic acid;
(4-{(Z)-3-[4-(3-Dimethylamino-prop-1-ynyl)-phenyl]-3-phenyl-allyloxy}-2-methyl-phenoxy)-acetic acid;
(2-Methyl-4-{(Z)-3-[4-(3-morpholin-4-yl-prop-1-ynyl)-phenyl]-3-phenyl-allyloxy}-phenoxy)-acetic acid;
{2-Methyl-4-[(Z)-3-phenyl-3-(4-pyridin-2-ylethynyl-phenyl)-allyloxy]-phenoxy}-acetic acid;
{2-Methyl-4-[(E)-3-phenyl-3-(4-pyridin-2-ylethynyl-phenyl)-allyloxy]-phenoxy}-acetic acid; or
a salt thereof with a pharmaceutically acceptable acid or base, or any optical isomer or mixture of optical isomers, including a racemic mixture, or any tautomeric forms.

Other examples of compounds of the invention are:
(E)-[4-[3-(4-Bromophenyl)-3-[4-[4-(hydroxymethyl)phenylethynyl]phenyl]allyloxy]-2-methylphenoxy]acetic acid;
(E)-1-[4-[4-[1-(4-Bromophenyl)-3-[4-(carboxymethoxy)-3-methylphenoxy]propenyl]-phenylethynyl]benzyl]piperidine-4-carboxylic acid;
(Z)-[4-[3-(4-Fluorophenyl)-3-[4-[3-(morpholin-4-yl)propynyl]phenyl]allyloxy]-2-methylphenoxy]acetic acid;
(E)-[2-Methyl-4-[3-(4-methylphenyl)-3-[4-[3-(morpholin-4-yl)propynyl]phenyl]allyloxy]-phenoxy]acetic acid;
(Z)-[4-[3-(4-Chlorophenyl)-3-[4-[3-(morpholin-4-yl)propynyl]phenyl]allyloxy]-2-methylphenoxy]acetic acid;

Methyl (E)-[2-Methyl-4-[3-[4-[3-(morpholin-4-yl)propynyl]phenyl]-3-(4-trifluoromethylphenyl)-allyloxy]phenoxy]acetate;

(Z)-[4-[3-(4-Chlorophenyl)-3-[4-[3-(morpholin-4-yl)propynyl]phenyl]allyloxy]-2-methylphenyl]-propionic acid;

(Z)-[2-Methyl-4-[3-[4-[3-(morpholin-4-yl)propynyl]phenyl]-3-(4-trifluoromethylphenyl)allyloxy]-phenoxy]acetic acid;

(Z)-[4-[3-(Benzo[b]thiophen-2-yl)-3-[4-[4-(trifluoromethyl)phenyl)ethynyl]phenyl]allyloxy]-2-methylphenoxy]acetic acid;

(E)-[7-[3-[4-[3-(Morpholin-4-yl)propynyl]phenyl]-3-(4-trifluoromethylphenyl)allyloxy]-benzo[b]furan-4-yl]oxyacetic acid; or a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The compounds of the present invention may form solvates with standard low molecular weight solvents using methods well known to the person skilled in the art. Such solvates are also contemplated as being within the scope of the present invention. Examples of solvates are the hydrates, which the present compounds are able to form.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

The invention also provides novel compounds of the formula I for use in therapy.

In an aspect, the present invention provides novel compounds or pharmaceutically acceptable salts thereof that are useful as PPAR-δ activators.

In another aspect, the present invention provides novel compounds that improve mitochondrial energy output.

In another aspect, the present invention provides novel pharmaceutical compositions comprising a pharmaceutically acceptable carrier and a therapeutically effective amount of at least one of the compounds of the present invention or a pharmaceutically acceptable salt thereof.

In another aspect, the present invention relates to a method of treating and/or preventing Type I or Type II diabetes.

In a still further aspect, the present invention relates to the use of one or more compounds of the general formula I or pharmaceutically acceptable salts thereof for the preparation of a pharmaceutical composition for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In a still further aspect, the present compounds are useful as pharmaceutical compositions having cholesterol and/or glucose lowering effects.

In a still further aspect, the present compounds reduce blood glucose and triglyceride levels.

In a still further aspect, the present compounds are useful in increasing insulin sensitivity.

In another aspect, the present compounds are cholesterol and/or glucose lowering and are accordingly useful in the treatment of diseases such as type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, atherosclerosis, hyperlipidemia, coronary artery disease, myocardial ischemia and other cardiovascular disorders.

In still another aspect, the present compounds are useful for the treatment and/or prophylaxis of diseases or complications related to atherosclerosis such as coronary artery diseases, coronary heart diseases, heart attack, myocardial infarct, coronary infarct, transient ischemic attack (TIA) or stroke.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

In yet another aspect, the invention also relates to the use of the present compounds, which after administration lower the bio-markers of atherosclerosis like, but not limited to, c-reactive protein (CRP), TNFα and IL-6.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, fenofibrate, bezafibrate, tesaglitazar, EML-4156, LY-518674, LY-519818, MK-767, atorvastatin, fluvastatin, lovastatin, pravastatin, simvastatin, cerivastin, acipimox, ezetimibe probucol, dextrothyroxine or nicotinic acid.

In yet another embodiment the present compounds are administered in combination with a thiazolidinedione e.g. troglitazone, ciglitazone, pioglitazone or rosiglitazone.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tableted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

If desired, the pharmaceutical composition of the invention may comprise the compound of formula (I) in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

Any novel feature or combination of features described herein is considered essential to this invention.

EXAMPLES

The following examples and general procedures refer to intermediate compounds and final products identified in the specification and in the synthesis schemes. The preparation of the compounds of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed nuclear magnetic resonance (NMR). NMR shifts (δ) are given in parts per million (ppm. Mp is melting point and is given in ° C.

The abbreviations as used in the examples have the following meaning:
THF: tetrahydrofuran
DMSO: dimethylsulfoxide
$CDCl_3$: deuterated chloroform
DMF: N,N-dimethylformamide
min: minutes
h: hours General Procedure (A)

Step A:
Reacting a compound of formula II

wherein, $X_3$ is defined as above, with propargyl alcohol using Sonogashira reaction conditions to give a compound of formula III

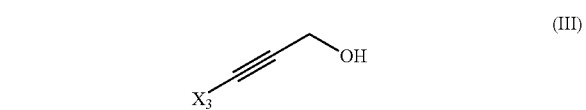

wherein $X_3$ is defined as above.

Step B:
Coupling compound III with halogen-$X_2$-halogen using LiAlH4 followed by direct Pd-coupling to give in a one-pot procedure a compound of formula IV

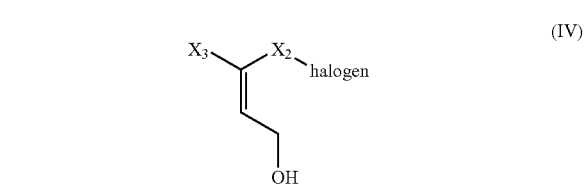

wherein $X_2$ and $X_3$ are defined as above, and

Step C:
Reacting the compound of formula IV, wherein $X_2$ and $X_3$ are defined as above, with a compound of formula V

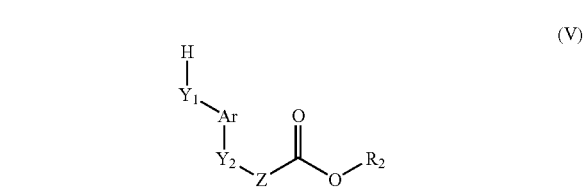

wherein $Y_1$, Ar, $Y_2$, Z and $R_2$ are defined as above, except that $R_2$ is not hydrogen, under Mitsunobu conditions, using a reagent such as triphenylphosphine/diethylazodicarboxylate and the like, to obtain a compound of formula VI

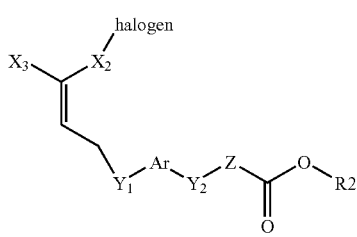
(VI)

wherein $X_2$, $X_3$, $Y_1$, $Y_2$, Ar, Z and $R_2$ are defined as above, except that $R_2$ is not hydrogen.

Step D:

Reacting a compound of formula VI, wherein $X_2$, $X_3$, $Y_1$, $Y_2$, Ar, Z and $R_2$ are defined as above, with a compound of formula VIII,

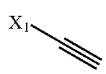
(VII)

wherein $X_1$ is as defined as above, using Sonogashira reaction conditions to give a compound of formula I, wherein $X_1$, $X_2$, $X_3$, $Y_1$, $Y_2$, Ar, Z and $R_2$ are defined as above, except that $R_2$ is not hydrogen.

General Procedure (B)

Step A:

Converting the —OH functionality in the compound of formula IV, wherein $X_2$ and $X_3$ are defined as above, to an appropriate leaving group (L) such as p-toluenesulfonate, methanesulfonate, halogen (for example by methods according to: Houben-Weyl, Methoden der organischen Chemie, Alkohole III, 6/1b, Thieme-Verlag 1984, 4th Ed., pp. 927-939; Comprehensive Organic Transformations. A guide to functional group preparations, VCH Publishers 1989, 1$^{st}$ Ed., pp. 353-363 and *J. Org. Chem.*, Vol. 36 (20), 3044-3045, 1971), triflate and the like, to give a compound of formula VIII

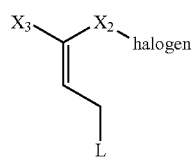
(VIII)

wherein, $X_2$ and $X_3$ are defined as above and L is a leaving group such as p-toluenesulfonate, methanesulfonate, halogen, triflate and the like.

Step B:

Reacting the compound of formula VIII,

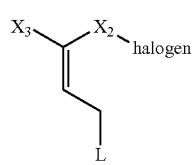
(VIII)

wherein L is a leaving group such as p-toluenesulfonate, methanesulfonate, halogen, triflate and the like and wherein $X_2$ and $X_3$ are defined as above with a compound of formula V

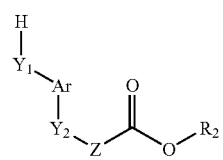
(V)

wherein $Y_1$, Ar, $Y_2$, Z and $R_2$ are defined as above, except that $R_2$ is not hydrogen, to give a compound of formula VI

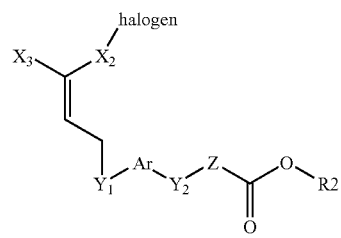
(VI)

wherein $X_2$, $X_3$, $Y_1$, $Y_2$, Ar, Z and $R_2$ are defined as above, except that $R_2$ is not hydrogen.

General Procedure (C)

Step A:

Reacting an compound of formula IX

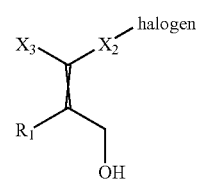
(IX)

wherein $X_2$, $X_3$ and $R_1$ are defined as above, with a compound of formula VII

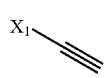
(VII)

wherein $X_1$ is as defined as above, under Sonogashira reaction conditions, to give a compound of formula X,

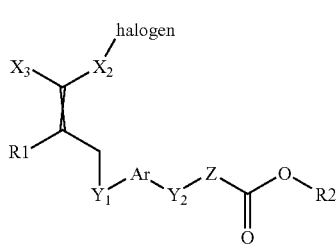

(X)

wherein $X_1$, $X_2$, $X_3$, $Y_1$, $Y_2$, Ar, Z, $R_1$ and $R_2$ are defined as above, except that $R_2$ is not hydrogen.

Step B:

Reacting a compound of formula X,

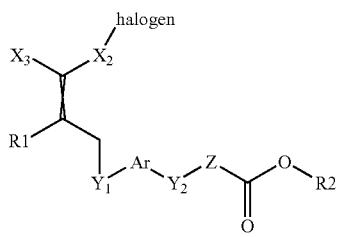

(X)

wherein $X_2$, $X_3$, $Y_1$, $Y_2$, Ar, Z, $R_1$ and $R_2$ are defined as above, with a compound of formula VII,

(VII)

wherein $X_1$ is as defined as above, using Sonogashira reaction conditions to give a compound of formula I, wherein $X_1$, $X_2$, $X_3$, $Y_1$, $Y_2$, Ar, Z and $R_2$ are defined as above, except that $R_2$ is not hydrogen.

General Procedure (D)

Step A:

By chemical or enzymatic saponification of a compound of formula I wherein $X_1$, $X_2$, $X_3$, $Y_1$, $Y_2$, Ar, Z, $R_1$ and $R_2$ are defined as above, except that $R_2$ is not hydrogen, to give a compound of formula I wherein $X_1$, $X_2$, $X_3$, $Y_1$, $Y_2$, Ar, Z, $R_1$ and $R_2$ are defined as above, except that $R_2$ is hydrogen.

General Procedure (E)

Step A:

Reacting a compound of formula XI

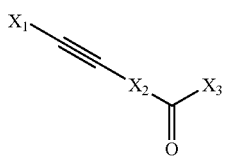

(XI)

wherein $X_1$, $X_2$ and $X_3$ are defined as above, through a Horner-Emmons-like process with for example $(EtO)_2PO(CHR_1)COOR_6$ (wherein $R_6$ is an alkyl group), in the presence of a base such as sodium hydride, EtONa and the like to give a compound of formula XII

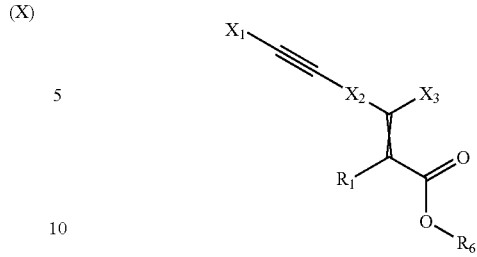

(XII)

wherein $X_1$, $X_2$, $X_3$, $R_1$ and $R_6$ are defined as above

Step B:

Reducing the compound of formula XII, wherein $X_1$, $X_2$, $X_3$, $R_1$ and $R_6$ are defined as above with a suitable reagent such as diisobutylaluminium hydride, to give a compound of formula XIII

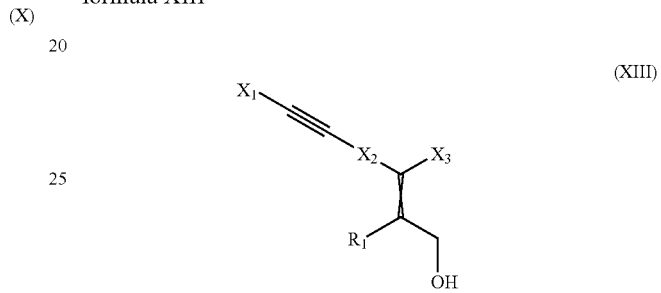

(XIII)

wherein $X_1$, $X_2$, $X_3$ and $R_1$ are defined as above, and

Step C:

Reacting the compound of formula XIII, wherein $X_1$, $X_2$, $X_3$ and $R_1$ are defined as above, with a compound of formula V, wherein $Y_1$, Ar, $Y_2$, Z and $R_2$ are defined as above, except that $R_2$ is not hydrogen, under Mitsunobu conditions, using a reagent such as triphenylphosphine/diethylazodicarboxylate and the like, to obtain a compound of formula I, wherein $X_1$, $X_2$, $X_3$, $X_4$, $Y_1$, $Y_2$, Ar, Z, $R_1$ and $R_2$ are defined as above, except that $R_2$ is not hydrogen.

Example 1

(E)-[2-Methyl-4-[3-phenyl-3-[4-(phenylethynyl)phenyl]allylsulfanyl]phenoxy]acetic Acid

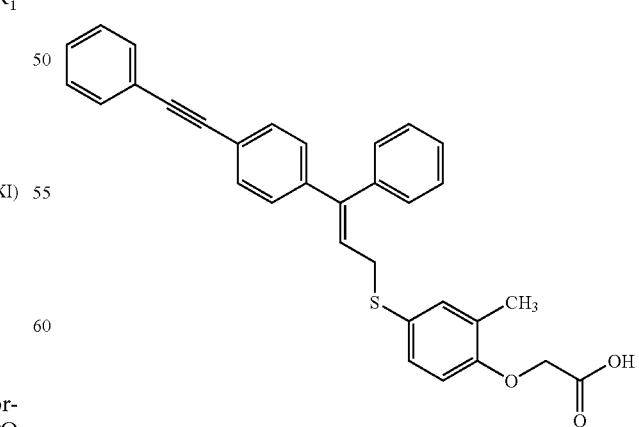

In argon atmosphere, 0.15 M Solution of tri-tert-butylphosphine in cyclohexane (12.0 mL, 18.0 mmol) was added to a stirred suspension of copper(I) iodide (350 mg, 1.8 mmol) and dichloro(bisbenzonitrile)palladium (350 mg, 0.9 mmol) in tetrahydrofuran (100 mL) at ambient temperature. The mixture was stirred for 5 min, N,N-diisopropylamine (4.5 mL, 30 mmol) was added, the mixture was stirred for next 5 min and then a solution of 4-bromobenzophenone (3.92 g, 15 mmol) and phenylacetylene (2.30 g, 22.5 mmol) in tetrahydrofuran (20 mL) was added dropwise during 15 min. The reaction mixture was stirred at ambient temperature overnight and then diluted with benzene (200 mL). The benzene solution was washed with water (2×80 mL) and 1.5 M aqueous solution of tartaric acid (30 mL); the organic solution was dried with anhydrous magnesium sulfate and subsequently evaporated in vacuo. The residue was purified by column chromatography (silica gel Fluka 60, hexane/ethyl acetate 95:5) yielding phenyl-[4-(phenylethynyl)phenyl]methanone.

Yield: 4.11 g (97%).

$R_F$ ($SiO_2$, benzene) 0.55.

$^1H$ NMR spectrum (200 MHz, $CDCl_3$, $\delta_H$): 7.82-7.76 (m, 4H); 7.67-7.44 (m, 7H); 7.42-7.30 (m, 3H).

A solution of triethyl phosphonoacetate (6.53 g, 29.1 mmol) in dry tetrahydrofuran (20 mL) was added dropwise to a suspension of sodium hydride (80% suspension in oil, 873 mg, 29.1 mmol; washed three times with hexane) in dry tetrahydrofuran (50 mL) under nitrogen atmosphere (20 min). When the gas evolution deceased, the suspension was heated to reflux for 10 min. The mixture was allowed to cool down, a solution of the above ketone in dry tetrahydrofuran (40 mL) was added dropwise and the resulting reaction mixture was refluxed for 90 min. The mixture was allowed to cool down and poured into 5% aqueous solution of citric acid (200 mL). Ether was added (100 mL), organic layer was separated and the aqueous layer was extracted with ether (50 mL). The combined organic solutions were washed with 10% aqueous solution of sodium hydrogen carbonate (50 mL), water (2×50 mL) and dried with anhydrous magnesium sulfate. The residue obtained by evaporation of the organic solution was purified by column chromatography (silica gel Fluka 60, hexane/ethyl acetate 95:5) yielding a mixture of both isomers (5.05 g). The product was recrystallized from the mixture of n-heptane/benzene/ethanol to give pure ethyl (E)-3-phenyl-3-[4-(phenylethynyl)phenyl]acrylate (configuration assigned according to NOE experiment).

Yield of (E)-isomer: 2.25 g (44%).

M.p. 86-88° C. (n-heptane/benzene/ethanol).

$R_F$ ($SiO_2$, hexane/ethyl acetate 95:5) 0.40.

$^1H$ NMR spectrum (200 MHz, DMSO-$d_6$, $\delta_H$): 7.65-7.05 (m, 14H); 6.38 (s, 1H); 4.08 (q, J=8.0 Hz, 2H); 1.16 (t, J=8.0 Hz, 3H).

Mother liquor from crystallization of the main crop was evaporated giving 2.45 g (48%) of mixture of both isomers.

In atmosphere of argon, 1 M solution of diisobutylaluminum hydride in tetrahydrofuran (5 mL, 5 mmol) was added dropwise to a cooled (−20° C.) solution of the above (E)-ester (1.90 g; 5.39 mmol) in dry tetrahydrofuran (30 mL). The reaction mixture was allowed to warm up to −15° C., stirred at the temperature for 30 min and then allowed to warm up to ambient temperature and stirred overnight. The mixture was cooled to −10° C. again, methanol (5 mL) and subsequently 15% aqueous hydrochloric acid (7 mL) were added and the mixture was allowed to warm up to ambient temperature. The mixture was diluted with ether (100 mL), the organic layer was washed with brine (30 mL), dried with anhydrous magnesium sulfate and subsequently evaporated in vacuo. The residue was purified by column chromatography (silica gel Fluka 60, hexane/ethyl acetate 85:15) giving a crystalline product which was recrystallized from a mixture ethanol/n-heptane (7:3, 10 mL) giving (E)-3-phenyl-3-[4-(phenylethynyl)phenyl]allyl alcohol.

Yield: 655 mg (39%).

M.p. 115-117° C.

$R_F$ ($SiO_2$, hexane/ethyl acetate 85:15) 0.25.

$^1H$ NMR spectrum (200 MHz, $CDCl_3$, $\delta_H$): 7.62-7.18 (m, ~14H); 6.27 (t, J=6.8 Hz, 1H); 4.27 (d, J=6.8 Hz, 2H); 1.54 (bs, 1H).

In atmosphere of nitrogen, tetrabromomethane (500 mg, 1.51 mmol) was added to an ice-water cooled solution of the above hydroxy derivative (470 mg, 1.51 mmol) and triphenylphosphine (420 mg, 1.60 mmol) in dry methylene chloride (20 mL). The mixture was stirred for 2 h under cooling and for further 2 h at ambient temperature, filtered through short path of silica gel and evaporated in vacuo. The residue was dissolved in tetrahydrofuran (19 mL), N,N-diisopropylethylamine (233 mg, 1.80 mmol) and subsequently a solution of ethyl (4-mercapto-2-methylphenoxy)acetate (404 mg, 1.90 mmol) in tetrahydrofuran (1 mL) were added and the resulting solution was stirred for 18 h. The mixture was evaporated in vacuo and the residue was purified by column chromatography (silica gel Fluka 60, hexane/ethyl acetate 95:5) yielding of ethyl (E)-[2-Methyl-4-[3-phenyl-3-[4-(phenylethynyl)phenyl]-allylsulfanyl]phenoxy]acetate as an oil.

Yield: 365 mg (47%).

$R_F$ ($SiO_2$, hexane/ethyl acetate 9:1) 0.45.

$^1H$ NMR spectrum (200 MHz, DMSO-$d_6$, $\delta_H$): 7.58-7.15 (m, ~15H); 6.81 (d, 2H); 6.56 (d, 1H); 6.13 (d, 1H); 4.62 (s, 1H); 4.23 (q, 2H); 3.52 (d, 2H); 2.22 (s, 3H); 1.25 (t, 3H).

In atmosphere of nitrogen, a solution of lithium hydroxide monohydrate (629 mg, 1.66 mmol) in distilled water (10 mL) was added to an ice-water cooled solution of the above ester (350 mg, 1.11 mmol) in a mixture of tetrahydrofuran (50 mL) and methanol (10 mL). The resulting solution was stirred for 2 h under cooling, 2 M aqueous solution of tartaric acid (2 mL) was added and the resulting solution was diluted with water (30 mL). The mixture was extracted with ether (3×30 mL); the collected organic solutions were washed with brine (30 mL), dried with anhydrous magnesium sulfate and evaporated in vacuo. The residue was purified by column chromatography (silica gel Fluka 60, chloroform/methanol 95:5) to yield the title acid.

Yield: 250 mg (46%).

$R_F$ ($SiO_2$, chloroform/methanol, 9:1): 0.25.

$^1H$ NMR spectrum (200 MHz, AcOH-$d_4$, $\delta_H$): 7.60-7.10 (m, ~14H); 6.88 (m, 2H); 6.79 (d, 1H); 6.16 (bp, 1H); 4.73 (s, 2H); 3.52 (d, 2H); 2.18 (s, 3H).

A solution of L-Lysine (64 mg, 0.438 mmol) in water (2 mL) was added to a solution of the above acid (226 mg, 0.461 mmol) in tetrahydrofuran (30 mL). The mixture was stirred for 1 h, evaporated in vacuo and the residue was three times triturated with anhydrous ether yielding L-lysinate of the title acid.

Yield: 190 mg (68%).

$^1H$ NMR spectrum (200 MHz, AcOH-$d_4$, $\delta_H$): 7.65-7.05 (m, ~6H); 6.88 (m, 2H); 6.79 (d, 1H); 6.16 (bp, 1H); 4.72 (s, ~2H); 4.05 (m, 1H); 3.53 (m, ~2H); 3.08 (m, 2H); 2.18 (s, ~3H); 1.95-1.40 (m, overlap, ~6H).

Example 2

(E)-[2-Methyl-4-[3-[4-[3-(morpholin-4-yl)propynyl]phenyl]-3-phenylallyloxy]phenoxy]acetic Acid

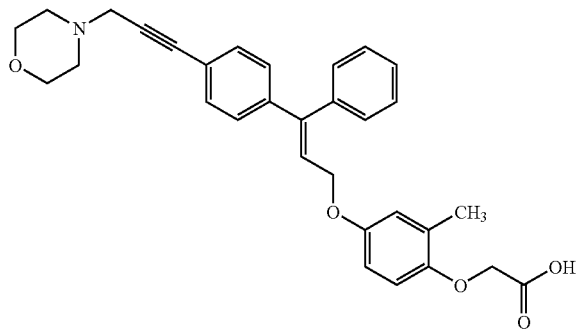

A solution of 1,4-dibromobenzene (23.6 g, 100.0 mmol) in dry tetrahydrofuran (100 mL) was degassed and copper(I) iodide (570 mg, 3.0 mmol), tetrakis(triphenylphosphine)palladium (3.4 g, 3.0 mmol) and diazabicycloundecene (18.2 g, 120.0 mmol) were added. The reaction solution was degassed again and propargyl alcohol (6.7 g, 120.0 mmol) was added dropwise under inert atmosphere at 0° C. The reaction was stirred at 0° C. for 1 h and next 4 h at 50° C. The solution was then treated with brine (20 mL) and acidified with 2 M hydrochloric acid (20 mL). The organic phase was isolated and the aqueous phase was extracted with ether (4×30 mL). The combined organic phases were dried with magnesium sulfate and concentrated in vacuo yielding brown solid. Product was purified by crystallization from hexane yielding yellowish dust of 3-(4-bromophenyl)prop-2-yn-1-ol.

Yield: 10 g (49%).

M.p.: 65-68° C. (hexane).

$R_f$ (hexane/ethyl acetate 90:10): 0.10.

Sodium methoxide (0.27 g, 0.5 mmol) was added to 1 M solution of lithium aluminum hydride in tetrahydrofuran (12 mL, 12 mmol). The mixture was cooled to 0° C. and a solution of 3-(4-bromophenyl)prop-2-yn-1-ol (0.422 g, 2.0 mmol) in tetrahydrofuran (50 mL) was slowly added. The reaction was stirred for at 0° C. for 3 h, ethyl acetate (2.6 mL, 30 mmol) was added and the mixture was stirred for further 10 min without cooling. Iodobenzene (2.7 g, 13 mmol), anhydrous zinc bromide (1.4 g, 6 mmol), and tris(dibenzylideneacetone)dipalladium chloroform complex (0.50 g, 0.5 mmol) were added and the mixture was evacuated and kept under nitrogen. A solution of tri-tert-butylphosphine in cyclohexane (6.7 mL, 1 mmol) was added and the mixture was heated at 60° C. for 16 h. Methanol (10 mL) was added and the resulting mixture was stirred for additional 1 h. The reaction mixture was poured into water, acidified with hydrochloric acid and extracted with ethyl acetate (3×100 mL). Organic layers were combined, dried with anhydrous sodium sulphate, evaporated in vacuo and the residue was purified by column chromatography (silica gel Fluka 60, hexanes/ethyl acetate 98:2-70:30) affording (E)-3-(4-bromophenyl)-3-phenylprop-2-en-1-ol.

Yield: 2.8 g (32%).

$R_F$ (SiO$_2$, hexanes/ethyl acetate 4:1) 0.30.

$^1$H NMR spectrum (300 MHz, CDCl$_3$, $\delta_H$): 7.42-7.34 (m, 5H); 7.15-7.05 (m, 4H); 6.23 (t, J=6.9 Hz, 1H); 4.21 (d, J=4.8 Hz, 2H).

The above allyl alcohol (0.889 g, 3.0 mmol), methyl (4-hydroxy-2-methylphenoxy)acetate (0.770 g, 3.9 mmol; see below) and triphenylphosphine (1.30 g, 5 mmol) were dissolved in a mixture of anhydrous toluene (12 mL) and tetrahydrofuran (4 mL). The mixture was cooled to 0° C., kept under nitrogen and diisopropyl azodicarboxylate (0.85 g, 4.2 mmol) was added dropwise. The reaction mixture was stirred at 0° C. for 3 h and then at 25° C. for 16 h. The solvents were evaporated in vacuo and the residue was submitted to column chromatography (silica gel Fluka 60, hexanes/ethyl acetate 98:2-90:10) affording methyl (E)-[4-[3-(4-bromophenyl)-3-phenylallyloxy]-2-methylphenoxy]acetate.

Yield: 0.70 g (50%).

$R_F$ (SiO$_2$, hexanes/ethyl acetate 4:1) 0.50.

$^1$H NMR spectrum (300 MHz, CDCl$_3$, $\delta_H$): 7.45-7.35 (m, 5H); 7.20-7.11 (m, 4H); 6.70-6.55 (m, 3H); 6.23 (t, J=6.6 Hz, 1H); 4.58 (s, 2H); 4.51 (d, J=6.6 Hz, 2H); 3.80 (s, 3H); 2.24 (s, 3H).

Dry triethylamine (8 mL), copper(I) iodide (29 mg, 0.152 mmol) and tetrakis(triphenylphosphine)palladium (68 mg, 0.059 mmol) were added to a degassed solution of the above ester (448 mg, 0.931 mmol) and N-propargylmorpholine (291 mg, 2.32 mmol) in dry tetrahydrofuran (18 mL). In atmosphere of argon, the resulting mixture was heated at 50° C. for 10 h, cooled down and subsequently evaporated in vacuo. The residue was dissolved in dichloromethane (20 mL); the solution was washed with water (3×10 mL), dried with anhydrous magnesium sulfate and evaporated in vacuo. The residue was purified by column chromatography (silica gel Fluka 60, hexanes/ethyl acetate 4:1-1:1) yielding methyl (E)-[2-methyl-4-[3-[4-[3-(morpholin-4-yl)propynyl]phenyl]-3-phenylallyloxy]phenoxy]acetate as an oil.

Yield: 138 mg (29%).

$R_F$ (SiO$_2$, hexanes/ethyl acetate 1:1) 0.10.

In atmosphere of argon, a solution of lithium hydroxide monohydrate (16.9 mg, 0.404 mmol) in distilled water (1 mL) was added to an ice-water cooled solution of the above ester (138 mg, 0.270 mmol) in tetrahydrofuran/methanol mixture (5:1; 6 mL). The resulting solution was stirred for 3 h under cooling. Saturated aqueous solution of ammonium chloride (15 mL) was added and the mixture was extracted with ether (3×10 mL). Combined ethereal solutions were dried with anhydrous magnesium sulfate and evaporated in vacuo yielding the title acid as a foam.

Yield: 102 mg (76%).

M.p.: - - - (foam).

$R_F$ (SiO$_2$, chloroform/methanol 9:1) 0.10.

A solution of L-lysine (29.9 mg, 0.205 mmol) in distilled water (0.5 mL) was added to a solution of the above acid (102 mg, 0.205 mmol) in dry tetrahydrofuran (7 mL). The resulting solution was stirred for 10 min, acetonitrile (50 mL) was added and the mixture was stirred for 2 h. The formed solid was filtered, washed with ether (2×30 mL) and dried yielding L-lysinate of the title acid.

Yield: 55.8 mg (42%).

M.p.: 162-180° C. (amorphous).

$^1$H NMR spectrum (300 MHz, DMSO-d$_6$, $\delta_H$): 7.48-7.15 (m, 9H); 6.61-6.50 (m, 3H); 6.34 (t, J=7.1 Hz, 1H); 4.42 (d, J=6.4 Hz, 2H); 4.12 (s, 2H); 3.58 (m, 4H); 3.49 (s, 2H); 3.38-3.08 (m, ~5H); 2.70 (bs, 2H); 2.08 (s, ~3H); 1.16-1.75 (m, ~6H).

(4-Hydroxy-2-methylphenoxy)acetic Acid Methyl Ester

Potassium carbonate (34.4 g, 0.250 mol) and solution of methyl bromoacetate (16.1 ml, 0.175 mol) in butanone (20 ml) were added to a solution of 4-hydroxy-3-methylacetophenone (25 g, 0.166 mol) in butanone (180 ml) and the mixture was refluxed for 1 h. After cooling to ambient temperature a white precipitated was filtered off and the filtrate evaporated in vacuo. The resulting solid was recrystallized by dissolving it in a mixture of hexanes/diethyl ether/dichloromethane (120:120:50 ml) and concentrating in vacuo. (4-Acetyl-2-methyl-phenoxy)acetic acid methyl ester was filtered and washed with hexanes (50 mL).

Yield: 35.0 g (95%).

R$_F$ (SiO$_2$, hexanes/ethyl acetate 1:1) 0.75.

$^1$H NMR spectrum (200 MHz, CDCl$_3$, $\delta_H$): 7.80-7.76 (m, 2H); 6.70 (d, J=9.0 Hz, 1H); 4.74 (s, 2H); 3.82 (s, 3H); 2.55 (s, 3H); 2.33 (s, 3H).

To a solution of the above ester (33.0 g, 0.148 mol) and p-toluenesulfonic acid monohydrate (0.281 g, 0.00148 mol) in dichloromethane (50 ml) a solution of 3-chloroperoxybenzoic acid (53.1 g, 0.237 mol; 77% in water) in dichloromethane was added (300 ml, dried over magnesium sulfate prior to addition). The mixture was stirred at ambient temperature for 20 h, a solution of sodium sulfite (1 M, 150 ml) was added and the two-phase mixture stirred for 20 min. Then a solution of sodium carbonate (2 M, 150 ml) was added and heterogeneous mixture was vigorously stirred for next 10 min. The organic layer was separated and the aqueous layer was extracted with dichloromethane (50 ml). The combined organic layers were washed with 10% solution of sodium carbonate (2×200 ml) and brine (300 ml). The organic solution was dried with anhydrous magnesium sulfate and its evaporation yielded (4-acetoxy-2-methyl-phenoxy)acetic acid methyl ester as yellowish solid.

Yield: 32.9 g (93%).

R$_F$ (SiO$_2$, hexanes/ethyl acetate 1:1) 0.80.

$^1$H NMR spectrum (200 MHz, CDCl$_3$, $\delta_H$): 6.90 (m, 2H); 6.68 (d, J=8.6, 1H); 4.64 (s, 2H); 3.80 (s, 3H); 2.28 (s, 6H).

A mixture of the above ester (32.9 g, 0.138 mol) and sodium methoxide (0.746 g, 0.0138 mol) in anhydrous methanol (250 ml) was stirred for 24 h. The mixture was evaporated to dryness and a solid residue was dissolved in ethyl acetate (200 ml). The turbid mixture was filtered and the filtrate was washed with saturated aqueous solution of sodium hydrogen carbonate (2×150 ml) and brine (200 ml). The organic solution was dried over anhydrous magnesium sulfate and evaporated in vacuo. The crude product was recrystallized from ethyl acetate/hexanes yielding the title compound as off-white crystals.

Yield: 24.0 g (89%).

R$_F$ (SiO$_2$, dichloromethane/methanol 99:1) 0.30.

$^1$H NMR spectrum (200 MHz, CDCl$_3$, $\delta_H$): 6.66-6.58 (m, 3H); 4.76 (s, 1H); 4.59 (s, 2H); 3.80 (s, 3H); 2.25 (s, 3H), 2.19 (s, 3H).

Example 3

(Z)-[2-Methyl-4-[3-(4-methylphenyl)-3-[4-[3-(morpholin-4-yl)propynyl]phenyl]allyloxy]-phenoxy] acetic Acid

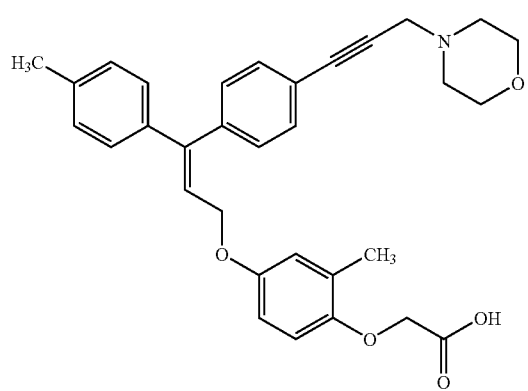

To a degassed solution of 4-bromotoluene (4.27 g, 25 mmol) in tetrahydrofuran (30 mL) was added in the following order: copper(I) iodide (143 mg, 0.75 mol), tetrakis(triphenylphosphine)palladium (0.85 g, 7.5 mmol), and 1,8-diazabicyclo[5.4.0]undec-7-ene (4.55 g, 30 mmol). The resulting mixture was degassed one more time, cooled in an ice bath and a solution of propargyl alcohol (1.68 g, 30 mmol) in tetrahydrofuran (5 mL) was added over period of 10 min. The reaction mixture was slowly heated up to 55° C. and then stirred at this temperature for 20 h. This mixture was then cooled to ambient temperature, diluted with ether (150 mL) and water (50 mL) and acidified with 5% hydrochloric acid. The ethereal layer was separated and the aqueous layer was extracted with ether (3×30 mL). The combined organic portions were washed with 5% hydrochloric acid (2×30 mL), saturated aqueous solution of sodium hydrogen carbonate (2×30 mL), dried with anhydrous magnesium sulfate and evaporated in vacuo. The residue was purified by flash column chromatography (silica gel Fluka 60, chloroform) affording 3-(4-methylphenyl)prop-2-yn-1-ol as oil.

Yield: 2.50 g (68%).

R$_F$ (SiO$_2$, chloroform) 0.20.

Sodium methoxide (12.5 mg, 0.225 mmol) was added to 1 M solution of lithium aluminum hydride in tetrahydrofuran (5 mL, 5 mmol) under argon. The mixture was cooled to 0° C. and a solution of the above hydroxy derivative (730 mg, 5 mmol) in tetrahydrofuran (12.5 mL) was added over 10 min. The reaction mixture was stirred at 0° C. for 3 h; dry ethyl acetate (0.825 mL) was added and the whole mixture was stirred at ambient temperature for 15 min. A degassed solution of 1,4-diiodobenzene (2.15 g, 6.5 mmol) in dry tetrahydrofuran (5 mL), anhydrous zinc chloride (0.408 g, 3 mmol), tris(dibenzylideneacetone)dipalladium chloroform complex (0.103 g, 0.1 mmol), and tri(2-furyl)phosphine (92.5 mg, 0.4 mmol) were added; the mixture was degassed and then heated at 65° C. for 20 h under nitrogen. The suspension was cooled down to ambient temperature, methanol (2.5 mL) was added and the mixture was stirred for additional 1 h. The reaction was diluted with ether (50 mL) and saturated aqueous solution of ammonium chloride (1.25 mL) was added. The mixture was filtered through a paddle of silica gel and the paddle was thoroughly washed with ether (100 mL). The solvents were evaporated and the residue was separated by flash column chromatography (silica gel Fluka 60, hexanes/ethyl acetate 4:1) affording (Z)-3-(4-iodophenyl)-3-(4-methylphenyl)prop-2-en-1-ol as solidifying oil.

Yield: 610 mg (35%).

$R_F$ (SiO$_2$, hexanes/ethyl acetate 3:1) 0.30.

The above allyl alcohol (420 mg, 1.2 mmol), methyl (4-hydroxy-2-methylphenoxy)acetate (0.259 mg, 1.32 mmol; example 2) and triphenylphosphine (378 mg, 1.44 mmol) were dissolved in a mixture of anhydrous toluene (20 mL) and tetrahydrofuran (7 mL). The solution was cooled to 0° C., kept under nitrogen and a degassed solution of diisopropyl azodicarboxylate (0.28 mL, 1.44 mmol) in anhydrous tetrahydrofuran (2.5 mL) was added dropwise over 10 min. The reaction mixture was allowed to warm up to the ambient temperature with the bath and then was stirred for 48 h. The solvents were evaporated in vacuo and the residue was submitted to flash column chromatography (silica gel Fluka 60, hexanes/ethyl acetate 4:1) affording methyl (Z)-[4-[3-(4-iodophenyl)-3-(4-methylphenyl)allyloxy]-2-methylphenoxy}acetate as solidifying yellow oil.

Yield: 520 mg (82%).

$R_F$ (SiO$_2$, hexanes/ethyl acetate 3:1) 0.55.

$^1$H NMR spectrum (300 MHz, CDCl$_3$, $\delta_H$): 7.71 (d, 2H); 6.93-7.11 (m, 6H); 6.55-6.68 (m, 3H); 6.27 (t, J=7.1 Hz, 1H); 4.58 (s, 2H); 4.47 (d, J=6.6 Hz, 2H); 3.79 (s, 3H); 2.34 (s, 3H); 2.25 (s, 3H).

A solution of the above ester (480 mg, 0.908 mmol) in a mixture of tetrahydrofuran (5 mL) and triethylamine (5 mL) was degassed and N-propargylmorpholine (237 mg, 1.89 mmol) was added under argon atmosphere. The solution was cooled, tetrakis(triphenylphosphine)palladium (84 mg, 0.073 mmol) and copper(I) iodide (27.6 mg, 0.145 mmol) were added. The reaction mixture was stirred at ambient temperature for 6 h and then left to stand overnight. The mixture was evaporated in vacuo; the residue was dissolved in dichloromethane (20 mL) and the formed solution was washed with water (2×10 mL). The organic solution was dried with anhydrous magnesium sulfate and subsequently evaporated in vacuo. The residue was purified by flash column chromatography (silica gel Fluka 60, hexanes/ethyl acetate 1:1) yielding methyl (Z)-[2-methyl-4-[3-(4-methylphenyl)-3-[4-[3-(morpholin-4-yl)propynyl]phenyl]allyloxy]phenoxy]acetate.

Yield: 252 mg (53%).

$R_F$ (SiO$_2$, hexanes/ethyl acetate 1:1) 0.10.

$^1$H NMR spectrum (300 MHz, CDCl$_3$, $\delta_H$): 7.45 (d, J=8.4 Hz, 2H); 7.07-7.16 (m, 6H); 6.54-6.67 (m, 3H); 6.26 (t, J=6.7 Hz, 1H); 4.58 (s, 2H); 4.48 (d, J=6.7 Hz, 2H); 3.79 (s, 3H); 3.76-3.79 (m, 4H); 3.53 (s, 2H); 2.66 (m, 4H); 2.33 (s, 3H); 2.24 (s, 3H).

To a solution of the above ester (233 mg, 0.443 mmol) in tetrahydrofuran/methanol mixture (5:1, 12 mL), a solution of lithium hydroxide monohydrate (28 mg, 0.665 mmol) in distilled water (2 mL) was added under cooling to 0° C. The solution was stirred for 1 h under cooling and 1 h under ambient temperature. The solution was diluted with ether (30 mL) and saturated solution of ammonium chloride (15 mL). The phases were separated; the organic layer was washed with water (2×10 mL), dried over anhydrous magnesium sulfate and evaporated in vacuo. The residue was triturated with hexanes yielding the title acid as tan solid.

Yield: 114 mg (64%).

M.p. 182-190° C.

$R_F$ (SiO$_2$, chloroform/methanol, 9:1) 0.30.

$^1$H NMR spectrum (300 MHz, CDCl$_3$, $\delta_H$): 7.39-7.06 (m, 8H); 6.66 (m, 1H); 6.57 (m, 1H); 6.39 (m, 1H); 6.30 (t, J=7.1 Hz, 1H); 4.55 (s, 2H); 4.44 (d, J=6.6 Hz, 2H); 3.82 (bs, 4H); 3.65 (s, 2H); 2.85 (bs, 4H); 2.33 (s, 3H); 2.23 (s, 3H).

Example 4

(E)-[2-Methyl-4-[3-[4-[3-(pyrazol-1-yl)prop-1-ynyl]phenyl]-3-(4-trifluoromethyl phenyl)allyloxy]phenoxy]acetic Acid

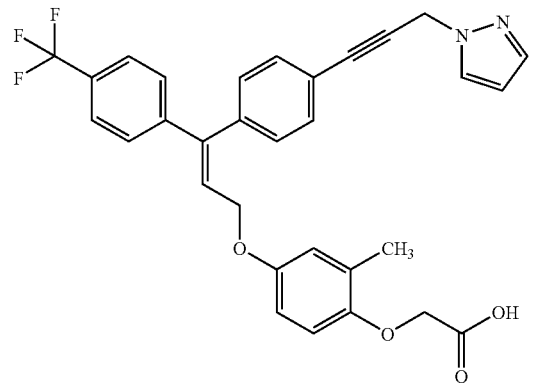

To a degassed solution of 1-bromo-4-trifluoromethylbenzene (5.62 g, 25 mmol) in tetrahydrofuran (25 ml) was added in the following order: copper(I) iodide (143 mg, 0.75 mL), tetrakis(triphenylphosphine)palladium (0.85 g, 7.5 mmol), and 1,8-diazabicyclo[5.4.0]undec-7-ene (4.55 g, 30 mmol). The resulting mixture was degassed one more time, cooled in an ice bath and a solution of propargyl alcohol (1.68 g, 30 mmol) in tetrahydrofuran (5 mL) was added over period of 10 min. The reaction mixture was slowly heated up to 55° C. and then stirred at this temperature for 3 h and then at ambient temperature overnight. The mixture was diluted with diethyl ether (100 mL), washed with water (50 mL), 5% hydrochloric acid (35 mL) and saturated aqueous solution of sodium hydrogen carbonate (30 mL). The organic solution was dried with anhydrous magnesium sulfate and evaporated in vacuo. The residue was purified by column chromatography (silica gel Fluka 60, dichloromethane) affording 3-(4-trifluoromethylphenyl)prop-2-yn-1-ol.

Yield: 4.25 g (90%).

$R_F$ (SiO$_2$, chloroform) 0.25.

Sodium methoxide (12.5 mg, 0.225 mmol) was added to 1 M solution of lithium aluminum hydride in tetrahydrofuran (5 mL, 5 mmol) under argon. The mixture was cooled to 0° C. and a solution of the above alcohol (1.00 g, 5 mmol) in tetrahydrofuran (12.5 mL) was added over 10 min. The reaction was stirred at 0° C. for 3 h; dry ethyl acetate (0.825 mL) was added and the whole mixture was stirred at ambient temperature for 15 min. A degassed solution of 1,4-diiodobenzene (2.15 g, 6.5 mmol) in dry tetrahydrofuran (5 mL), anhydrous zinc chloride (0.408 g, 3 mmol), tris(dibenzylideneacetone)dipalladium chloroform complex (0.103 g, 0.1 mmol), and tri(2-furyl)phosphine (92.5 mg, 0.4 mmol) were added; the mixture was degassed and then was heated at 65° C. for 15 h under nitrogen. The suspension was cooled down; methanol (2.5 mL) was added and the mixture was stirred for additional 1 h. The reaction was diluted with ether (50 mL) and saturated aqueous solution of ammonium chloride (1.25 mL) was added. The mixture was filtered through a paddle of silica gel and the paddle was thoroughly washed with ether (100 mL). The solvents were evaporated in vacuo and the residue was purified by flash column chromatography (silica gel Fluka 60, hexanes/ethyl acetate 5:1) affording (Z)-3-(4-iodophenyl)-3-(4-trifluoromethylphenyl)prop-2-en-1-ol as solidifying oil.

Yield: 815 mg (47%).

$R_F$ (SiO$_2$, hexanes/ethyl acetate 3:1) 0.35.

$^1$H NMR spectrum (300 MHz, CDCl$_3$, $\delta_H$): 7.73 (m, 2H); 7.54 (m, 2H); 7.33 (m, 2H); 6.90 (m, 2H); 6.30 (t, J=6.8 Hz, 1H); 4.24 (m, 2H).

The above allyl alcohol (810 mg, 2.0 mmol), methyl (4-hydroxy-2-methylphenoxy)acetate (431 mg, 2.2 mmol; example 2) and triphenylphosphine (630 mg, 2.4 mmol) were dissolved in a mixture of anhydrous toluene (32 mL) and tetrahydrofuran (12 mL). The mixture was cooled to 0° C., kept under nitrogen and a degassed solution of diisopropyl azodicarboxylate (0.47 mL, 2.4 mmol) in anhydrous tetrahydrofuran (4 mL) was added dropwise during 10 min. The reaction mixture was allowed to warm up to ambient temperature with the bath and then was stirred for 48 h. The solvents were evaporated in vacuo and the residue was submitted to flash column chromatography (silica gel Fluka 60, hexanes/ethyl acetate 85:15) affording methyl (Z)-[4-[3-(4-iodophenyl)-3-(4-trifluoromethylphenyl)allyloxy]-2-methylphenoxy]acetate as solidifying yellow oil.

Yield: 880 mg (76%).

$R_F$ (SiO$_2$, hexanes/ethyl acetate 3:1) 0.55.

$^1$H NMR spectrum (300 MHz, CDCl$_3$, $\delta_H$): 7.73 (d, J=10.5 Hz, 2H); 7.55 (d, J=10.5 Hz, 2H); 7.35 (d, J=10.5 Hz, 2H); 6.93 (d, J=10.5 Hz, 2H); 6.69-6.55 (m, 3H); 6.37 (t, J=7.1, 1H); 4.59 (s, 2H); 4.51 (d, 2H); 3.79 (s, 3H); 2.26 (s, 3H).

A solution of the above ester (375 mg, 0.644 mmol) in the mixture of tetrahydrofuran (5 mL) and triethylamine (5 mL) was degassed and 1-propargylpyrazole (123 mg, 1.16 mmol) was added in argon atmosphere. The solution was cooled down; tetrakis(triphenylphosphine)palladium (59.5 mg, 0.052 mmol) and copper(I) iodide (19.6 mg, 0.103 mmol) were added. The reaction mixture was stirred at ambient temperature for 48 h. The mixture was evaporated in vacuo and the residue was purified by flash column chromatography (silica gel Fluka 60, hexanes/ethyl acetate 7:3) yielding methyl (E)-[2-methyl-4-[3-[4-[3-(pyrazol-1-yl)prop-1-ynyl]phenyl]-3-(4-trifluoromethylphenyl)allyloxy]-phenoxy]acetate.

Yield: 340 mg (94%).

$R_F$ (SiO$_2$, hexanes/ethyl acetate 3:1) 0.20.

$^1$H NMR spectrum (300 MHz, CDCl$_3$, $\delta_H$): 7.68 (m, 1H); 7.49-7.48 (m, 5H); 7.35-7.14 (m, 4H); 6.67-6.54 (m, 3H); 6.37 (t, J=6.7 Hz, 1H); 6.31 (m, 1H); 5.20 (s, 2H); 4.58 (s, 2H); 4.51 (d, J=6.7 Hz, 2H); 3.79 (s, 3H); 2.25 (s, 3H).

To a solution of the above ester (330 mg, 0.589 mmol) in tetrahydrofuran/methanol mixture (3:5, 8 mL), a solution of lithium hydroxide monohydrate (37 mg, 0.883 mmol) in distilled water (1 mL) was added under cooling to 0° C. The solution was stirred for 1 h under cooling and 1 h at ambient temperature. The solution was diluted with chloroform (70 mL), water (10 mL) and saturated aqueous solution of ammonium chloride (15 mL) and the phases were separated. The organic layer was washed with brine (10 mL), dried with anhydrous magnesium sulfate and evaporated in vacuo. The residue was triturated with hexanes yielding the title acid as tan solid.

Yield: 142 mg (44%).

M.p. 123-125° C.

$R_F$ (SiO$_2$, chloroform/methanol 4:1) 0.50.

$^1$H NMR spectrum (300 MHz, CDCl$_3$, $\delta_H$): 7.67 (m, 1H); 7.58-7.49 (m, 5H); 7.36-7.11 (m, ~4H); 6.66-6.50 (m, 3H); 6.37 (t, J=6.6 Hz, 1H); 6.33 (m, 1H); 5.22 (s, 2H); 4.60 (s, 2H); 4.50 (d, J=6.7 Hz, 2H); 2.36 (s, 1H); 2.24 (s, 3H).

Example 5

(E)-[2-Methyl-4-[3-[4-(pyridin-2-ylethynyl)phenyl]-3-(4-trifluoromethylphenyl)allyloxy]-phenoxy]acetic Acid

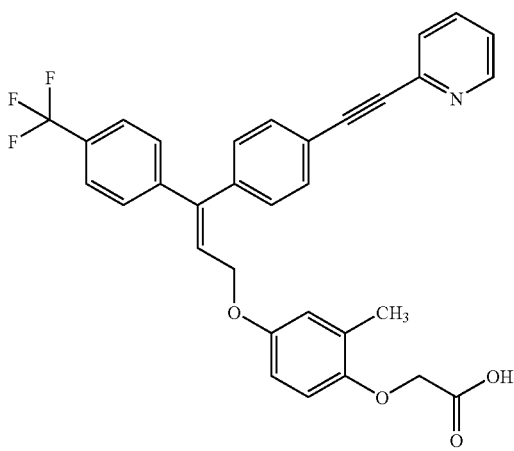

A solution of methyl (Z)-[4-[3-(4-iodophenyl)-3-(4-trifluoromethylphenyl)allyloxy]-2-methylphenoxy]acetate (370 mg, 0.636 mmol; example 4) in a mixture of tetrahydrofuran (5 mL) and triethylamine (5 mL) was degassed and 2-ethynylpyridine (118 mg, 1.144 mmol) was added under argon atmosphere. The solution was cooled; tetrakis(triphenylphosphine)palladium (59.0 mg, 0.051 mmol) and copper (I) iodide (19.3 mg, 0.102 mmol) were added. The reaction mixture was stirred at ambient temperature for 48 h. The mixture was evaporated in vacuo and the residue was dissolved in dichloromethane (60 mL). The solution was washed with water (2×20 mL), dried with anhydrous magnesium sulfate and evaporated in vacuo. The residue was purified by flash column chromatography (silica gel Fluka 60, hexanes/ethyl acetate 7:3) yielding methyl (E)-[2-methyl-4-[3-[4-(pyridin-2-ylethynyl)phenyl]-3-(4-trifluoromethyl phenyl)allyloxy]phenoxy]acetate.

Yield: 344 mg (94%).

$R_F$ (SiO$_2$, hexanes/ethyl acetate 65:35) 0.35.

$^1$H NMR spectrum (300 MHz, CDCl$_3$, $\delta_H$): 8.64 (bs, 1H); 7.73-7.54 (m, 6H); 7.38-7.18 (m, ~5H); 6.69-6.40 (m, 3H); 6.38 (t, J=6.7 Hz, 1H); 4.58 (s, 2H); 4.55 (d, J=6.7 Hz, 2H); 3.78 (s, 3H); 2.25 (s, 3H).

To a solution of the above ester (330 mg, 0.575 mmol) in tetrahydrofuran/methanol mixture (5:1, 18 mL), a solution of lithium hydroxide monohydrate (48.3 mg, 1.15 mmol) in distilled water (3 mL) was added under cooling to 0° C. The solution was stirred for 1 h under cooling and 1 h under ambient temperature. The reaction mixture was acidified with glacial acetic acid (66 µL, 1.15 mmol) and diluted with chloroform (50 mL); the phases were separated and the organic layer was washed with water (10 mL), brine (10 mL), dried with anhydrous magnesium sulfate and evaporated in vacuo. The residue was triturated with hexanes yielding the title acid as solid.

Yield: 255 mg (79%).

M.p. 161-165° C.

$R_F$ (SiO$_2$, chloroform/methanol 4:1) 0.35.

¹H NMR spectrum (300 MHz, CDCl₃, δ_H): 8.67 (bd, J=4.4 Hz, 1H); 7.77 (dt, J=7.7 and 1.4 Hz, 1H); 7.55 (m, 5H); 7.37-7.09 (m, 5H); 6.55 (m, 2H); 6.48 (m, 1H); 6.40 (t, J=6.7 Hz, 1H); 4.63 (s, 2H); 4.50 (d, J=6.8 Hz, 2H); 2.25 (s, 1H).

Example 6

(Z)-[4-[3-(4-Chlorophenyl)-3-[4-(4-methylphenylethynyl)phenyl]allyloxy]-2-methylphenoxy]-acetic Acid

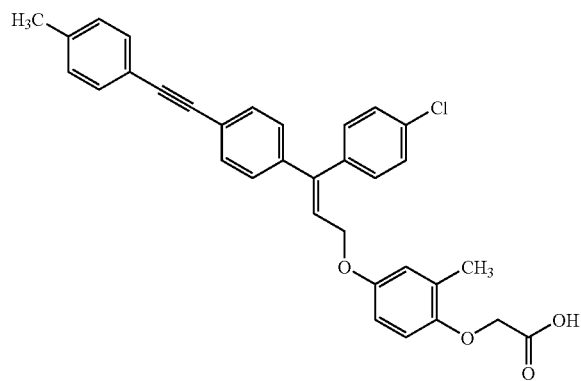

Sodium methoxide (0.02 g, 0.37 mmol) was added to 1 M solution of lithium aluminum hydride in tetrahydrofuran (8 mL, 8 mmol) under nitrogen. The mixture was cooled to 0° C. and a solution of 3-(4-bromophenyl)prop-2-yn-1-ol (1.69 g, 8.01 mmol; prepared as described in experimental part of the synthesis of compound VÚFB-21041) in tetrahydrofuran (8 mL) was added over 30 min. The reaction was stirred at 0° C. for 3.5 h; dry ethyl acetate (2.40 mL, 24.6 mmol) was added and the whole mixture was stirred at ambient temperature for 15 min. A degassed solution of 1-chloro-4-iodobenzene (2.01 g, 8.43 mmol) in dry tetrahydrofuran (5 mL), anhydrous zinc chloride (0.66 g, 4.84 mmol), tris(dibenzylideneacetone)dipalladium chloroform complex (0.18 g, 0.17 mmol), and tri-2-furyl phosphine (0.20 g, 0.86 mmol) were added; the mixture was degassed and then was heated at 65° C. for 18 h under nitrogen. The suspension was cooled down; methanol (4 mL) was added and the mixture was stirred for additional 1 h. The reaction was diluted with ether (40 mL) and saturated aqueous solution of ammonium chloride (2 mL) was added. The mixture was filtered through a paddle of silica gel and the paddle was thoroughly washed with ether (100 mL). Solvents were evaporated and the residue was separated by flash column chromatography (silica gel Fluka 60, hexanes/ethyl acetate 6:1) affording (E)-[3-(4-bromophenyl)-3-(4-chlorophenyl)]allyl alcohol as solidifying oil.

Yield: 1.45 g (56%).

R_F (SiO₂, hexanes/ethyl acetate 4:1) 0.20.

The above allyl alcohol (1.45 g, 4.44 mmol), methyl (4-hydroxy-2-methylphenoxy)acetate (0.96 g, 4.89 mmol; compound VÚFB-21004) and triphenylphosphine (1.35 g, 5.15 mmol) were dissolved in a mixture of anhydrous toluene (75 mL) and tetrahydrofuran (25 mL). The mixture was cooled to 0° C., kept under nitrogen and a degassed solution of diisopropyl azodicarboxylate (1.00 mL, 5.04 mmol) in anhydrous tetrahydrofuran (10 mL) was added dropwise during 15 min. The reaction mixture was allowed to warm up the ambient temperature with the bath and then was stirred overnight. The solvents were evaporated in vacuo and the residue was submitted to flash column chromatography (silica gel Fluka 60, hexanes/ethyl acetate 12:1) affording methyl (E)-[4-[3-(4-bromophenyl)-3-(4-chlorophenyl)allyloxy]-2-methylphenoxy]acetate as solidifying yellow oil.

Yield: 1.94 g (87%).

R_F (SiO₂, hexanes/ethyl acetate 9:1) 0.15.

In nitrogen atmosphere, bis(benzonitrile)palladium(II) chloride (14.6 mg, 0.038 mmol), copper(I) iodide (12.1 mg, 0.064 mmol) and 0.15 M solution of tri(tert-butyl)phosphine in cyclohexane (0.60 mL, 0.090 mmol) were added to a degassed solution of methyl (E)-[4-[3-(4-bromophenyl)-3-(4-chlorophenyl)allyloxy]-2-methylphenoxy]acetate (383 mg, 0.763 mmol), 4-ethynyltoluene (115 mg, 0.990 mmol) and diisopropyl amine (0.50 mL, 3.57 mmol) in dry tetrahydrofuran (6 mL). In atmosphere of nitrogen, the reaction mixture was stirred at 60° C. for 4 h, cooled down and evaporated in vacuo. The residue was purified by flash column chromatography (silica gel Fluka 60, hexanes/ethyl acetate 12:1) yielding methyl (Z)-[4-[3-(4-chlorophenyl)-3-[4-(4-methylphenylethynyl)phenyl]allyloxy]-2-methylphenoxy]acetate as brownish oil.

Yield: 315 mg (77%).

R_F (SiO₂, hexanes/ethyl acetate 9:1) 0.10.

¹H NMR spectrum (300 MHz, CDCl₃, δ_H): 7.45-7.37 (m, 6H); 7.23-7.13 (m, ~6H); 6.69-6.55 (m, 3H); 6.35 (t, J=6.6 Hz, 1H); 4.59 (s, 2H); 4.50 (d, J=6.6 Hz, 2H); 3.79 (s, 3H); 2.37 (s, 3H); 2.25 (s, 3H).

To a solution of the above ester (232 mg, 0.432 mmol) in tetrahydrofuran/methanol mixture (5:1, 6 mL), a solution of lithium hydroxide monohydrate (26 mg, 0.620 mmol) in distilled water (1 mL) was added under cooling (0° C.). The solution was stirred for 60 min under cooling, glacial acetic acid (0.05 mL, 0.874 mmol) was added and the mixture was stirred for further 10 min. The solution was diluted with ether (20 mL) and water (15 mL); the phases were separated and the aqueous phase was extracted with ether (3×10 mL). The combined organic layers were washed with water (2×10 mL) and brine (2×10 mL), dried with anhydrous magnesium sulfate and evaporated in vacuo. The residue was triturated with dichloromethane/hexanes mixture (1:10, 11 mL) yielding the title acid as grayish solid.

Yield: 183 mg (81%).

M.p. 157-175° C. (amorphous).

R_F (SiO₂, dichloromethane/methanol 90:10) 0.35.

¹H NMR spectrum (300 MHz, CDCl₃, δ_H): 7.46-7.37 (m, 6H); 7.23-7.14 (m, 6H); 6.68-6.57 (m, 3H); 6.35 (t, J=6.6 Hz, 1H); 4.62 (s, 2H); 4.51 (d, J=6.6 Hz, 2H); 2.37 (s, 3H); 2.25 (s, 3H).

Example 7

(E)-[4-[3-(4-Chlorophenyl)-3-[4-(3,3-dimethylbutynyl)phenyl]allyloxy]-2-methylphenoxy]acetic Acid

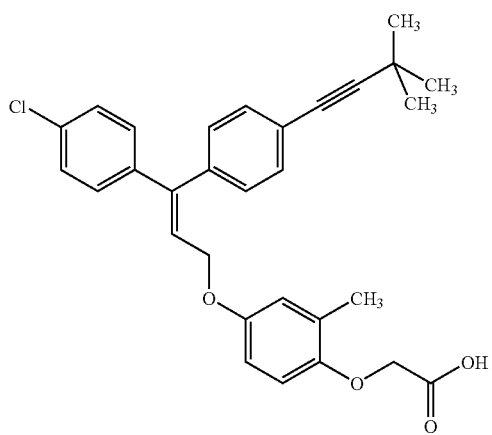

A solution of 1-chloro-4-iodobenzene (23.9 g, 100.0 mmol) in dry tetrahydrofuran (100 mL) was degassed and copper(I) iodide (570 mg, 3.0 mmol), tetrakis(triphenylphosphine)palladium (3.4 g, 3.0 mmol) and 1,8-diazabicyclo[5.4.0]undec-7-ene (18.2 g, 120.0 mmol) were added. The reaction solution was degassed again and propargyl alcohol (6.7 g, 120.0 mmol) was added under inert atmosphere at ambient temperature. The reaction mixture was stirred (initially under cooling with ice water) for 24 h, then treated with water (20 mL) and acidified with 2 M hydrochloric acid (20 mL). The organic phase was separated and the aqueous phase was extracted with ether (4×30 mL). The combined organic phases were dried with anhydrous magnesium sulfate and concentrated in vacuo yielding brown solid. The residue was purified by column chromatography (silica gel Fluka 60, chloroform) yielding 3-(4-chlorophenyl)prop-2-yn-1-ol.

Yield: 8.35 g (50%).
M.p.: 75.5-77.5° C. (hexane).
$R_F$ (SiO$_2$, hexane/ethyl acetate 90:10): 0.10.

Sodium methoxide (0.05 g, 0.9 mmol) was added to 1 M solution of lithium aluminum hydride in tetrahydrofuran (20 mL, 20 mmol). The mixture was cooled to 0° C., and a solution of the above alcohol (3.35 g, 20.1 mmol) in tetrahydrofuran (30 mL) was slowly added. The reaction mixture was stirred at 0° C. for 1.5 h and at ambient temperature for 1.5 h. Ethyl acetate (3.3 mL, 34 mmol) was added at 0° C., and the mixture was stirred for 20 min without cooling. 1,4-Diiodobenzene (6.6 g, 20 mmol), anhydrous zinc chloride (1.64 g, 12 mmol), tris(dibenzylideneacetone)dipalladium chloroform complex (0.41 g, 0.4 mmol), and tri-(2-furyl)phosphine (0.37 g, 1.6 mmol) were added; the mixture was evacuated and kept under nitrogen. Reaction mixture was heated at 65° C. for 16 h, and then cooled down. Methanol (10 mL) was added and the mixture was stirred for additional 1 h. The reaction suspension was diluted with ether (150 mL), and saturated aqueous solution of ammonium chloride (5 mL) was added. The mixture was filtered through a paddle of silica gel and the solid phase was thoroughly washed with ether. Solvents were evaporated in vacuo and the residue was submitted to column chromatography (silica gel Fluka 60; benzene-chloroform) affording (Z)-[3-(4-chlorophenyl)-3-(4-iodophenyl)]allyl alcohol as light brown solid.

Yield: 3.5 g (49%).
M.p.: 79-84° C.
$R_F$ (SiO$_2$, chloroform/ether 2:1): 0.40.
$^1$H NMR spectrum (300 MHz, CDCl$_3$, $\delta_H$): 7.71 (d, J=8.7 Hz, 2H); 7.26 (d, J=8.8 Hz, 2H); 7.15 (d, J=8.8 Hz, 2H); 6.90 (d, J=8.7 Hz, 2H); 6.22 (t, J=6.9 Hz, 1H); 4.20 (d, J=6.9 Hz, 2H); 1.55 (s, 1H).

The above allyl alcohol (3.45 g, 9.7 mmol), methyl (4-hydroxy-2-methylphenoxy)acetate (1.96 g, 10 mmol; example 2) and triphenylphosphine (2.9 g, 11 mmol) were dissolved in a mixture of anhydrous toluene (50 mL) and tetrahydrofuran (25 mL). The mixture was cooled to 0° C., kept under nitrogen and diisopropyl azodicarboxylate (2.3 g, 10.8 mmol) was added dropwise. The reaction mixture was stirred at 0° C. for 3 h and then at ambient temperature for 16 h. The solvents were evaporated in vacuo and the residue was submitted to column chromatography (silica gel Fluka 60, benzene) affording methyl (Z)-[4-[3-(4-chlorophenyl)-3-(4-iodophenyl)allyloxy]-2-methylphenoxy]acetate as solid.

Yield: 3.1 g (58%).
M.p.: 89-92° C.
$R_F$ (SiO$_2$, chloroform): 0.55.
$^1$H NMR spectrum (300 MHz, CDCl$_3$, $\delta_H$): 7.73 (d, J=8.4 Hz, 2H); 7.26 (d, J=8.7 Hz, 2H); 7.16 (d, J=8.7 Hz, 2H); 6.93 (d, J=8.4 Hz, 2H); 6.68 (d, J=2.7 Hz, 1H); 6.63 (d, J=8.7 Hz, 1H); 6.57 (dd, J=8.7 and 2.7 Hz); 6.29 (t, J=6.7 Hz, 1H); 4.59 (s, 2H); 4.48 (d, J=6.7 Hz, 2H); 3.79 (s, 3H); 2.26 (s, 3H).

t-Butylacetylene (220 mg, 2.7 mmol) was added under nitrogen atmosphere to a degassed solution of methyl (Z)-[4-[3-(4-chlorophenyl)-3-(4-iodophenyl)allyloxy]-2-methylphenoxy]acetate (500 mg, 0.91 mmol) in a mixture of tetrahydrofuran (8 mL) and triethylamine (8 mL) The solution was cooled, tetrakis(triphenylphosphine)palladium (96 mg, 0.083 mmol) and copper(I) iodide (27.6 mg, 0.145 mmol) were added. The reaction mixture was stirred at ambient temperature for 72 h, diluted with benzene (100 mL) and washed with water (2×50 mL). The organic solution was dried with anhydrous magnesium sulfate and subsequently evaporated in vacuo. The residue was purified by column chromatography (silica gel Fluka 60, hexanes/ethyl acetate 1:1) and recrystallized from ethanol yielding methyl E)-[4-[3-(4-chlorophenyl)-3-[4-(3,3-dimethylbutynyl)phenyl]allyloxy]-2-methylphenoxy]acetate.

Yield: 330 mg (72%).
M.p.: 115-116.5° C. (ethanol).
$R_F$ (SiO$_2$, cyclohexane/tetrahydrofuran 9:1): 0.35.
$^1$H NMR spectrum (300 MHz, CDCl$_3$, $\delta_H$): 7.41 (d, J=8.4 Hz, 2H); 7.25 (d, J=8.7 Hz, 2H); 7.15 (d, J=8.7 Hz, 2H); 7.09 (d, J=8.4 Hz, 2H); 6.66 (d, J=2.7 Hz, 1H); 6.61 (d, J=8.7 Hz, 1H); 6.55 (dd, J=8.7 and 2.7 Hz); 6.26 (t, J=6.7 Hz, 1H); 4.58 (s, 2H); 4.48 (d, J=6.7 Hz, 2H); 3.79 (s, 3H); 2.24 (s, 3H); 1.33 (s, 9H).

The above ester (0.33 g, 0.656 mmol) was dissolved in ethanol/tetrahydrofuran mixture (1:1, 30 mL); a solution of lithium hydroxide monohydrate (0.08 g, 1.9 mmol) in water (3 mL) was added and the mixture was left to stand for 72 h. The solvents were evaporated in vacuo; the residue was diluted with water (25 mL) and acidified with acetic acid (0.5 mL). The product was filtered off and dried in the air yielding the title compound.

Yield: 0.30 g (94%).
M.p.: 144-147° C.
$R_F$ (SiO$_2$, chloroform/ethanol 9:1): 0.30.
$^1$H NMR spectrum (300 MHz, CDCl$_3$, $\delta_H$): 7.41 (d, J=8.4 Hz, 2H); 7.24 (d, J=8.8 Hz, 2H); 7.15 (d, J=8.8 Hz, 2H); 7.09

(d, J=8.4 Hz, 2H); 6.62 (m, 2H); 6.54 (dd, J=8.5 and 3.0 Hz); 6.25 (t, J=6.6 Hz, 1H); 4.56 (s, 2H); 4.47 (d, J=6.6 Hz, 2H); 2.21 (s, 3H); 1.32 (s, 9H).

Example 8

(E)-[4-[3-(4-Chlorophenyl)-3-[4-[3-(dimethylamino)propynyl]phenyl]allyloxy]-2-methylphenoxy]acetic Acid

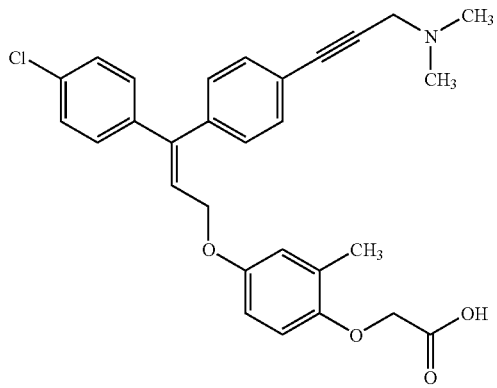

N,N-Dimethylpropargylamine (200 mg, 2.4 mmol) was added under nitrogen atmosphere to a degassed solution of methyl (Z)-[4-[3-(4-iodoophenyl)-3-(4-chlorophenyl)allyloxy]-2-methylphenoxy]acetate (500 mg, 0.91 mmol; example 7) in a mixture of tetrahydrofuran (8 mL) and triethylamine (8 mL) The solution was cooled, tetrakis(triphenylphosphine)palladium (96 mg, 0.083 mmol) and copper(I) iodide (27.6 mg, 0.145 mmol) were added. The reaction mixture was stirred at ambient temperature for 48 h, dissolved in benzene (100 mL) and washed with water (2×50 mL). The organic solution was dried with anhydrous potassium carbonate and subsequently evaporated in vacuo. The residue was purified by column chromatography (silica gel Fluka 60, benzene-chloroform/ether 2:1) yielding (E)-[4-[3-(4-chlorophenyl)-3-[4-[3-(dimethylamino)propynyl]phenyl]allyloxy]-2-methylphenoxy]acetate.

Yield: 400 mg (87%).

$R_F$ (SiO$_2$, chloroform/ethanol 9:1): 0.40.

$^1$H NMR spectrum (300 MHz, CDCl$_3$, $\delta_H$): 7.46 (d, J=8.1 Hz, 2H); 7.25 (d, J=8.7 Hz, 2H); 7.16 (d, J=8.7 Hz, 2H); 7.12 (d, J=8.1 Hz, 2H); 6.66 (d, J=2.7 Hz, 1H); 6.62 (d, J=8.7 Hz, 1H); 6.56 (dd, J=8.7 and 2.7 Hz); 6.27 (t, J=6.7 Hz, 1H); 4.58 (s, 2H); 4.49 (d, J=6.7 Hz, 2H); 3.78 (s, 3H); 3.49 (s, 2H); 2.38 (s, 6H); 2.24 (s, 3H).

The above ester (0.40 g, 0.794 mmol) was dissolved in ethanol (50 mL), a solution of lithium hydroxide monohydrate (0.10 g, 2.38 mmol) in water (4 mL) was added and the mixture was left to stand for 48 h. The solvents were evaporated in vacuo; the residue was diluted with water (25 mL), acidified with acetic acid (0.5 mL) and extracted with ethyl acetate (2×50 mL). The organic solution was dried with anhydrous potassium carbonate and subsequently evaporated in vacuo. The residue was purified by column chromatography (silica gel Fluka 60, chloroform/ethanol/ammonia 1:1:0.05) affording oil which was triturated with hexane yielding the title compound as amorphous solid.

Yield: 0.34 g (87.5%).

$R_F$ (SiO$_2$, chloroform/ethanol/ammonia 1:1:0.05): 0.05.

$^1$H NMR spectrum (300 MHz, CDCl$_3$, $\delta_H$): 7.45 (d, J=8.1 Hz, 2H); 7.25 (d, J=8.4 Hz, 2H); 7.15 (m, 4H); 6.64 (m, 2H); 6.48 (dd, J=8.7 and 2.7 Hz); 6.31 (t, J=6.6 Hz, 1H); 4.48 (s, 2H); 4.42 (d, J=6.6 Hz, 2H); 3.86 (s, 2H); 2.64 (s, 6H); 2.24 (s, 3H).

Example 9

(E)-[4-[3-(4-Chlorophenyl)-3-[4-(pyridin-2-ylethynyl)phenyl]allyloxy]-2-methylphenoxy]acetic Acid

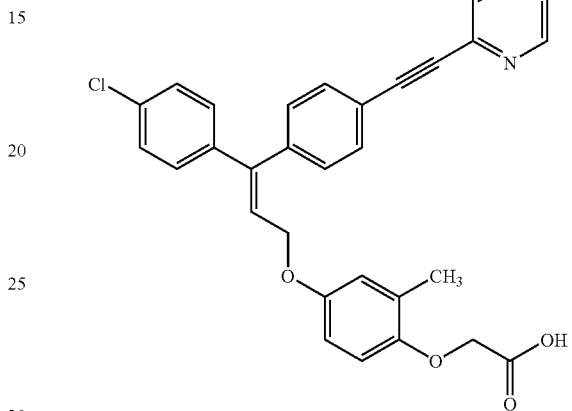

2-Ethynylpyridine (250 mg, 2.42 mmol) was added under nitrogen atmosphere to a degassed solution of methyl (Z)-[4-[3-(4-chlorophenyl)-3-(4-iodophenyl)allyloxy]-2-methylphenoxy]-acetate (500 mg, 0.91 mmol; example 7) in a mixture of tetrahydrofuran (8 mL) and triethylamine (8 mL) The solution was cooled, tetrakis(triphenylphosphine)palladium (96 mg, 0.083 mmol) and copper(I) iodide (27.6 mg, 0.145 mmol) were added. The reaction mixture was stirred at ambient temperature for 72 h, diluted with benzene (100 mL) and washed with water (2×50 mL). The organic solution was dried with anhydrous potassium carbonate and subsequently evaporated in vacuo. The residue was purified by column chromatography (silica gel Fluka 60, benzene-chloroform/ether 2:1) yielding methyl (E)-[4-[3-(4-chlorophenyl)-3-[4-(pyridin-2-ylethynyl)phenyl]allyloxy]-2-methylphenoxy]acetate.

Yield: 400 mg (84%).

$R_F$ (SiO$_2$, chloroform/ethanol 9:1): 0.70.

$^1$H NMR spectrum (300 MHz, CDCl$_3$, $\delta_H$): 8.63 (d, J=4.5 Hz, 1H); 7.70 (dt, 1H); 7.63 (d, J=8.3 Hz, 2H); 7.56 (d, J=7.8 Hz, 1H); 7.27 (m, 3H); 7.20 (m, 4H); 6.68 (d, J=2.7 Hz, 1H); 6.63 (d, J=8.8 Hz, 1H); 6.57 (dd, J=8.8 and 2.7 Hz); 6.30 (t, J=6.7 Hz, 1H); 4.58 (s, 2H); 4.51 (d, J=6.7 Hz, 2H); 3.78 (s, 3H); 2.25 (s, 3H).

The above ester (0.30 g, 0.57 mmol) was dissolved in ethanol (30 mL), a solution of lithium hydroxide monohydrate (0.08 g, 1.9 mmol) in water (4 mL) was added and the mixture was left to stand for 72 h. The solvents were evaporated in vacuo, the residue was diluted with water (25 mL), acidified with acetic acid (0.5 mL) and extracted with chloroform (2×50 mL). The organic solution was dried with anhydrous potassium carbonate and subsequently evaporated in vacuo. The residue was purified by column chromatography (silica gel Fluka 60, ethyl acetate) affording oil which was triturated with hexane yielding the title compound as amorphous solid.

Yield: 0.25 g (86%).
R$_F$ (SiO$_2$, chloroform/ethanol 9:1): 0.15.
$^1$H NMR spectrum (300 MHz, CDCl$_3$, δ$_H$): 8.69 (d, J=4.5 Hz, 1H); 7.75 (dt, 1H); 7.55 (m, 3H); 7.31 (m, 1H); 7.26 (m, 2H); 7.15 (m, 4H); 6.66 (m, 2H); 6.57 (dd, J=8.9 and 3.0 Hz); 6.29 (t, J=6.8 Hz, 1H); 4.62 (s, 2H); 4.47 (d, J=6.8 Hz, 2H); 2.24 (s, 3H).

Example 10

(E)-[4-[3-(4-Fluorophenyl)-3-[4-[3-(morpholin-4-yl)propynyl]phenyl]allyloxy]-2-methylphenoxy]acetic Acid

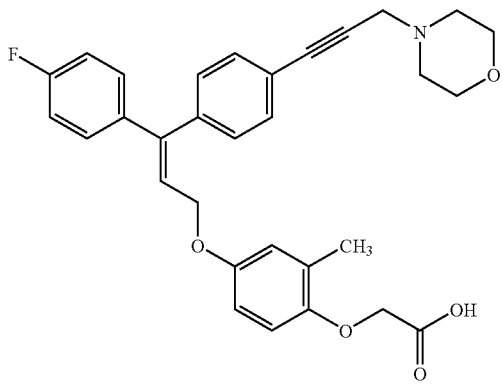

A solution of 4-fluoro-1-iodobenzene (11.0 g, 50.0 mmol) in anhydrous tetrahydrofuran (90 mL) was degassed and copper(I) iodide (0.29 g, 1.5 mmol), tetrakis(triphenylphosphine) palladium (1.75 g, 1.5 mmol) and 1,8-diazabicyclo[5.4.0]undec-7-ene (9.25 g, 60.0 mmol) were added. The reaction solution was degassed again and propargyl alcohol (3.5 mL, 60.0 mmol) was added dropwise under inert atmosphere at ambient temperature. The obtained yellow suspension was stirred at ambient temperature overnight, then treated with brine (10 mL) and acidified with 2 M hydrochloric acid to pH~2. The phases were separated and the aqueous phase was extracted with ether (4×50 mL). The combined organic phases were washed with water (3×30 mL) and brine (2×30 mL), dried over anhydrous magnesium sulfate and concentrated in vacuo yielding brown solid. The residue was purified by column chromatography (silica gel Fluka 60, hexanes/ethyl acetate 90:10) and the obtained light yellow solid was crystallized from hexane yielding 3-(4-fluorophenyl)prop-2-yn-1-ol as light yellow needles.
Yield: 6.2 g (83%).
M.p. 32-33° C. (hexane).
R$_F$ (hexanes/ethyl acetate 80:20) 0.30.
Sodium methoxide (0.05 g, 0.9 mmol) was added to 1 M solution of lithium aluminum hydride in tetrahydrofuran (20 mL, 20 mmol). The mixture was cooled to 0° C., and a solution of the above alcohol (3.0 g, 20.0 mmol) in tetrahydrofuran (30 mL) was slowly added. The reaction mixture was stirred at 0° C. for 3 h, ethyl acetate (5.5 mL, 60.1 mmol) was added and the mixture was stirred for further 10 min without cooling. 1,4-Diiodobenzene (6.3 g, 19.0 mmol), anhydrous zinc chloride (1.65 g, 12.0 mmol), tris(dibenzylideneacetone)dipalladium chloroform complex (0.42 g, 0.4 mmol) were added; the mixture was evacuated and kept under nitrogen. A solution of tri(2-furyl)phosphine (0.37 g, 1.6 mmol) was added and the mixture was heated at 50° C. overnight under nitrogen. Methanol (10 mL) was added and the mixture was stirred for additional 1 h. The reaction mixture was diluted with ether (100 mL) and saturated aqueous solution of ammonium chloride (5 mL) was added. The mixture was filtered through a paddle of silica gel, evaporated in vacuo and the residue was purified by column chromatography (silica gel Fluka 60, hexanes/ethyl acetate 90:10) affording (Z)-3-(4-fluorophenyl)-3-(4-iodophenyl)lallyl alcohol.
Yield: 3.1 g (43%).
R$_F$ (SiO$_2$, hexanes/ethyl acetate 80:20) 0.25.
The above allyl alcohol (3.0 g, 8.5 mmol) was dissolved in anhydrous tetrahydrofuran (50 mL) and anhydrous toluene (150 mL), methyl (4-hydroxy-2-methylphenoxy)acetate (1.83 g, 9.3 mmol; example 2) and triphenylphosphine (2.7 g, 10.3 mmol) were added to the solution. The mixture was evacuated and cooled to 0° C. under nitrogen. A degassed solution of diisopropyl azodicarboxylate (2.0 mL, 10.3 mmol) in anhydrous tetrahydrofuran (20 mL) was added dropwise during 30 min and the reaction mixture was allowed to warm up to the ambient temperature and then was stirred overnight. The solvents were evaporated in vacuo and the residue was submitted to flash column chromatography (silica gel Fluka 60, hexanes/ethyl acetate 90:10) affording methyl (Z)-[4-[3-(4-fluorophenyl)-3-(4-iodophenyl)allyloxy]-2-methylphenoxy]acetate as solidifying light yellow oil.
Yield: 3.0 g (67%).
R$_F$ (SiO$_2$, hexanes/ethyl acetate 80:20) 0.55.
Methyl (Z)-[4-[3-(4-Fluorophenyl)-3-(4-iodophenyl)allyloxy]-2-methylphenoxy]acetate (400 mg, 0.75 mmol) was dissolved in anhydrous tetrahydrofuran (10 mL); anhydrous triethylamine (20 mL) and a solution of 4-propargylmorpholine (190 mg, 1.51 mmol) in anhydrous tetrahydrofuran (2 mL) were added. The solution was degassed and copper(I) iodide (23 mg, 0.12 mmol) and tetrakis(triphenylphosphine) palladium (70 mg, 0.06 mmol) were added under nitrogen atmosphere. The mixture was stirred at ambient temperature overnight, the resulting suspension was filtered through a paddle of silica gel and silica gel was thoroughly washed with ethyl acetate. Filtrate was washed with water (2×30 mL) and brine (2×30 mL), dried over anhydrous magnesium sulfate and evaporated in vacuo. The residue was purified using column chromatography (silica gel Fluka 60, chloroform saturated with ammonia/methanol 99:1) yielding (E)-[4-[3-(4-fluorophenyl)-3-[4-[3-(morpholin-4-yl)propynyl]-phenyl]allyloxy]-2-methylphenoxy]acetate as yellow oil.
Yield: 370 mg (95%).
R$_F$ (SiO$_2$, chloroform saturated with ammonia/methanol 99:1): 0.15.
$^1$H NMR spectrum (300 MHz, CDCl$_3$, δ$_H$): 7.46 (d, J=8.2 Hz, 2H); 7.23-7.13 (m, 4H); 6.98 (t, J=8.6 Hz, 2H); 6.68-6.55 (m, 3H); 6.24 (t, J=6.7 Hz, 1H); 4.58 (s, 2H); 4.49 (d, J=6.7 Hz, 2H); 3.79-3.75 (m, 5H); 3.54 (s, 2H); 2.68-2.56 (m, 6H); 2.25 (s, 3H).
To a solution of the above ester (370 mg, 0.718 mmol) in tetrahydrofuran/methanol mixture (5:2, 7 mL), a solution of lithium hydroxide monohydrate (70 mg, 1.44 mmol) in distilled water (2.5 mL) was added and the solution was stirred for 60 min at ambient temperature. The mixture was neutralized with 2 M hydrochloric acid and diluted with ether (50 mL) and water (20 mL). The phases were separated and the aqueous layer was extracted with ether (2×15 mL). The combined organic layers were washed with water (2×15 mL) and brine (3×15 mL), dried with anhydrous magnesium sulfate and evaporated in vacuo. The residue was treated with hexane giving the title acid as brownish crystals.

Yield: 260 mg (72%).
M.p.: 145-171° C. (amorphous).
$R_F$ (SiO$_2$, chloroform/methanol 85:15): 0.25.
$^1$H NMR spectrum (300 MHz, DMSO-d$_6$, $\delta_H$): 7.50 (d, J=8.2 Hz, 2H); 7.25-7.14 (m, 6H); 6.72-6.69 (m, 2H); 6.61 (dm, J=8.9 and 2.9 Hz, 2H); 6.23 (t, J=6.7 Hz, 1H); 4.59 (s, 2H); 4.46 (d, J=6.7 Hz, 2H); 3.63-3.60 (m, 4H); 3.53 (s, 2H); 2.54-2.53 (m, 4H); 2.14 (s, 3H).

Example 11

(E)-[4-[3-(4-Fluorophenyl)-3-[4-[3-(methylsulfanyl)propynyl]phenyl]allyloxy]-2-methylphenoxy]acetic Acid

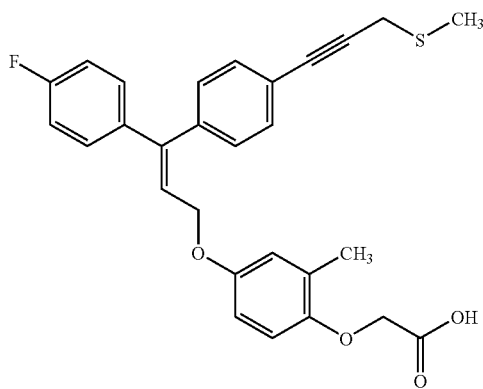

Methyl (Z)-[4-[3-(4-Fluorophenyl)-3-(4-iodophenyl)allyloxy]-2-methylphenoxy]acetate (400 mg, 0.75 mmol; example 10) was dissolved in anhydrous tetrahydrofuran (10 mL); anhydrous triethylamine (20 mL) and a solution of 3-(methylsulfanyl)propyne (130 mg, 1.51 mmol) in anhydrous tetrahydrofuran (2 mL) were added. Resulting solution was degassed and copper(I) iodide (23 mg, 0.12 mmol) and tetrakis(triphenylphosphine)palladium (70 mg, 0.06 mmol) were added under nitrogen atmosphere. Reaction mixture was stirred at ambient temperature overnight, the resulting suspension was filtered through a paddle of silica gel and silica gel was thoroughly washed with ethyl acetate. The filtrate was evaporated in vacuo; the obtained residue was dissolved in dichloromethane and the solution was washed with water (2×30 mL) and brine (2×30 mL), dried over anhydrous magnesium sulfate and evaporated in vacuo. The residue was purified by column chromatography (silica gel Fluka 60, hexanes/ethyl acetate 90:10) yielding methyl (E)-[4-[3-(4-fluorophenyl)-3-[4-[3-(methylsulfanyl)propynyl]phenyl]allyloxy]-2-methylphenoxy]acetate as yellow oil.
Yield: 310 mg (84%).
$R_F$ (SiO$_2$, hexanes/ethyl acetate 80:20): 0.45.
$^1$H NMR spectrum (300 MHz, CDCl$_3$, $\delta_H$): 7.45 (d, J=8.2 Hz, 2H); 7.23-7.12 (m, 4H); 7.00-6.95 (m, 2H); 6.67-6.54 (m, 3H); 6.24 (t, J=6.7 Hz, 1H); 4.58 (s, 2H); 4.49 (d, J=6.7 Hz, 2H); 3.79 (s, 3H); 3.49 (s, 2H); 2.31 (s, 3H); 2.25 (s, 3H).

To a solution of the above ester (300 mg, 0.611 mmol) in tetrahydrofuran (5 mL) and methanol (2 mL), a solution of lithium hydroxide monohydrate (60 mg, 1.22 mmol) in distilled water (2 mL) was added. The solution was stirred for 60 min at ambient temperature and subsequently neutralized with 2 M hydrochloric acid. The mixture was diluted with ether (50 mL) and water (20 mL); the phases were separated and the aqueous layer was extracted with ether (2×15 mL). The combined organic layers were washed with water (2×15 mL) and brine (3×15 mL), dried with anhydrous magnesium sulfate and evaporated in vacuo. The residue was treated with hexane giving the title acid as brownish crystals.
Yield: 260 mg (72%).
M.p.: 145-171° C. (amorphous).
$R_F$ (SiO$_2$, chloroform/methanol 85:15): 0.25.
$^1$H NMR spectrum (300 MHz, DMSO-d$_6$, $\delta_H$): 7.49 (d, J=8.1 Hz, 2H); 7.24-7.16 (m, 6H); 6.72-6.69 (m, 2H); 6.63-6.59 (m, 1H); 6.30 (t, J=6.7 Hz, 1H); 4.59 (s, 2H); 4.46 (d, J=6.7 Hz, 2H); 3.62 (s, 2H); 2.24 (s, 3H); 2.14 (s, 3H).

Example 12

(E)-[4-[3-(4-Fluorophenyl)-3-[4-[(pyridin-2-yl)ethynyl]phenyl]allyloxy]-2-methylphenoxy]acetic Acid

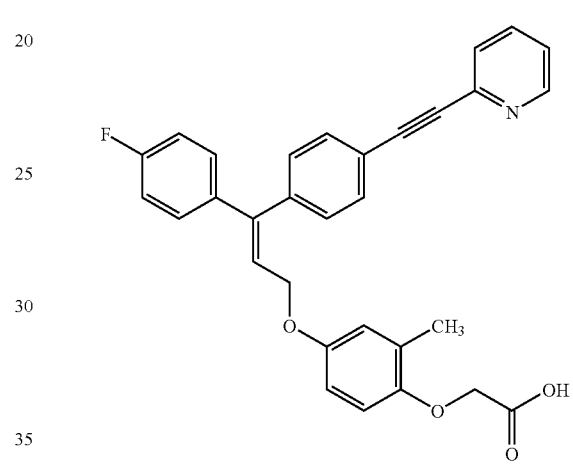

Methyl (Z)-[4-[3-(4-fluorophenyl)-3-(4-iodophenyl)allyloxy]-2-methylphenoxy]acetate (400 mg, 0.75 mmol; example 10) was dissolved in anhydrous tetrahydrofuran (10 mL). Anhydrous triethylamine (20 mL) and a solution of 2-ethynylpyridine (155 mg, 1.50 mmol) in anhydrous tetrahydrofuran (2 mL) were added. The solution was degassed and copper(I) iodide (23 mg, 0.12 mmol) and tetrakis(triphenylphosphine)palladium (70 mg, 0.06 mmol) were added. A mixture was stirred at ambient temperature under nitrogen atmosphere overnight; the resulting suspension was filtered through a paddle of silica gel and silica gel was thoroughly washed with ethyl acetate. The obtained filtrate was evaporated in vacuo and the residue was dissolved in ethyl acetate (50 mL). The solution was washed with water (2×30 mL) and brine (2×30 mL), dried over anhydrous magnesium sulfate and evaporated in vacuo. The residue was purified using column chromatography (silica gel Fluka 60, hexanes/ethyl acetate 90:10) yielding methyl (E)-[4-[3-(4-fluorophenyl)-3-[4-[(pyridin-2-yl)ethynyl]phenyl]allyloxy]-2-methylphenoxy]acetate as orange oil.
Yield: 310 mg (81%).
$R_F$ (SiO$_2$, hexanes/ethyl acetate 80:20): 0.65.
$^1$H NMR spectrum (300 MHz, CDCl$_3$, $\delta_H$): 8.64 (d, J=4.4 Hz, 1H); 7.73-7.68 (m, 1H); 7.69-7.63 (d, J=8.3 Hz, 2H); 7.55 (d, J=8.3 Hz, 1H); 7.25-7.19 (m, 5H); 6.97 (t, J=8.7 Hz, 2H); 6.69-6.56 (m, 3H); 6.26 (t, J=6.7 Hz, 1H); 4.59 (s, 2H); 4.51 (d, J=6.7 Hz, 2H); 3.79 (s, 3H); 2.25 (s, 3H).

To a solution of the above ester (300 mg, 0.591 mmol) in tetrahydrofuran/methanol mixture (5:2, 7 mL), a solution of lithium hydroxide monohydrate (60 mg, 1.22 mmol) in distilled water (2.0 mL) was added and reaction mixture was stirred for 60 min at ambient temperature. The solution was neutralized with 2 M hydrochloric acid and diluted with ether (50 mL) and water (20 mL). Phases were separated and the aqueous layer was extracted with ether (2×10 mL). The combined organic layers were washed with water (2×15 mL) and brine (3×15 mL), dried over anhydrous magnesium sulfate and evaporated in vacuo. The residue was treated with a mixture of hexane and dichloromethane (10:1, 7 mL) giving the title acid as grayish crystals.

Yield: 240 mg (82%).

M.p.: 90-95° C. (amorphous).

$R_F$ (SiO$_2$, chloroform/methanol 85:15): 0.30.

$^1$H NMR spectrum (300 MHz, DMSO-d$_6$, $\delta_H$): 8.62 (d, J=4.8 Hz, 1H); 7.87 (dt, J=7.7 and 1.8 Hz, 1H); 7.69-7.65 (m, 3H); 7.45-7.41 (m, 1H); 7.29-7.16 (m, 6H); 6.72-6.69 (m, 2H); 6.64-6.60 (m, 1H); 6.33 (t, J=6.7 Hz, 1H); 4.57 (s, 2H); 4.48 (d, J=6.7 Hz, 2H); 2.14 (s, 3H).

Example 13

(E)-[4-[3-[4-[3-(Dimethylamino)propynyl)phenyl]-3-(4-fluorophenyl)allyloxy]-2-methylphenoxy]acetic Acid

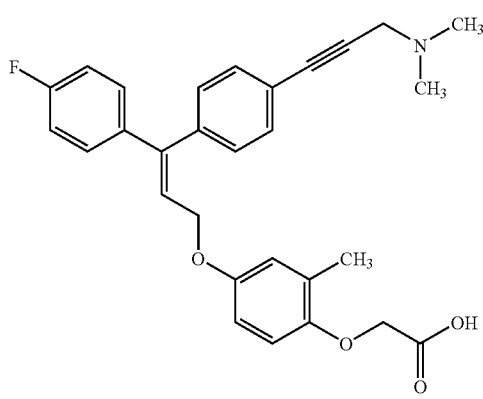

Methyl (Z)-[4-[3-(4-Fluorophenyl)-3-(4-iodophenyl)allyloxy]-2-methylphenoxy]acetate (400 mg, 0.75 mmol; example 10) was dissolved in a mixture of anhydrous tetrahydrofuran (10 mL) and anhydrous triethylamine (20 mL). The solution was degassed and a solution of N,N-dimethylpropargylamine (125 mg, 1.50 mmol) in anhydrous tetrahydrofuran (2 mL) was added under inert atmosphere. The resulting solution was degassed once more, copper(I) iodide (23 mg, 0.12 mmol) and tetrakis(triphenylphosphine)palladium (70 mg, 0.06 mmol) were added and the mixture was degassed again. The reaction mixture was stirred at ambient temperature overnight and the resulting suspension was filtered through a paddle of silica gel. Silica gel was washed thoroughly with ethyl acetate; the filtrate was evaporated in vacuo and the residue was dissolved in dichloromethane (50 mL). The solution was washed with water (2×30 mL) and brine (2×30 mL), dried over anhydrous magnesium sulfate and evaporated in vacuo. The residue was purified by column chromatography (silica gel Fluka 60, dichloromethane/methanol 99:1) yielding methyl (E)-[4-[3-[4-[3-(dimethylamino)propynyl)phenyl]-3-(4-fluorophenyl)allyloxy]-2-methylphenoxy]acetate as yellow oil.

Yield: 320 mg (87%).

$R_F$ (SiO$_2$, chloroform/methanol 95:5): 0.55.

$^1$H NMR spectrum (300 MHz, CDCl$_3$, $\delta_H$): 7.46 (d, J=8.3 Hz, 2H); 7.23-7.12 (m, 4H); 7.00-6.95 (m, 2H); 6.68-6.55 (m, 3H); 6.24 (t, J=6.7 Hz, 1H); 4.58 (s, 2H); 4.49 (d, J=6.7 Hz, 2H); 3.79 (s, 3H); 3.50 (s, 2H); 2.39 (s, 6H); 2.25 (s, 3H).

To a solution of the above ester (300 mg, 0.615 mmol) in tetrahydrofuran (5 mL) and methanol (2 mL), a solution of lithium hydroxide monohydrate (60 mg, 1.22 mmol) in distilled water (2 mL) was added. The solution was stirred for 60 min at ambient temperature, neutralized with saturated aqueous solution of ammonium chloride (10 mL) and extracted with ether (3×30 mL) and dichloromethane (3×30 mL). The combined organic extracts were washed with saturated aqueous solution of ammonium chloride (2×10 mL), dried over anhydrous magnesium sulfate and evaporated in vacuo. The residue was treated with of hexanes/dichloromethane mixture (10:1, 5 mL) giving the title acid as yellowish crystals.

Yield: 165 mg (57%).

M.p.: 115-143° C. (amorphous).

$R_F$ (SiO$_2$, chloroform/methanol 85:15): 0.10.

$^1$H NMR spectrum (300 MHz, DMSO-d$_6$, $\delta_H$): 7.49 (d, J=8.2 Hz, 2H); 7.27-7.14 (m, 6H); 6.70-6.68 (m, 2H); 6.62-6.58 (m, 1H); 6.23 (t, J=6.7 Hz, 1H); 4.54 (s, 2H); 4.46 (d, J=6.7 Hz, 2H); 3.49 (s, 2H); 2.26 (s, 6H); 2.13 (s, 3H).

Example 14

(E)-[4-[3-(4-Fluorophenyl)-3-[4-[3-(pyrazol-1-yl)propynyl]phenyl]allyloxy]-2-methylphenoxy]acetic Acid

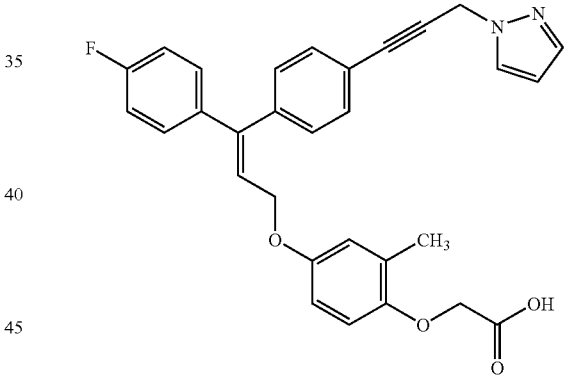

Methyl (Z)-[4-[3-(4-Fluorophenyl)-3-(4-iodophenyl)allyloxy]-2-methylphenoxy]acetate (400 mg, 0.75 mmol; example 10) was dissolved in a mixture of anhydrous tetrahydrofuran (10 mL) and anhydrous triethylamine (20 mL). The solution was degassed and a solution of 1-propargylpyrazol (160 mg, 1.50 mmol) in anhydrous tetrahydrofuran (2 mL) was added under inert atmosphere. The resulting solution was degassed and copper(I) iodide (23 mg, 0.12 mmol) and tetrakis(triphenylphosphine)palladium (70 mg, 0.06 mmol) were added and the mixture was degassed again. The reaction mixture was stirred at ambient temperature overnight; the resulting suspension was filtered through a paddle of silica gel. Silica gel was thoroughly washed with ethyl acetate; the filtrate was evaporated and the residue was dissolved in dichloromethane (30 mL). The solution was washed with water (2×30 mL) and brine (2×30 mL), dried over anhydrous magnesium sulfate and evaporated in vacuo. The residue was purified by column chromatography (silica gel Fluka 60, hexanes/ethyl acetate 80:20) yielding methyl (E)-[4-[3-(4-fluorophenyl)-3-[4-[3-(pyrazol-1-yl)propynyl]phenyl]-allyloxy]-2-methylphenoxy]acetate as orange oil.

Yield: 270 mg (70%).

$R_F$ (SiO$_2$, chloroform/methanol 95:5): 0.55.

$^1$H NMR spectrum (300 MHz, CDCl$_3$, $\delta_H$): 7.69 (d, J=2.3 Hz, 1H); 7.56 (d, J=1.7 Hz, 1H); 7.48 (d, J=8.2 Hz, 2H); 7.22-7.14 (m, 4H); 6.98 (t, J=8.7 Hz, 2H); 6.67-6.54 (m, 3H); 6.32 (t, J=2.1 Hz, 1H); 6.25 (t, J=6.7 Hz, 1H); 5.20 (s, 2H); 4.58 (s, 2H); 4.47 (d, J=6.7 Hz, 2H); 3.79 (s, 3H); 2.24 (s, 3H).

To a solution of the above ester (250 mg, 0.615 mmol) in tetrahydrofuran (5 mL) and methanol (2 mL), a solution of lithium hydroxide monohydrate (50 mg, 1.22 mmol) in distilled water (2 mL) was added. The solution was stirred for 2 hours at ambient temperature, neutralized 2 M hydrochloric acid and diluted with ether (30 mL) and water (20 mL). Layers were separated and the aqueous layer was extracted with ether (3×30 mL). The combined organic extracts were washed with water (2×30 mL) and brine (2×30 mL), dried over anhydrous magnesium sulfate and evaporated in vacuo. The residue was treated with hexane/dichloromethane mixture (10:1, 5 mL) giving the title acid as yellowish crystals.

Yield: 130 mg (53%).

M.p.: 35-56° C. (amorphous).

$R_F$ (SiO$_2$, chloroform/methanol 85:15): 0.20.

$^1$H NMR spectrum (300 MHz, DMSO-d$_6$, $\delta_H$): 7.88 (d, J=2.2 Hz, 1H); 7.54-7.51 (m, 3H); 7.26-7.13 (m, 6H); 6.72-6.69 (m, 2H); 6.60 (dd, J=8.8 and 2.9 Hz, 1H); 6.28-6.23 (m, 2H); 5.32 (s, 2H); 4.59 (s, 2H); 4.45 (d, J=6.7 Hz, 2H); 2.13 (s, 3H).

Example 15

(E)-[4-[3-(4-Chlorophenyl)-3-[4-[3-(pyrrolidin-1-yl)propynyl]phenyl]allyloxy]-2-methylphenoxy]acetic Acid

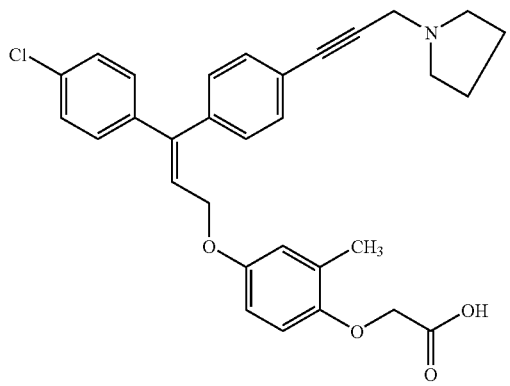

A solution of 1-chloro-4-iodobenzene (23.9 g, 100.0 mmol) in dry tetrahydrofuran (100 mL) was degassed and copper(I) iodide (570 mg, 3.0 mmol), tetrakis(triphenylphosphine)-palladium (3.4 g, 3.0 mmol) and 1,8-diazabicyclo[5.4.0]undec-7-ene (18.2 g, 120.0 mmol) were added. The reaction solution was degassed again and propargyl alcohol (6.7 g, 120.0 mmol) was added under inert atmosphere at ambient temperature. The reaction mixture was stirred (initially under cooling with ice water) for 24 h, then treated with water (20 mL) and acidified with 2 M hydrochloric acid (20 mL). The organic phase was separated and the aqueous phase was extracted with ether (4×30 mL). The combined organic phases were dried with anhydrous magnesium sulfate and concentrated in vacuo yielding brown solid. The residue was purified by column chromatography (silica gel Fluka 60, chloroform) yielding 3-(4-chlorophenyl)prop-2-yn-1-ol.

Yield: 8.35 g (50%).

M.p.: 75.5-77.5° C. (hexane).

$R_F$ (SiO$_2$, hexane/ethyl acetate 90:10): 0.10.

Sodium methoxide (0.05 g, 0.9 mmol) was added to 1 M solution of lithium aluminum hydride in tetrahydrofuran (20 mL, 20 mmol). The mixture was cooled to 0° C., and a solution of the above alcohol (3.35 g, 20.1 mmol) in tetrahydrofuran (30 mL) was slowly added. The reaction mixture was stirred at 0° C. for 1.5 h and at ambient temperature for 1.5 h. Ethyl acetate (3.3 mL, 34 mmol) was added at 0° C., and the mixture was stirred for 20 min without cooling. 1,4-Diiodobenzene (6.6 g, 20 mmol), anhydrous zinc chloride (1.64 g, 12 mmol), tris(dibenzylideneacetone)dipalladium chloroform complex (0.41 g, 0.4 mmol), and tri-(2-furyl)phosphine (0.37 g, 1.6 mmol) were added; the mixture was evacuated and kept under nitrogen. Reaction mixture was heated at 65° C. for 16 h, and then cooled down. Methanol (10 mL) was added and the mixture was stirred for additional 1 h. The reaction suspension was diluted with ether (150 mL), and saturated aqueous solution of ammonium chloride (5 mL) was added. The mixture was filtered through a paddle of silica gel and the solid phase was thoroughly washed with ether. Solvents were evaporated in vacuo and the residue was submitted to column chromatography (silica gel Fluka 60; benzene-chloroform) affording (Z)-[3-(4-chlorophenyl)-3-(4-iodophenyl)]allyl alcohol as light brown solid.

Yield: 3.5 g (49%).

M.p.: 79-84° C.

$R_F$ (SiO$_2$, chloroform/ether 2:1): 0.40.

$^1$H NMR spectrum (300 MHz, CDCl$_3$, $\delta_H$): 7.71 (d, J=8.7 Hz, 2H); 7.26 (d, J=8.8 Hz, 2H); 7.15 (d, J=8.8 Hz, 2H); 6.90 (d, J=8.7 Hz, 2H); 6.22 (t, J=6.9 Hz, 1H); 4.20 (d, J=6.9 Hz, 2H); 1.55 (s, 1H).

The above allyl alcohol (3.45 g, 9.7 mmol), methyl (4-hydroxy-2-methylphenoxy)acetate (1.96 g, 10 mmol; example 2) and triphenylphosphine (2.9 g, 11 mmol) were dissolved in a mixture of anhydrous toluene (50 mL) and tetrahydrofuran (25 mL). The mixture was cooled to 0° C., kept under nitrogen and diisopropyl azodicarboxylate (2.3 g, 10.8 mmol) was added dropwise. The reaction mixture was stirred at 0° C. for 3 h and then at ambient temperature for 16 h. The solvents were evaporated in vacuo and the residue was submitted to column chromatography (silica gel Fluka 60, benzene) affording methyl (Z)-[4-[3-(4-chlorophenyl)-3-(4-iodophenyl)allyloxy]-2-methylphenoxy]acetate as solid.

Yield: 3.1 g (58%).

M.p.: 89-92° C.

$R_F$ (SiO$_2$, chloroform): 0.55.

$^1$H NMR spectrum (300 MHz, CDCl$_3$, $\delta_H$): 7.73 (d, J=8.4 Hz, 2H); 7.26 (d, J=8.7 Hz, 2H); 7.16 (d, J=8.7 Hz, 2H); 6.93 (d, J=8.4 Hz, 2H); 6.68 (d, J=2.7 Hz, 1H); 6.63 (d, J=8.7 Hz, 1H); 6.57 (dd, J=8.7 and 2.7 Hz); 6.29 (t, J=6.7 Hz, 1H); 4.59 (s, 2H); 4.48 (d, J=6.7 Hz, 2H); 3.79 (s, 3H); 2.26 (s, 3H).

N-Propargylpyrrolidine (300 mg, 2.75 mmol) was added under nitrogen atmosphere to a degassed solution of methyl (Z)-[4-[3-(4-chlorophenyl)-3-(4-iodophenyl)allyloxy]-2-methylphenoxy]acetate (500 mg, 0.91 mmol) in a mixture of tetrahydrofuran (8 mL) and triethylamine (8 mL) The solution was cooled, tetrakis(triphenylphosphine)palladium (96 mg, 0.083 mmol) and copper(I) iodide (27.6 mg, 0.145 mmol) were added. The reaction mixture was stirred at ambient temperature for 72 h, diluted with benzene (100 mL) and the resulting mixture was washed with water (2×50 mL). The organic solution was dried with anhydrous potassium carbonate and subsequently evaporated in vacuo. The residue was purified by column chromatography (silica gel Fluka 60, benzene-chloroform/ether 2:1) yielding methyl (E)-[4-[3-(4-chlorophenyl)-3-[4-[3-(pyrrolidin-1-yl)propynyl]phenyl]allyloxy]-2-methylphenoxy]-acetate.

Yield: 350 mg (73%).

$R_F$ (SiO$_2$, chloroform/ethanol 9:1): 0.35.

$^1$H NMR spectrum (300 MHz, CDCl$_3$, $\delta_H$): 7.45 (d, J=8.2 Hz, 2H); 7.25 (d, J=8.7 Hz, 2H); 7.16 (d, J=8.7 Hz, 2H); 7.12 (d, J=8.2 Hz, 2H); 6.66 (d, J=3.0 Hz, 1H); 6.62 (d, J=8.7 Hz, 1H); 6.56 (dd, J=8.7 and 3.0 Hz); 6.27 (t, J=6.7 Hz, 1H); 4.58 (s, 2H); 4.49 (d, J=6.7 Hz, 2H); 3.79 (s, 3H); 3.65 (s, 2H); 2.71 (m, 4H); 2.24 (s, 3H); 1.85 (m, 4H).

The above ester (0.31 g, 0.585 mmol) was dissolved in ethanol (30 mL), a solution of lithium hydroxide monohydrate (0.08 g, 1.9 mmol) in water (4 mL) was added and the mixture was left to stand for 72 h. The solvents were evaporated in vacuo; the residue was diluted with water (25 mL), acidified with acetic acid (0.5 mL) and extracted with ethyl acetate (2×50 mL). The organic solution was dried with anhydrous potassium carbonate and subsequently evaporated in vacuo. The residue was purified by column chromatography (silica gel Fluka 60, chloroform/ethanol/ammonia 1:1:0.05) affording oil which was triturated with hexane yielding the title compound as amorphous solid.

Yield: 0.28 g (93%).

$R_F$ (SiO$_2$, chloroform/ethanol/ammonia 1:1:0.05): 0.05.

$^1$H NMR spectrum (300 MHz, CDCl$_3$, $\delta_H$): 7.43 (d, J=7.8 Hz, 2H); 7.25 (d, J=8.7 Hz, 2H); 7.15 (m, 4H); 6.64 (m, 2H); 6.46 (d, 1H); 6.31 (t, J=7.2 Hz, 1H); 4.48 (s, 2H); 4.41 (d, J=7.2 Hz, 2H); 4.06 (s, 2H); 3.25 (bs, 4H); 2.24 (s, 3H); 2.01 (bs, 4H).

Example 16

(E)-[4-[3-(4-Chlorophenyl)-3-[4-[3-(pyrazol-1-yl)propynyl]phenyl]allyloxy]-2-methylphenoxy]acetic Acid

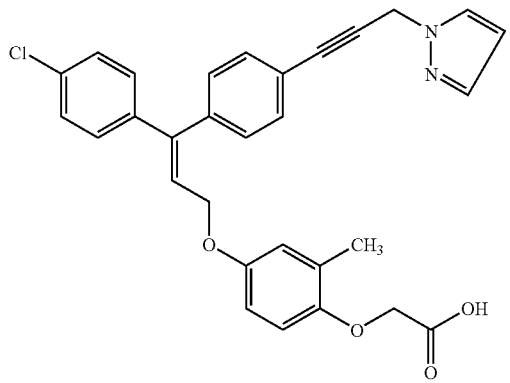

1-Propargylpyrazol (500 mg, 4.7 mmol) was added under nitrogen atmosphere to a degassed solution of methyl (Z)-[4-[3-(4-chlorophenyl)-3-(4-iodophenyl)allyloxy]-2-methylphenoxy]acetate (680 mg, 1.24 mmol; example 15) in a mixture of tetrahydrofuran (10 mL) and triethylamine (10 mL) The solution was cooled, tetrakis(triphenylphosphine)palladium (118 mg, 0.1 mmol) and copper(I) iodide (38 mg, 0.2 mmol) were added. The reaction mixture was stirred at ambient temperature for 48 h, diluted with benzene (100 mL) and the resulting mixture was washed with water (2×50 mL).

The organic solution was dried with anhydrous potassium carbonate and subsequently evaporated in vacuo. The residue was purified by column chromatography (silica gel Fluka 60, benzene-chloroform/ether 2:1) yielding methyl (E)-[4-[3-(4-chlorophenyl)-3-[4-[3-(pyrazol-1-yl)propynyl]phenyl]allyloxy]-2-methylphenoxy]acetate.

Yield: 610 mg (93%).

$R_F$ (SiO$_2$, chloroform/ethanol 9:1): 0.75.

$^1$H NMR spectrum (300 MHz, CDCl$_3$, $\delta_H$): 7.69 (d, J=2.3 Hz, 1H); 7.56 (d, J=1.7 Hz, 1H); 7.48 (d, J=8.2 Hz, 2H); 7.26 (d, J=8.6 Hz, 2H); 7.16 (m, 4H); 6.66 (d, J=2.8 Hz, 1H); 6.62 (d, J=8.8 Hz, 1H); 6.56 (dd, J=8.8 and 2.8 Hz, 1H); 6.29 (m, 2H); 5.20 (s, 2H); 4.58 (s, 2H); 4.47 (d, J=6.7 Hz, 2H); 3.79 (s, 3H); 2.24 (s, 3H).

The above ester (0.61 g, 1.16 mmol) was dissolved in ethanol (50 mL), a solution of lithium hydroxide monohydrate (0.09 g, 2.14 mmol) in water (4 mL) was added and the mixture was left to stand for 72 h. The solvents were evaporated in vacuo; the residue was diluted with water (25 mL) and neutralized with 2 M hydrochloric acid. The mixture was extracted with chloroform (2×50 mL); the organic solution was dried with anhydrous potassium carbonate and subsequently evaporated in vacuo. The residue was purified by column chromatography (silica gel Fluka 60, chloroform/ether 2:1) affording oil which was triturated with hexane yielding the title compound as amorphous solid.

Yield: 0.40 g (67%).

$R_F$ (SiO$_2$, chloroform/ethanol 90:10): 0.25.

$^1$H NMR spectrum (300 MHz, CDCl$_3$, $\delta_H$): 7.69 (s, 1H); 7.59 (s, 1H); 7.47 (d, J=7.2 Hz, 2H); 7.25 (d, J=8.1 Hz, 2H); 7.15 (m, 4H); 6.66 (d, 2H); 6.56 (d, 1H); 6.30 (m, 2H); 5.24 (s, 2H); 4.59 (s, 2H); 4.47 (d, J=6.6 Hz, 2H); 2.24 (s, 3H).

Example 17

(E)-[2-Methyl-4-[3-[4-(5-methylthiophen-2-yl)phenyl]-3-[4-[3-(morpholin-4-yl)propynyl]-phenyl]allyloxy]phenoxy]acetic Acid

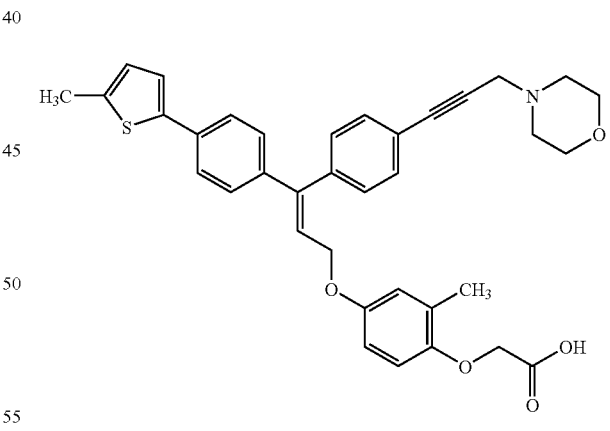

In nitrogen atmosphere, 0.15 M solution of tri(tert-butyl)phosphine in cyclohexane (6.60 mL, 0.990 mmol) and tris(dibenzylideneacetone)dipalladium chloroform complex (252 mg, 0.243 mmol) were added to a degassed solution of 3-(4-bromophenyl)propargyl alcohol (1.82 g, 8.62 mmol; example 2) and tributyl-(5-methylthiophen-2-yl)tin (4.18 g, 10.8 mmol; prepared according to J. Med. Chem. 2001, 44, 3355) in dry N,N-dimethylformamide (50 mL). The reaction mixture was stirred at 50° C. for 2 h, cooled down and 10% aqueous solution of potassium fluoride (5 mL) was added. The formed suspension was stirred for 15 min, filtered through a paddle of silica gel and the solid mass was thoroughly washed with ethyl acetate (180 mL). The combined filtrates were washed with brine (3×50 mL), 10% aqueous solution of potassium fluoride (2×50 mL), water (50 mL) and brine (2×50 mL). The organic solution was dried with anhydrous magnesium sulfate and its evaporation gave oil that was purified by flash column chromatography (silica gel Fluka 60, hexanes/ethyl acetate 5:1) yielding 3-[4-(5-methylthiophen-2-yl)phenyl]propargyl alcohol as brownish solid mass.

Yield: 1.16 g (59%).

$R_F$ (SiO$_2$, hexanes/ethyl acetate 4:1): 0.15.

$^1$H NMR spectrum (300 MHz, CDCl$_3$, $\delta_H$): 7.49 (dm, J=8.5 Hz, 2H); 7.41 (dm, J=8.6 Hz, 2H); 7.14 (d, J=3.6 Hz, 1H); 6.73 (dd, J=3.6 and 1.0 Hz, 1H); 4.51 (d, J=5.9 Hz, 2H); 2.51 (d, J=0.9 Hz, 1H); 1.67 (bt, J=5.6 Hz, 1H).

Sodium methoxide (16 mg, 0.296 mmol) was added to 1 M solution of lithium aluminum hydride in tetrahydrofuran (5.1 mL, 5.1 mmol) under nitrogen. The mixture was cooled to 0° C. and a solution of the above hydroxy derivative (1.16 g, 5.08 mmol) in tetrahydrofuran (5 mL) was added over 30 min. The reaction was stirred at 0° C. for 3.5 h; dry ethyl acetate (1.50 mL, 15.4 mmol) was added and the whole mixture was stirred at ambient temperature for 60 min. A degassed solution of 1,4-diiodobenzene (1.77 g, 5.37 mmol) in dry tetrahydrofuran (5 mL), anhydrous zinc chloride (0.42 g, 3.08 mmol), tris(dibenzylidene-acetone)dipalladium chloroform complex (0.11 g, 0.11 mmol), and tri-2-furylphosphine (0.13 g, 0.56 mmol) were added; the mixture was degassed and was then heated at 65° C. for 19 h under nitrogen. The suspension was cooled down; methanol (2.5 mL) was added and the mixture was stirred for additional 1 h. The reaction mixture was diluted with ether (25 mL) and saturated aqueous solution of ammonium chloride (1.5 mL) was added. The mixture was filtered through a paddle of silica gel and the paddle was thoroughly washed with ether (40 mL). Solvents were evaporated in vacuo and the residue was separated by flash column chromatography (silica gel Fluka 60, hexanes/ethyl acetate 5:1) affording (Z)-3-(4-iodophenyl)-3-[4-(5-methylthiophen-2-yl)phenyl]allyl alcohol as solidifying oil.

Yield: 0.65 g (30%).

$R_F$ (SiO$_2$, hexanes/ethyl acetate 4:1): 0.15.

$^1$H NMR spectrum (300 MHz, CDCl$_3$, $\delta_H$): 7.43 (dm, J=8.2 Hz, 2H); 7.48 (dm, J=8.3 Hz, 2H); 7.23 (dm, J=8.3 Hz, 2H); 7.13 (d, J=3.6 Hz, 1H); 6.96 (dm, J=8.2 Hz, 2H); 6.74 (dd, J=3.6 and 0.8 Hz, 1H); 6.26 (t, J=6.8 Hz, 1H); 4.23 (dd, J=6.8 and 5.6 Hz, 2H); 2.52 (d, J=0.9 Hz, 1H); 1.43 (t, J=5.6 Hz, 1H).

The above allyl alcohol (0.65 g, 1.50 mmol), methyl (4-hydroxy-2-methylphenoxy)acetate (0.33 g, 1.68 mmol; example 2) and triphenylphosphine (0.48 g, 1.83 mmol) were dissolved in a mixture of anhydrous toluene (30 mL) and tetrahydrofuran (10 mL). The mixture was cooled to 0° C., kept under nitrogen and a degassed solution of diisopropyl azodicarboxylate (0.35 mL, 1.77 mmol) in anhydrous tetrahydrofuran (5 mL) was added dropwise during 10 min. The reaction mixture was allowed to warm up the ambient temperature with the bath and then was stirred overnight. The solvents were evaporated in vacuo and the residue was submitted to flash column chromatography (silica gel Fluka 60, hexanes/ethyl acetate 6:1) affording methyl (Z)-[4-[3-(4-iodophenyl)-3-[4-(5-methylthiophen-2-yl)phenyl]-allyloxy]-2-methylphenoxy]acetate as solid mass.

Yield: 484 mg (53%).

$R_F$ (SiO$_2$, hexanes/ethyl acetate 4:1): 0.30.

$^1$H NMR spectrum (300 MHz, CDCl$_3$, $\delta_H$): 7.50 (dm, J=8.4 Hz, 2H); 7.48 (dm, J=8.5 Hz, 2H); 7.23 (dm, J=8.5 Hz, 2H); 7.13 (d, J=3.5 Hz, 1H); 6.99 (dm, J=8.3 Hz, 2H); 6.75 (dd, J=3.5 and 1.1 Hz, 1H); 6.71 (d, J=2.8 Hz, 1H); 6.65 (d, J=8.8 Hz, 1H); 6.61 (dd, J=9.0 and 2.9 Hz, 1H); 6.35 (t, J=6.7 Hz, 1H); 4.61 (s, 2H); 4.51 (d, J=6.8 Hz, 2H); 3.81 (s, 3H); 2.52 (bs, 3H); 2.28 (s, 3H).

4-Propargylmorpholine (80 mg, 0.639 mmol) and diisopropylamine (0.30 mL, 2.14 mmol) were added to a solution of the above iodo derivative (245 mg, 0.401 mmol) in tetrahydrofuran (5 mL). The mixture was degassed and copper(I) iodide (8 mg, 0.042 mmol) and bis(triphenylphosphine)palladium dichloride (15 mg, 0.021 mmol) were added. The reaction mixture was stirred at ambient temperature for 2 h, filtered and the filtrate was evaporated in vacuo. The residue was purified by flash column chromatography (silica gel Fluka 60, hexanes/ethyl acetate 1:1 with 0.1% of triethylamine) yielding methyl (E)-[2-methyl-4-[3-[4-(5-methylthiophen-2-yl)phenyl]-3-[4-[3-(morpholin-4-yl)propynyl]phenyl]allyloxy]-phenoxy]-acetate as solidifying oil.

Yield: 208 mg (85%).

$R_F$ (SiO$_2$, hexanes/ethyl acetate 1:1): 0.05.

$^1$H NMR spectrum (300 MHz, CDCl$_3$, $\delta_H$): 7.49 (dm, J=8.3 Hz, 2H); 7.48 (dm, J=8.5 Hz, 2H); 7.24 (dm, J=8.3 Hz, 2H); 7.19 (d, J=8.3 Hz, 2H); 7.13 (d, J=3.6 Hz, 1H); 6.74 (dd, J=3.5 and 1.0 Hz, 1H); 6.70 (d, J=2.7 Hz, 1H); 6.65 (d, J=8.9 Hz, 1H); 6.59 (dd, J=8.9 and 2.7 Hz, 1H); 6.35 (t, J=6.7 Hz, 1H); 4.60 (s, 2H); 4.52 (d, J=6.7 Hz, 2H); 3.81 (m, 7H); 3.56 (s, 2H); 2.68 (m, 4H); 2.52 (bs, 3H); 2.27 (s, 3H).

To a solution of the above ester (208 mg, 0.342 mmol) in tetrahydrofuran/methanol mixture (5:1, 6 mL), a solution of lithium hydroxide monohydrate (28.5 mg, 0.679 mmol) in distilled water (1 mL) was added under cooling to 0° C. The solution was stirred for 3 h under cooling, acetic acid (0.039 mL; 0.682 mmol) was added and the resulting mixture was stirred for further 10 min. The solution was diluted with dichloromethane (50 mL) and the resulting heterogeneous mixture was washed with water (2×15 mL) and brine (2×15 mL). The organic solution was dried with anhydrous magnesium sulfate and evaporated in vacuo. The residue was triturated with hexanes (3×5 mL) yielding the title acid as tan solid.

Yield: 112 mg (55%).

M.p.: 151-187° C. (amorphous).

$R_F$ (SiO$_2$, chloroform/methanol 85:15): 0.20.

$^1$H NMR spectrum (300 MHz, CDCl$_3$, $\delta_H$): 7.47 (dm, J=8.4 Hz, 2H); 7.43 (dm, J=8.1 Hz, 2H); 7.22 (dm, J=8.4 Hz, 2H); 7.13 (m, 3H); 6.73 (dd, J=3.5 and 1.0 Hz, 1H); 6.69 (d, J=2.9 Hz, 1H); 6.61 (d, J=9.0 Hz, 1H); 6.46 (dd, J=8.8 and 3.0 Hz, 1H); 6.37 (t, J=6.8 Hz, 1H); 4.57 (s, 2H); 4.57 (d, J=6.9 Hz, 2H); 3.85 (m, 4H); 3.70 (s, 2H); 2.90 (m, 4H); 2.52 (bs, 3H); 2.26 (s, 3H).

Example 18

(Z)-[2-Methyl-4-[3-(4-methylphenyl)-3-[4-(pyridin-2-ylethynyl)phenyl]allyloxy]phenoxy]acetic Acid

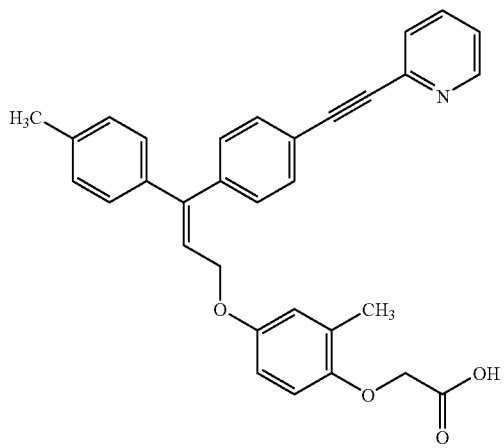

A solution of methyl (Z)-[2-methyl-4-[3-(4-iodophenyl)-3-(4-methylphenyl)]allyloxy]-phenoxy]acetate (310 mg, 0.587 mmol; example 3) in a mixture of tetrahydrofuran (9 mL) and triethylamine (9 mL) was degassed and 2-ethynylpyridine (121 mg, 1.17 mmol) was added in argon atmosphere. The solution was cooled down; tetrakis(triphenylphosphine)palladium (55 mg, 0.047 mmol) and copper(I) iodide (17.8 mg, 0.094 mmol) were added. The reaction mixture was stirred at ambient temperature for 48 h, then evaporated in vacuo and the residue was dissolved in ethyl acetate (20 mL). The solution was washed with water (3×15 mL), dried with anhydrous magnesium sulphate and evaporated in vacuo. The residue was purified by flash column chromatography (silica gel Fluka 60, hexanes/ethyl acetate 7:3) yielding methyl (Z)-[2-methyl-4-[3-(4-methylphenyl)-3-[4-(pyridin-2-ylethynyl)phenyl]allyloxy]-phenoxy]acetate.

Yield: 232 mg (79%).

$R_F$ (SiO$_2$, hexanes/ethyl acetate 3:1): 0.20.

$^1$H NMR spectrum (300 MHz, CDCl$_3$, $\delta_H$): 7.50-7.72 (m, 4H); 7.10-7.28 (m, 8H); 6.69 (m, 1H); 6.46 (m, 2H); 6.28 (t, J=6.8 Hz, 1H); 4.58 (s, 2H); 4.51 (d, J=6.8 Hz, 2H); 3.79 (s, 3H); 2.34 (s, 3H); 2.25 (s, 3H).

To a solution of the above ester (232 mg, 0.461 mmol) in tetrahydrofuran/methanol mixture (3:5, 11 mL), a solution of lithium hydroxide monohydrate (38.6 mg, 0.921 mmol) in distilled water (1 mL) was added under cooling to 0° C. The solution was stirred at ambient temperature for 4 h, then neutralized with acetic acid (38.6 mg, 0.921 mmol) and extracted with ether (2×30 mL). The extracts were washed with water (2×10 mL) and brine (10 mL), dried with anhydrous magnesium sulfate and evaporated in vacuo. The residue was triturated with hexanes yielding the title acid as tan solid.

Yield: 144 mg (64%).

M.p.: 121-130° C.

$R_F$ (SiO$_2$, chloroform/methanol 9:1): 0.25.

$^1$H NMR spectrum (300 MHz, CDCl$_3$, $\delta_H$): 8.68 (d, J=5.0 Hz, 1H); 7.75 (m, 1H); 7.55 (m, 3H); 7.31 (m, 1H); 7.17-7.08 (m, 6H); 6.68 (m, 2H); 6.50 (dd, J=8.6 and 2.9 Hz, 1H); 6.30 (t, J=6.8 Hz, 1H); 4.20 (s, 2H); 4.47 (d, J=6.8 Hz, 2H); 2.34 (s, 3H); 2.25 (s, 3H).

Example 19

(Z)-[2-Methyl-4-[3-(4-methylphenyl)-3-[4-(3-pyrazol-1-ylpropynyl)phenyl]allyloxy]phenoxy]-acetic Acid

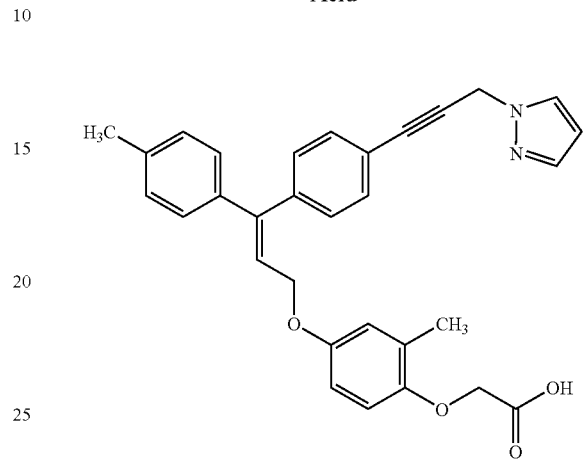

A solution of methyl (Z)-[2-methyl-4-[3-(4-iodophenyl)-3-(4-methylphenyl)]allyloxy]-phenoxy]acetate (310 mg, 0.587 mmol; example 3) in a mixture of tetrahydrofuran (9 mL) and triethylamine (9 mL) was degassed and 1-propargyl-1H-pyrazole (124 mg, 1.17 mmol) was added in argon atmosphere. The solution was cooled down; tetrakis(triphenylphosphine)palladium (54 mg, 0.046 mmol) and copper(I) iodide (17.8 mg, 0.094 mmol) were added. The reaction mixture was stirred at ambient temperature for 4 days, subsequently evaporated in vacuo and the residue was dissolved in ethyl acetate (20 mL). The solution was washed with water (3×15 mL), dried with anhydrous magnesium sulphate and evaporated in vacuo. The residue was purified by flash column chromatography (silica gel Fluka 60, hexanes/ethyl acetate 7:3) yielding methyl (Z)-[2-methyl-4-[3-(4-methylphenyl)-3-[4-(3-pyrazol-1-ylpropynyl)phenyl]allyloxy]phenoxy]acetate.

Yield: 214 mg (72%).

$R_F$ (SiO$_2$, hexanes/ethyl acetate 3:1): 0.15.

$^1$H NMR spectrum (300 MHz, CDCl$_3$, $\delta_H$): 7.69 (s, 1H); 7.56 (s, 1H); 7.47 (d, J=8.3 Hz, 2H); 7.08-7.18 (m, 6H); 6.54-6.68 (m, 3H); 6.32 (m, 1H); 6.28 (t, J=6.7 Hz, 1H); 5.20 (s, 2H); 4.58 (s, 2H); 4.47 (d, J=6.7 Hz, 2H); 3.79 (s, 3H); 2.34 (s, 3H); 2.24 (s, 3H).

To a solution of the above ester (214 mg, 0.422 mmol) in tetrahydrofuran/methanol mixture (3:5, 11 mL), a solution of lithium hydroxide monohydrate (35.4 mg, 0.845 mmol) in distilled water (1 mL) was added under cooling to 0° C. The solution was stirred at ambient temperature for 4 h, then neutralized with acetic acid (48.3 mg, 0.845 mmol) and extracted with ether (2×20 mL). The extracts were washed with water (2×10 mL) and brine (10 mL), dried with anhydrous magnesium sulfate and evaporated in vacuo. The residue was triturated with hexanes yielding the title acid as tan solid.

Yield: 129 mg (62%).

M.p.: 110-125° C.

$R_F$ (SiO$_2$, chloroform/methanol 9:1): 0.20.

¹H NMR spectrum (300 MHz, CDCl₃, δ_H): 7.69-7.08 (m, 10H); 6.65 (m, 2H); 6.55 (m, 1H); 6.32 (s, 1H); 6.28 (t, J=6.3 Hz, 1H); 5.22 (s, 2H); 4.60 (s, 2H); 4.46 (d, J=6.7 Hz, 2H); 2.33 (s, 3H); 2.24 (s, 3H).

Example 20

(E)-[2-Methyl-4-[3-[4-[3-(morpholin-4-yl)propynyl]phenyl]-3-(4-trifluoromethylphenyl)allyloxy]-phenoxy]acetic Acid

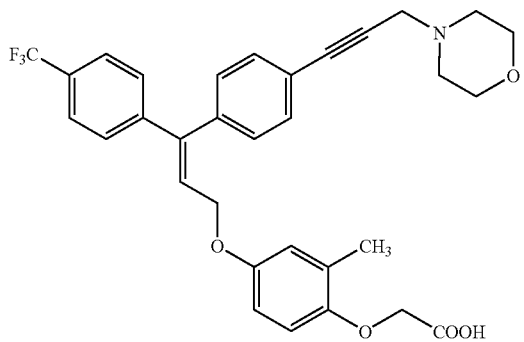

4-Propargylmorpholine (193 mg, 1.55 mmol) and diisopropylamine (0.51 mL, 3.64 mmol) were added to a solution of methyl (Z)-[4-[3-(4-iodophenyl)-3-(4-trifluoromethylphenyl)-allyloxy]-2-methylphenoxy]acetate (450 mg, 0.773 mmol; example 4) in tetrahydrofuran (10 mL). The mixture was degassed and copper(I) iodide (12 mg, 0.063 mmol) and bis(triphenylphosphine)palladium(II) dichloride (27 mg, 0.039 mmol) were added. The reaction mixture was stirred at ambient temperature for 19 h and evaporated in vacuo. The residue was purified by flash column chromatography (silica gel Fluka 60, dichloromethane/methanol 99:1) yielding methyl (E)-[2-methyl-4-[3-[4-[3-(morpholin-4-yl)propynyl]phenyl]-3-(4-trifluoromethylphenyl)allyloxy]phenoxy]acetate as brown oil.

Yield: 447 mg (99%).

R_F (SiO₂, chloroform saturated with ammonia/methanol 97:3): 0.70.

¹H NMR spectrum (300 MHz, CDCl₃, δ_H): 7.55 (d, J=8.3 Hz, 2H); 7.48 (d, J=8.2 Hz, 2H); 7.35 (d, J=8.2 Hz, 2H); 7.14 (d, J=8.2 Hz, 2H); 6.68 (d, J=2.7 Hz, 1H); 6.63 (d, J=8.8 Hz, 1H); 6.57 (dd, J=8.8 and 2.8 Hz, 1H); 6.37 (t, J=6.6 Hz, 1H); 4.59 (s, 2H); 4.53 (d, J=6.6 Hz, 2H); 3.79 (m, 7H); 3.54 (s, 2H); 2.66 (m, 4H); 2.25 (s, 3H).

To a solution of the above ester (435 mg, 0.751 mmol) in tetrahydrofuran/methanol mixture (5:1, 6 mL), a solution of lithium hydroxide monohydrate (47 mg, 1.12 mmol) in distilled water (1 mL) was added under cooling (0° C.). The solution was stirred for 2.5 h under cooling, glacial acetic acid (0.064 mL, 1.12 mmol) was added and the mixture was stirred for further 10 min. The solution was diluted with ether (40 mL) and water (30 mL); the phases were separated and the aqueous phase was extracted with ether (3×20 mL). The combined organic layers were washed with water (2×20 mL) and brine (2×20 mL), dried with anhydrous magnesium sulfate and evaporated in vacuo. The residue was triturated with hexanes (2×4 mL) yielding the title acid as white crystals.

Yield: 306 mg (72%).

M.p.: 150-157° C.

R_F (SiO₂, dichloromethane/methanol 90:10): 0.15.

¹H NMR spectrum (300 MHz, CDCl₃, δ_H): 7.54 (d, J=8.3 Hz, 2H); 7.43 (d, J=8.2 Hz, 2H); 7.34 (d, J=8.1 Hz, 2H); 7.09 (d, J=8.2 Hz, 2H); 6.67-6.58 (m, 2H); 6.47-6.43 (m, 1H); 6.38 (t, J=6.8 Hz, 1H); 4.55 (s, 2H); 4.48 (d, J=6.7 Hz, 2H); 3.83 (m, 4H); 3.69 (s, 2H); 2.88 (m, 4H); 2.24 (s, 3H).

Example 21

(E)-[4-[3-[4-[3-(4-Hydroxypiperidin-1-yl)propynyl]phenyl]-3-(4-trifluoromethylphenyl)allyloxy]-2-methylphenoxy]acetic Acid

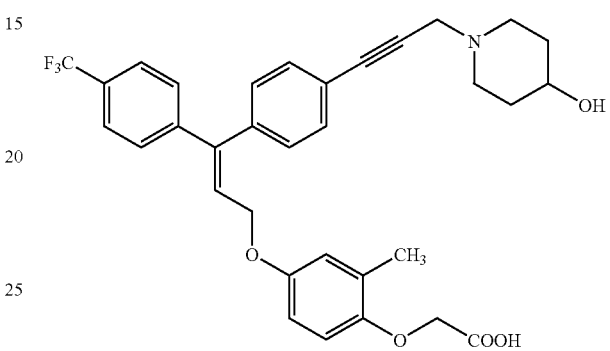

1-Propargylpiperidin-4-ol (215 mg, 1.55 mmol) and diisopropylamine (0.51 mL, 3.64 mmol) were added to a solution of methyl (Z)-[4-[3-(4-iodophenyl)-3-(4-trifluoromethylphenyl)-allyloxy]-2-methylphenoxy]acetate (450 mg, 0.773 mmol; example 4) in tetrahydrofuran (10 mL). The mixture was degassed and copper(I) iodide (12 mg, 0.063 mmol) and bis(triphenylphosphine)palladium(II) dichloride (27 mg, 0.039 mmol) were added. The reaction mixture was stirred at ambient temperature for 20 h and evaporated in vacuo. The residue was purified by flash column chromatography (silica gel Fluka 60, dichloromethane/methanol 98:2-97:3-95:5) yielding methyl (E)-[4-[3-[4-[3-(4-hydroxy-piperidin-1-yl)propynyl]-phenyl]-3-(4-trifluoromethylphenyl)allyloxy]-2-methylphenoxy]acetate as yellow oil.

Yield: 402 mg (88%).

R_F (SiO₂, chloroform saturated with ammonia/methanol 97:3): 0.25.

¹H NMR spectrum (300 MHz, CDCl₃, δ_H): 7.55 (d, J=8.3 Hz, 2H); 7.48 (d, J=8.2 Hz, 2H); 7.35 (d, J=8.2 Hz, 2H); 7.14 (d, J=8.2 Hz, 2H); 6.68 (d, J=2.7 Hz, 1H); 6.63 (d, J=8.8 Hz, 1H); 6.57 (dd, J=8.8 and 2.9 Hz, 1H); 6.36 (t, J=6.6 Hz, 1H); 4.59 (s, 2H); 4.52 (d, J=6.6 Hz, 2H); 3.79 (s, 3H); 3.74 (m, 1H); 3.54 (s, 2H); 2.90 (m, 2H); 2.45 (m, 2H); 2.25 (s, 3H); 1.96 (m, 2H); 1.69 (m, ~2H).

To a solution of the above ester (392 mg, 0.660 mmol) in tetrahydrofuran/methanol mixture (5:1, 6 mL), a solution of lithium hydroxide monohydrate (42 mg, 1.0 mmol) in distilled water (1 mL) was added under cooling (0° C.). The solution was stirred for 2 h under cooling, glacial acetic acid (0.057 mL, 0.997 mmol) was added and the mixture was stirred for further 10 min. The solution was diluted with ether (40 mL) and water (30 mL); the phases were separated and the aqueous phase was extracted with ether (7×20 mL). The combined organic layers were washed with brine (2×30 mL), dried with anhydrous magnesium sulfate and evaporated in vacuo. The residue was triturated with hexanes (2×4 mL) yielding the title acid as white crystals.

Yield: 62 mg (16%).

M.p.: 110-121° C.

$R_F$ (SiO$_2$, ethyl acetate/methanol 1:1): 0.25.

$^1$H NMR spectrum (300 MHz, CDCl$_3$, $\delta_H$): 7.54 (d, J=8.4 Hz, 2H); 7.42 (d, J=8.2 Hz, 2H); 7.35 (d, J=8.4 Hz, 2H); 7.07 (d, J=8.2 Hz, 2H); 6.66-6.55 (m, 2H); 6.41 (t, J=6.8 Hz, 1H); 6.33 (m, 1H); 4.50 (s, 2H); 4.44 (d, J=6.8 Hz, 2H); 3.93 (m, 1H); 3.82 (s, 2H); 3.24 (m, 2H); 2.94 (m, ~2H); 2.24 (s, 3H); 2.03 (m, 2H); 1.83 (m, 2H).

Example 22

(E)-[2-Methyl-4-[3-[4-[3-(N,N-dimethylamino)propynyl]phenyl]-3-(4-trifluoromethylphenyl)allyloxy]phenoxy]acetic Acid

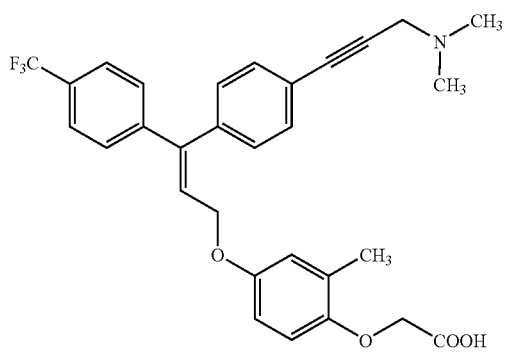

N,N-Dimethylpropargylamine (0.11 mL, 1.03 mmol) and diisopropylamine (0.34 mL, 2.42 mmol) were added to a solution of methyl (Z)-[4-[3-(4-iodophenyl)-3-(4-trifluoromethylphenyl)allyloxy]-2-methylphenoxy]acetate (300 mg, 0.515 mmol; example 4) in tetrahydrofuran (10 mL). The mixture was degassed and copper(I) iodide (8 mg, 0.042 mmol) and bis(triphenylphosphine)palladium(II) dichloride (18 mg, 0.026 mmol) were added. The reaction mixture was stirred at ambient temperature for 20 h and evaporated in vacuo. The residue was purified by flash column chromatography (silica gel Fluka 60, dichloromethane/methanol 98:2) yielding methyl (E)-[2-methyl-4-[3-[4-[3-(N,N-dimethylamino)propynyl]phenyl]-3-(4-trifluoromethylphenyl)allyloxy]phenoxy]acetate as brown oil.

Yield: 279 mg (99%).

$R_F$ (SiO$_2$, chloroform saturated with ammonia/methanol 97:3): 0.55.

$^1$H NMR spectrum (300 MHz, CDCl$_3$, $\delta_H$): 7.55 (d, J=8.3 Hz, 2H); 7.48 (d, J=8.0 Hz, 2H); 7.36 (d, J=8.2 Hz, 2H); 7.14 (d, J=8.0 Hz, 2H); 6.68 (d, J=2.6 Hz, 1H); 6.63 (d, J=8.8 Hz, 1H); 6.57 (dd, J=8.9 and 2.7 Hz, 1H); 6.36 (t, J=6.5 Hz, 1H); 4.59 (s, 2H); 4.53 (d, J=6.5 Hz, 2H); 3.79 (s, 3H); 3.50 (s, 2H); 2.39 (s, 6H); 2.25 (s, 3H).

To a solution of the above ester (266 mg, 0.495 mmol) in tetrahydrofuran/methanol mixture (5:1, 6 mL), a solution of lithium hydroxide monohydrate (62 mg, 1.48 mmol) in distilled water (1 mL) was added under cooling (0° C.). The solution was stirred for 3 h under cooling, glacial acetic acid (0.086 mL, 1.50 mmol) was added and the mixture was stirred for further 10 min. The solution was diluted with ether (30 mL) and water (20 mL); the phases were separated and the aqueous phase was extracted with ether (3×10 mL). The combined organic layers were washed with water (2×10 mL) and brine (2×10 mL), dried with anhydrous magnesium sulfate and evaporated in vacuo. The residue was triturated with hexanes (2×4 mL) yielding the title acid as yellow crystals.

Yield: 83 mg (32%).

M.p.: 49-64° C.

$R_F$ (SiO$_2$, ethyl acetate/methanol 1:1): 0.20.

$^1$H NMR spectrum (300 MHz, CDCl$_3$, $\delta_H$): 7.55 (d, J=8.3 Hz, 2H); 7.44 (d, J=8.0 Hz, 2H); 7.36 (d, J=8.2 Hz, 2H); 7.13 (d, J=8.0 Hz, 2H); 6.68 (s, 1H); 6.60 (d, J=9.1 Hz, 1H); 6.42 (t, 1H); 6.40 (m, 1H); 4.51 (s, 2H); 4.43 (d, J=6.7 Hz, 2H); 3.87 (s, 2H); 2.66 (s, ~6H); 2.25 (s, 3H).

Example 23

(E)-[2-Methyl-4-[3-[4-[(5-methylthiophen-2-yl)ethynyl]phenyl]-3-(4-trifluoromethylphenyl)allyloxy]phenoxy]acetic Acid

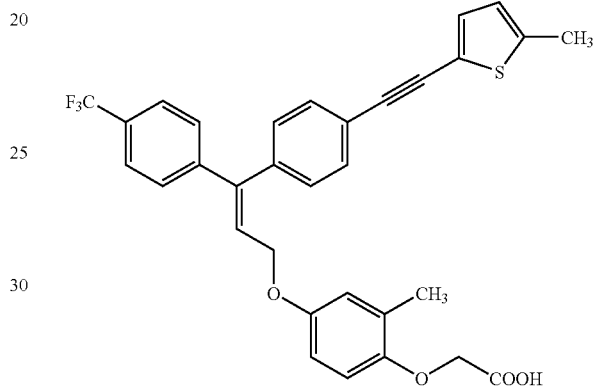

2-Ethynyl-5-methylthiophene (161 mg, 1.32 mmol) and diisopropylamine (0.43 mL, 3.10 mmol) were added to a solution of methyl (Z)-[4-[3-(4-iodophenyl)-3-(4-trifluoromethylphenyl)allyloxy]-2-methylphenoxy]acetate (384 mg, 0.659 mmol; example 4) in tetrahydrofuran (10 mL). The mixture was degassed and copper(I) iodide (10 mg, 0.053 mmol) and bis(triphenylphosphine)palladium(II) dichloride (23 mg, 0.033 mmol) were added. The reaction mixture was stirred at ambient temperature for 19 h and subsequently evaporated in vacuo. The residue was purified by flash column chromatography (silica gel Fluka 60, hexanes/ethyl acetate 15:1-12:1) yielding methyl (E)-[2-methyl-4-[3-[4-[(5-methylthiophen-2-yl)ethynyl]phenyl]-3-(4-trifluoromethylphenyl)allyloxy]phenoxy]acetate as brown oil.

Yield: 326 mg (86%).

$R_F$ (SiO$_2$, hexanes/ethyl acetate 9:1): 0.15.

$^1$H NMR spectrum (300 MHz, CDCl$_3$, $\delta_H$): 7.56 (d, J=8.0 Hz, 2H); 7.54 (d, J=8.0 Hz, 2H); 7.37 (d, J=8.2 Hz, 2H); 7.17 (d, J=8.2 Hz, 2H); 7.11 (d, J=3.6 Hz, 1H); 6.68 (s, 2H); 6.63 (d, J=8.8 Hz, 1H); 6.57 (dd, J=8.9 and 2.8 Hz, 1H); 6.37 (t, J=6.6 Hz, 1H); 4.59 (s, 2H); 4.55 (d, J=6.6 Hz, 2H); 3.79 (s, 3H); 2.50 (s, 3H); 2.25 (s, 3H).

To a solution of the above ester (319 mg, 0.553 mmol) in tetrahydrofuran/methanol mixture (5:1, 6 mL), a solution of lithium hydroxide monohydrate (70 mg, 1.67 mmol) in distilled water (1 mL) was added under cooling (0° C.). The solution was stirred for 2.5 h under cooling, glacial acetic acid (0.095 mL, 1.66 mmol) was added and the mixture was stirred for further 10 min. The solution was diluted with ether (30 mL) and water (20 mL); the phases were separated and the aqueous phase was extracted with ether (3×10 mL). The combined organic layers were washed with water (2×10 mL)

and brine (2×10 mL), dried with anhydrous magnesium sulfate and evaporated in vacuo. The residue was triturated with hexanes (2×4 mL) yielding the title acid as brown crystals.

Yield: 233 mg (75%).
M.p.: 127-134° C.
$R_F$ (SiO$_2$, dichloromethane/methanol 90:10): 0.25.
$^1$H NMR spectrum (300 MHz, CDCl$_3$, $\delta_H$): 7.56 (d, J=8.0 Hz, 2H); 7.54 (d, J=8.1 Hz, 2H); 7.36 (d, J=8.2 Hz, 2H); 7.17 (d, J=8.2 Hz, 2H); 7.11 (d, J=3.5 Hz, 1H); 6.69-6.65 (m, 3H); 6.59 (dd, J=8.8 and 2.7 Hz, 1H); 6.37 (t, J=6.6 Hz, 1H); 4.61 (s, 2H); 4.55 (d, J=6.6 Hz, 2H); 2.50 (s, 3H); 2.25 (s, 3H).

Example 24

(E)-[2-Methyl-4-[3-[4-(5-methylthiophen-2-yl)phenyl]-3-[4-[3-(pyrrolidin-1-yl)propynyl]phenyl]-allyloxy]phenoxy]acetic Acid

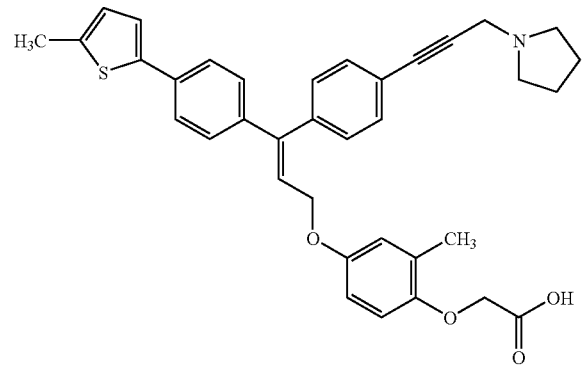

1-Propargylpyrrolidine (168 mg, 1.54 mmol) and diisopropylamine (0.27 mL, 1.93 mmol) were added to a solution of methyl (Z)-[4-[3-(4-iodophenyl)-3-[4-(5-methylthiophen-2-yl)phenyl]allyloxy]-2-methylphenoxy]acetate (235 mg, 0.385 mmol; prepared as described in example 17) in tetrahydrofuran (5 mL). The mixture was degassed and copper(I) iodide (15 mg, 0.079 mmol) and bis(triphenylphosphine)palladium(II) dichloride (27 mg, 0.038 mmol) were added. The reaction mixture was stirred at ambient temperature for 2.5 h and subsequently evaporated in vacuo. The residue was purified by flash column chromatography (silica gel Fluka 60, dichloromethane/methanol 98:2+0.5% of triethylamine) yielding methyl (E)-[2-methyl-4-[3-[4-(5-methylthiophen-2-yl)phenyl]-3-[4-[3-(pyrrolidin-1-yl)propynyl]phenyl]-allyloxy]phenoxy]acetate as brownish oil.

Yield: 186 mg (82%).
$R_F$ (SiO$_2$, dichloromethane/methanol 98:2): 0.10.
$^1$H NMR spectrum (300 MHz, CDCl$_3$, $\delta_H$): 7.46 (m, 4H); 7.21 (dm, J=8.6 Hz, 2H); 7.16 (dm, J=8.3 Hz, 2H); 7.11 (d, J=3.5 Hz, 1H); 6.72 (dd, J=3.5 and 1.0 Hz, 1H); 6.68 (d, J=2.9 Hz, 1H); 6.62 (d, J=8.8 Hz, 1H); 6.57 (dd, J=9.0 and 2.9 Hz, 1H); 6.32 (t, J=6.7 Hz, 1H); 4.58 (s, 2H); 4.50 (d, J=6.7 Hz, 2H); 3.76 (s, 3H); 3.67 (s, 2H); 2.73 (m, 4H); 2.50 (d, J=0.8 Hz, 3H); 2.25 (s, 3H); 1.86 (m, 4H).

To a solution of the above ester (186 mg, 0.314 mmol) in tetrahydrofuran/methanol mixture (5:1, 6 mL), a solution of lithium hydroxide monohydrate (29 mg, 0.691 mmol) in distilled water (1 mL) was added under cooling to 0° C. The solution was stirred for 45 min under cooling, acetic acid (0.040 mL; 0.699 mmol) was added and the resulting mixture was stirred for further 15 min. The solution was diluted with dichloromethane (50 mL) and the resulting heterogeneous mixture was washed with water (3×15 mL) and brine (2×15 mL). The organic solution was dried with anhydrous magnesium sulfate and evaporated in vacuo. The residue was triturated with hexanes/dichloromethane (1:5, 6 mL) and subsequently with pure hexanes (2×5 mL) yielding the title acid as tan solid.

Yield: 100 mg (55%).
M.p.: 172-177° C. (amorphous).
$R_F$ (SiO$_2$, chloroform/methanol 85:15): 0.10.
$^1$H NMR spectrum (300 MHz, CDCl$_3$+CD$_3$COOD, $\delta_H$): 7.47 (dm, J=8.3 Hz, 2H); 7.45 (dm, J=8.6 Hz, 2H); 7.19 (dm, J=8.1 Hz, 4H); 7.09 (d, J=3.6 Hz, 1H); 6.70 (dd, J=3.6 and 1.0 Hz, 1H); 6.67 (d, J=2.8 Hz, 1H); 6.62 (d, J=9.0 Hz, 1H); 6.54 (dd, J=9.0 and 2.9 Hz, 1H); 6.35 (t, J=6.8 Hz, 1H); 4.59 (s, 2H); 4.47 (d, J=6.8 Hz, 2H); 4.26 (s, 2H); 3.51 (m, 4H); 2.48 (d, J=0.8 Hz, 3H); 2.22 (s, 3H) 2.10 (m, overlap).

Example 25

(E)-[2-Methyl-4-[3-(2-methylbenzo[b]furan-5-yl)-3-[4-(3-(pyrrolidin-1-yl)propynyl)phenyl]-allyloxy]phenoxy]acetic Acid

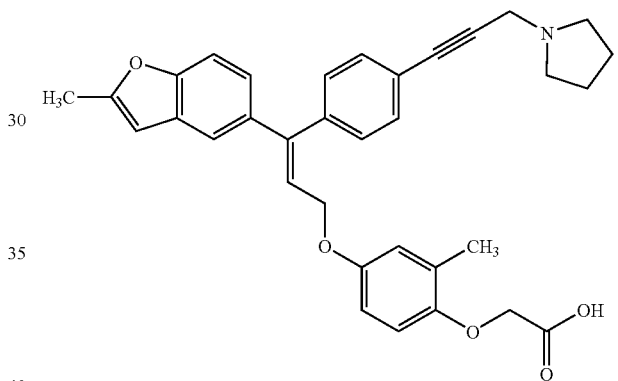

A solution of 5-iodo-2-methylbenzo[b]furan (12.1 g, 46.9 mmol) in dry tetrahydrofuran (50 mL) was degassed and copper(I) iodide (280 mg, 1.5 mmol), tetrakis(triphenylphosphine)palladium (1.7 g, 1.5 mmol) and 1,8-diazabicyclo[5.4.0]undec-7-ene (9.1 g, 60.0 mmol) were added. The reaction solution was degassed again and propargyl alcohol (3.4 g, 60.7 mmol) was added under inert atmosphere at ambient temperature. The reaction mixture was stirred (initially under cooling with ice water) for 48 h, then treated with water (20 mL) and acidified with 2 M hydrochloric acid (20 mL). The organic phase was separated and the aqueous phase was extracted with ether (4×30 mL). The combined organic phases were dried with anhydrous magnesium sulfate and concentrated in vacuo yielding brown solid. The residue was purified by column chromatography (silica gel Fluka 60, benzene) yielding 3-(2-methyl benzo[b]furan-5-yl)prop-2-yn-1-ol.

Yield: 6.4 g (73%).
M.p.: 101.5-102.5° C. (hexane).
$R_F$ (SiO$_2$, chloroform): 0.20.
$^1$H NMR spectrum (300 MHz, CDCl$_3$, $\delta_H$): 7.55 (s, 1H); 7.29 (m, 2H); 6.32 (s, 1H); 4.51 (s, 2H); 2.43 (s, 3H); 2.05 (bs, 1H).

Sodium methoxide (0.05 g, 0.9 mmol) was added to 1 M solution of lithium aluminum hydride in tetrahydrofuran (20 mL, 20 mmol). The mixture was cooled to 0° C., and a solution of the above alcohol (3.67 g, 19.7 mmol) in tetrahydrofuran (30 mL) was slowly added. The reaction mixture was stirred at 0° C. for 1.5 h and subsequently for 1.5 h at ambient temperature. Ethyl acetate (3.3 mL, 34 mmol) was added at 0° C. and the mixture was then stirred for 20 min without cooling. 1,4-Diiodobenzene (6.6 g, 20 mmol), anhydrous zinc chloride (1.64 g, 12 mmol), tris(dibenzylideneacetone)dipalladium chloroform complex (0.41 g, 0.4 mmol), and tri-(2-furyl)phosphine (0.37 g, 1.6 mmol) were added; the mixture was evacuated and kept under nitrogen. Reaction mixture was heated at 65° C. for 16 h, and then cooled down. Methanol (10 mL) was added and the mixture was stirred for additional 1 h. The reaction suspension was diluted with ether (150 mL), and saturated aqueous solution of ammonium chloride (5 mL) was added. The mixture was filtered through a paddle of silica gel and the solid phase was thoroughly washed with ether. Solvents were evaporated in vacuo and the residue was submitted to column chromatography (silica gel Fluka 60; benzene/chloroform 1:0-0:1) affording (Z)-3-(4-iodophenyl)-3-(2-methylbenzo[b]furan-5-yl)allyl alcohol as light brown solid.

Yield: 2.4 g (31%).

M.p.: 103-113° C.

$R_F$ (SiO$_2$, chloroform/ether 2:1): 0.45.

$^1$H NMR spectrum (300 MHz, CDCl$_3$, $\delta_H$): 7.66 (d, J=7.9 Hz, 2H); 7.27 (m, 2H); 7.07 (d, J=8.5, 1H); 6.89 (d, J=7.9 Hz, 2H); 6.27 (s, 1H); 6.18 (t, J=6.9 Hz, 1H); 4.17 (d, J=6.9 Hz, 2H); 2.41 (s, 3H); 2.08 (bs, 1H).

The above allyl alcohol (2.20 g, 5.64 mmol), methyl (4-hydroxy-2-methylphenoxy)acetate (1.20 g, 6.1 mmol; prepared as in example 2) and triphenylphosphine (1.70 g, 6.48 mmol) were dissolved in a mixture of anhydrous toluene (20 mL) and tetrahydrofuran (10 mL). The mixture was cooled to 0° C., kept under nitrogen and diisopropyl azodicarboxylate (1.50 g, 7.0 mmol) was added dropwise. The reaction mixture was stirred at 0° C. for 3 h and then at ambient temperature for 72 h. The solvents were evaporated in vacuo and the residue was submitted to column chromatography (silica gel Fluka 60, benzene) affording methyl (Z)-[4-[3-(4-iodophenyl)-3-(2-methylbenzo[b]furan-5-yl)allyloxy]-2-methylphenoxy]acetate as solid mass.

Yield: 1.64 g (50%).

M.p.: 121-128° C.

$R_F$ (SiO$_2$, chloroform): 0.60.

$^1$H NMR spectrum (300 MHz, CDCl$_3$, $\delta_H$): 7.71 (d, J=8.2 Hz, 2H); 7.28 (m, 2H); 7.10 (dd, J=8.6 and 1.2 Hz, 2H); 6.97 (d, J=8.2 Hz, 2H); 6.69 (d, J=2.3 Hz, 1H); 6.63 (d, J=8.7 Hz, 1H); 6.58 (dd, J=8.7 and 2.3 Hz); 6.30 (s, 1H); 6.27 (t, J=6.7 Hz, 1H); 4.59 (s, 2H); 4.49 (d, J=6.7 Hz, 2H); 3.79 (s, 3H); 2.44 (s, 3H); 2.25 (s, 3H).

N-Propargylpyrrolidine (250 mg, 2.29 mmol) was added under nitrogen atmosphere to a degassed solution of the above ester (400 mg, 0.68 mmol) in a mixture of tetrahydrofuran (6 mL) and triethylamine (6 mL) The solution was cooled, tetrakis(triphenylphosphine)palladium (71 mg, 0.061 mmol) and copper(I) iodide (21 mg, 0.11 mmol) were added. The reaction mixture was stirred at ambient temperature for 96 h, diluted with benzene (100 mL), decanted and evaporated in vacuo. The residue was purified by column chromatography (silica gel Fluka 60, benzene/ethyl acetate 1:0-0:1) yielding methyl (E)-[2-methyl-4-[3-(2-methyl benzo[b]furan-5-yl)-3-[4-[3-(pyrrolidin-1-yl)propynyl]phenyl]allyloxy]phenoxy]acetate.

Yield: 180 mg (48%).

$R_F$ (SiO$_2$, chloroform/ethanol 5:1): 0.50.

$^1$H NMR spectrum (300 MHz, CDCl$_3$, $\delta_H$): 7.45 (d, J=8.3 Hz, 2H); 7.29 (m, 2H); 7.16 (d, J=8.3 Hz, 2H); 7.11 (dd, J=8.6 and 1.8 Hz, 1H); 6.68 (d, J=2.7 Hz, 1H); 6.62 (d, J=8.7 Hz, 1H); 6.58 (dd, J=8.7 and 2.7 Hz), 1H); 6.29 (s, 1H); 6.26 (t, J=6.7 Hz, 1H); 4.58 (s, 2H); 4.51 (d, J=6.7 Hz, 2H); 3.79 (s, 3H); 3.66 (s, 2H); 2.71 (m, 4H); 2.44 (s, 3H); 2.25 (s, 3H); 1.85 (m, 4H).

The above ester (0.16 g, 0.29 mmol) was dissolved in ethanol (20 mL), a solution of lithium hydroxide monohydrate (0.05 g, 1.19 mmol) in water (2 mL) was added and the mixture was left to stand for 48 h. The solvents were evaporated in vacuo; the residue was diluted with water (25 mL), acidified with acetic acid (0.2 mL) and extracted with chloroform (2×50 mL). The organic solution was dried with anhydrous potassium carbonate and subsequently evaporated in vacuo affording oil which was triturated with hexanes yielding the title compound as amorphous solid.

Yield: 0.12 g (77%).

$R_F$ (SiO$_2$, chloroform/ethanol/ammonia 1:1:0.05): 0.10.

$^1$H NMR spectrum (300 MHz, CDCl$_3$, $\delta_H$): 7.43 (d, J=8.1 Hz, 2H); 7.28 (m, 2H); 7.18 (d, J=8.1 Hz, 2H); 7.09 (dd, J=8.6 and 1.4 Hz, 1H); 6.65 (m, 2H); 6.49 (dd, J=8.7 and 2.6 Hz, 1H); 6.30 (t, J=6.9 Hz, 1H); 6.28 (s, 1H); 4.48 (s, 2H); 4.44 (d, J=6.9 Hz, 2H); 4.09 (s, 2H); 3.31 (bs, 4H); 2.43 (s, 3H); 2.25 (s, 3H); 2.02 (bs, 4H).

Example 26

(E)-[2-Methyl-4-[3-(2-methylbenzo[b]furan-5-yl)-3-[4-(3-(morpholin-4-yl)propynyl)phenyl]allyloxy]phenoxy]acetic Acid

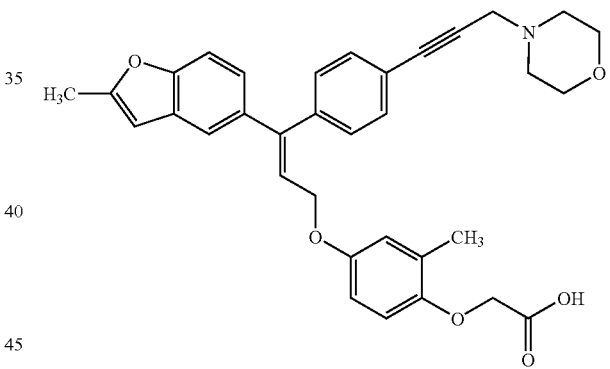

N-Propargylmorpholine (270 mg, 2.16 mmol) was added under nitrogen atmosphere to a degassed solution of methyl (Z)-[4-[3-(4-iodophenyl)-3-(2-methylbenzo[b]furan-5-yl)allyloxy]-2-methylphenoxy]acetate (400 mg, 0.68 mmol; prepared as described in example 25) in a mixture of tetrahydrofuran (6 mL) and triethylamine (6 mL) The solution was cooled to 0° C., tetrakis(triphenylphosphine)palladium (71 mg, 0.061 mmol) and copper(I) iodide (21 mg, 0.11 mmol) were added. The reaction mixture was stirred at ambient temperature for 96 h, diluted with benzene (100 mL), decanted and evaporated in vacuo. The residue was purified by column chromatography (silica gel Fluka 60, benzene/ethyl acetate 1:0-0:1) yielding methyl (E)-[2-methyl-4-[3-(2-methyl benzo[b]furan-5-yl)-3-[4-[3-(morpholin-4-yl)propynyl]phenyl]-allyloxy]phenoxy]acetate.

Yield: 340 mg (88%).

$R_F$ (SiO$_2$, chloroform/ethanol 5:1): 0.70.

$^1$H NMR spectrum (300 MHz, CDCl$_3$, $\delta_H$): 7.46 (d, J=8.3 Hz, 2H); 7.29 (m, 2H); 7.17 (d, J=8.3 Hz, 2H); 7.11 (dd, J=8.6 and 1.8 Hz, 1H); 6.68 (d, J=2.7 Hz, 1H); 6.62 (d, J=8.7 Hz, 1H); 6.58 (dd, J=8.7 and 2.7 Hz); 6.29 (s, 1H); 6.26 (t, J=6.7 Hz, 1H); 4.58 (s, 2H); 4.51 (d, J=6.7 Hz, 2H); 3.79 (s, 3H); 3.78 (m, 4H); 3.53 (s, 2H); 2.66 (m, 4H); 2.43 (s, 3H); 2.25 (s, 3H).

The above ester (0.34 g, 0.60 mmol) was dissolved in ethanol (30 mL), a solution of lithium hydroxide monohydrate (0.08 g, 1.9 mmol) in water (3 mL) was added and the mixture was left to stand for 48 h. The solvents were evaporated in vacuo; the residue was diluted with water (25 mL) and acidified with acetic acid (0.3 mL). The formed precipitate was filtered off and dried in the air yielding the title compound as amorphous solid.

Yield: 0.32 g (96%).
$R_F$ (SiO$_2$, chloroform/ethanol/ammonia 1:1:0.05): 0.10.
$^1$H NMR spectrum (300 MHz, CDCl$_3$, $\delta_H$): 7.42 (d, J=8.2 Hz, 2H); 7.27 (m, 2H); 7.14 (d, J=8.2 Hz, 2H); 7.09 (dd, J=8.7 and 1.7 Hz, 1H); 6.68 (d, J=2.7 Hz, 1H); 6.62 (d, J=8.8 Hz, 1H); 6.49 (dd, J=8.8 and 2.7 Hz, 1H); 6.28 (s and t, 2H); 4.53 (s, 2H); 4.46 (d, J=6.8 Hz, 2H); 3.83 (bs, 4H); 3.71 (s, 2H); 2.90 (bs, 4H); 2.43 (s, 3H); 2.24 (s, 3H).

Example 27

(E)-[2-Methyl-4-[3-(2-methylbenzo[b]furan-5-yl)-3-[4-(3-(dimethylamino)propynyl)phenyl]-allyloxy]phenoxy]acetic Acid

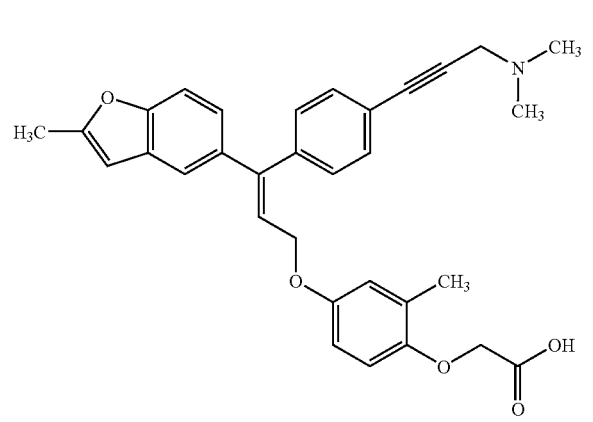

Under nitrogen atmosphere, 3-(N,N-dimethylamino)propyne (250 mg, 3.00 mmol) was added to a degassed solution of methyl (Z)-[4-[3-(4-iodophenyl)-3-(2-methylbenzo[b]furan-5-yl)allyloxy]-2-methylphenoxy]acetate (370 mg, 0.63 mmol; prepared as described in example 25) in a mixture of tetrahydrofuran (6 mL) and triethylamine (6 mL) The solution was cooled to 0° C., tetrakis(triphenylphosphine)palladium (71 mg, 0.06 mmol) and copper(I) iodide (21 mg, 0.11 mmol) were added. The reaction mixture was stirred at ambient temperature for 72 h, diluted with benzene (100 mL), decanted and evaporated in vacuo. The residue was purified by column chromatography (silica gel Fluka 60, benzene/ethyl acetate 1:0-0:1) yielding methyl (E)-[2-methyl-4-[3-(2-methylbenzo[b]furan-5-yl)-3-[4-[3-(dimethylamino)propynyl]phenyl]-allyloxy]phenoxy]acetate.

Yield: 260 mg (78%).
$R_F$ (SiO$_2$, chloroform/ethanol 5:1): 0.55.
$^1$H NMR spectrum (300 MHz, CDCl$_3$, $\delta_H$): 7.46 (d, J=8.3 Hz, 2H); 7.29 (m, 2H); 7.17 (d, J=8.3 Hz, 2H); 7.11 (dd, J=8.6 and 1.8 Hz, 1H); 6.68 (d, J=2.7 Hz, 1H); 6.63 (d, J=8.7 Hz, 1H); 6.58 (dd, J=8.7 and 2.7 Hz); 6.29 (s, 1H); 6.26 (t, J=6.7 Hz, 1H); 4.58 (s, 2H); 4.51 (d, J=6.7 Hz, 2H); 3.79 (s, 3H); 3.50 (s, 2H); 2.44 (s, 3H); 2.39 (s, 6H); 2.25 (s, 3H).

The above ester (0.26 g, 0.50 mmol) was dissolved in ethanol (30 mL), a solution of lithium hydroxide monohydrate (0.08 g, 1.9 mmol) in water (3 mL) was added and the mixture was left to stand for 48 h. The solvents were evaporated in vacuo; the residue was diluted with water (25 mL), acidified with acetic acid (0.25 mL) and extracted with chloroform (2×50 mL). The organic solution was dried with anhydrous potassium carbonate and subsequently evaporated in vacuo affording oil which was triturated with hexanes yielding the title compound as amorphous solid.

Yield: 0.24 g (95%).
$R_F$ (SiO$_2$, chloroform/ethanol/ammonia 1:1:0.05): 0.10.
$^1$H NMR spectrum (300 MHz, CDCl$_3$, $\delta_H$): 7.45 (d, J=8.1 Hz, 2H); 7.29 (m, 2H); 7.19 (d, J=8.1 Hz, 2H); 7.09 (dd, J=8.5 and 1.5 Hz, 1H); 6.65 (m, 2H); 6.53 (dd, J=8.6 and 2.5 Hz, 1H); 6.29 (s and t, 2H); 4.49 (s, 2H); 4.45 (d, J=6.9 Hz, 2H); 3.90 (s, 2H); 2.67 (s, 6H); 2.42 (s, 3H); 2.26 (s, 3H).

Example 28

(E)-[4-[3-[4-[3-[N-(2-Hydroxyethyl)-N-methylamino]propynyl]phenyl]-3-(2-methylbenzo[b]-furan-5-yl)allyloxy]-2-methylphenoxy]acetic Acid

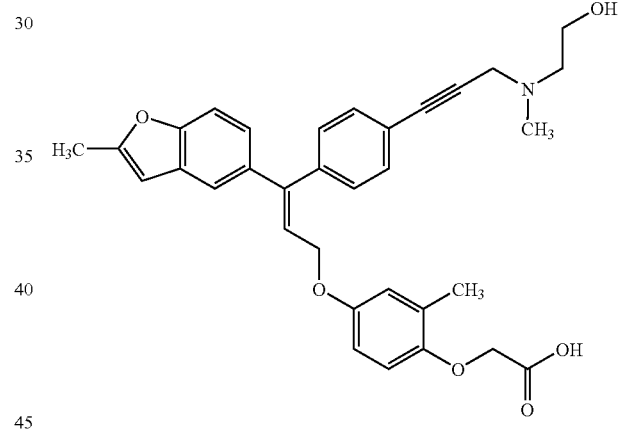

2-(N-Methyl-N-propargylamino)ethanol (440 mg, 3.89 mmol) was added under nitrogen atmosphere to a degassed solution of methyl (Z)-[4-[3-(4-iodophenyl)-3-(2-methylbenzo[b]furan-5-yl)allyloxy]-2-methylphenoxy]acetate (400 mg, 0.68 mmol; prepared as described in example 25) in a mixture of tetrahydrofuran (6 mL) and triethylamine (6 mL). The solution was cooled to 0° C. and tetrakis(triphenylphosphine)palladium (71 mg, 0.061 mmol) and copper(I) iodide (21 mg, 0.11 mmol) were added. The reaction mixture was stirred at ambient temperature for 72 h, diluted with benzene (100 mL), decanted and evaporated in vacuo. The residue was purified by column chromatography (silica gel Fluka 60, benzene/ethyl acetate 1:0-0:1) yielding methyl (E)-[4-[3-[4-[3-[N-(2-hydroxyethyl)-N-methylamino]-propynyl]phenyl]-3-(2-methyl benzo[b]furan-5-yl)allyloxy]-2-methylphenoxy]acetate.

Yield: 340 mg (89%).
$R_F$ (SiO$_2$, chloroform/ethanol 1:1): 0.60.
$^1$H NMR spectrum (300 MHz, CDCl$_3$, $\delta_H$): 7.45 (d, J=8.1 Hz, 2H); 7.23 (m, 2H); 7.17 (d, J=8.1 Hz, 2H); 7.11 (dd, J=8.6 and 1.8 Hz, 1H); 6.68 (d, J=2.7 Hz, 1H); 6.63 (d, J=8.7 Hz, 1H); 6.58 (dd, J=8.7 and 2.7 Hz); 6.29 (s, 1H); 6.27 (t, J=6.7 Hz, 1H); 4.58 (s, 2H); 4.51 (d, J=6.7 Hz, 2H); 3.79 (s, 3H); 3.66 (t, J=5.2 Hz, 2H); 3.62 (s, 2H); 2.72 (t, J=5.2 Hz, 2H); 2.43 (s, 3H); 2.25 (s, 3H).

The above ester (0.34 g, 0.61 mmol) was dissolved in ethanol (30 mL), a solution of lithium hydroxide monohydrate (0.08 g, 1.90 mmol) in water (3 mL) was added and the mixture was left to stand for 48 h. The solvents were evaporated in vacuo; the residue was diluted with water (25 mL), acidified with acetic acid (0.25 mL) and extracted with chloroform (2×50 mL). The organic solution was dried with anhydrous potassium carbonate and subsequently evaporated in vacuo affording oil which was triturated with hexanes yielding the title compound as amorphous solid.

Yield: 0.29 g (88%).

$R_F$ (SiO$_2$, chloroform/ethanol/ammonia 1:1:0.05): 0.05.

$^1$H NMR spectrum (300 MHz, CDCl$_3$, $\delta_H$): 7.43 (d, J=8.1 Hz, 2H); 7.29 (m, 2H); 7.17 (d, J=8.1 Hz, 2H); 7.09 (dd, J=8.7 and 1.5 Hz, 1H); 6.67 (d, J=2.7 Hz, 1H); 6.63 (d, J=8.7 Hz, 1H); 6.49 (dd, J=8.7 and 2.7 Hz, 1H); 6.29 (s and t, 2H); 4.49 (s, 2H); 4.43 (d, J=6.9 Hz, 2H); 3.97 (s, 2H); 3.85 (bs, 2H); 3.08 (bs, 2H); 2.72 (s, 3H); 2.43 (s, 3H); 2.24 (s, 3H).

Example 29

(E)-[2-Methyl-4-[3-[4-[3-(pyrrolidin-1-yl)propynyl]phenyl]-3-(4-trifluoromethylphenyl)allyloxy]-phenoxy]acetic Acid

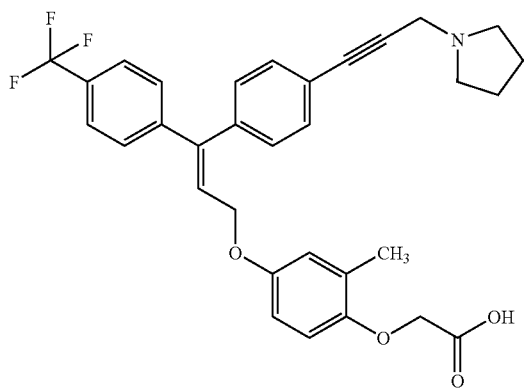

N-Propargylpyrrolidine (113 mg, 1.04 mmol) and diisopropylamine (0.339 mL, 2.42 mmol) were added to a solution of methyl (Z)-[4-[3-(4-iodophenyl)-3-(4-trifluoromethylphenyl)-allyloxy]-2-methylphenoxy]acetate (300 mg, 0.515 mmol; prepared as described in example 4) in tetrahydrofuran (10 mL). The mixture was degassed and copper(I) iodide (8 mg, 0.042 mmol) and bis(triphenylphosphine)palladium(II) dichloride (18 mg, 0.026 mmol) were added. The reaction mixture was stirred at ambient temperature for 21 h. Further portions of N-propargylpyrrolidine (113 mg, 1.04 mmol), diisopropylamine (0.339 mL, 2.42 mmol), copper(I) iodide (8 mg, 0.042 mmol) and bis(triphenylphosphine)palladium(II) dichloride (18 mg, 0.026 mmol) were added and reaction mixture was stirred at 50° C. for further 5 h and then evaporated in vacuo. The residue was purified by flash column chromatography (silica gel Fluka 60, dichloromethane/methanol 99:1-98:2) yielding methyl (E)-[2-methyl-4-[3-[4-[3-(pyrrolidin-1-yl)propynyl]phenyl]-3-(4-trifluoromethylphenyl)allyloxy]phenoxy]acetate as brown oil.

Yield: 249 mg (86%).

$R_F$ (SiO$_2$, chloroform saturated with ammonia/methanol 97:3): 0.50.

$^1$H NMR spectrum (300 MHz, CDCl$_3$, $\delta_H$): 7.55 (d, J=8.2 Hz, 2H); 7.49 (d, J=8.3 Hz, 2H); 7.35 (d, J=8.2 Hz, 2H); 7.15 (d, J=8.3 Hz, 2H); 6.68 (d, J=2.8 Hz, 1H); 6.63 (d, J=8.8 Hz, 1H); 6.57 (dd, J=8.9 and 2.9 Hz, 1H); 6.37 (t, J=6.6 Hz, 1H); 4.59 (s, 2H); 4.52 (d, J=6.6 Hz, 2H); 3.79 (s, 3H); 3.78 (s, 2H); 2.89 (m, 4H); 2.25 (s, 3H); 1.93 (m, 4H).

To a solution of the above ester (242 mg, 0.429 mmol) in tetrahydrofuran/methanol mixture (5:1, 6 mL), a solution of lithium hydroxide monohydrate (54 mg, 1.29 mmol) in distilled water (1 mL) was added under cooling (0° C.). The solution was stirred for 2 h under cooling, glacial acetic acid (0.074 mL, 1.29 mmol) was added and the mixture was stirred for further 10 min. The solution was diluted with ether (30 mL) and water (20 mL); the phases were separated and the aqueous phase was extracted with ether (3×10 mL). The combined organic layers were washed with water (2×10 mL) and brine (2×10 mL), dried with anhydrous magnesium sulfate and evaporated in vacuo. The residue was purified by preparative HPLC yielding the title acid as brown oil.

Yield: 58 mg (25%).

M.p.: - - - (oil).

$R_F$ (SiO$_2$, ethyl acetate/methanol 1:1): 0.15.

$^1$H NMR spectrum (300 MHz, CDCl$_3$, $\delta_H$): 7.50 (d, J=7.0 Hz, ~2H); 7.43 (d, J=6.8 Hz, ~2H); 7.29 (d, J=9.4 Hz, ~2H); 7.10 (d, J=7.2 Hz, 2H); 6.57 (m, 2H); 6.41 (m, ~1H); 6.33 (m, ~1H); 4.36 (m. 4H); 3.97 (s, 2H); 3.14 (s, 4H); 2.14 (s, 3H); 1.96 (s, 4H).

Example 30

(Z)-[4-[3-(4-tert-Butylphenyl)-3-[4-[3-(morpholin-4-yl)propynyl]phenyl]allyloxy]-2-methylphenoxy]acetic Acid

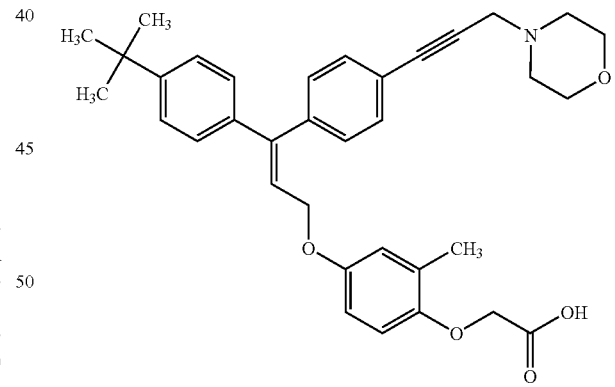

To a degassed solution of 1-bromo-4-tert-butylbenzene (5 g, 23.5 mmol) in tetrahydrofuran (25 mL) was added in the following order: copper(I) iodide (134 mg, 0.704 mmol), tetrakis(triphenylphosphine)palladium (813 mg, 0.704 mmol), and 1,8-diazabicyclo[5.4.0]-undec-7-ene (4.2 mL, 28.1 mmol). The resulting mixture was degassed again and a solution of propargyl alcohol (1.64 mL, 28.2 mmol) in tetrahydrofuran (2 mL) was added over period of 10 min. The reaction mixture was slowly heated up to 50° C. and then stirred at this temperature over night. The mixture was diluted with ether (50 mL), washed with water (20 mL), 15% hydrochloric acid (2×20 mL) and saturated aqueous solution of sodium hydrogen carbonate (25 mL). The organic solution was dried with anhydrous magnesium sulfate and evaporated in vacuo. The residue was purified by column chromatography (silica gel Fluka 60, hexanes/ethyl acetate 5:1) affording 3-(4-tert-butylphenyl)prop-2-yn-1-ol.

Yield: 4.3 g (97%).

$R_F$ (SiO$_2$, hexanes/ethyl acetate 4:1): 0.20.

$^1$H NMR spectrum (300 MHz, CDCl$_3$, $\delta_H$): 7.38 (d, J=8.7 Hz, 2H); 7.33 (d, J=8.7 Hz, 2H); 4.49 (d, J=5.7 Hz, 2H); 1.31 (s, 9H).

Sodium methoxide (62 mg, 1.15 mmol) was added to 1 M solution of lithium aluminum hydride in tetrahydrofuran (22.8 mL, 22.8 mmol) under nitrogen. The mixture was cooled to 0° C. and a solution of the above hydroxy derivative (4.3 g, 22.8 mmol) in tetrahydrofuran (22 mL) was added over 30 min. The reaction was stirred at 0° C. for 3 h; dry ethyl acetate (6.9 mL, 70.6 mmol) was added and the whole mixture was stirred at ambient temperature for 10 min. A degassed solution of 1,4-diiodobenzene (7.9 g, 24.0 mmol) in dry tetrahydrofuran (28 mL), anhydrous zinc chloride (1.9 g, 13.9 mmol), tris(dibenzylideneacetone)dipalladium chloroform complex (0.43 g, 0.415 mmol), and tri-2-furylphosphine (0.583 g, 2.51 mmol) were added; the mixture was degassed and then heated at 50° C. for 19 h under nitrogen. The suspension was cooled down; methanol (11.5 mL) was added and the mixture was stirred for additional 1 h. The reaction mixture was diluted with ether (110 mL) and saturated aqueous solution of ammonium chloride (5.8 mL) was added. The mixture was filtered through a paddle of silica gel and the paddle was thoroughly washed with ether (500 mL). Solvents were evaporated in vacuo and the residue was separated by flash column chromatography (silica gel Fluka 60, hexanes/ethyl acetate 6:1) affording (Z)-3-(4-tert-butylphenyl)-3-(4-iodophenyl)allyl alcohol as an oil.

Yield: 2.5 g (28%).

$R_F$ (SiO$_2$, hexanes/ethyl acetate 2:1): 0.50.

$^1$H NMR spectrum (300 MHz, CDCl$_3$, $\delta_H$): 7.73 (d, J=8.3 Hz, 2H); 7.33 (d, J=8.5 Hz, 2H); 7.19 (d, J=8.6 Hz, 2H); 6.95 (d, J=8.3 Hz, 2H); 6.26 (t, J=6.9 Hz, 1H); 4.20 (d, ~2H (overlapped)); 1.33 (s, 9H).

The above allyl alcohol (2.46 g, 6.27 mmol), methyl (4-hydroxy-2-methylphenoxy)acetate (1.35 g, 6.88 mmol; example 2) and triphenylphosphine (1.97 g, 7.51 mmol) were dissolved in a mixture of anhydrous toluene (135 mL) and tetrahydrofuran (45 mL). The mixture was cooled to 0° C., kept under nitrogen and a degassed solution of diisopropyl azodicarboxylate (1.5 mL, 7.57 mmol) in anhydrous tetrahydrofuran (15 mL) was added dropwise during 30 min. The reaction mixture was allowed to warm up the ambient temperature with the bath and then stirred over night. The solvents were evaporated in vacuo and the residue was submitted to flash column chromatography (silica gel Fluka 60, hexanes/ethyl acetate 12:1-10:1) affording methyl (Z)-[4-[3-(4-tert-butylphenyl)-3-(4-iodophenyl)allyloxy]-2-methylphenoxy]acetate as yellow oil.

Yield: 2.38 g (67%).

$R_F$ (SiO$_2$, hexanes/ethyl acetate 4:1): 0.35.

$^1$H NMR spectrum (300 MHz, CDCl$_3$, $\delta_H$): 7.72 (d, J=8.3 Hz, 2H); 7.31 (d, J=8.5 Hz, 2H); 7.17 (d, J=8.5 Hz, 2H); 6.96 (d, J=8.3 Hz, 2H); 6.68 (d, J=2.7 Hz, 1H); 6.63 (d, J=8.8 Hz, 1H); 6.57 (dd, J=8.8 and 2.8 Hz, 1H); 6.29 (t, J=6.7 Hz, 1H); 4.58 (s, 2H); 4.48 (d, J=6.7 Hz, 2H); 3.79 (s, 3H); 2.25 (s, 3H); 1.31 (s, ~9H).

4-Propargylmorpholine (153 mg, 1.22 mmol) and diisopropylamine (0.40 mL, 2.85 mmol) were added to a solution of the above iodo derivative (350 mg, 0.614 mmol) in tetrahydrofuran (5 mL). The mixture was degassed and copper(I) iodide (10 mg, 0.053 mmol) and bis(triphenylphosphine)palladium dichloride (22 mg, 0.031 mmol) were added. The reaction mixture was stirred at ambient temperature overnight, filtered and the filtrate was evaporated in vacuo. The residue was purified by flash column chromatography (silica gel Fluka 60, dichloromethane/methanol 99:1) yielding methyl (Z)-[4-[3-(4-tert-butylphenyl)-3-[4-[3-(morpholin-4-yl)propynyl]phenyl]allyloxy]-2-methylphenoxy]acetate as oil.

Yield: 334 mg (96%).

$R_F$ (SiO$_2$, dichloromethane/methanol 95:5): 0.35.

$^1$H NMR spectrum (300 MHz, CDCl$_3$, $\delta_H$): 7.46 (d, J=8.2 Hz, 2H); 7.31 (d, J=8.5 Hz, 2H); 7.17 (d, J=8.5 Hz, 2H); 7.16 (d, J=8.2 Hz, 2H); 6.67 (d, J=2.7 Hz, 1H); 6.62 (d, J=8.8 Hz, 1H); 6.56 (dd, J=8.9 and 2.8 Hz, 1H); 6.29 (t, J=6.6 Hz, 1H); 4.58 (s, 2H); 4.49 (d, J=6.7 Hz, 2H); 3.79 (s, 3H); 3.78 (m, 4H); 3.54 (s, 2H); 2.66 (m, 4H); 2.24 (s, 3H); 1.31 (s, 9H).

To a solution of the above ester (325 mg, 0.573 mmol) in tetrahydrofuran/methanol mixture (5:1, 6 mL), a solution of lithium hydroxide monohydrate (71 mg, 1.69 mmol) in distilled water (1 mL) was added under cooling to 0° C. The solution was stirred for 2.5 h under cooling, acetic acid (0.097 mL; 1.70 mmol) was added and the resulting mixture was stirred for further 10 min. The solution was diluted with ethyl acetate (40 mL) and water (30 mL); the phases were separated and the aqueous phase was extracted with ethyl acetate (3×20 mL). The combined organic layers were washed with water (2×20 mL) and brine (2×20 mL). The organic solution was dried with anhydrous magnesium sulfate and evaporated in vacuo. The residue was triturated with hexanes (2×4 mL) yielding the title acid as yellow solid.

Yield: 227 mg (72%).

M.p.: 68-75° C.

$R_F$ (SiO$_2$, ethyl acetate/methanol 1:1): 0.30.

$^1$H NMR spectrum (300 MHz, CDCl$_3$, $\delta_H$): 7.41 (d, J=8.3 Hz, 2H); 7.30 (d, J=8.5 Hz, 2H); 7.17 (d, J=8.5 Hz, 2H); 7.10 (d, J=8.1 Hz, 2H); 6.66 (m, 1H); 6.58 (d, J=8.9 Hz, 1H); 6.43 (dd, J=8.5 and 2.3 Hz, 1H); 6.31 (t, J=6.8 Hz, 1H); 4.53 (s, 2H); 4.44 (d, J=6.8 Hz, 2H); 3.82 (m, 4H); 3.66 (s, 2H); 2.86 (m, ~4H); 2.23 (s, 3H); 1.30 (s, 9H).

Example 31

(Z)-[4-[3-(4-tert-Butylphenyl)-3-[4-(2-methyl-1,1-dioxobenzo[b]thiophen-5-ylethynyl)phenyl]-allyloxy]-2-methylphenoxy]acetic Acid

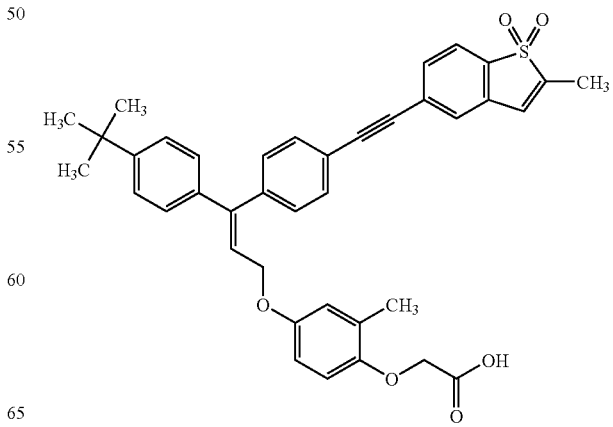

5-Bromo-2-methylbenzo[b]thiophene (8.0 g, 35.2 mmol; prepared according to J. Med. Chem. 1986, 29, 1643) was dissolved in acetic acid (200 mL); 30% hydrogen peroxide (50 mL) was added and the mixture was refluxed for 4 h. Water (500 mL) was added and the mixture was extracted with benzene (300 mL). The organic layer was evaporated in vacuo and the residue was purified by column chromatography (silica gel Fluka 60, benzene) affording 5-bromo-2-methylbenzo[b]thiophene-1,1-dioxide.

Yield: 5.88 g (64%).
M.p.: 149-151° C.
$^1$H NMR spectrum (300 MHz, CDCl$_3$, $\delta_H$): 7.57 (s, 2H); 7.43 (s, 1H); 6.74 (s, 1H); 2.23 (s, 3H).

A mixture of the above sulfone (5.88 g, 22.7 mmol), bis(triphenylphosphine)palladium(II) dichloride (0.175 g, 0.25 mmol), copper(II) acetate (50 mg, 0.275 mmol), ethynyltrimethylsilane (5.5 g, 56.0 mmol) and triethylamine (60 mL) was refluxed under stirring for 6 h. After cooling, the separated 5-trimethylsilylethynyl-2-methylbenzo[b]thiophene-1,1-dioxide was collected by filtration and washed with benzene.

Yield: 3.80 g (61%).
M.p.: 195-197° C.
$^1$H NMR spectrum (300 MHz, CDCl$_3$, $\delta_H$): 7.64 (d, J=7.8 Hz, 1H); 7.51 (d, J=7.8 Hz, 1H); 7.35 (s, 1H); 6.74 (s, 1H); 2.22 (s, 3H); 0.26 (s, 9H).

The above derivative (3.80 g, 13.7 mmol) and potassium carbonate (0.35 g, 2.5 mmol) were stirred for 4 h with methanol (50 mL); methanol was evaporated in vacuo and the residue was dissolved in dichloromethane and filtered through a paddle of silica gel affording 5-ethynyl-2-methylbenzo[b]thiophene-1,1-dioxide.

Yield: 2.10 g (74%).
M.p.: 165-166° C.
$^1$H NMR spectrum (300 MHz, CDCl$_3$, $\delta_H$): 7.65 (d, J=7.8 Hz, 1H); 7.53 (d, J=7.8 Hz, 1H); 7.35 (s, 1H); 6.75 (s, 1H); 3.28 (s, 1H); 2.22 (s, 3H).

The above aryl acetylene (251 mg, 1.23 mmol) and diisopropylamine (0.40 mL, 2.85 mmol) were added to a solution of methyl (Z)-[4-[3-(4-tert-butylphenyl)-3-(4-iodophenyl)allyloxy]-2-methylphenoxy]acetate (350 mg, 0.614 mmol; prepared as described in example 30) in tetrahydrofuran (10 mL). The mixture was degassed and copper(I) iodide (10 mg, 0.053 mmol) and bis(triphenylphosphine)palladium(II) dichloride (22 mg, 0.031 mmol) were added. The reaction mixture was stirred at ambient temperature over night, filtered and the filtrate was evaporated in vacuo. The residue was purified by flash column chromatography (silica gel Fluka 60, hexanes/ethyl acetate 4:1) yielding methyl (Z)-[4-[3-(4-tert-butylphenyl)-3-[4-(2-methyl-1,1-dioxobenzo[b]thiophen-5-ylethynyl)phenyl]allyloxy]-2-methylphenoxy]-acetate as yellow solidifying oil.

Yield: 346 mg (87%).
R$_F$ (SiO$_2$, hexanes/ethyl acetate 1:1): 0.40.
$^1$H NMR spectrum (300 MHz, CDCl$_3$, $\delta_H$): 7.70 (d, J=7.8 Hz, 1H); 7.61 (d, J=1.2 Hz, 1H); 7.57 (d, J=8.4 Hz, 2H); 7.43 (s, 1H); 7.32 (d, J=8.5 Hz, 2H); 7.24 (d, J=8.3 Hz, 2H); 7.19 (d, J=8.5 Hz, 2H); 6.79 (m, 1H); 6.69 (d, J=2.7 Hz, 1H); 6.63 (d, J=8.8 Hz, 1H); 6.57 (dd, J=8.8 and 2.8 Hz, 1H); 6.32 (t, J=6.7 Hz, 1H); 4.58 (s, 2H); 4.51 (d, J=6.7 Hz, 2H); 3.79 (s, 3H); 2.25 (s, 3H); 2.24 (s, 3H); 1.31 (s, 9H).

To a solution of the above ester (339 mg, 0.524 mmol) in tetrahydrofuran/methanol mixture (5:1, 6 mL), a solution of lithium hydroxide monohydrate (72 mg, 1.72 mmol) in distilled water (1 mL) was added under cooling to 0° C. The solution was stirred for 1.5 h under cooling, acetic acid (0.098 mL; 1.71 mmol) was added and the resulting mixture was stirred for further 10 min. The solution was diluted with ethyl acetate (40 mL) and water (30 mL); the phases were separated and the aqueous phase was extracted with ethyl acetate (3×20 mL). The combined organic layers were washed with water (2×20 mL) and brine (2×20 mL). The organic solution was dried with anhydrous magnesium sulfate and evaporated in vacuo. The residue was triturated with hexanes (2×4 mL) yielding the title acid as white solid.

Yield: 207 mg (63%).
M.p.: 104-116° C.
R$_F$ (SiO$_2$, ethyl acetate/methanol 1:1): 0.60.
$^1$H NMR spectrum (300 MHz, CDCl$_3$, $\delta_H$): 7.70 (d, J=7.9 Hz, 1H); 7.60 (m, 1H); 7.57 (d, J=8.1 Hz, 2H); 7.42 (s, 1H); 7.32 (d, J=8.4 Hz, 2H); 7.24 (d, J=8.2 Hz, 2H); 7.19 (d, J=8.5 Hz, 2H); 6.78 (s, 1H); 6.69 (d, J=2.5 Hz, 1H); 6.66 (d, 1H); 6.59 (dd, J=9.0 and 2.8 Hz, 1H); 6.32 (t, J=6.7 Hz, 1H); 4.59 (s, 2H); 4.51 (d, J=6.7 Hz, 2H); 2.24 (s, 6H); 1.31 (s, 9H).

Example 32

(E)-[2-Methyl-4-[3-[4-[3-(morpholin-4-yl)propynyl]phenyl]-3-(6-phenylpyridin-3-yl)allyloxy]-phenoxy] acetic Acid

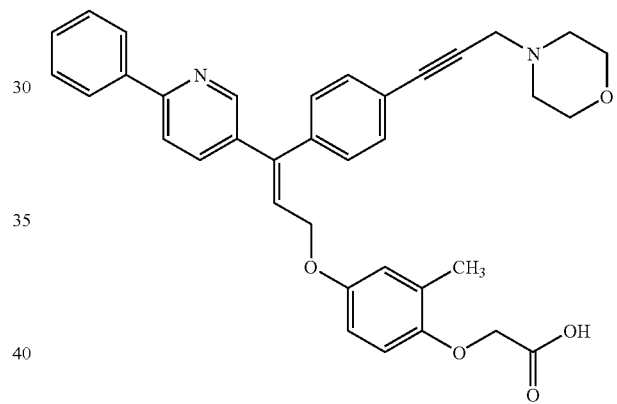

2,5-Dibromopyridine (0.948 g, 4 mmol), phenylboronic acid (0.488 g, 4 mmol) and tetrakis(triphenylphosphine)palladium (0.116 g, 0.1 mmol) were dissolved in anhydrous tetrahydrofuran (6 mL) and a solution of sodium carbonate (0.848 g, 8 mmol) in water (6 mL) was added. The mixture was put under nitrogen and stirred at 75° C. for 16 h. The mixture was concentrated in vacuo. The residue was dissolved in water (10 mL) and extracted with dichloromethane (3×5 mL). The combined organic extracts were dried with anhydrous sodium sulphate. Column chromatography of the residue (silica gel Fluka 60, hexanes/dichloromethane 1:1) afforded 3-bromo-6-phenylpyridine as a white crystalline product.

Yield: 0.74 g (79%).
R$_F$ (SiO$_2$, hexanes/dichloromethane 1:1): 0.30.

In nitrogen atmosphere, the above bromo derivative (0.468 g, 2 mmol), bis(triphenylphosphine)palladium(II) dichloride (0.042 g, 0.06 mmol) and copper(I) iodide (0.011 g, 0.06 mmol) were dissolved in tetrahydrofuran (50 mL). Propargyl alcohol (0.14 mL, 2.4 mmol) and 1,8-diazabicyclo[5.4.0]undec-7-ene (0.36 mL, 2.4 mmol) were added via syringe. Traces of air were removed; the mixture was stirred at ambient temperature for 3 h and then at 50° C. for 16 h under nitrogen. The reaction mixture was concentrated in vacuo; the residue was mixed with water (8 mL) and extracted with dichloromethane (4×3 mL). The combined organic layers were dried with anhydrous sodium sulphate, concentrated in vacuo and the obtained residue was submitted to column chromatography (silica gel Fluka 60, hexanes/ethyl acetate 1:1) affording 3-(6-phenylpyridin-3-yl)prop-2-yn-1-ol.

Sodium methoxide (2.5 mg, 0.045 mmol) was added to 1 M solution of lithium aluminum hydride in tetrahydrofuran (1.43 mL, 1.43 mmol). The mixture was cooled to 0° C. and a solution of 3-(6-phenylpyridin-3-yl)prop-2-yn-1-ol (300 mg, 1.43 mmol) in tetrahydrofuran (6 mL) was slowly added. The reaction mixture was stirred at 0° C. for 2 h and then at ambient temperature for 2 h. The reaction mixture was cooled to 0° C. again, ethyl acetate (0.24 mL, 2.4 mmol) was added and the mixture was stirred for further 10 min without cooling. 1,4-Diiodobenzene (527 mg, 1.60 mmol), anhydrous zinc chloride (108 mg, 1.23 mmol), tris(dibenzylideneacetone)dipalladium chloroform complex (29.5 mg, 0.029 mmol) and tri-(2-furyl)phosphine (26.6 mg, 0.118 mmol) were added, the mixture was degassed and kept under argon. The mixture was heated at 60° C. for 20 h; methanol (0.7 mL) was added and the mixture was stirred for additional 1 h. The reaction mixture was diluted with ether (30 mL) and subsequently saturated aqueous solution of ammonium chloride (0.36 mL) was added. The formed suspension was filtered through a paddle of silica gel and the paddle was thoroughly washed with ethyl acetate. The combined filtrates were concentrated in vacuo and the residue was submitted to column chromatography (silica gel Fluka 60, hexanes/ethyl acetate 1:1) affording (E)-3-(4-iodophenyl)-3-(6-phenylpyridin-3-yl)prop-2-en-1-ol.

Yield: 0.240 g (46%).

$R_F$ (SiO$_2$, hexanes/ethyl acetate 1:1): 0.60.

$^1$H NMR spectrum (300 MHz, CDCl$_3$, $\delta_H$): 8.61 (d, J=1.9 Hz, 1H); 7.80 (m, 2H); 7.73-7.41 (m, 7H); 6.94 (d, J=8.3 Hz, 2H); 6.34 (t, J=6.8 Hz, 1H); 4.25 (bt, J=6.5 Hz, 2H).

The above allyl alcohol (238 mg, 0.0.65 mmol), methyl (4-hydroxy-2-methylphenoxy)acetate (140 mg, 0.715 mmol; example 2) and triphenylphosphine (205 mg, 0.78 mmol) were dissolved in a mixture of anhydrous toluene (8 mL) and tetrahydrofuran (6 mL). The mixture was cooled to 0° C., kept under argon and a degassed solution of diisopropyl azodicarboxylate (0.163 mL, 0.78 mmol) in anhydrous tetrahydrofuran (1 mL) was added dropwise during 10 min. The reaction mixture was allowed to warm up to ambient temperature with the bath and then was stirred for 3 days. The solvents were evaporated in vacuo and the residue was submitted to flash column chromatography (silica gel Fluka 60, hexanes/ethyl acetate 85:15) affording methyl (E)-[4-[3-(4-iodophenyl)-3-(6-phenylpyridin-3-yl)allyloxy]-2-methylphenoxy]acetate as oil.

Yield: 130 mg (35%).

$R_F$ (SiO$_2$, hexanes/ethyl acetate 3:1): 0.60.

$^1$H NMR spectrum (300 MHz, CDCl$_3$, $\delta_H$): 8.60 (d, J=1.9 Hz, 1H); 7.99 (d, J=6.8 Hz, 2H); 7.77-7.45 (m, 7H); 6.99 (d, J=8.2 Hz, 2H); 6.70-6.57 (m, 3H); 6.41 (t, J=6.6 Hz, 1H); 4.59 (s, 2H); 4.53 (d, J=6.7 Hz, 2H); 3.79 (s, 3H); 2.26 (s, 3H).

4-Propargylmorpholine (51 mg, 0.405 mmol) was added to a solution of the above iodo derivative (130 mg, 0.225 mmol) in a mixture of tetrahydrofuran (3 mL) and triethylamine (3 mL). The mixture was degassed and copper(I) iodide (7 mg, 0.036 mmol) and tetrakis(triphenylphosphine)-palladium (21 mg, 0.018 mmol) were added. The reaction mixture was stirred at ambient temperature for 2 days, filtered and the filtrate was evaporated in vacuo. The residue was purified by flash column chromatography (silica gel Fluka 60, hexanes/ethyl acetate 4:6) yielding methyl (E)-[2-methyl-4-[3-[4-[3-(morpholin-4-yl)propynyl]phenyl]-3-(6-phenylpyridin-3-yl)allyloxy]-phenoxy]acetate as oil.

Yield: 135 mg (89%).

$R_F$ (SiO$_2$, hexanes/ethyl acetate 1:9): 0.15.

$^1$H NMR spectrum (300 MHz, CDCl$_3$, $\delta_H$): 8.60 (bs, 1H); 7.99 (d, J=7.0 Hz, 2H); 7.72-7.26 (m, 7H); 7.19 (d, J=7.9 Hz, 2H); 6.69-6.60 (m, 3H); 6.41 (t, J=6.6 Hz, 1H); 4.59 (s, 2H); 4.54 (d, J=6.7 Hz, 2H); 3.79 (s, 3H); 3.77 (m, 4H); 3.54 (s, 2H); 2.66 (bs, 4H); 2.26 (s, 3H).

To a solution of the above ester (115 mg, 0.20 mmol) in tetrahydrofuran/methanol mixture (1:1, 2 mL), a solution of lithium hydroxide monohydrate (12 mg, 0.278 mmol) in distilled water (0.3 mL) was added under cooling (0° C.). The solution was stirred for 3 h at ambient temperature, glacial acetic acid (0.060 mL) was added and the mixture was stirred for further 10 min. The solution was diluted with chloroform (20 mL), washed with water (2×3 mL), dried with anhydrous magnesium sulfate and evaporated in vacuo. The residue was triturated with hexanes (2×20 mL) yielding the title acid.

Yield: 104 mg (93%).

M.p.: 79-83° C.

$R_F$ (SiO$_2$, chloroform/methanol 4:1): 0.20.

$^1$H NMR spectrum (300 MHz, CDCl$_3$+AcOH-d$_4$): 11.46 (s, ~2H); 8.67 (s, 1H); 7.93-7.40 (m, ~9H); 7.20 (d, J=8.1 Hz, 2H); 6.55-6.71 (m, 3H); 6.45 (t, J=6.7 Hz, 1H); 4.58 (s, 2H); 4.53 (d, J=6.7 Hz, 2H); 3.87 (m, 4H); 3.85 (s, 2H); 3.04 (m, 4H); 2.26 (s, 3H).

Example 33

(E)-[4-[3-(4-Chlorophenyl)-3-[4-[3-(N-cyclopropylamino)propynyl]phenyl]allyloxy]-2-methylphenoxy]acetic Acid

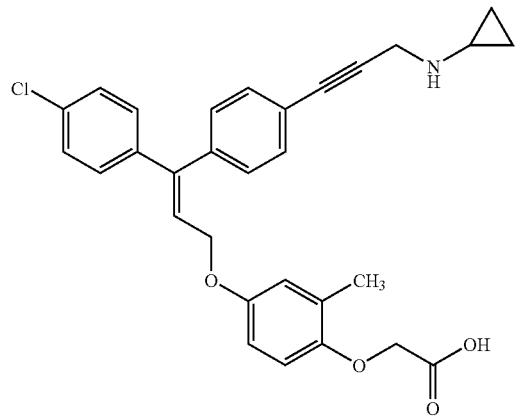

N-Cyclopropyl-N-(prop-2-ynyl)amine (105 mg, 1.103 mmol) was added to a solution of methyl (Z)-[4-[3-(4-chlorophenyl)-3-(4-iodophenyl)allyloxy]-2-methylphenoxy]acetate (336 mg, 0.613 mmol; prepared as described in example 7) in a mixture of tetrahydrofuran (5 mL) and triethylamine (5 mL). The mixture was degassed and copper(I) iodide (19 mg, 0.1 mmol) and tetrakis(triphenylphosphine)palladium (58 mg, 0.05 mmol) were added. The reaction mixture was stirred at ambient temperature for 2 days, diluted with dichloromethane (40 mL), washed with water (2×15 mL), dried with anhydrous magnesium sulfate and evaporated in vacuo. The residue was purified by flash column chromatography (silica gel Fluka 60, hexanes/ethyl acetate 7:3) yielding methyl (E)-[4-[3-(4-chlorophenyl)-3-[4-[3-(N-cyclopropylamino)propynyl]phenyl]allyloxy]-2-methylphenoxy]acetate as oil.

Yield: 205 mg (65%).

$R_F$ (SiO$_2$, hexanes/ethyl acetate 1:1): 0.15.

$^1$H NMR spectrum (300 MHz, CDCl$_3$, $\delta_H$): 7.45 (d, J=8.0 Hz, 2H); 7.27-7.11 (m, 6H); 6.69-6.54 (m, 3H); 6.27 (t, J=6.7 Hz, 1H); 4.58 (s, 2H); 4.49 (d, J=6.7 Hz, 2H); 3.79 (s, 3H); 3.77 (m, 2H); 2.24 (s, 3H); 0.94 (m, 1H); 0.50 (m, 4H).

To a solution of the above ester (200 mg, 0.388 mmol) in tetrahydrofuran/methanol mixture (1:1, 6 mL), a solution of lithium hydroxide monohydrate (24.4 mg, 0.58 mmol) in distilled water (0.5 mL) was added. The solution was stirred for 2 h at ambient temperature, glacial acetic acid (0.08 mL) was added and the mixture was stirred for further 10 min. The solution was diluted with dichloromethane (30 mL), washed with water (2×10 mL), dried with anhydrous magnesium sulfate and evaporated in vacuo. The residue was triturated with hexanes (2×20 mL) yielding the title acid.

Yield: 120 mg (62%).

M.p.: 92-95° C.

$R_F$ (SiO$_2$, chloroform/methanol 4:1): 0.15.

$^1$H NMR spectrum (300 MHz, CDCl$_3$+AcOH-d$_4$): 7.46-7.12 (m, 8H); 6.67-6.49 (m, 3H); 6.30 (t, J=6.6 Hz, 1H); 4.55 (s, 2H); 4.46 (d, J=6.7 Hz, 2H); 4.11 (s, 2H); 2.23 (s, 3H); 2.07 (m, 1H); 1.08 (m, 2H); 0.83 (s, 2H).

Example 34

(E)-[2-Methyl-4-[3-[4-[3-(pyrazol-1-yl)propynyl]phenyl]-3-(3-trifluoromethylphenyl)allyloxy]-phenoxy]acetic Acid

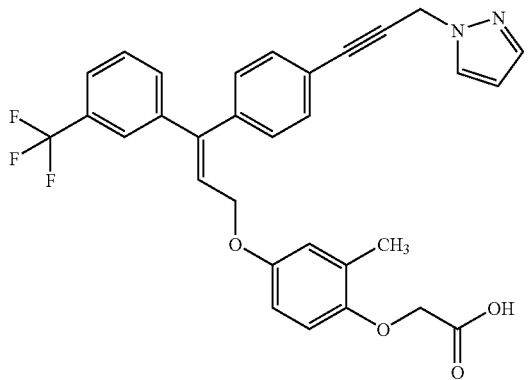

To a degassed solution of 1-bromo-3-trifluoromethylbenzene (20.0 g, 88.8 mmol) in tetrahydrofuran (160 ml) were in the following order added: copper(I) iodide (506 mg, 2.66 mmol), tetrakis(triphenylphosphine)palladium (3.06 g, 26.6 mmol), and 1,8-diazabicyclo-[5.4.0]undec-7-ene (16.22 g, 106.6 mmol). The resulting mixture was degassed one more time, cooled in an ice bath and a solution of propargyl alcohol (5.94 g, 106.6 mmol) in tetrahydrofuran (10 mL) was added over period of 20 min. The reaction mixture was slowly heated up to 55° C. and then stirred at this temperature for 16 h. The mixture was diluted with diethyl ether (400 mL), washed with water (100 mL), 5% hydrochloric acid (100 mL) and saturated aqueous solution of sodium hydrogen carbonate (80 mL). The organic solution was dried with anhydrous magnesium sulfate and evaporated in vacuo. The residue was purified by column chromatography (silica gel Fluka 60, hexanes/ethyl acetate 85:15) affording 3-(3-trifluoromethylphenyl)prop-2-yn-1-ol.

Yield: 4.40 g (50%).

$R_F$ (SiO$_2$, hexanes/ethyl acetate 3:1): 0.25.

$^1$H NMR spectrum (300 MHz, CDCl$_3$, $\delta_H$): 7.70 (s, 1H); 7.59 (t, J=7.8 Hz, 2H); 7.44 (t, J=7.8 Hz, 1H); 4.52 (d, J=6.1 Hz, 2H); 1.89 (t, J=6.1 Hz, 1H).

Sodium methoxide (90 mg, 1.67 mmol) was added to 1 M solution of lithium aluminum hydride in tetrahydrofuran (33 mL, 33 mmol) under argon. The mixture was cooled to 0° C. and a solution of the above alcohol (6.7 g, 33.5 mmol) in tetrahydrofuran (25 mL) was added over 10 min. The reaction was stirred at 0° C. for 3 h; dry ethyl acetate (10 mL, 103 mmol) was added and the whole mixture was stirred at ambient temperature for 15 min. A degassed solution of 1,4-diiodobenzene (13.25 g, 40.1 mmol) in dry tetrahydrofuran (25 mL), anhydrous zinc chloride (2.73 g, 20.0 mmol), tris(dibenzylideneacetone)dipalladium chloroform complex (0.692 g, 0.66 mmol), and tri(2-furyl)phosphine (0.854 g, 3.6 mmol) were added; the mixture was degassed and then was heated at 60° C. for 15 h under argon. The suspension was cooled down; methanol (16 mL) was added and the mixture was stirred for additional 1 h. The reaction was diluted with ether (350 mL) and saturated aqueous solution of ammonium chloride (9 mL) was added. The mixture was filtered through a paddle of silica gel and the paddle was thoroughly washed with ether (100 mL). The solvents were evaporated in vacuo and the residue was purified by flash column chromatography (silica gel Fluka 60, hexanes/ethyl acetate 5:1) affording (E)-3-(4-iodophenyl)-3-(3-trifluoromethylphenyl)prop-2-en-1-ol as solidifying oil.

Yield: 4.14 mg (31%).

$R_F$ (SiO$_2$, hexanes/ethyl acetate 4:1): 0.20.

$^1$H NMR spectrum (300 MHz, CDCl$_3$, $\delta_H$): 7.73 (d, J=7.4 Hz, 2H); 7.82 (m, 2H); 7.33 (m, 2H); 6.91 (m, 2H); 6.28 (t, J=6.8 Hz, 1H); 4.22 (m, 2H).

The above allyl alcohol (2.0 g, 4.94 mmol), methyl (4-hydroxy-2-methylphenoxy)acetate (1.08 g, 5.54 mmol; example 2) and triphenylphosphine (1.50 g, 6.02 mmol) were dissolved in a mixture of anhydrous toluene (40 mL) and tetrahydrofuran (20 mL). The mixture was cooled to 0° C., kept under argon and a degassed solution of diisopropyl azodicarboxylate (1.15 mL, 5.82 mmol) in anhydrous tetrahydrofuran (10 mL) was added dropwise during 10 min. The reaction mixture was allowed to warm up to ambient temperature with the bath and then was stirred for 20 h. The solvents were evaporated in vacuo and the residue was submitted to flash column chromatography (silica gel Fluka 60, hexanes/ethyl acetate 9:1) affording methyl (E)-[4-[3-(4-iodophenyl)-3-(3-trifluoromethylphenyl)allyloxy]-2-methylphenoxy]acetate as yellow oil.

Yield: 1.99 g (69%).

$R_F$ (SiO$_2$, hexanes/ethyl acetate 3:1): 0.25.

$^1$H NMR spectrum (300 MHz, CDCl$_3$, $\delta_H$): 7.74 (d, J=8.3 Hz, 2H); 7.53 (m, 2H); 7.41 (m, 2H); 6.95 (d, J=8.3 Hz, 2H); 6.68-6.56 (m, 3H); 6.36 (t, J=6.7 Hz, 1H); 4.59 (s, 2H); 4.50 (d, J=6.7 Hz, 2H); 3.79 (s, 3H); 2.26 (s, 3H).

A solution of the above ester (400 mg, 0.68 mmol) in a mixture of tetrahydrofuran (12 mL) and triethylamine (12 mL) was degassed and 1-propargylpyrazole (144 mg, 1.36 mmol) was added in argon atmosphere. The solution was cooled down; tetrakis(triphenylphosphine)palladium (62 mg, 0.054 mmol) and copper(I) iodide (20 mg, 0.108 mmol) were added and the resulting mixture was stirred at ambient temperature for 30 h. The mixture was evaporated in vacuo; the residue was dissolved in ethyl acetate (20 mL) and the formed solution was washed with water (2×15 mL) and brine (10 mL). The organic solution was dried with anhydrous magnesium sulfate and evaporated in vacuo. The residue was purified by flash column chromatography (silica gel Fluka 60, hexanes/ethyl acetate 7:3) yielding methyl (E)-[2-methyl-4-[3-[4-[3-(pyrazol-1-yl)propynyl]phenyl]-3-(trifluoromethyl phenyl)allyloxy]-phenoxy]acetate.

Yield: 287 mg (75%).
RF (SiO$_2$, hexanes/ethyl acetate 3:1): 0.15.
1H NMR spectrum (300 MHz, CDCl$_3$, $\delta_H$): 7.69 (d, J=2.3 Hz, 1H); 7.57-7.37 (m, 7H); 7.16 (d J=8.3 Hz, 2H); 6.68-6.55 (m, 3H); 6.36 (t, J=6.7 Hz, 1H); 6.34 (m, 1H); 5.20 (s, 2H); 4.58 (s, 2H); 4.51 (d, J=6.7 Hz, 2H); 3.79 (s, 3H); 2.25 (s, 3H).

To a solution of the above ester (265 mg, 0.47 mmol) in tetrahydrofuran/methanol mixture (1:5, 11 mL), a solution of lithium hydroxide monohydrate (39.6 mg, 0.945 mmol) in distilled water (1 mL) was added under cooling to 0° C. The solution was stirred for 1 h under cooling and 2 h at ambient temperature. The solution was acidified with acetic acid (0.054 mL, 0.945 mmol) and evaporated in vacuo. The residue was dissolved in ethyl acetate (40 mL); the solution was washed with water (2×15 mL), brine (10 mL), dried with anhydrous magnesium sulfate and evaporated in vacuo. The residue was triturated with hexanes yielding the title acid as tan solid.

Yield: 118 mg (45%).
M.p.: - - - (foam).
R$_F$ (SiO$_2$, chloroform/methanol 9:1): 0.25.
$^1$H NMR spectrum (300 MHz, CDCl$_3$, $\delta_H$): 7.69 (m, 1H); 7.60-7.39 (m, ~7H); 7.14 (d, J=8.1 Hz, 2H); 6.68-6.53 (m, 3H); 6.36 (t, J=6.7 Hz, 1H); 6.33 (m, 1H); 5.23 (s, 2H); 4.61 (s, 2H); 4.50 (d, J=6.7 Hz, 2H); 2.25 (s, 3H).

Example 35

(E)-[2-Methyl-4-[3-[4-[3-(morpholin-4-yl)propynyl]phenyl]-3-(3-trifluoromethylphenyl)allyloxy]phenoxy]acetic Acid

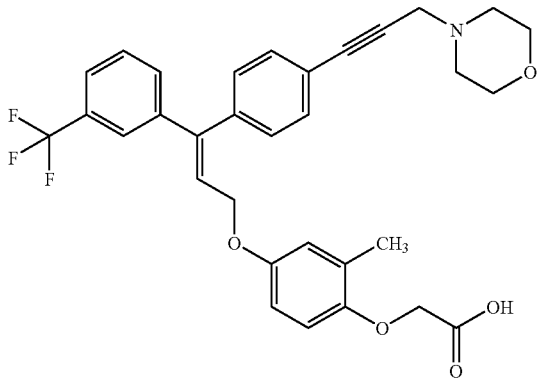

N-Propargylmorpholine (171 mg, 1.37 mmol) was added to a solution of methyl (E)-[4-[3-(4-iodophenyl)-3-(3-trifluoromethylphenyl)allyloxy]-2-methylphenoxy]acetate (400 mg, 0.68 mmol; prepared as described in example 34) in a mixture of tetrahydrofuran (12 mL) and triethylamine (12 mL). The mixture was degassed and copper(I) iodide (20 mg, 0.108 mmol) and tetrakis(triphenylphosphine)-palladium (62 mg, 0.054 mmol) were added. The reaction mixture was degassed once more and then stirred at ambient temperature for 2 days under argon. The mixture was evaporated in vacuo; the residue was dissolved in ethyl acetate (50 mL) and the solution was washed with water (2×15 mL) and brine (10 mL). The organic solution was dried with anhydrous magnesium sulfate and its evaporation gave oil that was purified by flash column chromatography (silica gel Fluka 60, hexanes/ethyl acetate 1:1) yielding methyl (E)-[2-methyl-4-[3-[4-[3-(morpholin-4-yl)propynyl]phenyl]-3-(3-trifluoromethylphenyl)allyl-oxy]phenoxy]acetate as oil.

Yield: 382 mg (95%).
R$_F$ (SiO$_2$, hexanes/ethyl acetate 1:1): 0.10.
1H NMR spectrum (300 MHz, CDCl$_3$, $\delta_H$): 7.58-7.40 (m, 6H); 7.15 (d, J=8.2 Hz, 2H); 6.69-6.56 (m, 3H); 6.35 (t, J=6.6 Hz, 1H); 4.59 (s, 2H); 4.52 (d, J=6.6 Hz, 2H); 3.80 (s, 3H); 3.78 (m, 4H); 3.54 (s, 2H); 2.66 (m, 4H); 2.25 (s, 3H).

To a solution of the above ester (367 mg, 0.633 mmol) in tetrahydrofuran/methanol mixture (5:1, 11 mL), a solution of lithium hydroxide monohydrate (53 mg, 0.126 mmol) in distilled water (1 mL) was added under cooling (0° C.). The solution was stirred for 2 h at ambient temperature, glacial acetic acid (0.072 mL) was added and the mixture was stirred for further 10 min. The solution was diluted with diethyl ether (20 mL), the solution was washed with water (2×15 mL, brine (10 mL), dried with anhydrous magnesium sulfate and evaporated in vacuo. The residue was triturated with hexanes (2×20 mL) yielding the title acid.

Yield: 168 mg (47%).
M.p.: 61-70° C.
R$_F$ (SiO$_2$, chloroform/methanol 9:1): 0.30.
$^1$H NMR spectrum (300 MHz, CDCl$_3$, $\delta_H$): 7.55-7.34 (m, ~6H); 7.12 (m, 2H); 6.68-6.60 (m, 3H); 6.37 (t, J=6.7 Hz, 1H); 4.54 (s, 2H); 4.48 (d, J=6.7 Hz, 2H); 3.84 (m, 4H); 3.73 (s, 2H); 2.91 (m, 4H); 2.25 (s, 3H).

Example 36

(E)-[4-[3-[4-[3-(4-Hydroxypiperidin-1-yl)propynyl]phenyl]-3-(3-trifluoromethylphenyl)allyloxy]-2-methylphenoxy]acetic Acid

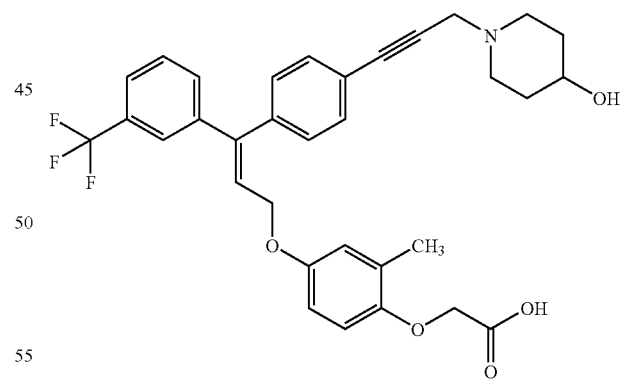

1-Propargylpiperidin-4-ol (191 mg, 1.374 mmol) and diisopropylamine (0.45 mL, 3.23 mmol) were added to a solution of methyl (E)-[4-[3-(4-iodophenyl)-3-(3-trifluoromethylphenyl)-allyloxy]-2-methylphenoxy]acetate (400 mg, 0.687 mmol; prepared as described in example 34) in tetrahydrofuran (10 mL). The mixture was degassed and copper(I) iodide (10.4 mg, 0.055 mmol) and bis(triphenylphosphine) palladium(II) dichloride (24.1 mg, 0.034 mmol) were added. The reaction mixture was stirred at ambient temperature for 20 h and evaporated in vacuo. The residue was purified by flash column chromatography (silica gel Fluka 60, chloroform/methanol 96:4) yielding methyl (E)-[4-[3-[4-[3-(4-hydroxypiperidin-1-yl)propynyl]phenyl]-3-(3-trifluoromethylphenyl)allyloxy]-2-methylphenoxy]acetate as yellow oil.

Yield: 420 mg (99%).

$R_F$ (SiO$_2$, chloroform/methanol 9:1): 0.15.

$^1$H NMR spectrum (300 MHz, CDCl$_3$, $\delta_H$): 7.55-7.39 (m, 6H); 7.14 (d, J=8.3 Hz, 2H); 6.69-6.55 (m, 3H); 6.35 (t, J=6.6 Hz, 1H); 4.57 (s, 2H); 4.52 (d, J=6.6 Hz, 2H); 3.79 (s, 3H); 3.54 (s, 2H); 2.88 (m, 2H); 2.44 (m, 2H); 2.25 (s, 3H); 1.98 (m, 2H); 1.68 (m, 2H).

To a solution of the above ester (404 mg, 0.68 mmol) in tetrahydrofuran/methanol mixture (4:1, 15 mL), a solution of lithium hydroxide monohydrate (57 mg, 1.3 mmol) in distilled water (1 mL) was added under cooling (0° C.). The solution was stirred for 2 h under cooling, glacial acetic acid (0.065 mL) was added and the mixture was stirred for further 10 min. The solution was diluted with ether (40 mL) and water (15 mL); the phases were separated and the organic phase was washed with water (2×15 mL), dried with anhydrous magnesium sulfate and evaporated in vacuo. The residue was triturated with hexanes (2×10 mL) yielding the title acid as pale solid.

Yield: 147 mg (37%).

M.p.: 82-91° C.

$R_F$ (SiO$_2$, chloroform/methanol 4:1): 0.15.

$^1$H NMR spectrum (300 MHz, CDCl$_3$+AcOH-d$_4$, $\delta_H$): 10.13 (bs, ~4H); 7.55-7.39 (m, 6H); 7.14 (d, J=8.2 Hz, 2H); 6.70-6.46 (m, 3H); 6.38 (t, J=6.8 Hz, 2H); 4.52 (s, 2H); 4.45 (d, J=6.8 Hz, 2H); 4.08 (s, 2H); 3.99 (bs, 1H); 3.49 (m, 2H); 3.22 (m, 2H); 2.23 (s, 3H); 2.12 (m, 2H); 1.93 (m, 2H).

Example 37

(E)-[4-[3-[4-[3-(N,N-Dimethylamino)propynyl]phenyl]-3-(3-trifluoromethylphenyl)allyloxy]-2-methylphenoxy]acetic Acid

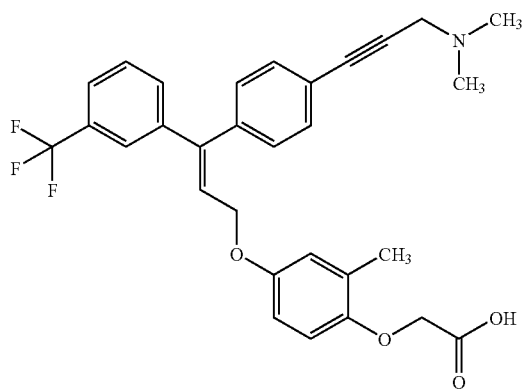

Dimethyl(prop-2-ynyl)amine (114 mg, 1.374 mmol) was added to a solution of methyl (E)-[4-[3-(4-iodophenyl)-3-(3-trifluoromethylphenyl)allyloxy]-2-methylphenoxy]acetate (400 mg, 0.687 mmol; prepared as described in example 34) in a mixture of tetrahydrofuran (12 mL) and triethylamine (12 mL). The mixture was degassed and copper(I) iodide (20 mg, 0.109 mmol) and tetrakis(triphenylphosphine)palladium (63 mg, 0.054 mmol) were added. The reaction mixture was stirred at ambient temperature for 24 h. Further portions of dimethyl(prop-2-ynyl)amine (57 mg, 0.687 mmol), copper(I) iodide (10 mg, 0.0545 mmol) and tetrakis(triphenylphosphine)palladium (31.5 mg, 0.027 mmol) were added and the reaction mixture was stirred under argon for additional 20 h. The mixture was evaporated in vacuo; the residue was dissolved in ethyl acetate (30 mL) and was washed with water (2×15 mL) and brine (10 mL). The organic solution was dried with anhydrous magnesium sulfate and evaporated in vacuo. The residue was purified by flash column chromatography (silica gel Fluka 60, hexanes/ethyl acetate 3:5) yielding methyl (E)-[4-[3-[4-[3-(N,N-dimethylamino)propynyl]phenyl]-3-(3-trifluoromethyl phenyl)allyloxy]-2-methylphenoxy]acetate as oil.

Yield: 230 mg (62%).

$R_F$ (SiO$_2$, hexanes/ethyl acetate 1:1): 0.15.

$^1$H NMR spectrum (300 MHz, CDCl$_3$, $\delta_H$): 7.52-7.39 (m, 6H); 7.14 (d, J=8.3 Hz, 2H); 6.69-6.57 (m, 3H); 6.35 (t, J=6.7 Hz, 1H); 4.59 (s, 2H); 4.52 (d, J=6.7 Hz, 2H); 3.79 (s, 3H); 3.50 (s, 2H); 2.39 (s, 6H); 2.25 (s, 3H).

To a solution of the above ester (218 mg, 0.40 mmol) in tetrahydrofuran/methanol mixture (4:1, 11 mL), a solution of lithium hydroxide monohydrate (34 mg, 0.81 mmol) in distilled water (1 mL) was added under cooling (0° C.). The solution was stirred at ambient temperature for 2 h. Glacial acetic acid (0.046 mL) was added and the mixture was stirred for further 10 min. The solution was diluted with ether (30 mL), washed with water (2×15 mL) and brine (10 mL), dried with anhydrous magnesium sulfate and evaporated in vacuo. The residue was triturated with hexanes (2×10 mL) yielding the title acid as pale solid.

Yield: 147 mg (37%).

M.p.: 55-64° C.

$R_F$ (SiO$_2$, chloroform/methanol 9:1): 0.15.

$^1$H NMR spectrum (300 MHz, CDCl$_3$+AcOH-d$_4$, $\delta_H$): 7.55-7.34 (m, ~6H); 7.12 (m, ~2H); 6.69-6.52 (m, 3H); 6.40 (t, J=6.6 Hz, 1H); 4.57 (s, 2H); 4.49 (d, J=6.7 Hz, 2H); 4.17 (s, 2H); 2.90 (s, 6H); 2.25 (s, 3H).

Example 38

(Z)-[4-[3-(4-Cyclopropylphenyl)-3-[4-[3-(morpholin-4-yl)propynyl]phenyl]allyloxy]-2-methylphenoxy]acetic Acid

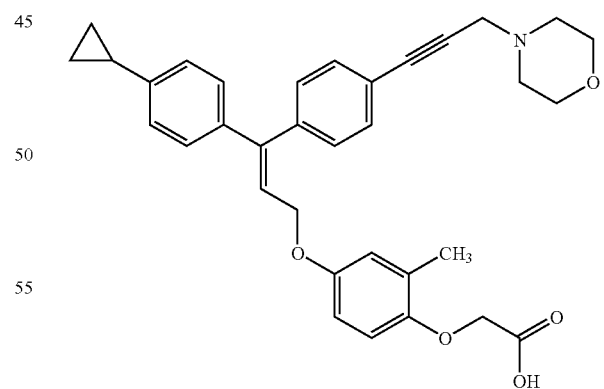

To a degassed solution of 1-bromo-4-cyclopropylbenzene (4.4 g, 22.3 mmol; prepared according to J. Org. Chem. 1976, 41, 2262) in anhydrous tetrahydrofuran (22 mL), copper(I) iodide (134 mg, 0.70 mol) and tetrakis(triphenylphosphine) palladium (773 mg, 0.67 mmol) were added and the mixture was cooled down with ice bath. 1,8-Diazabicyclo[5.4.0]-undec-7-ene (4 mL, 26.8 mmol) was added and the reaction mixture was degassed again. A degassed solution of prop-2-yn-1-ol (1.56 mL, 26.8 mmol) in anhydrous tetrahydrofuran (3 mL) was added dropwise afterwards and the reaction mixture was stirred at 50° C. over night under nitrogen. After cooling, the mixture was diluted with ether (100 mL) and washed with water (40 mL) and 15% hydrochloric acid (2×40 mL). The aqueous layer was extracted with ether (5×40 mL). Combined organic extracts were finally washed with 10% aqueous solution of sodium hydrogen carbonate (40 mL) and brine (2×40 mL) and dried with anhydrous magnesium sulfate. The crude product was purified by column chromatography (silica gel Fluka 60, hexanes/ethyl acetate 10:1-8:1) yielding 3-(4-cyclopropylphenyl)prop-2-yn-1-ol as yellow oil, which solidified in refrigerator.

Yield: 1.30 g (34%).

$R_F$ (SiO$_2$, hexanes/ethyl acetate 4:1): 0.20.

$^1$H NMR spectrum (300 MHz, CDCl$_3$, $\delta_H$): 7.34 (d, J=8.2 Hz, 2H); 7.02 (d, J=8.2 Hz, 2H); 4.51 (d, J=6.1 Hz, 2H); 1.90 (m, 1H); 1.69 (t, J=6.1 Hz, 1H); 1.01 (m, 2H); 0.73 (m, 2H).

1 M Solution of lithium aluminum hydride in tetrahydrofuran (11.3 mL, 11.3 mmol) was added to sodium methoxide (19 mg, 0.350 mmol) under nitrogen. The mixture was cooled to 0° C. and a solution of the above hydroxy derivative (1.30 g, 7.50 mmol) in dry tetrahydrofuran (12 mL) was added dropwise. The reaction mixture was stirred at 0° C. for 3.5 h; dry ethyl acetate (2.25 mL, 22.9 mmol) was added and the whole mixture was stirred at ambient temperature for 30 min. A degassed solution of 1,4-diiodobenzene (2.47 g, 7.50 mmol) in anhydrous tetrahydrofuran (12 mL), anhydrous zinc chloride (0.611 g, 4.53 mmol), tris(dibenzylidene-acetone) dipalladium chloroform complex (0.165 g, 0.16 mmol) and tri-(2-furyl)phosphine (0.191 g, 0.82 mmol) were added; the mixture was degassed and stirred at 65° C. for 22 h under atmosphere of nitrogen. The suspension was cooled down; methanol (3.5 mL) was added and the mixture was stirred for additional 1 h. After dilution with ether (40 mL) and saturated aqueous solution of ammonium chloride (2 mL), the mixture was filtered through a paddle of silica gel and the paddle was thoroughly washed with ether (80 mL). Solvents were evaporated in vacuo and the residue was separated by flash column chromatography (silica gel Fluka 60, dichloromethane/ethyl acetate 20:1) affording (Z)-3-(4-cyclopropylphenyl)-3-(4-iodophenyl)prop-2-en-1-ol as yellow oil, which solidifies at 0° C.

Yield: 0.98 g (35%).

$R_F$ (SiO$_2$, dichloromethane/ethyl acetate 20:1): 0.50.

$^1$H NMR spectrum (300 MHz, CDCl$_3$, $\delta_H$): 7.72 (d, J=8.3 Hz, 2H); 7.14 (d, J=8.4 Hz, 2H); 7.01 (d, J=8.3 Hz, 2H); 6.93 (d, J=8.3 Hz, 2H); 6.22 (t, J=6.9 Hz, 1H); 4.20 (m, 2H); 1.90 (m, 1H); 1.49 (t, J=5.4 Hz, 1H); 0.99 (m, 2H); 0.71 (m, 2H).

The above allyl alcohol (0.98 g, 2.60 mmol), methyl (4-hydroxy-2-methylphenoxy)acetate (0.545 g, 2.78 mmol; compound VÚFB-21004) and triphenylphosphine (0.782 g, 2.98 mmol) were dissolved in a mixture of anhydrous toluene (12 mL) and tetrahydrofuran (4 mL). The mixture was cooled to 0° C., kept under nitrogen and a degassed solution of diisopropyl azodicarboxylate (0.587 mL, 2.98 mmol) in anhydrous tetrahydrofuran (5 mL) was added dropwise. The reaction mixture was allowed to warm up to ambient temperature and then was stirred over night. The solvents were evaporated in vacuo and the residue was submitted to flash column chromatography (silica gel Fluka 60, hexanes/ethyl acetate 8:1) affording methyl (Z)-[4-[3-(4-cyclopropylphenyl)-3-(4-iodophenyl)allyloxy]-2-methylphenoxy]-acetate as solid mass.

Yield: 890 mg (62%).

$R_F$ (SiO$_2$, hexanes/ethyl acetate 4:1): 0.45.

$^1$H NMR spectrum (300 MHz, CDCl$_3$, $\delta_H$): 7.73 (d, J=8.2 Hz, 2H); 7.14 (d, J=8.2 Hz, 2H); 7.00 (d, J=8.2 Hz, 2H); 6.94 (d, J=8.2 Hz, 2H); 6.70 (d, J=2.5 Hz, 1H); 6.65 (d, J=8.8 Hz, 1H); 6.59 (dd, J=8.8 and 2.7 Hz, 1H); 6.28 (t, J=6.7 Hz, 1H); 4.60 (s, 2H); 4.49 (d, J=6.7 Hz, 2H); 3.81 (s, 3H); 2.27 (s, 3H); 1.89 (m, 1H); 0.99 (m, 2H); 0.71 (m, 2H).

To a degassed solution of the above ester (392 mg, 0.707 mmol), N-propargylmorpholine (176 mg, 1.41 mmol) and diisopropyl amine (0.466 mL, 3.3 mmol) in anhydrous tetrahydrofuran (11 mL), bis(triphenylphosphine)palladium(II) dichloride (37 mg, 0.053 mmol) and copper(I) iodide (12.0 mg, 0.063 mmol) were added. The reaction mixture was stirred at ambient temperature for 7 h under nitrogen. The solvents were evaporated in vacuo and the residue was purified by flash column chromatography (silica gel Fluka 60, chloroform/methanol 100:0-95:5) yielding methyl (Z)-[4-[3-(4-cyclopropylphenyl)-3-[4-[3-(morpholin-4-yl)propynyl]phenyl]allyloxy]-2-methylphenoxy]acetate as yellow oil.

Yield: 370 mg (95%).

$R_F$ (SiO$_2$, chloroform/methanol 95:5): 0.45.

$^1$H NMR spectrum (300 MHz, CDCl$_3$, $\delta_H$): 7.45 (d, J=8.1 Hz, 2H); 7.14 (d, J=8.0 Hz, 2H); 7.13 (d, J=8.1 Hz, 2H); 6.98 (d, J=8.2 Hz, 2H); 6.67 (d, J=2.5 Hz, 1H); 6.62 (d, J=8.8 Hz, 1H); 6.56 (dd, J=8.9 and 2.8 Hz, 1H); 6.26 (t, J=6.7 Hz, 1H); 4.58 (s, 2H); 4.48 (d, J=6.7 Hz, 2H); 3.78 (m, 7H); 3.53 (s, 2H); 2.66 (t, J=4.5 Hz, 4H); 2.24 (s, 3H); 1.87 (m, 1H); 0.97 (m, 2H); 0.69 (m, 2H).

The above ester (360 mg, 0.65 mmol) was dissolved in a mixture of tetrahydrofuran (10 mL) and methanol (5 mL) and a solution of lithium hydroxide monohydrate (62 mg, 1.47 mmol) in distilled water (2.5 mL) was added. The mixture was stirred over night and then diluted with saturated aqueous solution of ammonium chloride (53 mL). The resulting mixture was extracted with ether (3×50 mL); the organic layers were combined, dried with anhydrous magnesium sulfate and evaporated in vacuo. The residue was triturated with hexanes (2×10 mL) yielding the title acid as white powder.

Yield: 177 mg (51%).

M.p.: 178-182° C.

$R_F$ (SiO$_2$, chloroform/methanol 4:1): 0.50.

$^1$H NMR spectrum (300 MHz, CDCl$_3$, $\delta_H$): 7.45 (d, J=8.1 Hz, 2H); 7.15 (d, J=8.1 Hz, 2H); 7.13 (d, J=8.2 Hz, 2H); 6.99 (d, J=8.3 Hz, 2H); 6.68 (d, J=2.8 Hz, 1H); 6.66 (d, J=8.8 Hz, 1H); 6.54 (dd, J=8.8 Hz; 2.9 Hz, 1H); 6.28 (t, J=6.8 Hz, 1H); 4.60 (s, 2H); 4.48 (d, J=6.8 Hz, 2H); 3.88 (t, J=4.6 Hz, 4H); 3.81 (s, 2H); 3.00 (t, J=4.5 Hz, 4H); 2.24 (s, 3H); 1.88 (m, 1H); 0.98 (m, 2H); 0.70 (m, 2H).

Example 39

(Z)-[4-[3-(4-Cyclopropylphenyl)-3-[4-[3-(N,N-dimethylamino)propynyl]phenyl]allyloxy]-2-methylphenoxy]acetic Acid

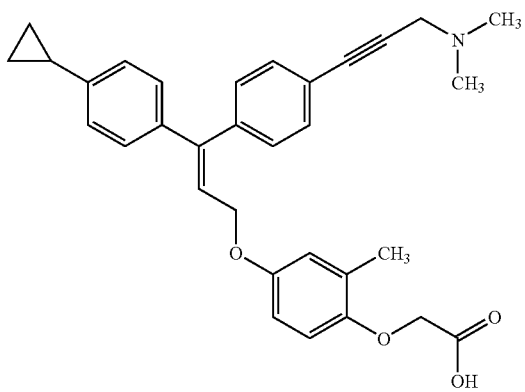

To a degassed solution of the ester (486 mg, 0.877 mmol; prepared as described in example 38), 1-(N,N-dimethylamino)prop-2-yne (150 mg, 1.80 mmol) and diisopropyl amine (0.589 mL, 4.24 mmol) in anhydrous tetrahydrofuran (12 mL), bis(triphenylphosphine)palladium(II) dichloride (47 mg, 0.067 mmol) and copper(I) iodide (14.0 mg, 0.074 mmol) were added. The reaction mixture was stirred at ambient temperature for 6 h under nitrogen. The solvents were evaporated in vacuo and the residue was purified by flash column chromatography (silica gel Fluka 60, chloroform/methanol 100:0-95:5) yielding methyl (Z)-[4-[3-(4-cyclopropylphenyl)-3-[4-[3-(N,N-dimethylamino)propynyl]phenyl]allyloxy]-2-methylphenoxy]acetate as yellow oil.

Yield: 431 mg (96%).

$R_F$ (SiO$_2$, chloroform/methanol 95:5): 0.30.

$^1$H NMR spectrum (300 MHz, CDCl$_3$, $\delta_H$): 7.47 (d, J=8.3 Hz, 2H); 7.16 (d, J=8.3 Hz, 2H); 7.14 (d, J=8.3 Hz, 2H); 7.00 (d, J=8.3 Hz, 2H); 6.69 (d, J=2.7 Hz, 1H); 6.64 (d, J=8.8 Hz, 1H); 6.58 (dd, J=8.8 and 2.8 Hz, 1H); 6.27 (t, J=6.7 Hz, 1H); 4.60 (s, 2H); 4.51 (d, J=6.7 Hz, 2H); 3.81 (s, 3H); 3.51 (s, 2H); 2.40 (s, 6H); 2.26 (s, 3H); 1.89 (m, 1H); 0.98 (m, 2H); 0.70 (m, 2H).

The above ester (420 mg, 0.824 mmol) was dissolved in a mixture of tetrahydrofuran (14 mL) and methanol (7 mL) and a solution of lithium hydroxide monohydrate (78 mg, 1.85 mmol) in distilled water (3 mL) was added. The mixture was stirred over night and then diluted with saturated aqueous solution of ammonium chloride (68 mL). The resulting mixture was extracted with ether (3×60 mL); the organic layers were combined, dried with anhydrous magnesium sulfate and evaporated in vacuo. The residue was triturated with hexanes yielding the title acid as white powder.

Yield: 267 mg (65%).

M.p.: 130-134° C.

$R_F$ (SiO$_2$, chloroform/methanol 4:1): 0.30.

$^1$H NMR spectrum (300 MHz, CDCl$_3$, $\delta_H$): 7.47 (d, J=8.1 Hz, 2H); 7.18 (d, J=8.1 Hz, 2H); 7.13 (d, J=8.2 Hz, 2H); 6.99 (d, J=8.3 Hz, 2H); 6.68 (d, J=2.8 Hz, 1H); 6.64 (d, J=8.9 Hz, 1H); 6.53 (dd, J=8.9 and 2.9 Hz, 1H); 6.30 (t, J=6.8 Hz, 1H); 4.56 (s, 2H); 4.45 (d, J=6.8 Hz, 2H); 4.15 (s, 2H); 2.88 (s, 6H); 2.24 (s, 3H); 1.88 (m, 1H); 0.98 (m, 2H); 0.70 (m, 2H)

Example 40

(E)-[2-Methyl-4-[3-(4-methylsulfanylphenyl)-3-[4-[3-(morpholin-4-yl)propynyl]phenyl]-allyloxy]phenoxy]acetic Acid

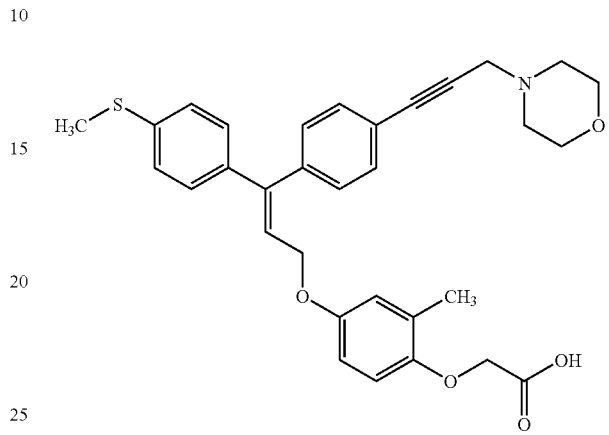

To a degassed solution of 4-bromothioanisole (10.15 g, 50.0 mmol) in tetrahydrofuran (50 mL) were in the following order added: copper(I) iodide (286 mg, 1.5 mmol), tetrakis(triphenylphosphine)palladium (1.73 g, 1.5 mmol), and 1,8-diazabicyclo[5.4.0]undec-7-ene (9.05 mL, 60.0 mmol). The resulting mixture was degassed one more time and a solution of propargyl alcohol (3.5 mL, 60.0 mmol) in tetrahydrofuran (5 mL) was added over period of 10 min. The reaction mixture was slowly heated up to 50° C. and then stirred at this temperature over night (~20 h). The mixture was diluted with ether (350 mL) and 5% hydrochloric acid (100 mL) was added. The mixture was filtered and the phases were separated. The aqueous phase was extracted with ether (2×60 mL) and collected ethereal solutions were washed with 1 M hydrochloric acid (30 mL) and saturated aqueous solution of sodium hydrogen carbonate (2×50 mL), dried with anhydrous magnesium sulfate and evaporated in vacuo. The residue was purified by column chromatography (silica gel Fluka 60, chloroform) affording 3-(4-methylsulfanylphenyl)prop-2-yn-1-ol.

Yield: 8.5 g (95%).

$R_F$ (SiO$_2$, chloroform): 0.25.

$^1$H NMR spectrum (300 MHz, CDCl$_3$, $\delta_H$): 7.35 (d, J=8.5 Hz, 2H); 7.18 (d, J=8.5 Hz, 2H); 4.50 (d, J=4.9 Hz, 2H); 2.49 (s, 3H); 1.94 (m, 1H).

Sodium methoxide (106 mg, 2 mmol) was added to 1 M solution of lithium aluminum hydride in tetrahydrofuran (43.8 mL, 43.8 mmol) under argon. The mixture was cooled to 0° C. and a solution of the above hydroxy derivative (7.8 g, 43.8 mmol) in tetrahydrofuran (100 mL) was added over 30 min. The reaction mixture was stirred at 0° C. for 3 h; dry ethyl acetate (7.1 mL, 72 mmol) was added and the whole mixture was stirred at ambient temperature for further 20 min. A degassed solution of 1,4-diiodobenzene (20.2 g, 61.3 mmol) in dry tetrahydrofuran (30 mL), anhydrous zinc chloride (3.58 g, 26.3 mmol), tris(dibenzylideneacetone)dipalladium chloroform complex (0.91 g, 0.875 mmol), and tri-2-furylphosphine (0.813 g, 3.5 mmol) were added; the mixture was degassed and then heated at 55° C. for 20 h under argon. The suspension was cooled down; methanol (22 mL) was added and the mixture was stirred for additional 1 h. The reaction mixture was diluted with ether (450 mL) and saturated aqueous solution of ammonium chloride (11 mL) was added. The mixture was filtered through a paddle of silica gel and the paddle was thoroughly washed with ether (150 mL). Solvents were evaporated in vacuo and the residue was separated by flash column chromatography (silica gel Fluka 60, hexanes/ethyl acetate 4:1) affording (Z)-3-(4-iodophenyl)-3-(4-methylsulfanylphenyl)prop-2-en-1-ol as solidifying oil.

Yield: 5.45 g (33%).

M.p.: 91-95° C.

$R_F$ (SiO$_2$, hexanes/ethyl acetate 3:1): 0.20.

$^1$H NMR spectrum (300 MHz, CDCl$_3$, $\delta_H$): 7.71 (d, J=8.3 Hz, 2H); 7.15 (m, 4H); 6.91 (d, J=8.3 Hz, 2H); 6.22 (t, J=6.9 Hz, 1H); 4.19 (d, J=6.9 Hz, 2H); 2.47 (s, 3H); 1.53 (bs, 1H).

The above allyl alcohol (4.97 g, 13.0 mmol), methyl (4-hydroxy-2-methylphenoxy)acetate (2.81 g, 14.3 mmol; example 2) and triphenylphosphine (4.09 g, 15.6 mmol) were dissolved in a mixture of anhydrous toluene (200 mL) and tetrahydrofuran (75 mL). The mixture was cooled to 0° C., kept under argon and a degassed solution of diisopropyl azodicarboxylate (3.32 mL, 15.6 mmol) in anhydrous tetrahydrofuran (25 mL) was added dropwise during 30 min. The reaction mixture was allowed to warm up the ambient temperature with the bath and then was stirred for 2 days. The solvents were evaporated in vacuo and the residue was submitted to flash column chromatography (silica gel Fluka 60, hexanes/ethyl acetate 9:1) affording methyl (Z)-[4-[3-(4-iodophenyl)-3-(4-methylsulfanyl-phenyl)allyloxy]-2-methylphenoxy]acetate as solid mass.

Yield: 3.95 g (54%).

$R_F$ (SiO$_2$, hexanes/ethyl acetate 3:1): 0.45.

$^1$H NMR spectrum (300 MHz, CDCl$_3$, $\delta_H$): 7.71 (d, J=8.0 Hz, 2H); 7.15 (m, 4H); 6.94 (d, J=8.0 Hz, 2H); 6.67-6.34 (m, 3H); 6.28 (t, J=6.6 Hz, 1H); 4.58 (s, 2H); 4.47 (d, J=6.6 Hz, 2H); 3.79 (s, 3H); 2.47 (s, 3H); 2.25 (s, 3H).

4-Propargylmorpholine (1.40 g, 2.50 mmol) was added to a solution of the above iodo derivative (1.40 g, 2.50 mmol) in tetrahydrofuran (18 mL) and triethylamine (18 mL). The mixture was degassed and copper(I) iodide (76 mg, 0.40 mmol) and tris(triphenylphosphine)palladium (231 mg, 0.20 mmol) were added. The reaction mixture was stirred under argon at ambient temperature for 20 h, filtered and the filtrate was evaporated in vacuo. The residue was purified by flash column chromatography (silica gel Fluka 60, hexanes/ethyl acetate 2:1) yielding methyl (E)-[2-methyl-4-[3-(4-methylsulfanylphenyl)-3-[4-[3-(morpholin-4-yl)propynyl]-phenyl]allyloxy]phenoxy]acetate.

Yield: 1.62 g (97%).

$R_F$ (SiO$_2$, hexanes/ethyl acetate 2:1): 0.15.

$^1$H NMR spectrum (300 MHz, CDCl$_3$, $\delta_H$): 7.46 (d, J=8.2 Hz, 2H); 7.36 (m, 2H); 7.14 (d, J=8.2 Hz, 2H); 6.67-6.54 (m, 3H); 6.28 (t, J=6.7 Hz, 1H); 4.58 (s, 2H); 4.48 (d, J=6.7 Hz, 2H); 3.80 (s, 3H); 3.77 (m, 4H); 3.53 (s, 2H); 2.66 (m, 4H); 2.47 (s, 3H); 2.25 (s, 3H).

To a solution of the above ester (1.36 g, 2.44 mmol) in tetrahydrofuran/methanol mixture (1:2, 60 mL), a solution of lithium hydroxide monohydrate (0.205 g, 4.88 mmol) in distilled water (6 mL) was added. The solution was stirred for 2 h at ambient temperature and acetic acid (0.56 mL; 9.8 mmol) was added. The resulting mixture was stirred for further 10 min and then evaporated in vacuo. The residue was dissolved in chloroform (80 mL), washed with water (2×20 mL), dried with anhydrous magnesium sulfate and evaporated in vacuo. The residue was triturated with hexanes (3×15 mL) yielding the title acid as tan solid.

Yield: 925 mg (68%).

M.p.: 179-184° C.

$R_F$ (SiO$_2$, chloroform/methanol 4:1): 0.40.

$^1$H NMR spectrum (300 MHz, CDCl$_3$, $\delta_H$): 7.49 (d, J=8.1 Hz, 2H); 7.16 (m, 6H); 6.68-6.54 (m, 3H); 6.31 (t, J=6.8 Hz, 1H); 4.60 (s, 2H); 4.48 (d, J=6.8 Hz, 2H); 4.04 (s, 2H); 3.95 (m, 4H); 3.25 (m, 4H); 2.47 (s, 3H); 2.24 (s, 3H).

Example 41

(E)-[2-Methyl-4-[3-(4-methylsulfinylphenyl)-3-[4-[3-(morpholin-4-yl)propynyl]phenyl]allyloxy]-phenoxy]acetic Acid

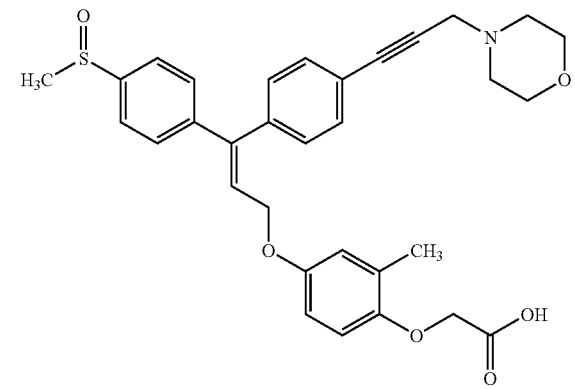

30% Aqueous hydrogen peroxide (0.0613 mL, 0.6 mmol) was added to a solution of (E)-[2-methyl-4-[3-(4-methylsulfanylphenyl)-3-[4-[3-(morpholin-4-yl)propynyl]phenyl]-allyloxy]-phenoxy]acetic acid (272 mg, 0.5 mmol; example 40) in glacial acetic acid (7 mL) at 5° C. under stirring. The mixture was left to stand over night at ambient temperature, diluted with water and extracted with ethyl acetate (2×30 mL). The collected extracts were alkalized with 15% solution of ammonium hydroxide; the solution was decanted from the separated oil and the oil was and dissolved in chloroform (45 mL). The solution was washed with water (2×10 mL), dried with anhydrous magnesium sulphate and evaporated in vacuo. The residue was triturated with hexanes (3×15 mL) to yield the title compound as pale solid.

Yield: 162 mg (58%).

M.p.: 137-142° C. (amorphous).

$R_F$ (SiO$_2$, chloroform/methanol 4:1): 0.35.

$^1$H NMR spectrum (300 MHz, CDCl$_3$, AcOH-d$_4$, $\delta_H$): 7.61 (d, J=8.3 Hz, 2H); 7.49 (d, J=8.0 Hz, 2H); 7.41 (d, J=8.3 Hz, 2H); 7.16 (d, J=8.0 Hz, 2H); 6.68-6.53 (m, 3H); 6.40 (t, J=6.6

Hz, 1H); 4.55 (s, 2H); 4.52 (d, J=6.6 Hz, 2H); 3.91 (s, 2H); 3.10 (m, 4H); 3.25 (m, 4H); 2.81 (s, 3H); 2.24 (s, 3H).

Example 42

(E)-[2-Methyl-4-[3-[4-[(5-methylthiophen-2-yl)ethynyl]phenyl]-3-(3-trifluoromethylphenyl)allyloxy]phenoxy]acetic Acid

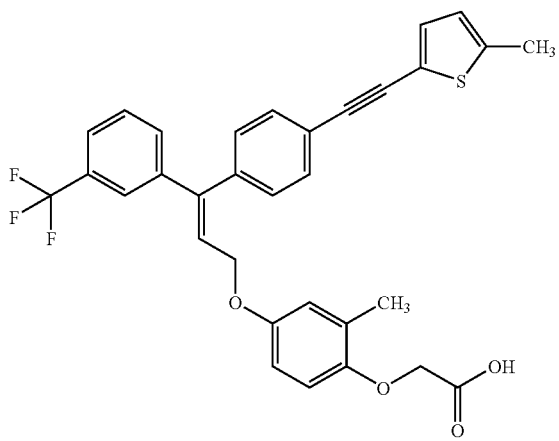

2-Ethynyl-5-methylthiophene (176 mg, 1.442 mmol) and diisopropylamine (0.475 mL, 3.39 mmol) were added to a solution of methyl (E)-[4-[3-(4-iodophenyl)-3-(3-trifluoromethylphenyl)allyloxy]-2-methylphenoxy]acetate (420 mg, 0.721 mmol; prepared as described in example 34) in tetrahydrofuran (10 mL). The mixture was degassed and copper(I) iodide (11.0 mg, 0.0576 mmol) and bis(triphenylphosphine)palladium(II) dichloride (25.3 mg, 0.0361 mmol) were added. The reaction mixture was stirred at ambient temperature for 20 h and evaporated in vacuo. The residue was purified by flash column chromatography (silica gel Fluka 60, hexanes/ethyl acetate 19:1) yielding methyl (E)-[2-methyl-4-[3-[4-[(5-methylthiophen-2-yl)ethynyl]phenyl]-3-(3-trifluoromethyl phenyl)allyloxy]phenoxy]acetate as yellow oil.

Yield: 291 mg (70%).

$R_F$ (SiO$_2$, chloroform/methanol 9:1): 0.15.

$^1$H NMR spectrum (300 MHz, CDCl$_3$, $\delta_H$): 7.53 (m, 4H); 7.41 (m, 2H); 7.17 (d, J=8.3 Hz, 2H); 7.10 (d, J=3.6 Hz, 1H); 6.69-6.56 (m, 3H); 6.36 (t, J=6.7 Hz, 1H); 4.59 (s, 2H); 4.53 (d, J=6.7 Hz, 2H); 3.79 (s, 3H); 2.49 (s, 3H); 2.25 (s, 3H).

To a solution of the above ester (201 mg, 0.509 mmol) in tetrahydrofuran/methanol mixture (4:1, 11 mL), a solution of lithium hydroxide monohydrate (42.3 mg, 1.0 mmol) in distilled water (1 mL) was added under cooling (0° C.). The solution was stirred at ambient temperature for 2 h, acidified with acetic acid (0.32 mL) and the mixture was stirred for further 10 min. The solution was diluted with ether (30 mL); the mixture was washed with water (2×15 mL) and brine (10 mL), dried with anhydrous magnesium sulfate and evaporated in vacuo. The residue was triturated with hexanes (2×10 mL) yielding the title acid as pale solid.

Yield: 144 mg (51%).

M.p.: 129-134° C.

$R_F$ (SiO$_2$, chloroform/methanol 9:1): 0.20.

$^1$H NMR spectrum (300 MHz, CDCl$_3$, $\delta_H$): 7.53 (m, 4H); 7.41 (m, 2H); 7.18 (d, J=8.2 Hz, 2H); 7.10 (d, J=3.6 Hz, 1H); 6.70-6.58 (m, 4H); 6.35 (t, J=6.6 Hz, 1H); 4.62 (s, 2H); 4.54 (d, J=6.6 Hz, 2H); 2.49 (s, 3H); 2.25 (s, 3H).

Example 43

(Z)-[4-[3-(4-tert-Butyl phenyl)-3-[4-[3-(N,N-dimethylamino)propynyl]phenyl]allyloxy]-2-methylphenoxy]acetic Acid

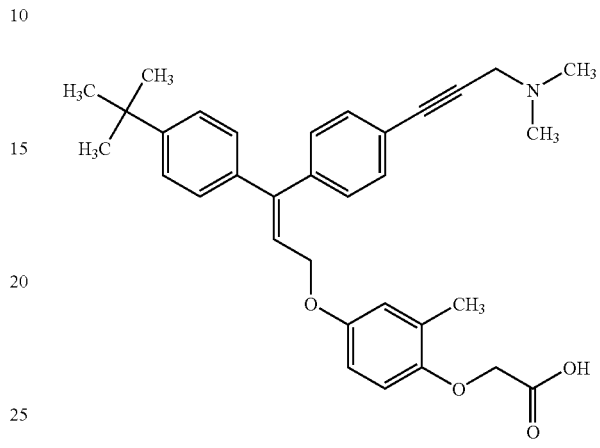

1-(N,N-Dimethylamino)prop-2-yne (0.131 mL, 1.23 mmol) and diisopropylamine (0.40 mL, 2.85 mmol) were added to a solution of the methyl (Z)-[4-[3-(4-tert-butylphenyl)-3-(4-iodophenyl)allyloxy]-2-methylphenoxy]acetate (350 mg, 0.614 mmol; prepared as described in example 30) in tetrahydrofuran (10 mL). The mixture was degassed and copper(I) iodide (10 mg, 0.053 mmol) and bis(triphenylphosphine)palladium(II) dichloride (22 mg, 0.031 mmol) were added. The reaction mixture was stirred at ambient temperature over night, filtered and the filtrate was evaporated in vacuo. The residue was purified by flash column chromatography (silica gel Fluka 60, dichloromethane/methanol 98:2) yielding methyl (Z)-[4-[3-(4-tert-butyl phenyl)-3-[4-[3-(N,N-dimethylamino)propynyl]phenyl]allyloxy]-2-methylphenoxy]acetate as oil.

Yield: 263 mg (82%).

$R_F$ (SiO$_2$, chloroform saturated with ammonia/methanol 97:3): 0.60.

$^1$H NMR spectrum (300 MHz, CDCl$_3$, $\delta_H$): 7.46 (d, J=8.2 Hz, 2H); 7.31 (d, J=8.5 Hz, 2H); 7.18 (d, J=8.5 Hz, 2H); 7.16 (d, J=8.2 Hz, 2H); 6.67 (d, J=2.8 Hz, 1H); 6.62 (d, J=8.8 Hz, 1H); 6.56 (dd, J=8.8 and 2.8 Hz, 1H); 6.29 (t, J=6.6 Hz, 1H); 4.58 (s, 2H); 4.50 (d, J=6.7 Hz, 2H); 3.79 (s, 3H); 3.51 (s, 2H); 2.39 (s, 6H); 2.24 (s, 3H); 1.31 (s, 9H).

To a solution of the above ester (255 mg, 0.485 mmol) in tetrahydrofuran/methanol mixture (5:1, 6 mL), a solution of lithium hydroxide monohydrate (61 mg, 1.45 mmol) in distilled water (1 mL) was added under cooling to 0° C. The solution was stirred for 1.5 h under cooling, acetic acid (0.083 mL; 1.45 mmol) was added and the resulting mixture was stirred for further 10 min. The solution was diluted with chloroform (40 mL) and water (30 mL); the phases were separated and the aqueous phase was extracted with chloroform (3×20 mL). The combined organic layers were washed with water (2×20 mL) and brine (2×20 mL). The organic solution was dried with anhydrous magnesium sulfate and evaporated in vacuo. The residue was triturated with hexanes (2×4 mL) yielding the title acid as white solid.

Yield: 206 mg (83%).
M.p.: 165-173° C.
$R_F$ (SiO$_2$, ethyl acetate/methanol 1:1): 0.20.
$^1$H NMR spectrum (300 MHz, CDCl$_3$, $\delta_H$): 7.42 (d, J=8.1 Hz, 2H); 7.32 (d, J=8.5 Hz, 2H); 7.20 (d, J=8.5 Hz, 2H); 7.15 (d, J=8.1 Hz, 2H); 6.70 (d, J=2.8 Hz, 1H); 6.58 (d, J=8.4 Hz, 1H); 6.36 (m, 2H); 4.52 (s, 2H); 4.38 (d, J=7.0 Hz, 2H); 3.86 (s, 2H); 2.67 (s, ~6H); 2.25 (s, 3H); 1.31 (s, 9H).

Example 44

(E)-[4-[3-(4-Chlorophenyl)-3-[4-[3-(4-methylpiperazin-1-yl)propynyl]phenyl]allyloxy]-2-methylphenoxy]acetic Acid

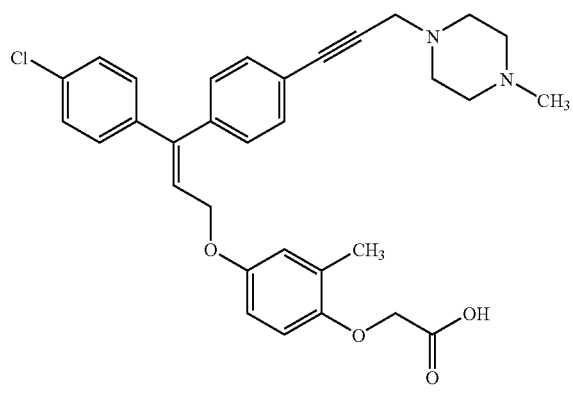

Under nitrogen atmosphere, 1-methyl-4-propargylpiperazine (380 mg, 2.75 mmol) was added to a degassed solution of methyl (Z)-[4-[3-(4-chlorophenyl)-3-(4-iodophenyl)allyloxy]-2-methylphenoxy]acetate (450 mg, 0.82 mmol; prepared as described in example 7) in a mixture of tetrahydrofuran (10 mL) and triethylamine (8 mL) The solution was cooled, tetrakis(triphenylphosphine)palladium (85 mg, 0.073 mmol) and copper(I) iodide (22 mg, 0.115 mmol) were added. The reaction mixture was stirred at ambient temperature for 48 h, diluted with benzene (100 mL) and washed with water (2×50 mL). The organic solution was dried with anhydrous potassium carbonate and subsequently evaporated in vacuo. The residue was purified by column chromatography (silica gel Fluka 60, benzene/ethanol 1:0-1:2) yielding methyl (E)-[4-[3-(4-chlorophenyl)-3-[4-[3-(4-methylpiperazin-1-yl)propynyl]phenyl]-allyloxy]-2-methylphenoxy]acetate.
Yield: 360 mg (80%).
$R_F$ (SiO$_2$, chloroform/ethanol 5:1): 0.45.
$^1$H NMR spectrum (300 MHz, CDCl$_3$, $\delta_H$): 7.46 (d, J=8.1 Hz, 2H); 7.26 (d, J=8.6 Hz, 2H); 7.16 (d, J=8.6 Hz, 2H); 7.12 (d, J=8.1 Hz, 2H); 6.67 (d, J=2.4 Hz, 1H); 6.62 (d, J=8.8 Hz, 1H); 6.56 (dd, J=8.8 and 2.4 Hz, 1H); 6.28 (t, J=6.7 Hz, 1H); 4.58 (s, 2H); 4.49 (d, J=6.7 Hz, 2H); 3.79 (s, 3H); 3.56 (s, 2H); 2.77 (bs, 4H); 2.64 (bs, 4H); 2.38 (s, 6H); 2.25 (s, 3H).

The above ester (0.36 g, 0.658 mmol) was dissolved in ethanol (30 mL), a solution of lithium hydroxide monohydrate (0.10 g, 2.38 mmol) in water (4 mL) was added and the mixture was left to stand for 72 h. The solvents were evaporated in vacuo; the residue was diluted with water (25 mL), acidified with acetic acid (0.25 mL) and extracted with chloroform (2×50 mL). The organic solution was dried with anhydrous potassium carbonate and subsequently evaporated in vacuo. The residue was triturated with hexanes (2×20 mL) yielding the title compound as amorphous solid.
Yield: 0.30 g (86%).
$R_F$ (SiO$_2$, chloroform/ethanol/ammonia 1:1:0.05): 0.10.
$^1$H NMR spectrum (300 MHz, CDCl$_3$, $\delta_H$): 7.41 (d, J=8.0 Hz, 2H); 7.23 (d, J=8.5 Hz, 2H); 7.13 (d, J=8.5 Hz, 2H); 6.99 (d, J=8.0 Hz, 2H); 6.61 (d, J=2.7 Hz, 1H); 6.54 (d, J=9.0 Hz, 1H); 6.27 (m, 2H); 4.41 (m, 4H); 3.61 (s, 2H); 3.10 (bs, 4H); 2.88 (s, 4H); 2.61 (s, 3H); 2.22 (s, 3H).

Example 45

(E)-[4-[3-(4-Chlorophenyl)-3-[4-(3-[N-(2-hydroxyethyl)-N-methylamino]propynyl]phenyl]-allyloxy]-2-methylphenoxy]acetic Acid

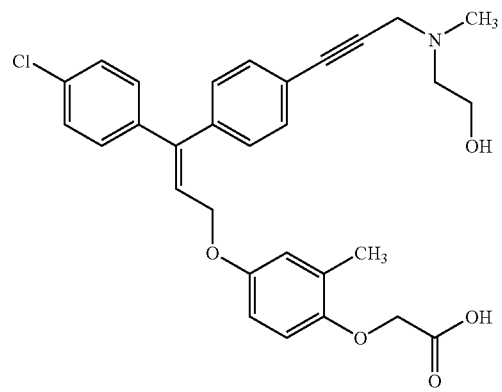

N-(2-Hydroxyethyl)-N-propargylmethylamine (300 mg, 2.65 mmol) was added under nitrogen atmosphere to a degassed solution of methyl (Z)-[4-[3-(4-chlorophenyl)-3-(4-iodophenyl)allyloxy]-2-methylphenoxy]acetate (450 mg, 0.82 mmol; prepared as described in example 7) in a mixture of tetrahydrofuran (10 mL) and triethylamine (8 mL) The solution was cooled to 0° C., tetrakis(triphenylphosphine)palladium (85 mg, 0.073 mmol) and copper(I) iodide (22 mg, 0.115 mmol) were added. The reaction mixture was stirred at ambient temperature for 48 h, dissolved in benzene (100 mL), decanted and evaporated in vacuo. The residue was purified by column chromatography (silica gel Fluka 60, benzene/ethyl acetate 1:0-0:1) yielding methyl (E)-[4-[3-(4-chlorophenyl)-3-[4-(3-[N-(2-hydroxyethyl)-N-methylamino]-propynyl]-phenyl]allyloxy]-2-methylphenoxy]acetate.
Yield: 360 mg (82%).
$R_F$ (SiO$_2$, chloroform/ethanol 5:1): 0.50.
$^1$H NMR spectrum (300 MHz, CDCl$_3$, $\delta_H$): 7.46 (d, J=8.1 Hz, 2H); 7.26 (d, J=8.5 Hz, 2H); 7.16 (d, J=8.5 Hz, 2H); 7.14 (d, J=8.1 Hz, 2H); 6.67 (d, J=2.7 Hz, 1H); 6.62 (d, J=8.8 Hz, 1H); 6.56 (dd, J=8.8 and 2.7 Hz, 1H); 6.29 (t, J=6.7 Hz, 1H); 4.97 (bs, 2H); 4.58 (s, 2H); 4.49 (d, J=6.7 Hz, 2H); 3.79 (s, 3H); 3.75 (bs, 2H); 2.87 (bs, 2H); 2.25 (s, 3H); 2.09 (s, 1H).

The above ester (0.36 g, 0.674 mmol) was dissolved in ethanol (30 mL), a solution of lithium hydroxide monohydrate (0.10 g, 2.38 mmol) in water (4 mL) was added and the mixture was left to stand for 72 h. The solvents were evaporated in vacuo; the residue was diluted with water (25 mL), acidified with acetic acid (0.25 mL) and extracted with chloroform (2×50 mL). The organic solution was dried with anhydrous potassium carbonate and subsequently evaporated in vacuo. The residue was purified by chromatography on silica gel (Fluka 60, ethyl acetate/methanol 9:1-1:1) and the crude product was triturated with hexanes yielding the title compound as amorphous solid.

Yield: 0.22 g (63%).

$R_F$ (SiO$_2$, chloroform/ethanol/ammonia 1:1:0.05): 0.10.

$^1$H NMR spectrum (300 MHz, CDCl$_3$ and CD$_3$COOD, $\delta_H$): 7.52 (d, J=8.0 Hz, 2H); 7.27 (d, J=8.4 Hz, 2H); 7.18 (m, 4H); 6.66 (m, 2H); 6.56 (dd, J=1.7 and 8.7 Hz, 1H); 6.34 (t, J=6.7 Hz, 1H); 4.59 (s, 2H); 4.49 (d, J=6.7 Hz, 2H); 4.36 (s, 2H); 4.02 (s, 2H); 3.43 (s, 2H); 3.02 (s, 3H); 2.23 (s, 3H); 2.06 (s, 1H).

Example 46

(E)-[4-[3-(4-Chlorophenyl)-3-[4-[3-(morpholin-4-yl)propynyl]phenyl]allyloxy]-2-methylphenoxy]acetic Acid

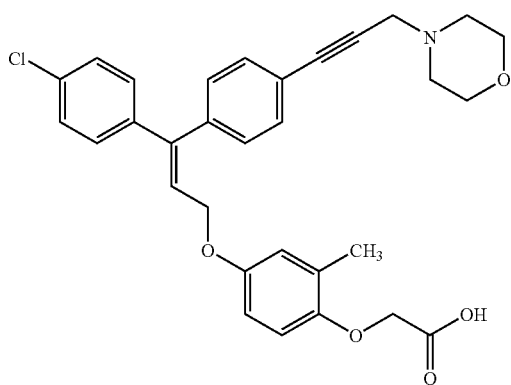

4-Propargylmorpholine (320 mg, 2.4 mmol) was added under nitrogen atmosphere to a degassed solution of methyl (Z)-[4-[3-(4-chlorophenyl)-3-(4-iodophenyl)allyloxy]-2-methylphenoxy]acetate (450 mg, 0.82 mmol; prepared as described in example 7) in a mixture of tetrahydrofuran (10 mL) and triethylamine (8 mL) The solution was cooled to 0° C. and tetrakis(triphenylphosphine)palladium (85 mg, 0.073 mmol) and copper(I) iodide (22 mg, 0.115 mmol) were added. The reaction mixture was stirred at ambient temperature for 72 h, diluted with benzene (100 mL) and washed with water (2×50 mL). The organic solution was dried with anhydrous potassium carbonate and subsequently evaporated in vacuo. The residue was purified by column chromatography (silica gel Fluka 60, benzene/ethyl acetate 1:0-0:1) yielding methyl (E)-[4-[3-(4-chlorophenyl)-3-[4-[3-(morpholin-4-yl)propynyl]phenyl]-allyloxy]-2-methylphenoxy]acetate contaminated with ca. 20% of 1,6-bis(morpholin-4-yl)-2,4-hexadiyne.

Yield: 500 mg (89% calculated on pure ester).

$R_F$ (SiO$_2$, chloroform/ethanol 9:1): 0.65.

$^1$H NMR spectrum (300 MHz, CDCl$_3$, $\delta_H$, signals belonging to the ester): 7.46 (d, J=8.1 Hz, 2H); 7.26 (d, J=8.6 Hz, 2H); 7.16 (d, J=8.6 Hz, 2H); 7.13 (d, J=8.1 Hz, 2H); 6.67 (d, J=2.7 Hz, 1H); 6.62 (d, J=8.8 Hz, 1H); 6.56 (dd, J=8.8 and 2.7 Hz, 1H); 6.28 (t, J=6.7 Hz, 1H); 4.58 (s, 2H); 4.49 (d, J=6.7 Hz, 2H); 3.79 (s, 3H); 3.76 (m, 4H); 3.53 (s, 2H); 2.66 (m, 4H); 2.25 (s, 3H).

The above mixture (0.47 g, 0.688 mmol) was dissolved in ethanol (30 mL), a solution of lithium hydroxide monohydrate (0.10 g, 2.38 mmol) in water (4 mL) was added and the mixture was left to stand for 72 h. The solvents were evaporated in vacuo; the residue was diluted with water (25 mL), acidified with acetic acid (0.25 mL) and extracted with chloroform (2×50 mL). The organic solution was dried with anhydrous potassium carbonate and subsequently evaporated in vacuo. The residue was purified by chromatography on silica gel (Fluka 60, chloroform/ethanol 20:1-1:1) yielding insufficiently pure title compound that was further purified using preparative HPLC on reverse phase column (gradient elution with 0.1% formic acid/acetonitrile). This afforded the pure title compound as amorphous solid.

Yield: 0.16 g (44%).

$R_F$ (SiO$_2$, chloroform/ethanol/ammonia 1:1:0.05): 0.15.

$^1$H NMR spectrum (300 MHz, CDCl$_3$, $\delta_H$): 7.45 (d, J=8.1 Hz, 2H); 7.25 (d, J=8.5 Hz, 2H); 7.13 (m, 4H); 6.65 (d, J=2.7 Hz, 1H); 6.62 (d, J=8.7 Hz, 1H); 6.51 (dd, J=2.7 and 8.7 Hz, 1H); 6.29 (t, J=6.6 Hz, 1H); 4.52 (s, 2H); 4.45 (d, J=6.6 Hz, 2H); 3.86 (bs, 4H); 3.80 (s, 2H); 2.99 (s, 4H); 2.24 (s, 3H).

Example 47

(E)-[4-[3-(4-Chlorophenyl)-3-[4-[3-(4-hydroxypiperidin-1-yl)propynyl]phenyl]allyloxy]-2-methylphenoxy]acetic Acid

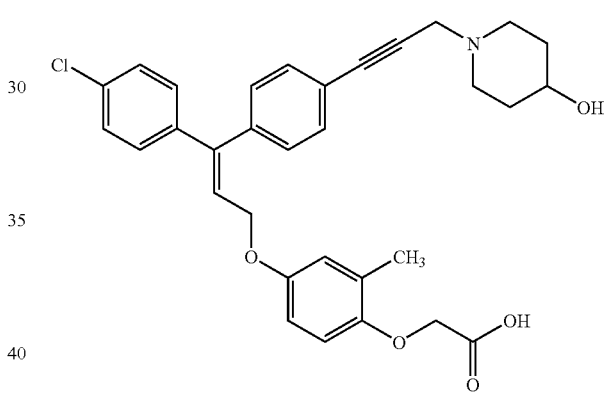

4-Hydroxy-1-propargylpiperidine (280 mg, 2.01 mmol) was added under nitrogen atmosphere to a degassed solution of methyl (Z)-[4-[3-(4-chlorophenyl)-3-(4-iodophenyl)allyloxy]-2-methylphenoxy]acetate (450 mg, 0.82 mmol; prepared as described in example 7) in a mixture of tetrahydrofuran (10 mL) and triethylamine (8 mL) The solution was cooled to 0° C.; tetrakis(triphenylphosphine)palladium (85 mg, 0.073 mmol) and copper(I) iodide (22 mg, 0.115 mmol) were added. The reaction mixture was stirred at ambient temperature for 72 h, diluted with benzene (100 mL), decanted and evaporated in vacuo. The residue was purified by column chromatography (silica gel Fluka 60, benzene/methanol 10:0-4:6) yielding methyl (E)-[4-[3-(4-chlorophenyl)-3-[4-[3-(4-hydroxypiperidin-1-yl)propynyl]phenyl]allyloxy]-2-methylphenoxy]acetate.

Yield: 390 mg (85%).

$R_F$ (SiO$_2$, chloroform/ethanol 5:1): 0.45.

$^1$H NMR spectrum (300 MHz, CDCl$_3$, $\delta_H$): 7.46 (d, J=8.2 Hz, 2H); 7.26 (d, J=8.7 Hz, 2H); 7.16 (d, J=8.7 Hz, 2H); 7.13 (d, J=8.2 Hz, 2H); 6.67 (d, J=2.7 Hz, 1H); 6.62 (d, J=8.7 Hz, 1H); 6.56 (dd, J=8.7 and 2.7 Hz, 1H); 6.28 (t, J=6.7 Hz, 1H); 4.58 (s, 2H); 4.49 (d, J=6.7 Hz, 2H); 3.79 (s, 4H); 3.57 (s, 2H); 2.94 (m, 2H); 2.50 (m, 2H); 2.25 (s, 3H); 2.00 (m, 2H); 1.70 (m, 2H).

The above ester (0.39 g, 0.696 mmol) was dissolved in ethanol (30 mL), a solution of lithium hydroxide monohydrate (0.10 g, 2.38 mmol) in water (4 mL) was added and the mixture was left to stand for 72 h. The solvents were evaporated in vacuo; the residue was diluted with water (25 mL), acidified with acetic acid (0.25 mL) and extracted with chloroform (2×50 mL). The organic solution was dried with anhydrous potassium carbonate and subsequently evaporated in vacuo. The residue was triturated with hexanes yielding the title compound as amorphous solid.

Yield: 0.34 g (89%).

$R_F$ (SiO$_2$, chloroform/ethanol/ammonia 1:1:0.05): 0.30.

$^1$H NMR spectrum (300 MHz, CDCl$_3$, $\delta_H$): 7.42 (d, J=8.1 Hz, 2H); 7.25 (d, J=8.5 Hz, 2H); 7.15 (d, J=8.5 Hz, 2H); 7.09 (d, J=8.1 Hz, 2H); 6.64 (d, J=2.5 Hz, 1H); 6.59 (d, J=8.9 Hz, 1H); 6.41 (dd, J=8.9 and 2.5 Hz, 1H); 6.30 (t, J=6.8 Hz, 1H); 4.47 (s, 2H); 4.40 (d, J=6.8 Hz, 2H); 3.82 (m, 3H); 3.21 (m, 2H); 2.89 (m, 2H); 2.22 (s, 3H); 2.03 (m, 2H); 1.77 (m, 2H).

Example 48

(E)-[2-Methyl-4-[3-(4-methylsulfanylphenyl)-3-[4-[3-(pyrazol-1-yl)propynyl]phenyl]allyloxy]-phenoxy]acetic Acid

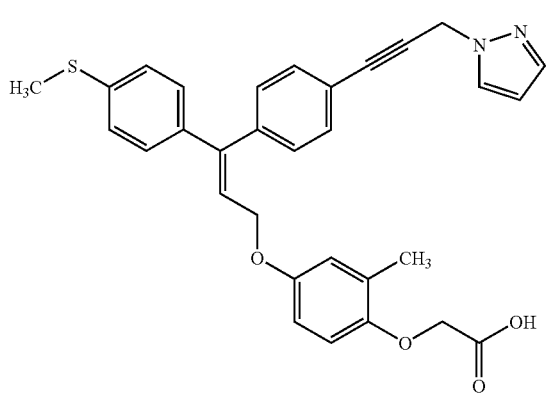

1-Propargylpyrazole (0.530 g, 5.0 mmol) and diisopropylamine (1.6 mL, 11.7 mmol) were added to a solution of methyl (Z)-[4-[3-(4-iodophenyl)-3-(4-methylsulfanylphenyl)allyloxy]-2-methylphenoxy]acetate (1.40 g, 2.5 mmol; prepared as described in example 40) in tetrahydrofuran (35 mL). The mixture was degassed and copper(I) iodide (38.0 mg, 0.2 mmol) and bis(triphenylphosphine)palladium(II) dichloride (87.5 mg, 0.12 mmol) were added. The reaction mixture was stirred at ambient temperature for 20 h and evaporated in vacuo. The residue was purified by flash column chromatography (silica gel Fluka 60, hexanes/ethyl acetate 7:3) yielding methyl (E)-[2-methyl-4-[3-(4-methylsulfanyl phenyl)-3-[4-[3-(pyrazol-1-yl)propynyl]phenyl]allyloxy]-phenoxy]acetate as yellow oil.

Yield: 1.04 g (80%).

$R_F$ (SiO$_2$, hexanes/ethyl acetate 4:1): 0.15.

$^1$H NMR spectrum (300 MHz, CDCl$_3$, $\delta_H$): 7.69 (d, J=2.3 Hz, 1H); 7.57 (d, J=1.7 Hz, 1H); 7.48 (d, J=8.2 Hz, 2H); 7.15 (m, 6H); 6.66 (t, J=2.0 Hz, 1H); 6.29 (t, J=6.7 Hz, 1H); 5.20 (s, 2H); 4.58 (s, 3H); 4.47 (d, J=6.7 Hz, 2H); 3.79 (s, 3H); 2.47 (s, 3H); 2.24 (s, 3H).

To a solution of the above ester (1.02 g, 1.89 mmol) in tetrahydrofuran/methanol mixture (5:1, 30 mL), a solution of lithium hydroxide monohydrate (0.15 g, 3.78 mmol) in distilled water (5 mL) was added. The solution was stirred for 2 h at ambient temperature; the precipitated solid was filtered and then suspended in 10% aqueous solution of ammonium chloride (5 mL). Acetic acid was added (2 drops) and the mixture was extracted with chloroform (3×15 mL). The collected extracts were washed with brine (15 mL), dried with anhydrous magnesium sulfate and evaporated in vacuo. The residue was triturated with hexanes (2×15 mL) yielding the title acid as tan solid.

Yield: 564 mg (66%).

M.p.: 131-137° C.

$R_F$ (SiO$_2$, chloroform/methanol 9:1): 0.25.

$^1$H NMR spectrum (300 MHz, CDCl$_3$+AcOH-d$_4$, $\delta_H$): 7.71 (d, J=2.2 Hz, 1H); 7.59 (d, J=1.6 Hz, 1H); 7.16 (m, 6H); 7.14 (d, J=8.1 Hz, 2H); 6.68-6.55 (m, 3H); 6.33 (t, J=2.1 Hz, 1H); 6.29 (t, J=6.8 Hz, 1H); 5.24 (s, 2H); 4.61 (s, 2H); 4.68 (d, J=6.8 Hz, 2H); 2.47 (s, 3H); 2.24 (s, 3H).

Example 49

(E)-[4-[3-(4-Chlorophenyl)-3-[4-[3-[4-(hydroxymethyl)piperidin-1-yl]propynyl]phenyl]allyloxy]-2-methylphenoxy]acetic Acid

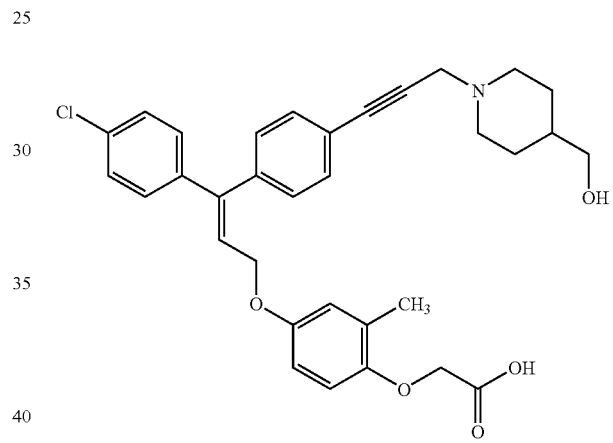

Under nitrogen atmosphere, (1-propargylpiperidin-4-yl)methanol (122 mg, 0.8 mmol) and diisopropylamine (370 mg, 0.56 mmol) were added to a degassed solution of methyl (Z)-[4-[3-(4-chlorophenyl)-3-(4-iodophenyl)allyloxy]-2-methylphenoxy]acetate (220 mg, 0.4 mmol; prepared as described in example 7) in tetrahydrofuran (15 mL). Subsequently, bis(triphenylphosphine)palladium(II) dichloride (30 mg, 0.042 mmol) and copper(I) iodide (15 mg, 0.075 mmol) were added; the reaction mixture was degassed again and then stirred under inert atmosphere at ambient temperature over night. The reaction mixture was diluted with ethyl acetate (20 mL) and filtered through a paddle of silica gel. The paddle was thoroughly washed with ethyl acetate (4×20 mL) and the combined filtrates were concentrated in vacuo. The residue was purified by column chromatography (silica gel Fluka 60, chloroform/methanol 95:5) yielding methyl (E)-[4-[3-(4-chlorophenyl)-3-[4-[3-[4-(hydroxymethyl)piperidin-1-yl]propynyl]phenyl]allyloxy]-2-methyl phenoxy]acetate.

Yield: 210 mg (91%).

$R_F$ (chloroform/methanol 85:15): 0.55.

$^1$H NMR spectrum (300 MHz, CDCl$_3$, $\delta_H$): 7.46 (d, J=8.2 Hz, 2H); 7.27-7.24 (m, overlapped); 7.19-7.12 (m, 4H); 6.67 (d, J=2.8 Hz, 1H); 6.62 (d, J=8.8 Hz, 1H); 6.56 (dd, J=8.9 and 2.8 Hz, 1H); 6.28 (t, J=6.7 Hz, 1H); 4.58 (s, 2H); 4.49 (d, J=6.7 Hz, 2H); 3.79 (s, 3H); 3.58 (s, 2H); 3.07 (d, J=11.3 Hz, 2H); 2.33 (t, J=11.8 Hz, 2H); 2.25 (s, 3H); 2.08 (s, 3H); 1.82 (d, J=11.9 Hz, 2H); 1.47-1.38 (m, 3H).

The above ester (210 mg, 0.37 mmol) was dissolved in a mixture of tetrahydrofuran (5 mL) and methanol (2 mL). A solution of lithium hydroxide monohydrate (36 mg, 0.73 mmol) in water (2 mL) was added and the mixture was stirred for 2 h at ambient temperature. The reaction mixture was diluted with water (15 mL) and acidified with 2 M hydrochloric acid to pH~6. A saturated solution of ammonium chloride (5 mL) was added and the mixture was extracted with ethyl acetate (4×15 mL). The organic extracts were washed with 10% aqueous solution of ammonium chloride (2×20 mL) and brine (2×15 mL), dried with anhydrous magnesium sulfate and subsequently evaporated in vacuo. The residue was triturated with hexanes (2×10 mL) yielding the title compound as amorphous solid.

Yield: 95 mg (46%).
M.p.: 94-104° C. (amorphous).
$R_F$ (SiO$_2$, chloroform/methanol 80:20): 0.10.
$^1$H NMR spectrum (300 MHz, CDCl$_3$, $\delta_H$): 7.44 (d, J=8.0 Hz, 2H); 7.34 (d, J=8.4 Hz, 2H); 7.17-7.12 (m, 4H); 6.64-6.53 (m, 3H); 6.29 (t, J=6.4 Hz, 1H); 4.51 (bs, 2H); 4.40 (d, J=6.5 Hz, 2H); 3.51 (s, 2H); 3.18 (d, J=5.9 Hz, 2H); 2.88-2.84 (m, 2H); 2.21-2.17 (m, 2H); 2.08 (s, 3H); 1.64-1.60 (m, 2H); 1.17-1.01 (m, 3H).

Example 50

(Z)-[4-[3-(4-tert-Butyl phenyl)-3-[4-[3-(4-hydroxypiperidin-1-yl)propynyl]phenyl]allyloxy]-2-methylphenoxy]acetic Acid

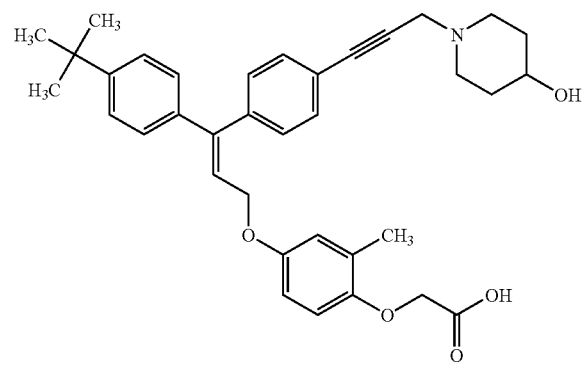

4-Hydroxy-1-propargylpiperidine (171 mg, 1.23 mmol) and diisopropylamine (0.40 mL, 2.85 mmol) were added to a solution of the methyl (Z)-[4-[3-(4-tert-butylphenyl)-3-(4-iodohenyl)allyloxy]-2-methylphenoxy]acetate (350 mg, 0.614 mmol; prepared as described in example 30) in tetrahydrofuran (10 mL). The mixture was degassed and copper(I) iodide (10 mg, 0.053 mmol) and bis(triphenylphosphine)palladium(II) dichloride (22 mg, 0.031 mmol) were added. The reaction mixture was stirred at ambient temperature overnight, filtered and the filtrate was evaporated in vacuo. The residue was purified by flash column chromatography (silica gel Fluka 60, dichloromethane/methanol 97:3) yielding methyl (Z)-[4-[3-(4-tert-butyl phenyl]-3-[4-[3-(4-hydroxypiperidin-1-yl)propynyl]phenyl]allyloxy]-2-methylphenoxy]-acetate as white solid.

Yield: 216 mg (61%).
$R_F$ (SiO$_2$, chloroform saturated with ammonia/methanol 97:3): 0.15.

$^1$H NMR spectrum (300 MHz, CDCl$_3$, $\delta_H$): 7.46 (d, J=8.3 Hz, 2H); 7.31 (d, J=8.6 Hz, 2H); 7.17 (d, J=8.5 Hz, 2H); 7.16 (d, J=8.3 Hz, 2H); 6.67 (d, J=2.8 Hz, 1H); 6.62 (d, J=8.8 Hz, 1H); 6.56 (dd, J=8.9 and 2.8 Hz, 1H); 6.29 (t, J=6.7 Hz, 1H); 4.58 (s, 2H); 4.49 (d, J=6.7 Hz, 2H); 3.79 (s, 3H); 3.56 (s, 2H); 2.92 (m, 2H); 2.47 (m, 2H); 2.24 (s, 3H); 1.99 (m, 2H); 1.69 (m, ~2H); 1.31 (s, 9H).

To a solution of the above ester (209 mg, 0.359 mmol) in tetrahydrofuran/methanol mixture (5:1, 6 mL), a solution of lithium hydroxide monohydrate (45 mg, 1.07 mmol) in distilled water (1 mL) was added under cooling to 0° C. The solution was stirred for 1.5 h under cooling, acetic acid (0.062 mL; 1.08 mmol) was added and the resulting mixture was stirred for further 10 min. The solution was diluted with ethyl acetate (40 mL) and water (30 mL); the phases were separated and the aqueous phase was extracted with ethyl acetate (3×20 mL). The combined organic layers were washed with water (2×20 mL) and brine (2×20 mL). The organic solution was dried with anhydrous magnesium sulfate and evaporated in vacuo. The residue was triturated with hexanes (2×4 mL) yielding the title acid as yellow solid.

Yield: 34 mg (17%).
M.p.: 95-110° C.
$R_F$ (SiO$_2$, ethyl acetate/methanol 1:1): 0.35.
$^1$H NMR spectrum (300 MHz, CDCl$_3$, $\delta_H$): 7.41 (d, J=8.1 Hz, 2H); 7.31 (d, J=8.5 Hz, 2H); 7.17 (d, J=8.5 Hz, 2H); 7.10 (d, J=8.1 Hz, 2H); 6.66 (d, J=3.0 Hz, 1H); 6.57 (d, J=8.9 Hz, 1H); 6.34 (m, 2H); 4.50 (s, 2H); 4.39 (d, J=7.0 Hz, 2H); 3.88 (m, 3H); 3.29 (m, 2H); 3.00 (m, overlapped); 2.22 (s, 3H); 2.08 (m, ~2H); 1.85 (m, ~2H); 1.30 (s, ~9H (overlapped)).

Example 51

(Z)-[4-[3-(4-tert-Butylphenyl)-3-[4-[3-[N-(2-hydroxyethyl)-N-methylamino]propynyl]phenyl]-allyloxy]-2-methylphenoxy]acetic Acid

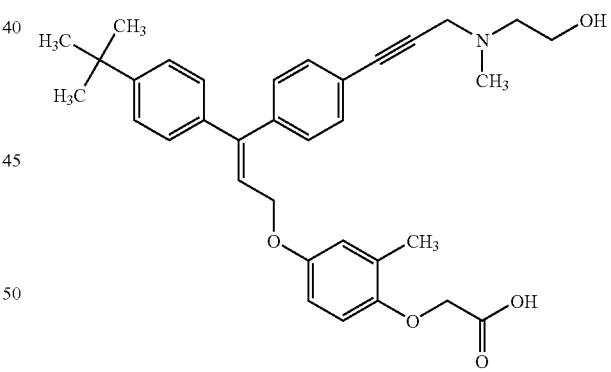

2-[N-Methyl-N-(2-propynyl)amino]ethanol (139 mg, 1.23 mmol) and diisopropylamine (0.40 mL, 2.85 mmol) were added to a solution of methyl (Z)-[4-[3-(4-tert-butylphenyl)-3-(4-iodophenyl)allyloxy]-2-methylphenoxy]acetate (350 mg, 0.614 mmol; prepared as described in example 30) in tetrahydrofuran (10 mL). The mixture was degassed and copper(I) iodide (10 mg, 0.053 mmol) and bis(triphenylphosphine)palladium(II) dichloride (22 mg, 0.031 mmol) were added. The reaction mixture was stirred at ambient temperature for 72 h, filtered and the filtrate was evaporated in vacuo. The residue was purified by flash column chromatography (silica gel Fluka 60, dichloromethane/ethanol 97:3) yielding methyl (Z)-[4-[3-(4-tert-butylphenyl)-3-[4-[3-[N-(2-hydroxyethyl)-N-methylmino]ropynyl]phenyl]-allyloxy]-2-methylphenoxy]acetate as brown oil.

Yield: 193 mg (57%).

$R_F$ (SiO$_2$, dichloromethane/methanol 95:5): 0.25.

$^1$H NMR spectrum (300 MHz, CDCl$_3$, $\delta_H$): 7.45 (d, J=8.2 Hz, 2H); 7.31 (d, J=8.5 Hz, 2H); 7.18 (d, J=8.5 Hz, 2H); 7.17 (d, J=8.2 Hz, 2H); 6.68 (d, J=2.6 Hz, 1H); 6.62 (d, J=8.8 Hz, 1H); 6.56 (dd, J=8.7 and 2.8 Hz, 1H); 6.29 (t, J=6.7 Hz, 1H); 4.58 (s, 2H); 4.49 (d, J=6.7 Hz, 2H); 3.79 (s, 3H); 3.64 (m, 2H); 3.63 (s, 2H); 2.72 (m, 2H); 2.44 (s, 3H); 2.24 (s, 3H); 1.31 (s, 9H).

To a solution of the above ester (187 mg, 0.337 mmol) in tetrahydrofuran/methanol mixture (5:1, 6 mL), a solution of lithium hydroxide monohydrate (42 mg, 1.00 mmol) in distilled water (1 mL) was added under cooling to 0° C. The solution was stirred for 1 h under cooling, acetic acid (0.057 mL; 1.00 mmol) was added and the resulting mixture was stirred for further 10 min. The solution was diluted with chloroform (40 mL) and water (30 mL); the phases were separated and the aqueous phase was extracted with chloroform (3×20 mL). The combined organic layers were washed with water (2×20 mL) and brine (2×20 mL). The organic solution was dried with anhydrous magnesium sulfate and evaporated in vacuo. The residue was triturated with hexanes (2×5 mL) yielding the title acid as white solid.

Yield: 139 mg (76%).

M.p.: 165-172° C.

$R_F$ (SiO$_2$, ethyl acetate/methanol 1:1): 0.20.

$^1$H NMR spectrum (300 MHz, CDCl$_3$+AcOH-d$_6$, $\delta_H$): 7.46 (d, J=8.1 Hz, 2H); 7.32 (d, J=8.5 Hz, 2H); 7.18 (m, 4H); 6.67 (d, J=2.6 Hz, 1H); 6.63 (d, J=8.8 Hz, 1H); 6.52 (dd, J=8.8 and 2.9 Hz, 1H); 6.33 (t, J=6.8 Hz, 1H); 4.55 (s, 2H); 4.45 (d, J=6.8 Hz, 2H); 4.26 (s, 2H); 3.98 (m, 2H); 3.33 (m, 2H); 2.95 (s, 3H); 2.24 (s, 3H); 1.31 (s, 9H).

Example 52

(Z)-[4-[3-(4-tert-Butylphenyl)-3-[4-[3-(pyrazol-1-yl)propynyl]phenyl]allyloxy]-2-methylphenoxy]acetic Acid

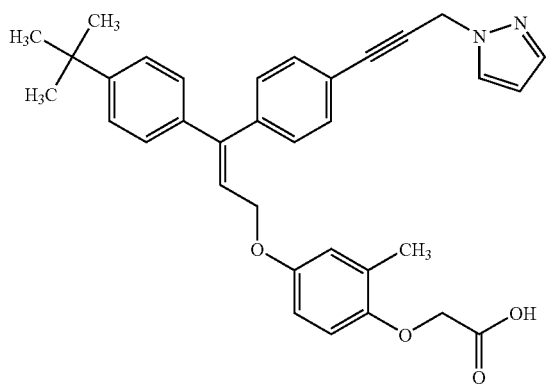

N-Propargylpyrazole (130 mg, 1.23 mmol) and diisopropylamine (0.40 mL, 2.85 mmol) were added to a solution of methyl (Z)-[4-[3-(4-tert-butylphenyl)-3-(4-iodophenyl)allyloxy]-2-methylphenoxy]cetate (350 mg, 0.614 mmol; prepared as described in example 30) in tetrahydrofuran (10 mL). The mixture was degassed and copper(I) iodide (10 mg, 0.053 mmol) and bis(triphenylphosphine)alladium(II) dichloride (22 mg, 0.031 mmol) were added. The reaction mixture was stirred at ambient temperature over night, filtered and the filtrate was evaporated in vacuo. The residue was purified by flash column chromatography (silica gel Fluka 60, hexanes/ethyl acetate 4:1-3:1) yielding methyl (Z)-[4-[3-(4-tert-butyl-phenyl)-3-[4-[3-(pyrazol-1-yl)propynyl]phenyl]allyloxy]-2-methylphenoxy]acetate as brown oil.

Yield: 205 mg (61%).

$R_F$ (SiO$_2$, dichloromethane/methanol 98:2): 0.40.

$^1$H NMR spectrum (300 MHz, CDCl$_3$, $\delta_H$): 7.71 (d, J=2.2 Hz, 1H); 7.57 (d, J=1.6 Hz, 1H); 7.49 (d, J=8.3 Hz, 2H); 7.31 (d, J=8.6 Hz, 2H); 7.18 (d, J=8.3 Hz, 2H); 7.17 (d, J=8.6 Hz, 2H); 6.67 (d, J=2.8 Hz, 1H); 6.62 (d, J=8.8 Hz, 1H); 6.56 (dd, J=8.9 and 2.8 Hz, 1H); 6.33 (m, 1H); 6.30 (t, J=6.7 Hz, 1H); 5.21 (s, 2H); 4.58 (s, 2H); 4.48 (d, J=6.7 Hz, 2H); 3.79 (s, 3H); 2.24 (s, 3H); 1.31 (s, 9H).

To a solution of the above ester (199 mg, 0.363 mmol) in tetrahydrofuran/methanol mixture (5:1, 6 mL), a solution of lithium hydroxide monohydrate (46 mg, 1.10 mmol) in distilled water (1 mL) was added under cooling to 0° C. The solution was stirred for 1 h under cooling, acetic acid (0.063 mL; 1.10 mmol) was added and the resulting mixture was stirred for further 10 min. The solution was diluted with chloroform (40 mL) and water (30 mL); the phases were separated and the aqueous phase was extracted with chloroform (3×20 mL). The combined organic layers were washed with water (2×20 mL) and brine (2×20 mL), dried with anhydrous magnesium sulfate and evaporated in vacuo. The residue was triturated with hexanes (2×5 mL) yielding the title acid as white solid.

Yield: 134 mg (70%).

M.p.: 144-147° C.

$R_F$ (SiO$_2$, ethyl acetate/methanol 1:1): 0.50.

$^1$H NMR spectrum (300 MHz, CDCl$_3$, $\delta_H$): 7.68 (m, 1H); 7.59 (m, 1H); 7.46 (d, J=8.2 Hz, 2H); 7.31 (d, J=8.5 Hz, 2H); 7.17 (d, J=8.3 Hz, 2H); 7.15 (d, J=8.1 Hz, 2H); 6.67 (d, J=2.7 Hz, 1H); 6.65 (d, 1H); 6.53 (dd, J=8.9 and 2.9 Hz, 1H); 6.33 (m, 1H); 6.31 (t, J=6.7 Hz, 1H); 5.21 (s, 2H); 4.60 (s, 2H); 4.47 (d, J=6.8 Hz, 2H); 2.24 (s, ~3H); 1.30 (s, 9H).

Example 53

(E)-[4-[3-(4-Cyclopropylsulfanylphenyl)-3-[4-[3-(morpholin-4-yl)propynyl]phenyl]allyloxy]-2-methylphenoxy]acetic Acid

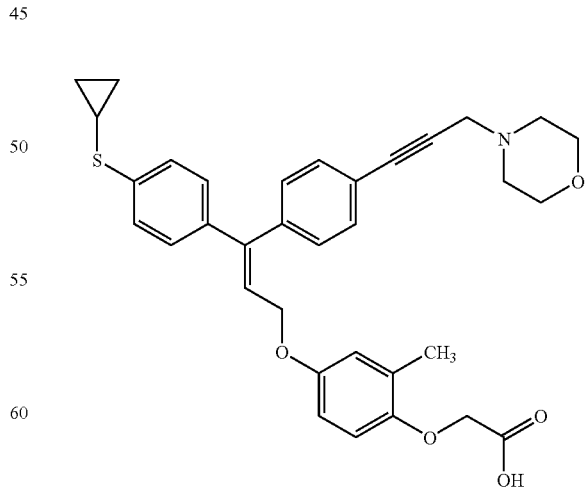

To a degassed solution of potassium tert-butoxide (2.08 g, 18.51 mmol) in dry dimethylsulphoxide (6 mL), 4-bromobenzenethiol (3.5 g, 18.5 mmol) was added and the mixture was stirred for 15 min at ambient temperature under nitrogen. Bromocyclopropane (4.4 mL, 55.5 mmol) was added afterwards and the reaction mixture was heated at 80° C. for 24 h in a sealed vessel. The mixture was cooled, diluted with ether (150 mL) and washed with water (100 mL). The aqueous layer was extracted with ether (3×50 mL). Combined organic extracts were finally dried with anhydrous magnesium sulfate. 1-Bromo-4-cyclopropylsulfanyl-benzene was obtained after evaporation of the solvent as yellow liquid.

Yield: 3.49 g (82%).

$R_F$ (SiO$_2$, hexanes/ethyl acetate 4:1): 0.70.

$^1$H NMR spectrum (300 MHz, CDCl$_3$, $\delta_H$): 7.40 (d, J=8.6 Hz, 2H); 7.23 (d, J=8.5 Hz, 2H); 2.16 (m, 1H); 1.08 (m, 2H); 0.69 (m, 2H).

To a degassed solution of the above bromide (5.8 g, 25.3 mmol) in anhydrous tetrahydrofuran (33 mL), copper(I) iodide (145 mg, 0.759 mol) and tetrakis(triphenylphosphine)palladium (878 mg, 0.760 mmol) were added and the mixture was cooled down with ice bath. 1,8-Diazabicyclo[5.4.0]undec-7-ene (5.68 mL, 38.0 mmol) was added and the reaction mixture was degassed again. A degassed solution of propargyl alcohol (2.20 mL, 38.0 mmol) in anhydrous tetrahydrofuran (5 mL) was added dropwise afterwards and the reaction mixture was stirred at 50° C. overnight under nitrogen. After cooling the mixture was diluted with ether (100 mL) and washed with water (40 mL) and 15% hydrochloric acid (2×40 mL). The aqueous layer was extracted with ether (5×40 mL), the combined organic extracts were washed with 10% sodium hydrogen carbonate (40 mL) and brine (2×40 mL) and dried with anhydrous magnesium sulfate. The crude product was purified by column chromatography (silica gel Fluka 60, hexanes/ethyl acetate 10:1-8:1) yielding 3-(4-cyclopropylsulfanylphenyl)-prop-2-yn-1-ol as yellow oil, which solidifies in refrigerator.

Yield: 4.45 g (86%).

$R_F$ (SiO$_2$, hexanes/ethyl acetate 4:1): 0.15.

$^1$H NMR spectrum (300 MHz, CDCl$_3$, $\delta_H$): 7.37 (d, J=8.4 Hz, 2H); 7.31 (d, J=8.4 Hz, 2H); 4.51 (d, J=6.1 Hz, 2H); 2.18 (m, 1H); 1.77 (t, J=6.1 Hz, 1H); 1.11 (m, 2H); 0.71 (m, 2H).

1 M Solution of lithium aluminum hydride in tetrahydrofuran (21.8 mL, 21.8 mmol) was added to sodium methoxide (55 mg, 1.01 mmol) under nitrogen. The mixture was cooled to 0° C. and a solution of the above hydroxy derivative (4.45 g, 21.8 mmol) in dry tetrahydrofuran (30 mL) was added dropwise. The reaction mixture was stirred at 0° C. for 3.5 h; dry ethyl acetate (6.90 mL, 70.2 mmol) was added and the whole mixture was stirred at ambient temperature for 30 min. A degassed solution of 1,4-diiodobenzene (7.26 g, 21.8 mmol) in anhydrous tetrahydrofuran (22 mL), anhydrous zinc chloride (1.8 g, 13.3 mmol), tris(dibenzylidene-acetone)dipalladium chloroform complex (0.480 g, 0.464 mmol), and tri-(2-furyl)phosphine (0.556 g, 2.39 mmol) were added; the mixture was degassed and stirred at 65° C. for 24 h under nitrogen. The suspension was cooled down; methanol (12 mL) was added and the mixture was stirred for additional 1 h. The reaction mixture was diluted with ether (100 mL) and saturated aqueous solution of ammonium chloride (7 mL), filtered through a paddle of silica gel and the paddle was thoroughly washed with ether (80 mL). The solvents were evaporated in vacuo and the residue was separated by flash column chromatography (silica gel Fluka 60, dichloromethane/ethyl acetate 20:1) affording (Z)-3-(4-cyclopropylsulfanylphenyl)-3-(4-iodophenyl)prop-2-en-1-ol as yellow oil.

Yield: 3.44 g (39%).

$R_F$ (SiO$_2$, dichloromethane/ethyl acetate 20:1): 0.55.

$^1$H NMR spectrum (300 MHz, CDCl$_3$, $\delta_H$): 7.71 (d, J=8.3 Hz, 2H); 7.28 (d, J=8.5 Hz, 2H); 7.15 (d, J=8.5 Hz, 2H); 6.92 (d, J=8.3 Hz, 2H); 6.23 (t, J=6.9 Hz, 1H); 4.19 (m, 2H); 2.17 (m, 1H); 1.43 (t, J=5.3 Hz, 1H); 1.07 (m, 2H); 0.69 (m, 2H).

The above allyl alcohol (3.40 g, 8.30 mmol), methyl (4-hydroxy-2-methylphenoxy)acetate (1.79 g, 9.13 mmol; compound VÚFB-21004) and triphenylphosphine (2.5 g, 9.55 mmol) were dissolved in a mixture of anhydrous toluene (38 mL) and tetrahydrofuran (13 mL). The mixture was cooled to 0° C., kept under nitrogen and a degassed solution of diisopropyl azodicarboxylate (1.88 mL, 9.55 mmol) in anhydrous tetrahydrofuran (5 mL) was added dropwise. The reaction mixture was allowed to warm up to ambient temperature and then was stirred overnight. The solvents were evaporated in vacuo and the residue was submitted to flash column chromatography (silica gel Fluka 60, hexanes/ethyl acetate 10:1-8:1) affording methyl (Z)-[4-[3-(4-cyclopropylsulfanylphenyl)-3-(4-iodophenyl)allyloxy]-2-methylphenoxy]acetate as yellowish oil.

Yield: 2.56 g (52%).

$R_F$ (SiO$_2$, hexanes/ethyl acetate 4:1): 0.50.

$^1$H NMR spectrum (300 MHz, CDCl$_3$, $\delta_H$): 7.74 (d, J=8.2 Hz, 2H); 7.30 (d, J=8.4 Hz, 2H); 7.17 (d, J=8.3 Hz, 2H); 6.97 (d, J=8.2 Hz, 2H); 6.69 (d, J=2.3 Hz, 1H); 6.64 (d, J=8.8 Hz, 1H); 6.59 (dd, J=8.8 and 2.7 Hz, 1H); 6.30 (t, J=6.7 Hz, 1H); 4.60 (s, 2H); 4.49 (d, J=6.7 Hz, 2H); 3.81 (s, 3H), 2.27 (s, 3H); 2.19 (m, 1H); 1.09 (m, 2H); 0.70 (m, 2H).

To a degassed solution of the above ester (1 g, 1.705 mmol), N-propargylmorpholine (440 mg, 3.515 mmol) and diisopropylamine (1.12 mL, 7.96 mmol) in anhydrous tetrahydrofuran (27 mL), bis(triphenylphosphine)palladium(II) dichloride (95 mg, 0.135 mmol) and copper(I) iodide (27.0 mg, 0.142 mmol) were added. The reaction mixture was stirred at 50° C. overnight under nitrogen. The solvents were evaporated in vacuo and the residue was twice purified by flash column chromatography (silica gel Fluka 60, chloroform/methanol 100:0-95:5 and then chloroform/ethyl acetate/methanol 80:13:7) yielding methyl (E)-[4-[3-(4-cyclopropylsulfanylphenyl)-3-[4-[3-(morpholin-4-yl)propynyl]phenyl]allyloxy]-2-methylphenoxy]acetate as yellow oil.

Yield: 680 mg (68%).

$R_F$ (SiO$_2$, chloroform/methanol 95:5): 0.55.

$^1$H NMR spectrum (300 MHz, CDCl$_3$, $\delta_H$): 7.48 (d, J=7.9 Hz, 2H); 7.29 (d, J=7.9 Hz, 2H); 7.18 (d, J=8.2 Hz, 4H); 6.69 (d, J=2.6 Hz, 1H); 6.65 (d, J=8.8 Hz, 1H); 6.58 (dd, J=8.8 and 2.7 Hz, 1H); 6.30 (t, J=6.7 Hz, 1H); 4.60 (s, 2H); 4.51 (d, J=6.7 Hz, 2H); 3.80 (m, 7H); 3.56 (s, 2H); 2.68 (t, J=4.5 Hz, 4H); 2.26 (s, 3H); 2.20 (m, 1H); 1.09 (m, 2H); 0.71 (m, 2H).

The above ester (690 mg, 1.18 mmol) was dissolved in a mixture of tetrahydrofuran (20 mL) and methanol (10 mL) and a solution of lithium hydroxide monohydrate (112 mg, 2.66 mmol) in distilled water (4 mL) was added. The mixture was stirred overnight and then diluted with saturated aqueous solution of ammonium chloride (112 mL). The resulting mixture was extracted with ether (3×50 mL); the combined organic layers were dried with anhydrous magnesium sulfate and evaporated in vacuo. The residue was triturated with hexanes yielding the title acid as white powder.

Yield: 440 mg (65%).

M.p.: 78-82° C.

$R_F$ (SiO$_2$, chloroform/methanol 4:1): 0.60.

$^1$H NMR spectrum (300 MHz, CDCl$_3$, $\delta_H$): 7.46 (d, J=8.1 Hz, 2H); 7.27 (d, J=8.4 Hz, 2H), 7.16 (d, J=8.4 Hz, 4H); 6.68 (d, J=2.7 Hz, 1H); 6.64 (d, J=8.8 Hz, 1H); 6.54 (dd, J=8.8 and 2.9 Hz, 1H); 6.30 (t, J=6.8 Hz, 1H); 4.59 (s, 2H); 4.48 (d, J=6.8 Hz, 2H); 3.89 (t, J=4.6 Hz, 4H); 3.80 (s, 2H); 2.99 (t, J=4.5 Hz, 4H); 2.24 (s, 3H); 2.19 (m, 1H); 1.07 (m, 2H); 0.69 (m, 2H).

Example 54

(E)-[4-[3-(4-Cyclopropylsulfanylphenyl)-3-[4-[3-(N,N-dimethylamino)propynyl]phenyl]-allyloxy]2-methylphenoxy]acetic Acid

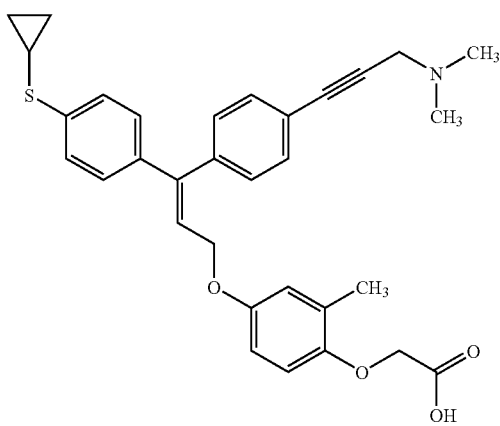

To a degassed solution of methyl (Z)-[4-[3-(4-cyclopropylsulfanylphenyl)-3-(4-iodophenyl)allyloxy]-2-methylphenoxy]acetate (480 mg, 0.818 mmol; prepared as described in example 53), N,N-dimethylpropargylamine (0.175 mL, 1.64 mmol) and diisopropylamine (0.539 mL, 3.85 mmol) in anhydrous tetrahydrofuran (10 mL), bis(triphenylphosphine)palladium(II) dichloride (29 mg, 0.041 mmol) and copper(I) iodide (13 mg, 0.068 mmol) were added. The reaction mixture was stirred at ambient temperature over night under nitrogen. The solvents were evaporated in vacuo and the residue was purified by flash column chromatography (silica gel Fluka 60, dichloromethane/methanol 99:1-98:2) yielding methyl (E)-[4-[3-(4-cyclopropylsulfanylphenyl)-3-[4-[3-(N,N-dimethylamino)propynyl]phenyl]allyloxy]-2-methylphenoxy]acetate as yellow oil.

Yield: 367 mg (83%).

$R_F$ (SiO$_2$, dichloromethane/methanol 95:5): 0.25.

$^1$H NMR spectrum (300 MHz, CDCl$_3$, $\delta_H$): 7.47 (d, J=8.2 Hz, 2H); 7.28 (d, J=8.4 Hz, ~2H); 7.16 (d, J=8.6 Hz, 2H); 7.15 (d, J=8.2 Hz, 2H); 6.68 (d, J=2.8 Hz, 1H); 6.63 (d, J=8.8 Hz, 1H); 6.57 (dd, J=8.8 and 2.8 Hz, 1H); 6.28 (t, J=6.7 Hz, 1H); 4.58 (s, 2H); 4.49 (d, J=6.7 Hz, 2H); 3.79 (s, 3H); 3.51 (s, 2H); 2.39 (s, 6H); 2.25 (s, 3H); 2.17 (m, 1H); 1.07 (m, 2H); 0.69 (m, 2H).

To a solution of the above ester (362 mg, 0.668 mmol) in tetrahydrofuran/methanol mixture (5:1, 6 mL), a solution of lithium hydroxide monohydrate (84 mg, 2.00 mmol) in distilled water (1 mL) was added under cooling to 0° C. The solution was stirred for 1.5 h under cooling, acetic acid (0.115 mL; 2.01 mmol) was added and the resulting mixture was stirred for further 10 min. The solution was diluted with chloroform (40 mL) and water (30 mL); the phases were separated and the aqueous phase was extracted with chloroform (3×20 mL). The combined organic layers were washed with water (2×20 mL) and brine (2×20 mL), dried with anhydrous magnesium sulfate and evaporated in vacuo. The residue was triturated with hexanes (2×5 mL) yielding the title acid as white solid.

Yield: 186 mg (53%).

M.p.: 82-86° C.

$R_F$ (SiO$_2$, ethyl acetate/methanol 1:1): 0.20.

$^1$H NMR spectrum (300 MHz, CDCl$_3$, $\delta_H$): 7.43 (d, J=8.2 Hz, 2H); 7.28 (d, ~2H); 7.17 (d, J=8.5 Hz, 2H); 7.16 (d, J=8.1 Hz, 2H); 6.69 (d, J=2.7 Hz, 1H); 6.61 (d, J=8.8 Hz, 1H); 6.43 (dd, J=8.7 and 2.9 Hz, 1H); 6.34 (t, J=6.9 Hz, 1H); 4.52 (s, 2H); 4.39 (d, J=7.0 Hz, 2H); 3.89 (s, 2H); 2.67 (s, 6H); 2.25 (s, 3H); 2.17 (m, 1H); 1.07 (m, 2H); 0.69 (m, 2H).

Example 55

(E)-[4-[3-(4-Cyclopropylsulfinylphenyl)-3-[4-[3-(morpholin-4-yl)propynyl]phenyl]allyloxy]-2-methylphenoxy]acetic Acid

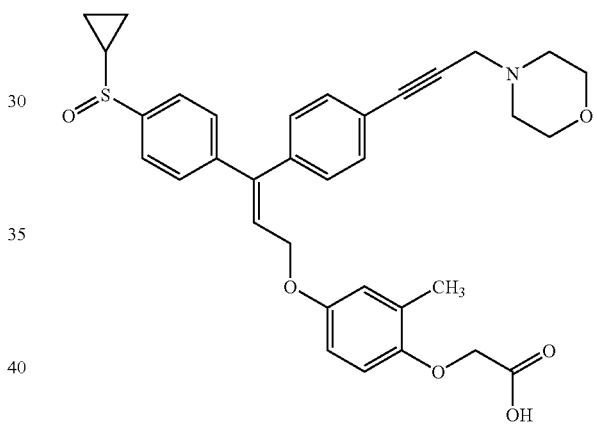

A solution of (E)-[4-[3-(4-cyclopropylsulfanylphenyl)-3-[4-[3-(morpholin-4-yl)propynyl]phenyl]allyloxy]-2-methylphenoxy]acetic acid (290 mg, 0.509 mmol; example 53) in acetic acid (8 mL) was cooled down with crushed ice and 30% aqueous hydrogen peroxide (62 μL, 0611 mmol) was added. The mixture was allowed to stand overnight at ambient temperature. The mixture was diluted with water (20 mL) and extracted with ethyl acetate (3×20 mL). The combined organic layers were dried with anhydrous magnesium sulfate and evaporated in vacuo. The crude product was purified by column chromatography (silica gel Fluka 60, chloroform/methanol 80:20) affording the title acid as yellowish powder.

Yield: 160 mg (54%).

$R_F$ (SiO$_2$, chloroform/methanol 95:5): 0.50.

$^1$H NMR spectrum (300 MHz, CDCl$_3$, $\delta_H$): 7.62 (d, J=8.3 Hz, 2H); 7.48 (d, J=8.1 Hz, 2H); 7.39 (d, J=8.4 Hz, 2H); 7.15 (d, J=8.1 Hz, 2H); 6.68 (d, J=2.8 Hz, 1H), 6.64 (d, J=8.9 Hz, 1H); 6.54 (dd, J=8.9 and 2.9 Hz, 1H); 6.39 (t, J=6.7 Hz, 1H); 4.58 (s, 2H); 4.52 (d, J=6.7 Hz, 2H); 3.87 (t, J=4.4 Hz, 4H); 3.77 (s, 2H); 2.96 (t, J=4.5 Hz, 4H); 2.35 (m, 1H); 2.24 (s, 3H); 1.06-0.85 (m, 4H).

Example 56

(E)-[2-Methyl-4-[[3-[4-[3-(morpholin-4-yl)propynyl]phenyl]-3-[4-(trifluoromethylsulfanyl)phenyl]allyloxy]phenoxy]acetic Acid

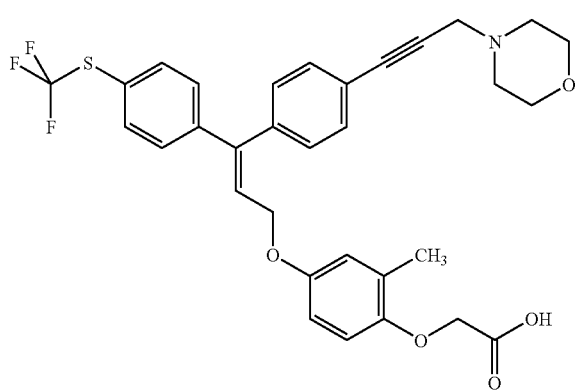

To a degassed solution of 1-bromo-4-(trifluoromethylsulfanyl)benzene (4.8 g, 18.7 mmol) in tetrahydrofuran (40 mL) was added in the following order: copper(I) iodide (106 mg, 0.56 mmol), tetrakis(triphenylphosphine)palladium (647 mg, 0.56 mmol) and 1,8-diazabicyclo[5.4.0]undec-7-ene (3.36 mL, 22.3 mmol). The resulting mixture was degassed one more time and a solution of propargyl alcohol (1.30 mL, 22.3 mmol) in tetrahydrofuran (5 mL) was added over period of 10 min. The reaction mixture was slowly heated up to 50° C. and then stirred at this temperature for 6 h and then left to stand at ambient temperature over night. The mixture was diluted with ether (50 mL) and acidified with 5% hydrochloric acid to pH 2. Ethereal solution was washed with water (2×15 mL), saturated solution of sodium hydrogen carbonate (15 mL) and brine (15 mL), dried with anhydrous magnesium sulfate and evaporated in vacuo. The residue was purified by column chromatography (silica gel Fluka 60, hexanes/ethyl acetate 85:15) affording 3-[4-(trifluoromethylsulfanyl)phenyl]prop-2-yn-1-ol.

Yield: 3.85 g (90%).

$R_F$ (SiO$_2$, hexanes/ethyl acetate 3:1): 0.25.

$^1$H NMR spectrum (300 MHz, CDCl$_3$, $\delta_H$): 7.60 (d, J=8.5 Hz, 2H); 7.47 (d, J=8.5 Hz, 2H); 4.52 (d, J=6.1 Hz, 2H); 1.84 (t, J=6.2 Hz, 1H).

Sodium methoxide (44 mg, 0.8 mmol) was added to 1 M solution of lithium aluminum hydride in tetrahydrofuran (16.0 mL, 16.0 mmol) under argon. The mixture was cooled to 0° C. and a solution of the above hydroxy derivative (3.78 g, 16.3 mmol) in tetrahydrofuran (50 mL) was added over 30 min. The reaction was stirred at 0° C. for 3 h; dry ethyl acetate (4.9 mL, 50 mmol) was added and the whole mixture was stirred at ambient temperature for 10 min. A degassed solution of 1,4-diiodobenzene (6.44 g, 19.5 mmol) in dry tetrahydrofuran (10 mL), anhydrous zinc chloride (1.33 g, 9.76 mmol), tris(dibenzylideneacetone)dipalladium chloroform complex (0.33 g, 0.325 mmol), and tri-2-furylphosphine (0.416 g, 1.78 mmol) were added; the mixture was degassed and then heated at 50-60° C. for 24 h under argon. The suspension was cooled down; methanol (8 mL) was added and the mixture was stirred for additional 1 h. The reaction mixture was diluted with ether (200 mL) and saturated aqueous solution of ammonium chloride (4.5 mL) was added. The suspension was filtered through a paddle of silica gel and the paddle was thoroughly washed with ether (50 mL). The filtrate was evaporated in vacuo and the residue was separated by flash column chromatography (silica gel Fluka 60, hexanes/ethyl acetate 9:1) affording (Z)-3-(4-iodo-phenyl)-3-[4-(trifluoromethylsulfanyl)phenyl]prop-2-en-1-ol.

Yield: 1.04 g (15%).

$R_F$ (SiO$_2$, chloroform): 0.15.

$^1$H NMR spectrum (300 MHz, CDCl$_3$, $\delta_H$): 7.74-7.04 (m, 8H); 6.31 (t, J=6.8 Hz, 1H); 4.22 (d, J=7.0 Hz, 2H); 2.36 (s, 1H).

The above allyl alcohol (1.09 g, 2.4 mmol), methyl (4-hydroxy-2-methylphenoxy)acetate (0.549 g, 27.9 mmol; example 2) and triphenylphosphine (0.755 g, 28.8 mmol) were dissolved in a mixture of anhydrous toluene (20 mL) and tetrahydrofuran (10 mL). The mixture was cooled to 0° C., kept under argon and a degassed solution of diisopropyl azodicarboxylate (0.56 mL, 28.8 mmol) in anhydrous tetrahydrofuran (5 mL) was added dropwise during 30 min. The reaction mixture was allowed to warm up the ambient temperature with the bath and then was stirred for 5 h. The solvents were evaporated in vacuo and the residue was submitted to flash column chromatography (silica gel Fluka 60, hexanes/ethyl acetate 10:1) affording methyl (Z)-[4-[3-(4-iodophenyl)-3-[4-(trifluoromethyl-sulfanyl)phenyl]allyloxy]-2-methylphenoxy]acetate as solid mass.

Yield: 0.70 g (73%).

$R_F$ (SiO$_2$, hexanes/ethyl acetate 3:1): 0.55.

$^1$H NMR spectrum (300 MHz, CDCl$_3$, $\delta_H$): 7.75 (d, J=8.3 Hz, 2H); 7.57 (d, J=8.3 Hz, 2H); 7.28 (d, J=8.3 Hz, 2H); 6.94 (d, J=8.3 Hz, 2H); 6.68-6.56 (m, 3H); 6.37 (t, J=6.6 Hz, 1H); 4.59 (s, 2H); 4.49 (d, J=6.6 Hz, 2H); 3.79 (s, 3H); 2.25 (s, 3H).

N-Propargylmorpholine (146 mg, 1.17 mmol) was added to a solution of the above iodo derivative (360 mg, 0.586 mmol) and diisopropylamine (0.38 mL, 2.7 mmol) in tetrahydrofuran (9 mL). The mixture was degassed and copper(I) iodide (8.9 mg, 0.046 mmol) and bis(triphenylphosphine) palladium(II) dichloride (20.5 mg, 0.029 mmol) were added. The reaction mixture was stirred under argon at ambient temperature for 20 h, filtered and the filtrate was evaporated in vacuo. The residue was purified by flash column chromatography (silica gel Fluka 60, chloroform/methanol 99:1) yielding (E)-[2-methyl-4-[[3-[4-[3-(morpholin-4-yl)propynyl]phenyl]-3-[4-(trifluoromethylsulfanyl)phenyl]allyloxy]phenoxy]acetate.

Yield: 204 mg (57%).

$R_F$ (SiO$_2$, chloroform/methanol 19:1): 0.55.

$^1$H NMR spectrum (300 MHz, CDCl$_3$, $\delta_H$): 7.58 (d, J=8.3 Hz, 2H); 7.49 (d, J=8.3 Hz, 2H); 7.30 (d, J=8.3 Hz, 2H); 7.16 (d, J=8.3 Hz, 2H); 6.69-6.56 (m, 3H); 6.38 (t, J=6.7 Hz, 1H); 4.60 (s, 2H); 4.53 (d, J=6.7 Hz, 2H); 3.80 (s, 3H); 3.78 (m, 4H); 3.55 (s, 2H); 2.68 (m, 4H); 2.27 (s, 3H).

To a solution of the above ester (184 mg, 0.30 mmol) in tetrahydrofuran/methanol mixture (5:1, 11 mL), a solution of lithium hydroxide monohydrate (25.2 mg, 0.60 mmol) in distilled water (1 mL) was added. The solution was stirred for 2 h at ambient temperature, acetic acid (34.3 mL; 0.60 mmol) was added and the mixture was diluted with ethyl acetate (20 mL). The solution was washed with water (2×10 mL), dried with anhydrous magnesium sulfate and evaporated in vacuo. The residue was triturated with hexanes (3×15 mL) yielding the title acid as tan solid.

Yield: 132 mg (74%).

M.p.: 71-80° C.

$R_F$ (SiO$_2$, chloroform/methanol 4:1): 0.50.

$^1$H NMR spectrum (300 MHz, CDCl$_3$, $\delta_H$): 7.56 (d, 2H); 7.45 (d, 2H); 7.27 (d, J=8.2 Hz, 2H); 7.11 (d, J=8.2 Hz, 2H);

6.63 (m, 2H); 6.47 (m, 1H); 6.38 (t, J=6.7 Hz, 1H); 4.54 (s, 2H); 4.47 (d, J=6.7 Hz, 2H); 3.84 (m, 4H); 3.76 (s, 2H); 2.95 (m, 4H); 2.24 (s, 3H).

Example 57

(E)-[4-[3-[4-[3-(4-Hydroxypiperidin-1-yl)propynyl]phenyl]-3-[4-(trifluoromethylsulfanyl)-phenyl]allyloxy]-2-methylphenoxy]acetic Acid

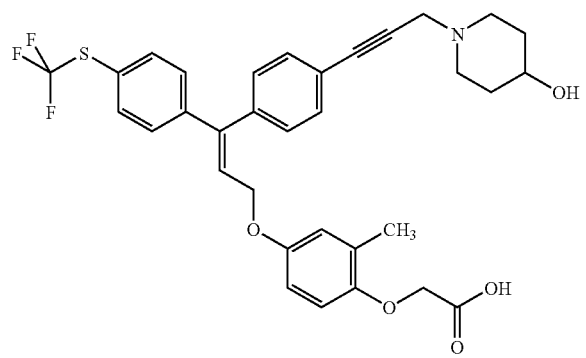

1-Propargylpiperidin-4-ol (154 mg, 1.10 mmol) was added to a solution of methyl (Z)-[4-[3-(4-iodophenyl)-3-[4-(trifluoromethyl-sulfanyl)phenyl]allyloxy]-2-methylphenoxy]-acetate (340 mg, 0.553 mmol; prepared as described in example 56) and diisopropylamine (0.35 mL, 2.49 mmol) in tetrahydrofuran (9 mL). The mixture was degassed and copper(I) iodide (8.4 mg, 0.044 mmol) and bis(triphenylphosphine)palladium(II) dichloride (19.3 mg, 0.027 mmol) were added. The reaction mixture was stirred under argon at ambient temperature for 20 h, filtered and the filtrate was evaporated in vacuo. The residue was purified by flash column chromatography (silica gel Fluka 60, chloroform/methanol 97:3) yielding methyl (E)-[4-[3-[4-[3-(4-hydroxypiperidin-1-yl)propynyl]phenyl]-3-[4-(trifluoromethylsulfanyl)phenyl]-allyloxy]-2-methylphenoxy]acetate.

Yield: 243 mg (70%).

$R_F$ (SiO$_2$, chloroform/methanol 19:3): 0.40.

$^1$H NMR spectrum (300 MHz, CDCl$_3$, $\delta_H$): 7.57 (d, J=8.1 Hz, 2H); 7.50 (d, J=8.1 Hz, 2H); 7.27 (d, J=8.1 Hz, 2H); 7.16 (d, J=8.1 Hz, 2H); 6.67-6.61 (m, 2H); 6.53-6.50 (m, 1H); 6.40 (t, J=6.7 Hz, 1H); 4.57 (s, 2H); 4.48 (d, J=6.7 Hz, 2H); 4.17 (s, 2H); 4.05 (m, 1H); 3.52 (m, 2H); 3.31 (m, 2H); 2.23 (s, 3H); 2.22 (m, 2H); 2.02 (m, 2H).

To a solution of the above ester (224 mg, 0.357 mmol) in tetrahydrofuran/methanol mixture (5:1, 11 mL), a solution of lithium hydroxide monohydrate (30.0 mg, 0.715 mmol) in distilled water (1 mL) was added. The solution was stirred for 2 h at ambient temperature, acetic acid (40.8 μL; 0.715 mmol) was added and the mixture was diluted with ethyl acetate (20 mL). The solution was washed with water (2×10 mL), dried with anhydrous magnesium sulfate and evaporated in vacuo. The residue was triturated with hexanes (3×15 mL) yielding the title acid as tan solid.

Yield: 159 mg (73%).

M.p.: 87-96° C.

$R_F$ (SiO$_2$, chloroform/methanol 4:1): 0.10.

$^1$H NMR spectrum (300 MHz, CDCl$_3$+AcOH-d$_4$, $\delta_H$): 7.58 (d, 2H); 7.50 (d, 2H); 7.28 (d, J=8.2 Hz, 2H); 7.16 (d, J=8.2 Hz, 2H); 6.66 (m, 2H); 6.51 (m, 1H); 6.41 (t, J=6.7 Hz, 1H); 4.57 (s, 2H); 4.47 (d, J=6.7 Hz, 2H); 4.17 (s, 2H); 4.05 (m, 1H); 3.53 (m, 2H); 3.31 (m, 2H); 2.23 (m, 2H); 2.23 (s, 3H); 2.02 (m, 2).

Example 58

(E)-[4-[3-[4-(Methylsulfinyl)phenyl]-3-[4-[3-(pyrazol-1-yl)propynyl]phenyl]allyloxy]-2-methylphenoxy]acetic Acid

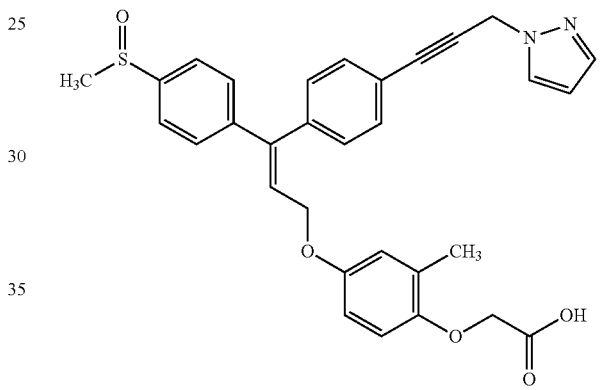

30% Aqueous hydrogen peroxide (0.0618 mL, 0.6 mmol) was added to a solution of (E)-[4-[3-[4-(methylsulfanyl)phenyl]-3-[4-[3-(pyrazol-1-yl)propynyl]phenyl]allyloxy]-2-methylphenoxy]acetic acid (262 mg, 0.5 mmol; example 48) in glacial acetic acid (7 mL) at 5° C. under stirring. The mixture was left to stand over night at ambient temperature, diluted with water (40 mL) and extracted with ethyl acetate (2×20 mL). The combined extracts were alkalized with 15% aqueous solution of ammonium hydroxide; the solution was washed with water (10 mL) and brine (10 mL), dried with anhydrous magnesium sulphate and evaporated in vacuo. The residue was triturated with hexanes (3×15 mL) to yield the title compound as pale solid.

Yield: 121 mg (45%).

M.p.: 139-145° C.

$R_F$ (SiO$_2$, chloroform/methanol 4:1): 0.25.

$^1$H NMR spectrum (300 MHz, CDCl$_3$, $\delta_H$): 7.68 (d, J=2.2 Hz, 1H); 7.59-7.36 (m, 7H); 7.14 (d, J=8.2 Hz, 2H); 6.64 (m, 2H); 6.55 (m, 1H); 6.37 (t, J=6.6 Hz, 1H); 6.33 (t, J=2.1 Hz, 1H); 5.22 (s, 2H); 4.57 (s, 2H); 4.50 (d, J=6.6 Hz, 2H); 2.76 (s, 3H); 2.24 (s, 3H).

Example 59

(E)-[4-[3-[4-[-(4-Hydroxypiperidin-1-yl)propynyl]phenyl]-3-[4-(methylsulfanyl)phenyl]-allyloxy]-2-methylphenoxy]acetic Acid

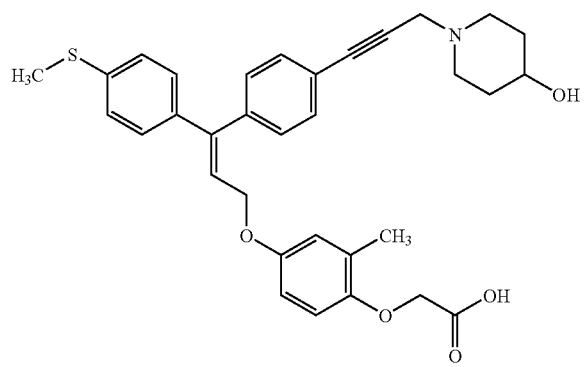

1-Propargylpiperidin-4-ol (0.401 g, 2.88 mmol) and diisopropylamine (1.6 mL, 11.73 mmol) were added to a solution of methyl (Z)-[4-[3-(4-iodophenyl)-3-[4-(methylsulfanyl)phenyl]allyloxy]-2-methylphenoxy]acetate (1.40 g, 2.5 mmol; prepared as described in example 40) in tetrahydrofuran (12 mL) and triethylamine (12 mL). The mixture was degassed and copper(I) iodide (49.0 mg, 0.256 mmol) and tetrakis(triphenylphosphine)palladium (148 g, 0.128 mmol) were added. The reaction mixture was stirred at ambient temperature for 20 h and evaporated in vacuo. The residue was purified by flash column chromatography (silica gel Fluka 60, chloroform/methanol 97:3) yielding methyl (E)-[4-[3-[4-[3-(4-hydroxypiperidin-1-yl)propynyl]phenyl]-3-[4-(methylsulfanyl)phenyl]-allyloxy]-2-methylphenoxy]acetate as yellow oil.

Yield: 800 mg (88%).

$R_F$ (SiO$_2$, chloroform/methanol 9:1): 0.40.

$^1$H NMR spectrum (300 MHz, CDCl$_3$, $\delta_H$): 7.45 (d, J=8.3 Hz, 2H); 7.16 (s, 4H); 7.14 (d, J=8.3 Hz, 2H); 6.67-6.54 (m, 3H); 6.27 (t, J=6.7 Hz, 1H); 4.58 (s, 2H); 4.48 (d, J=6.7 Hz, 2H); 3.79 (s, 3H); 3.74 (m, 1H); 3.56 (s, 2H); 2.88 (m, 2H); 2.47 (s, 3H); 2.44 (m, 2H); 2.24 (s, 3H); 1.95 (m, 2H); 1.67 (m, 2H).

To a solution of the above ester (800 mg, 1.41 mmol) in ethanol (15 mL), a 4.4 M solution of sodium hydroxide (0.64 mL, 2.82 mmol) was added. The mixture was stirred for 2 h at ambient temperature and then acetic acid (0.166 mL) and chloroform (100 mL) were added. The solid mass was filtered off, washed with chloroform (20 mL) and water (2×20 mL) and dried in vacuo. This afforded the title acid as white solid.

Yield: 482 mg (62%).

M.p.: 160-162° C.

$R_F$ (SiO$_2$, chloroform/methanol 7:3): 0.15.

$^1$H NMR spectrum (300 MHz, DMSO-d$_6$, $\delta_H$): 7.56 (d, J=8.2 Hz, 2H); 7.24 (d, J=8.2 Hz, 2H); 7.17 (s, 4H); 6.69 (m, 2H); 6.58 (dd, J=8.9 and 2.8 Hz, 1H); 6.36 (t, J=6.7 Hz, 1H); 4.65 (s, 2H); 4.50 (d, J=6.7 Hz, 2H); 4.29 (s, 2H); 3.56 (bs, ~1H); 2.45 (s, 3H); 2.22 (m, ~4H); 2.20 (s, 3H); 2.05 (m, ~4H).

Example 60

(Z)-[4-[3-(4-tert-Butyl phenyl)-3-[4-[4-(hydroxymethyl)phenylethynyl]phenyl]allyloxy]-2-methylphenoxy]acetic Acid

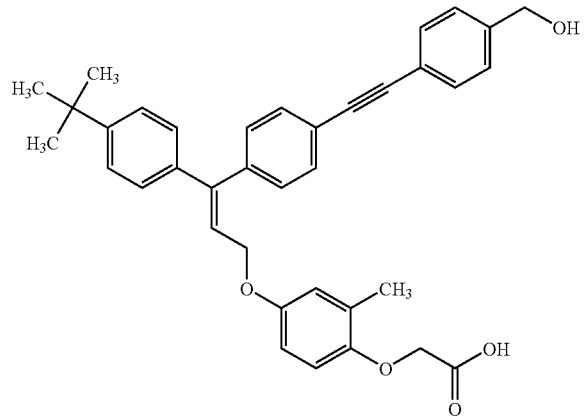

1-Ethynyl-4-(hydroxymethyl)benzene (169 mg, 1.28 mmol) and diisopropylamine (0.40 mL, 2.85 mmol) were added to a solution of methyl (Z)-[4-[3-(4-tert-butylphenyl)-3-(4-iodophenyl)allyloxy]-2-methylphenoxy]acetate (364 mg, 0.638 mmol; prepared as described in example 30) in tetrahydrofuran (10 mL). The mixture was degassed and copper(I) iodide (10 mg, 0.053 mmol) and bis(triphenylphosphine)palladium(II) dichloride (22 mg, 0.031 mmol) were added. The reaction mixture was stirred at ambient temperature overnight, filtered and the filtrate was evaporated in vacuo. The residue was purified by flash column chromatography (silica gel Fluka 60, dichloromethane/methanol 99:1) yielding methyl (Z)-[4-[3-(4-tert-butylphenyl)-3-[4-[4-(hydroxymethyl)phenylethynyl]phenyl]allyloxy]-2-methylphenoxy]acetate as brown oil.

Yield: 335 mg (92%).

$R_F$ (SiO$_2$, dichloromethane/methanol 95:5): 0.60.

$^1$H NMR spectrum (300 MHz, CDCl$_3$, $\delta_H$): 7.56 (d, J=8.3 Hz, ~2H); 7.55 (d, J=8.2 Hz, ~2H); 7.37 (d, J=8.2 Hz, ~2H); 7.32 (d, J=8.5 Hz, ~2H); 7.21 (d, J=8.2 Hz, ~2H); 7.19 (d, J=8.4 Hz, ~2H); 6.68 (d, J=2.7 Hz, 1H); 6.63 (d, J=8.7 Hz, 1H); 6.57 (dd, J=8.9 and 2.8 Hz, 1H); 6.30 (t, J=6.6 Hz, 1H); 4.72 (m, ~2H); 4.58 (s, 2H); 4.51 (d, J=6.7 Hz, 2H); 3.79 (s, 3H); 2.25 (s, 3H); 1.31 (s, 9H).

To a solution of the above ester (335 mg, 0.583 mmol) in tetrahydrofuran/methanol mixture (5:1, 6 mL), a solution of lithium hydroxide monohydrate (74 mg, 1.76 mmol) in distilled water (1 mL) was added under cooling to 0° C. The solution was stirred for 0.5 h under cooling, acetic acid (0.101 mL; 1.76 mmol) was added and the resulting mixture was stirred for further 10 min. The solution was diluted with chloroform (40 mL) and water (30 mL); the phases were separated and the aqueous phase was extracted with chloroform (3×20 mL). The combined organic layers were washed with water (2×20 mL) and brine (2×20 mL). The organic solution was dried with anhydrous magnesium sulfate and evaporated in vacuo. This afforded the title acid as brown solid.

Yield: 186 mg (57%).
M.p.: 62-73° C.
$R_F$ (SiO$_2$, ethyl acetate/methanol 1:1): 0.55.
$^1$H NMR spectrum (300 MHz, CDCl$_3$, $\delta_H$): 7.58 (d, J=8.3 Hz, 2H); 7.57 (d, J=8.2 Hz, 2H); 7.39 (d, J=8.3 Hz, 2H); 7.34 (d, J=8.5 Hz, 2H); 7.23 (d, J=8.2 Hz, 2H); 7.22 (d, J=8.5 Hz, 2H); 6.71 (d, J=2.9 Hz, 1H); 6.68 (d, 1H); 6.61 (dd, J=8.8 and 2.8 Hz, 1H); 6.32 (t, J=6.6 Hz, 1H); 4.75 (s, 2H); 4.62 (s, 2H); 4.54 (d, J=6.7 Hz, 2H); 2.26 (s, 3H); 1.33 (s, ~9H).

Example 61

(E)-[4-[3-(4-Bromophenyl)-3-[4-[3-(morpholin-4-yl)propynyl]phenyl]allyloxy]-2-methylphenoxy]acetic Acid

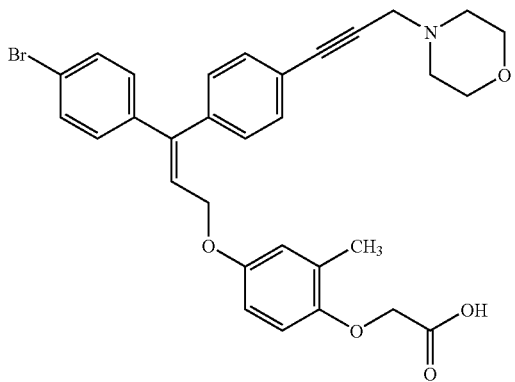

Under nitrogen atmosphere, N-propargylmorpholine (190 mg, 1.52 mmol) and diisopropylamine (360 mg, 3.56 mmol) were added to a degassed solution of methyl (Z)-[4-[3-(4-iodophenyl)-3-(4-bromophenyl)allyloxy]-2-methylphenoxy]acetate (445 mg, 0.75 mmol) in tetrahydrofuran (15 mL). Bis(triphenylphosphine)palladium(II) dichloride (30 mg, 0.042 mmol) and copper(I) iodide (15 mg, 0.078 mmol) were added; the reaction mixture was degassed again and then stirred at ambient temperature over night under inert atmosphere. The reaction mixture was filtered through a paddle of silica gel; the paddle was washed with ethyl acetate (4×15 mL) and the combined organic filtrates were evaporated in vacuo. The residue was purified by column chromatography (silica gel Fluka 60, dichloromethane/methanol 98:2) yielding (E)-[4-[3-(4-bromophenyl)-3-[4-[3-(morpholin-4-yl)propynyl]phenyl]allyloxy]-2-methylphenoxy]acetate.

Yield: 350 mg (79%).
$R_F$ (SiO$_2$, chloroform/methanol 95:5): 0.55.
$^1$H NMR spectrum (300 MHz, CDCl$_3$, $\delta_H$): 7.46 (d, J=8.2 Hz, 2H); 7.41 (d, J=8.6 Hz, 2H); 7.14-7.09 (m, 4H); 6.67 (d, J=2.8 Hz, 1H); 6.62 (d, J=8.8 Hz, 1H); 6.56 (dd, J=8.8 and 2.8 Hz, 1H); 6.29 (t, J=6.7 Hz, 1H); 4.58 (s, 2H); 4.49 (d, J=6.6 Hz, 2H); 3.79-3.78 (m, 7H); 3.54 (s, 2H); 2.68-2.65 (m, 3H), 2.25 (s, 3H).

A solution of the above ester (0.35 g, 0.59 mmol) in a mixture of tetrahydrofuran (5 mL) and methanol (2 mL) was cooled to 0° C. A solution of lithium hydroxide monohydrate (60 mg, 1.22 mmol) in distilled water (2.5 mL) was added and the mixture was stirred for 2 h. The reaction mixture was acidified with 2 M HCl to pH~6 and then diluted with 10% aqueous solution of ammonium chloride (20 mL) and ethyl acetate (20 mL). The phases were separated, the aqueous phase was washed with ethyl acetate (4×15 mL); the combined organic extracts were washed with 10% aqueous solution of ammonium chloride (2×15 mL) and brine (2×15 mL), dried with anhydrous magnesium sulfate and concentrated in vacuo. The residue was purified using flash column chromatography (silica gel Fluka 60, dichloromethane/methanol/acetic acid 95:5:1) affording oil which was triturated with hexanes (2×7 mL) yielding the title compound as amorphous white solid.

Yield: 0.210 g (67%).
$R_F$ (SiO$_2$, chloroform/methanol 85:15): 0.15.
M.p.: 132-149° C.
$^1$H NMR spectrum (300 MHz, DMSO-d$_6$, $\delta_H$): 7.53-7.48 (m, 4H); 7.19-7.13 (m, 4H); 6.68-6.58 (m, 3H); 6.34 (t, J=6.1 Hz, 1H); 4.55 (s, 2H); 4.45 (d, J=6.1 Hz, 2H); 3.60 (bs, 4H); 3.52 (s, 2H); ~2.50 (m, overlapped); 2.12 (s, 3H).

Example 62

(E)-[4-[3-(4-Bromophenyl)-3-[4-[3-(4-hydroxypiperidin-1-yl)propynyl]phenyl]allyloxy]-2-methylphenoxy]acetic Acid

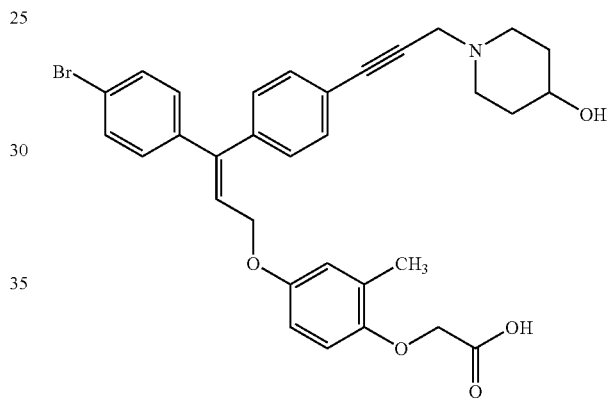

Under nitrogen atmosphere, 4-hydroxy-1-propargylpiperidine (210 mg, 1.50 mmol) and diisopropylamine (360 mg, 3.56 mmol) were added to a degassed solution of methyl (Z)-[4-[3-(4-iodoophenyl)-3-(4-bromophenyl)allyloxy]-2-methylphenoxy]acetate (445 mg, 0.75 mmol) in tetrahydrofuran (15 mL). Bis(triphenylphosphine)palladium(II) dichloride (30 mg, 0.042 mmol) and copper(I) iodide (15 mg, 0.078 mmol) were added; the reaction mixture was degassed again and stirred at ambient temperature overnight under inert atmosphere. The reaction mixture was filtered through a paddle of silica gel; the paddle was washed with ethyl acetate (4×15 mL) and the combined organic filtrates were evaporated in vacuo. The residue was purified using column chromatography (silica gel Fluka 60, dichloromethane/methanol 95:5) yielding (E)-[4-[3-(4-bromophenyl)-3-[4-[3-(4-hydroxypiperidin-1-yl)propynyl]phenyl]-allyloxy]-2-methylphenoxy]acetate.

Yield: 110 mg (24%).
$R_F$ (SiO$_2$, chloroform/methanol 95:5): 0.20.
$^1$H NMR spectrum (300 MHz, CDCl$_3$, $\delta_H$): 7.46 (d, J=8.2 Hz, 2H); 7.42 (d, J=8.5 Hz, 2H); 7.14-7.09 (m, 4H); 6.67 (d, J=2.7 Hz, 1H); 6.62 (d, J=8.8 Hz, 1H); 6.56 (dd, J=8.9 and 2.9 Hz, 1H); 6.29 (t, J=6.7 Hz, 1H); 4.58 (s, 2H); 4.49 (d, J=6.7 Hz, 2H); 3.79 (s, 3H); 3.55 (s, 2H); 2.93-2.88 (m, 2H); 2.49-2.42 (m, 2H); 2.25 (s, 3H); 1.97-1.95 (m, 2H); 1.73-1.62 (m, 3H).

A solution of the above ester (0.11 g, 0.18 mmol) in a mixture of tetrahydrofuran (5 mL) and methanol (2 mL) was cooled to 0° C. A solution of lithium hydroxide monohydrate (20 mg, 0.40 mmol) in distilled water (1.5 mL) was added and the mixture was stirred for 2 h. The reaction mixture was acidified with 2 M HCl to pH~6 and then diluted with 10% aqueous solution of ammonium chloride (15 mL) and ethyl acetate (15 mL). Phases were separated and the aqueous phase was washed with ethyl acetate (4×15 mL). The combined organic extracts were washed with 10% aqueous solution of ammonium chloride (2×15 mL) and brine (2×15 mL), dried with anhydrous magnesium sulfate and concentrated in vacuo. The residue was triturated with hexanes (2×5 mL) yielding the title compound as amorphous grayish solid.

Yield: 0.050 g (46%).

$R_F$ (SiO$_2$, chloroform/methanol 85:15): 0.20.

$^1$H NMR spectrum (300 MHz, DMSO-d$_6$, $\delta_H$): 7.53-7.47 (m, 4H); 7.18-7.13 (m, 4H); 6.70-6.67 (m, 2H); 6.59 (dd, J=8.6 and 2.5 Hz, 1H); 6.34 (t, J=6.6 Hz, 1H); 4.55 (s, 2H); 4.45 (d, J=6.6 Hz, 2H); 3.62-3.59 (m, 4H); 3.52 (s, 2H); 2.12 (s, 3H); 1.88-1.86 (m, 5H).

Example 63

(E)-[4-[3-(4-Chlorophenyl)-3-[4-[3-(morpholin-4-yl)propynyl]phenyl]allyloxy]-2-methyl phenyl]-propionic Acid

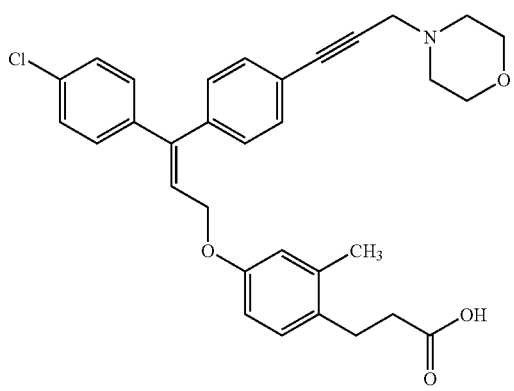

A mixture of 4-hydroxy-2-methylacetophenone (13.8 g, 91.8 mmol), benzyl chloride (12.7 g, 100 mmol), potassium carbonate (13.8 g, 100 ml) and 2-butanone (100 mL) was refluxed under stirring for 10 h, filtered and evaporated in vacuo. The residue was purified by column chromatography (silica gel Fluka 60, benzene) affording 4-benzyloxy-2-methylacetophenone.

Yield 16.7 g (76%).

$R_F$ (SiO$_2$, chloroform): 0.40.

M.p.: 51-53° C.

$^1$H NMR spectrum (300 MHz, CDCl$_3$, $\delta_H$): 7.74 (d, J=8.7 Hz, 2H); 7.39 (m, 5H); 6.81 (m, 2H); 5.09 (s, 2H); 2.56 (s, 3H); 2.53 (s, 3H).

Diethyl carbonate (19.5 g, 165 mmol) was dissolved in ether (100 mL) and 50% suspension of sodium hydride in oil (8.0 g, 167 mmol) was carefully added. A solution of the above acetophenone (16.7 g, 69.3 mmol) in benzene (100 mL) was added and the mixture was refluxed for 5 h. After cooling, the mixture was poured on ice with concentrated hydrochloric acid (50 mL); the organic layer was separated, dried with anhydrous potassium carbonate and evaporated in vacuo. The residue was purified by column chromatography (silica gel Fluka 60, benzene/chloroform 1:1) affording ethyl 4-benzyloxy-2-methylbenzoylacetate.

Yield: 16.1 g (74%).

M.p.: 59-60° C.

$^1$H NMR spectrum (300 MHz, CDCl$_3$, $\delta_H$): 7.69 (d, J=8.4 Hz, 2H); 7.39 (m, 5H); 6.82 (m, 2H); 5.10 (s, 2H); 4.19 (q, J=7.1 Hz, 2H); 3.91 (s, 2H); 2.57 (s, 3H); 1.24 (t, J=7.1 Hz, 3H).

5% Palladium on carbon (4.0 g) was added to a solution of the above keto-ester (10.4 g, 33.3 mmol) in ethyl acetate (300 mL) and the mixture was hydrogenated at atmospheric pressure and ambient temperature for 5 h. After filtration of the catalyst, the solvent was evaporated in vacuo and the residue was purified by column chromatography on silica gel (Fluka 60, chloroform/ethyl acetate 1:1) affording ethyl 3-(4-hydroxy-2-methylphenyl)propionate.

Yield 6.15 g (89%).

$R_F$ (SiO$_2$, chloroform): 0.10.

$^1$H NMR spectrum (300 MHz, CDCl$_3$, $\delta_H$): 6.97 (d, J=8.1 Hz, 1H); 6.64 (d, J=2.5 Hz, 1H); 6.60 (dd, J=2.5 and 8.1 Hz, 1H); 4.14 (q, J=7.1 Hz, 2H); 2.86 (t, J=8.4 Hz, 2H); 2.54 (t, J=8.4 Hz, 3H); 2.25 (s, 3H); 1.25 (t, J=7.1 Hz, 3H).

The above ester (0.60 g, 2.88 mmol), (Z)-[3-(4-chlorophenyl)-3-(4-iodophenyl)]allyl alcohol (0.78 g, 2.2 mmol, prepared as described in example 7) and triphenylphosphine (0.80 g, 3.05 mmol) were dissolved in a mixture of anhydrous toluene (10 mL) and tetrahydrofuran (8 mL). The mixture was cooled to 0° C., kept under nitrogen and diisopropyl azodicarboxylate (0.70 g, 3.28 mmol) was added dropwise. The reaction mixture was stirred at 0° C. for 3 h and then at ambient temperature for 24 h. The solvents were evaporated in vacuo and the residue was submitted to column chromatography (silica gel Fluka 60, benzene) affording ethyl (Z)-[4-[3-(4-chlorophenyl)-3-(4-iodophenyl)allyloxy]-2-methylphenyl]propionate as solid mass.

Yield: 0.85 g (69%).

$R_F$ (SiO$_2$, benzene): 0.30.

$^1$H NMR spectrum (300 MHz, CDCl$_3$, $\delta_H$): 7.72 (d, J=8.3 Hz, 2H); 7.25 (d, J=8.7 Hz, 2H); 7.17 (d, J=8.7 Hz, 2H); 7.01 (d, J=8.3 Hz, 1H); 6.94 (d, J=8.3 Hz, 2H); 6.64 (d, J=2.4 Hz, 1H); 6.60 (dd, J=8.3 and 2.4 Hz, 1H); 6.30 (t, J=6.7 Hz, 1H); 4.50 (d, J=6.7 Hz, 2H); 4.13 (q, J=7.1 Hz, 2H); 2.86 (t, J=8.4 Hz, 2H); 2.52 (t, J=8.4 Hz, 2H); 2.27 (s, 3H); 1.24 (t, J=7.1 Hz, 3H).

4-Propargylmorpholine (400 mg, 3.2 mmol) was added under nitrogen atmosphere to a degassed solution of the above ester (410 mg, 0.78 mmol) in a mixture of tetrahydrofuran (10 mL) and triethylamine (8 mL). The solution was cooled to 0° C., tetrakis(triphenylphosphine)palladium (90 mg, 0.078 mmol) and copper(I) iodide (22 mg, 0.115 mmol) were added. The reaction mixture was stirred at ambient temperature for 72 h, diluted with benzene (100 mL), decanted and evaporated in vacuo. The residue was purified by column chromatography (silica gel Fluka 60, benzene/ethyl acetate 10:0-4:6) yielding ethyl (E)-[4-[3-(4-chlorophenyl)-3-[4-[3-(morpholin-4-yl)propynyl]phenyl]allyloxy]-2-methylphenyl]propionate Yield: 350 mg (86%).

$R_F$ (SiO$_2$, chloroform/ethanol 5:1): 0.65.

$^1$H NMR spectrum (300 MHz, CDCl$_3$, $\delta_H$): 7.46 (d, J=8.3 Hz, 2H); 7.26 (d, J=8.4 Hz, 2H); 7.16 (m, 4H); 7.01 (d, J=8.3 Hz, 1H); 6.63 (d, J=2.5 Hz, 1H); 6.59 (dd, J=8.3 and 2.5 Hz, 1H); 6.29 (t, J=6.6 Hz, 1H); 4.52 (d, J=6.6 Hz, 2H); 4.13 (q, J=7.1 Hz, 2H); 3.78 (m, 4H); 3.53 (s, 2H); 2.86 (t, J=7.4 Hz, 2H); 2.66 (m, 4H); 2.52 (t, J=7.4 Hz, 2H) 2.27 (s, 3H); 1.24 (t, J=7.1, 3H).

The above ester (0.35 g, 0.627 mmol) was dissolved in ethanol (30 mL), a solution of lithium hydroxide monohydrate (0.10 g, 2.38 mmol) in water (4 mL) was added and the mixture was left to stand for 24 h. The solvents were evaporated in vacuo; the residue was diluted with water (25 mL), acidified with acetic acid (0.25 mL) and extracted with chloroform (2×50 mL). The organic solution was dried with anhydrous potassium carbonate and subsequently evaporated in vacuo. The residue was triturated with hexanes yielding the title compound as amorphous solid.

Yield: 0.26 g (78%).

$R_F$ (SiO$_2$, chloroform/ethanol/ammonia 1:1:0.05): 0.50.

$^1$H NMR spectrum (300 MHz, CDCl$_3$, $\delta_H$): 7.45 (d, J=8.1 Hz, 2H); 7.25 (d, J=6.0 Hz, 2H); 7.15 (t, 4H); 7.02 (d, J=8.1 Hz, 1H); 6.63 (d, J=2.5 Hz, 1H); 6.59 (dd, J=8.1 and 2.5 Hz, 1H); 6.30 (t, J=6.6 Hz, 1H); 4.51 (d, J=6.6 Hz, 2H); 3.79 (bs, 4H); 3.57 (s, 2H); 2.87 (t, J=7.7 Hz, 2H); 2.72 (bs, 4H); 2.57 (t, J=7.7 Hz, 2H) 2.26 (s, 3H).

Example 64

{4-[(Z)-3-(4-Fluoro-phenyl)-3-(4-phenylethynyl-phenyl)-allyloxy]-2-methyl-phenoxy}-acetic Acid

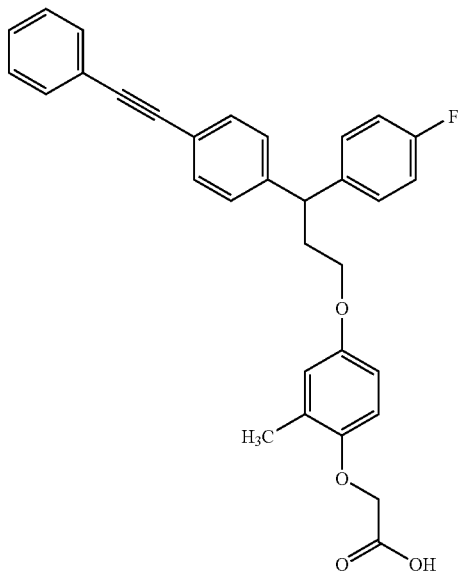

To a solution of sodium (0.42 g, 18.4 mmol) in ethanol (200 ml) was added triethyl phosphonoacetate (4.12 g, 18.4 mmol) and the reaction mixture was stirred for 5 min. To the mixture was added (4-fluoro-phenyl)-(4-phenylethynyl-phenyl)-methanone (3.94 g, 13.12 mmol) and refluxed for 48 hours. The cooled reaction mixture was evaporated in vacuo and purified by preparative HPLC method yielding both isomers. (E)-3-(4-Fluoro-phenyl)-3-(4-phenylethynyl-phenyl)-acrylic acid ethyl ester was isolated as an oil in 308 mg (6.3%) yield.

$^1$H NMR spectrum (300 MHz, CDCl$_3$, $\delta_H$): 7.60-6.95 (m, 13H); 6.30 (s, 1H); 4.10 (q, J=7.2 Hz, 2H); 1.16 (t, J=7.1 Hz, 3H).

(Z)-3-(4-Fluoro-phenyl)-3-(4-phenylethynyl-phenyl)-acrylic acid ethyl ester was isolated as solid in 323 mg (6.7%) yield.

$^1$H NMR spectrum (300 MHz, CDCl$_3$, $\delta_H$): 7.55-7.05 (m, 13H); 6.40 (s, 1H); 4.05 (q, J=7.2 Hz, 2H); 1.15 (t, J=7.1 Hz, 3H).

A 1 M solution of diisobutylaluminum hydride in tetrahydrofuran (4 mL, 4 mmol) was added dropwise to a cooled (0° C.) solution of the above (Z)-ester (0.323 g; 0.87 mmol) in dry tetrahydrofuran (40 mL). The reaction was stirred at the temperature for 4 hr. Then saturated ammoniumchloride (30 ml) after 30 min DCM (150 ml) and hyflo super cell medium (15 g) were added to the mixture, which was stirred at ambient temperature overnight. The mixture was filtered and subsequently evaporated in vacuo. The crude product were taken up in DCM (150 ml) and washed with water (2×50 ml), dried with anhydrous magnesium sulfate and subsequently evaporated in vacuo. The residue was purified by ISCO combiflash 16 (silica gel, hexane/ethyl acetate 85:15) giving (Z)-3-(4-fluoro-phenyl)-3-(4-phenylethynyl-phenyl)-prop-2-en-1-ol.

Yield: 100 mg (34%).

$^1$H NMR spectrum (300 MHz, CDCl$_3$, $\delta_H$): 7.55-7.05 (m, 13H); 6.29 (t, J=6.78 Hz, 1H); 4.12 (d, J=6.78 Hz, 2H).

To a solution of the above alcohol (100 mg, 0.305 mmol) in dry tetrahydrofuran (20 ml), was added tributylphosphine (0.11 ml, 0.61 mmol). The mixture was cooled to 0° C. and added 1,1'-(azodicarbonyl)dipiperidine (153 mg, 0.61 mmol), and after 10 min. (4-hydroxy-2-methyl-phenoxy)-acetic acid methyl ester (65 mg, 0.34 mmol) were added. The reaction mixture was stirred for 1.5 hours at 0° C. and then allowed to warm up to ambient temperature overnight. To the reaction mixture was added silica gel Fluka 60 (10 g) and the reaction mixture was evaporated in vacuo. The residue was purified by ISCO combiflash 16 (silica gel, hexane/ethyl acetate 85:15) giving {4-[(Z)-3-(4-fluoro-phenyl)-3-(4-phenylethynyl-phenyl)allyloxy]-2-methyl-phenoxy}-acetic acid methyl ester as an oil.

Yield: 102 mg (66%).

$^1$H NMR spectrum (300 MHz, CDCl$_3$, $\delta_H$): 7.58-7.15 (m, 13H); 6.70-6.55 (m, 3H); 6.35 (t, J=6.78 Hz, 1H); 4.58 (s, 2H); 4.50 (d, J=6.78 Hz, 2H); 3.79 (s, 3H); 2.25 (s, 3H).

To a solution of the above ester (102 mg, 0.201 mmol) in dioxane (100 ml) was added 1 N NaOH (1.6 ml, 1.6 mmol) and the reaction mixture was stirred for 48 hours, evaporated in vacuo and added water (10 ml) and DCM (50 ml) and 1N HCl (3 ml). The DCM phase were dried with anhydrous magnesium sulfate and subsequently evaporated in vacuo yielding the title compound as light yellow solid.

Yield: 96 mg (97%).

$^1$H NMR spectrum (300 MHz, CDCl$_3$, $\delta_H$): 7.55-7.05 (m, 13H); 6.70-6.55 (m, 3H); 6.35 (t, J=6.78 Hz, 1H); 4.61 (s, 2H); 4.51 (d, J=6.78 Hz, 2H); 2.25 (s, 3H).

Example 65

(4-{(E)-3-[4-(3-Dimethylamino-prop-1-ynyl)-phenyl]-3-phenyl-allyloxy}-2-methyl-phenoxy)acetic Acid

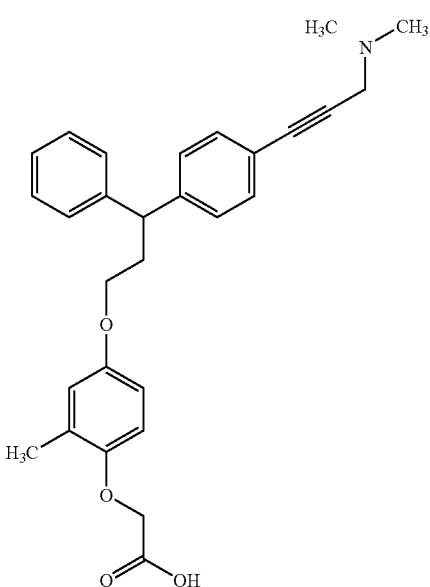

A solution of (E)-3-(4-bromo-phenyl)-3-phenyl-acrylic acid ethyl ester (0.728 g, 2.2 mmol), dimethyl-prop-2-ynyl-amine (0.56 ml, 6.58 mmol), bis(triphenylphosphine) palladium(II) chloride (0.061 g, 0.088 mmol), copper(I) iodide (1.25 mg, 0.0065 mmol) in dry triethylamine (7 ml) were heated to 100° C. by microwave irradiation for 20 min. To the cooled reaction mixture was added dichloromethane (20 ml) and silica gel Fluka 60 (5 g) and the reaction mixture was evaporated in vacuo. The residue was purified by ISCO combiflash 16 (silica gel, hexane/ethyl acetate 85:15) giving (E)-3-[4-(3-dimethylamino-prop-1-ynyl)-phenyl]-3-phenyl-acrylic acid ethyl ester as an oil.

Yield: 640 mg (87%).

$^1$H NMR spectrum (300 MHz, CDCl$_3$, δ$_H$): 7.45-7.15 (m, 9H); 6.36 (s, 1H); 4.04 (q, J=7.16 Hz, 2H); 3.48 (s, 2H); 2.37 (s, 6H); 1.11 (t, J=7.16 Hz, 3H).

A 1 M solution of diisobutylaluminum hydride in tetrahydrofuran (6 ml) was added drop wise to a cooled (0° C.) solution of the above ester (0.600 g; 1.80 mmol) in dry tetrahydrofuran (50 ml). The reaction stirred at the temperature for 4 hours and then added saturated ammoniumchloride (30 ml). After stirring 30 min dichloromethane (150 ml) and hyflo super cell medium (15 g) were added. The mixture was stirred at ambient temperature 2 hours, filtered and evaporated in vacuo. The crude product was taken up in dichloromethane (150 ml) and washed with water (2×50 ml), dried with anhydrous magnesium sulfate and subsequently evaporated in vacuo giving (E)-3-[4-(3-dimethylamino-prop-1-ynyl)-phenyl]-3-phenylprop-2-en-1-ol.

Yield: 430 mg (81%).

$^1$H NMR spectrum (300 MHz, CDCl$_3$, δ$_H$): 7.45-7.30 (m, 5H); 7.20-7.10 (m, 4H); 6.30 (t, J=6.78 Hz, 1H); 4.20 (d, J=6.78 Hz, 2H); 3.45 (s, 2H); 2.20 (s, 6H).

To a solution of the above alcohol (407 mg, 1.397 mmol) in dry tetrahydrofuran (40 mL) was added tributylphosphine (0.50 ml, 2.79 mmol). To the mixture was cooled to 0° C. and added 1,1'-(azodicarbonyl)dipiperidine (703 mg, 2.79 mmol) and after 10 min. (4-hydroxy-2-methyl-phenoxy)-acetic acid methyl ester (301 mg, 1.536 mmol) was added. After stirring for 1.5 hr at 0° C. the mixture was allowed to warm up to ambient temperature and stirred overnight. The reaction mixture was added silica gel Fluka 60 (10 g) and evaporated in vacuo. The residue was purified by ISCO combiflash 16 (silica gel, hexane/ethyl acetate 85:15) giving (4-{(E)-3-[4-(3-dimethylamino-prop-1-ynyl)-phenyl]-3-phenyl-allyloxy}-2-methylphenoxy)-acetic acid methyl ester as an oil.

Yield: 347 mg (53%).

$^1$H NMR spectrum (300 MHz, CDCl$_3$, δ$_H$): 7.45-7.30 (m, 5H); 7.15 (br d, 4H); 6.70-6.55 (m, 3H); 6.30 (t, 1H); 4.55-4.45 (m, 4H); 3.70 (s, 2H); 3.50 (s, 3H); 2.40 (s, 6H); 2.25 (s, 3H).

To a solution of the above ester (164 mg, 0.349 mmol) in ethanol (40 ml) was added 1 N NaOH (1.25 ml) and the reaction mixture was stirred for 3 hours. The mixture was evaporated in vacuo and the resulting residue was dissolved in dichloromethane (50 mL) and extracted with water (10 ml). The aqueous phase was neutralized with 1N HCl (1 ml) and extracted with ethyl acetate (20 ml). The ethyl acetate phase was dried with anhydrous magnesium sulfate and subsequently evaporated in vacuo yielding the title acid as light yellow solid.

Yield: 72 mg (45%).

$^1$H NMR spectrum (300 MHz, CDCl$_3$, δ$_H$): 7.40-7.30 (m, 5H); 7.15 (br d, 4H); 6.60 (m, 2H); 6.35 (d, 1H); 6.25 (t, 1H); 4.55-4.45 (m, 4H); 3.70 (s, 2H); 2.55 (s, 6H); 2.20 (s, 3H).

Example 66

(4-{(Z)-3-[4-(3-Dimethylamino-prop-1-ynyl)-phenyl]-3-phenyl-allyloxy}-2-methyl-phenoxy)acetic Acid

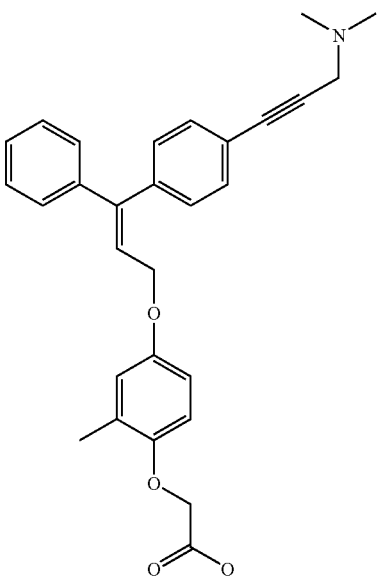

A solution of (Z)-3-(4-bromo-phenyl)-3-phenyl-acrylic acid ethyl ester (1.200 g, 3.6 mmol), dimethyl-prop-2-ynyl-amine (0.9 ml, 10.88 mmol), bis(triphenylphosphine) palladium(II) chloride (0.102 g, 0.144 mmol), copper(I) iodide (2.06 mg, 0.0108 mmol) in dry triethylamine (10 ml) were heated to 100° C. by microwave irradiation for 20 min. The cooled reaction mixture was added dichloromethane (20 ml) and silica gel Fluka 60 (10 g) and evaporated in vacuo. The resulting residue was purified by ISCO combiflash 16 (silica gel, hexane/ethyl acetate 85:15) giving (Z)-3-[4-(3-Dimethylamino-prop-1-ynyl)-phenyl]-3-phenyl-acrylic acid ethyl ester as an oil.

Yield: 6488 mg (54%).

$^1$H NMR spectrum (300 MHz, CDCl$_3$, $\delta_H$): 7.45-7.15 (m, 9H); 6.34 (s, 1H); 4.10 (q, J=7.16 Hz, 2H); 3.50 (s, 2H); 2.40 (s, 6H); 1.11 (t, J=7.16 Hz, 3H).

A 1 M solution of diisobutylaluminum hydride in tetrahydrofuran (8 mL) was added drop wise to a cooled (0° C.) solution of the above ester (0.650 g; 1.80 mmol) in dry tetrahydrofuran (50 mL). The reaction stirred at the temperature for 3 hours and then added saturated ammonium chloride (30 ml). The resulting mixture was stirred for 30 min, and the mixture was then added dichloromethane (150 ml) and hyflo super cell medium (15 g). The resulting suspension was stirred at ambient temperature 2 hours. The mixture was filtered and subsequently evaporated in vacuo. The crude product were taken up in dichloromethane (150 ml) and washed with water (2×50 ml). The dichloromethane phase was dried with anhydrous magnesium sulfate and subsequently evaporated in vacuo giving (Z)-3-[4-(3-dimethylamino-prop-1-ynyl)-phenyl]-3-phenyl-prop-2-en-1-ol Yield: 469 mg (82%).

$^1$H NMR spectrum (300 MHz, CDCl$_3$, $\delta_H$): 7.45-7.10 (m, 9H); 6.25 (t, J=6.78 Hz, 1H); 4.25 (d, J=6.78 Hz, 2H); 3.80 (s, 2H); 2.65 (s, 6H).

To a solution of the above alcohol (291 mg, 0.999 mmol) in dry tetrahydrofuran (30 mL) was added tributylphosphine (0.27 ml, 1.5 mmol). The mixture was cooled to 0° C. and added 1,1'-(azodicarbonyl)dipiperidine (377.5 mg, 1.5 mmol), and after 10 min (4-Hydroxy-2-methyl-phenoxy)-acetic acid methyl ester (2151 mg, 1.1 mmol) was added. After 1.5 hr at 0° C. the reaction was allowed to warm up to ambient temperature and stirred overnight. The reaction mixture was added silica gel Fluka 60 (10 g) and evaporated in vacuo. The residue was purified by ISCO combiflash 16 (silica gel, hexane/ethyl acetate 85:15) yielding (4-{(E)-3-[4-(3-dimethylamino-prop-1-ynyl)-phenyl]-3-phenyl-allyloxy}-2-methyl-phenoxy)-acetic acid methyl ester as an oil.

Yield: 140 mg (30%).

$^1$H NMR spectrum (300 MHz, CDCl$_3$, $\delta_H$): 7.45 (d, J=8.29 Hz, 2H) 7.25 (m, 5H); 7.15 (d, J=8.29 Hz, 2H); 6.70-6.55 (m, 3H); 6.30 (t, 1H); 4.55-4.45 (m, 4H); 3.80 (s, 2H); 3.45 (s, 3H); 2.39 (s, 6H); 2.25 (s, 3H).

To a solution of the above ester (140 mg, 0.298 mmol) in ethanol (40 ml) was added 1N NaOH (0.6 ml) and the reaction mixture was stirred for 3 hr. The mixture was evaporated in vacuo and the resulting residue was dissolved in dichloromethane (50 mL) and extracted with water (10 ml). The aqueous phase was neutralized with 1N HCl (1 ml) and extracted with ethyl acetate (20 ml). The ethyl acetate phase was dried with anhydrous magnesium sulfate and evaporated in vacuo yielding the title acid as light yellow solid.

Yield: 36 mg (27%).

$^1$H NMR spectrum (300 MHz, CDCl$_3$, $\delta_H$): 7.44 (d, J=8.29 Hz, 2H) 7.26 (m, 5H); 7.17 (d, J=8.29 Hz, 2H); 6.68-6.61 (m, 3H); 6.35 (t, 1H); 4.51-4.42 (m, 4H); 3.88 (s, 2H); 2.67 (s, 6H); 2.25 (s, 3H).

Example 67

(2-Methyl-4-{(Z)-3-[4-(3-morpholin-4-yl-prop-1-ynyl)-phenyl]-3-phenyl-allyloxy}-phenoxy)acetic Acid

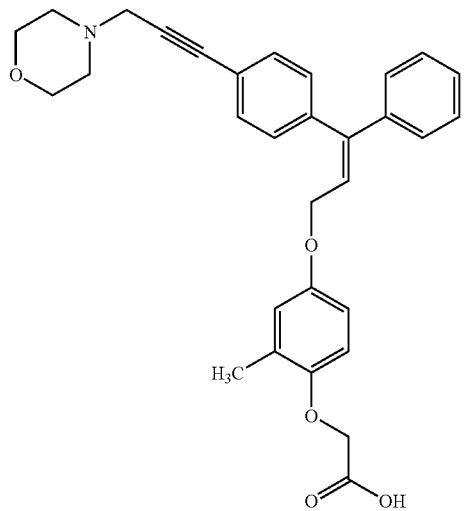

To a solution of (Z)-3-(4-Iodo-phenyl)-3-phenyl-prop-2-en-1-ol (756 mg, 2.249 mmol) in dry tetrahydrofuran (40 mL) was added tributylphosphine (0.61 ml, 3.37 mmol). The mixture was cooled to 0° C. and added 1,1'-(azodicarbonyl)dipiperidine (850 mg, 3.37 mmol) and after 10 min (4-Hydroxy-2-methyl-phenoxy)-acetic acid methyl ester (485 mg, 2.47 mmol) was added. After 1.5 hr at 0° C. the reaction was allowed to warm up to ambient temperature and stirred overnight. The reaction mixture was added silica gel Fluka 60 (10 g) and evaporated in vacuo. The residue was purified by ISCO combiflash 16 (silica gel, DCM/MeOH 90:10) giving (Z)-{4-[3-(4-iodo-phenyl)-3-phenyl-allyloxy]-2-methyl-phenoxy}-acetic acid methyl ester as an oil.

Yield: 782 mg (68%).

$^1$H NMR spectrum (300 MHz, CDCl$_3$, $\delta_H$): 7.72 (d, J=8.29 Hz, 2H) 7.27 (m, 5H); 6.95 (d, J=8.29 Hz, 2H); 6.68-6.61 (m, 3H); 6.31 (t, J=6.78 Hz 1H); 4.58 (s, 2H); 4.50 (d, J=6.78 Hz, 2H); 3.80 (s, 3H); 2.25 (s, 3H).

A solution of (Z)-{4-[3-(4-iodo-phenyl)-3-phenyl-allyloxy]-2-methyl-phenoxy}-acetic acid methyl ester (172 mg, 0.33 mmol), 4-prop-2-ynly-morpholine (0.9 ml, 10.88 mmol), bis(triphenylphosphine) palladium(II) chloride (0.009 g, 0.013 mmol), copper(I) iodide (0.19 mg, 0.001 mmol) in dry triethylamine (2 ml) were heated to 100° C. by microwave irradiation for 20 min. The cooled reaction mixture was added dichloromethane (20 ml) and silica gel Fluke 60 (10 g) and evaporated in vacuo. The residue was purified by ISCO combiflash 16 (silica gel, hexane/ethyl acetate 85:15) yielding (2-Methyl-4-{(Z)-3-[4-(3-morpholin-4-yl-prop-1-ynyl)-phenyl]-3-phenyl-allyloxy}-phenoxy)-acetic acid methyl ester as an oil.

Yield: 78 mg (54%).

¹H NMR spectrum (300 MHz, CDCl₃, δ_H): 7.46 (d, J=8.29 Hz, 2H) 7.27 (m, 5H); 7.20 (d, J=8.29 Hz, 2H); 6.68-6.58 (m, 3H); 6.30 (t, J=6.59 Hz 1H); 4.58 (s, 2H); 4.50 (d, J=6.59 Hz, 2H); 3.80 (s, 3H); 3.75 (m, 4H); 3.58 (s, 3H); 2.67 (m, 4H); 2.25 (s, 3H).

To a solution of the above ester (78 mg, 0.146 mmol) in ethanol (30 ml) was added 1N NaOH (0.43 ml) and stirred for 3 hr. The reaction mixture was then evaporated in vacuo. The resulting residue was dissolved in dichloromethane (50 mL) and extracted with water (10 ml). The aqueous phase was neutralized with 1N HCl (1 ml) and extracted with ethyl acetate. The ethyl acetate phase was dried with anhydrous magnesium sulfate and subsequently evaporated in vacuo yielding the title acid as light yellow solid.

Yield: 67 mg (89%).

¹H NMR spectrum (300 MHz, CDCl₃, δ_H): 7.41 (d, J=8.28 Hz, 2H), 7.26 (m, 5H); 7.17 (d, J=8.28 Hz, 2H); 6.67-6.58 (m, 2H); 6.42 (m, 1H) 6.32 (t, J=6.97 Hz, 1H); 4.57 (s, 2H); 4.45 (d, J=6.97 Hz, 2H); 3.82 (m, 4H); 3.68 (s, 2H); 2.88 (m, 4H); 2.24 (s, 3H).

Example 68

{2-Methyl-4-[(Z)-3-phenyl-3-(4-pyridin-2-ylethynyl-phenyl)-allyloxy]-phenoxy}-acetic Acid

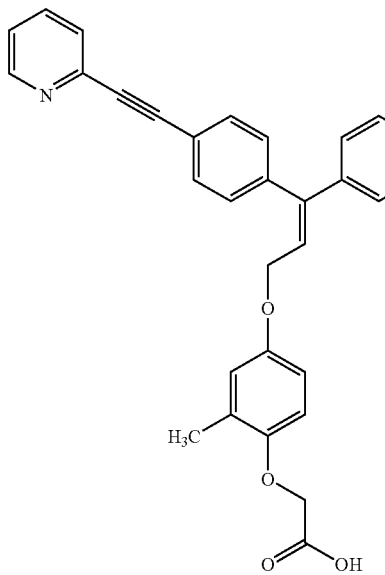

A solution of (Z)-{4-[3-(4-iodo-phenyl)-3-phenyl-allyloxy]-2-methyl-phenoxy}-acetic acid methyl ester (283 mg, 0.55 mmol), 2-Ethynyl-pyridine (0.167 ml, 1.65 mmol), bis(triphenylphosphine) palladium(II) chloride (0.015 g, 0.022 mmol), copper(I) iodide (0.31 mg, 0.002 mmol) in dry triethylamine (4 ml) were heated to 120° C. by microwave irradiation for 20 min. The cooled reaction mixture was added dichloromethane (20 ml) and silica gel Fluka 60 (10 g) and evaporated in vacuo. The residue was purified by ISCO combiflash 16 (silica gel, hexane/ethyl acetate 85:15) yielding {2-Methyl-4-[(Z)-3-phenyl-3-(4-pyridin-2-ylethynyl-phenyl)-allyloxy]-phenoxy}-acetic acid methyl ester as a yellow solid.

Yield: 239 mg (88%).

¹H NMR spectrum (300 MHz, CDCl₃, δ_H): 8.63 (d, J=4.9 Hz, 1H), 7.70 (m, 1H), 7.62 (d, J=7.91 Hz, 2H), 7.54 (d, J=7.51 Hz, 1H), 7.27 (m, 6H); 7.21 (d, J=7.91 Hz, 2H); 6.61 (m, 3H); 6.32 (t, J=6.59 Hz, 1H); 4.58 (s, 2H); 4.53 (d, J=6.97 Hz, 2H); 3.78 (s, 3H); 2.25 (s, 3H).

To a solution of the above ester (239 mg, 0.488 mmol) in methanol (40 ml) was added 1N NaOH (0.975 ml, 0.975 mmol) and the mixture were refluxed for 2 hr. After cooling to room temperature the mixture were evaporated in vacuo. The residue was dissolved in dichloromethane (50 mL) and extracted with water (10 ml). The aqueous phase was acidified with 1N HCl (1 ml) pH 3 and extracted with dichloromethane (20 ml). The dichloromethane phase were dried with anhydrous magnesium sulfate and subsequently evaporated in vacuo yielding the title acid as light green foam.

Yield: 178 mg (76%).

¹H NMR spectrum (300 MHz, CDCl₃, δ_H): 8.65 (d, J=4.52 Hz, 1H), 7.74 (m, 1H), 7.51 (m, 3H), 7.26 (m, 5H); 7.11 (d, J=7.91 Hz, 2H); 6.66 (m, 2H); 6.45 (dd, J=8.85 and 3.2 Hz 1H) 6.35 (t, J=6.97 Hz, 1H); 4.63 (s, 2H); 4.48 (d, J=6.97 Hz, 2H); 2.26 (s, 3H).

Example 69

{2-Methyl-4-[(E)-3-phenyl-3-(4-pyridin-2-ylethynyl-phenyl)-allyloxy]-phenoxy}-acetic Acid

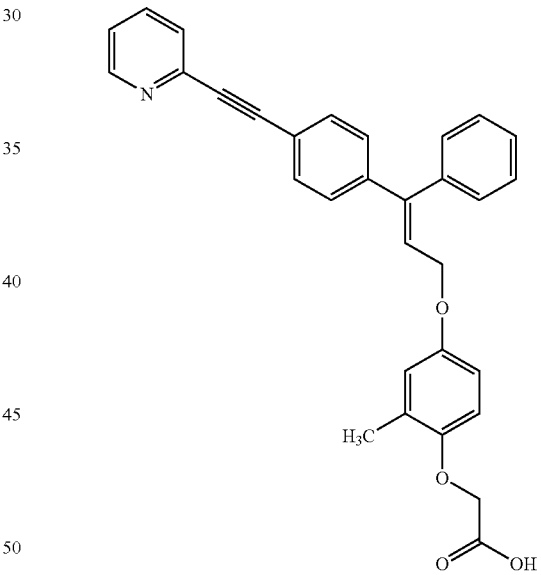

A solution of (E)-{4-[3-(4-iodo-phenyl)-3-phenyl-allyloxy]-2-methyl-phenoxy}-acetic acid methyl ester (250 mg, 0.55 mmol), 2-ethynyl-pyridine (0.147 ml, 1.458 mmol), bis(triphenylphosphine) palladium(II) chloride (0.013 g, 0.019 mmol), copper(I) iodide (0.27 mg, 0.001 mmol) in dry triethylamine (4 ml) were heated to 120° C. by microwave irradiation for 20 min. The cooled reaction mixture was then added dichloromethane (20 ml) and silica gel Fluka 60 (10 g) and evaporated in vacuo. The residue was purified by ISCO combiflash 16 (silica gel, hexane/ethyl acetate 85:15) {2-methyl-4-[(E)-3-phenyl-3-(4-pyridin-2-ylethynyl-phenyl)-allyloxy]-phenoxy}-acetic acid methyl ester as a yellow oil.

Yield: 172 mg (73%).

¹H NMR spectrum (300 MHz, CDCl₃, δ_H): 8.63 (d, J=4.9 Hz, 1H), 7.68 (m, 1H), 7.52 (m, 3H), 7.39 (m, 3H); 7.27 (m, 3H); 7.21 (d, 2H); 6.61 (m, 3H); 6.32 (t, J=6.59 Hz, 1H); 4.58 (s, 2H); 4.53 (d, J=6.59 Hz, 2H); 3.79 (s, 3H); 2.24 (s, 3H).

To a solution of the above ester (172 mg, 0.351 mmol) in methanol (30 ml) was added 1N NaOH (0.700 ml) and the mixture were refluxed for 2 hr. The cooled mixture was evaporated in vacuo. The residue was dissolved in dichloromethane (50 ml) and extracted with water (10 ml). The aqueous phase was acidified with 1N HCl (1 ml) pH 2 and extracted with ethyl acetate. The ethyl acetate phase was dried with anhydrous magnesium sulfate and subsequently evaporated in vacuo yielding the title acid as light green foam.

Yield: 145 mg (87%).

$^1$H NMR spectrum (300 MHz, CDCl$_3$, $\delta_H$): 8.65 (d, J=4.52 Hz, 1H), 7.74 (m, 1H), 7.51 (m, 1H), 7.43 (m, 5H); 7.22 (m, 5H); 6.66 (m, 2H); 6.53 (dd, J=8.67 and 3.01 Hz, 1H) 6.37 (t, J=6.59 Hz, 1H); 4.62 (s, 2H); 4.50 (d, J=6.97 Hz, 2H); 2.25 (s, 3H).

Example 70

(E)-[4-[3-(4-Bromophenyl)-3-[4-[4-(hydroxymethyl)phenylethynyl]phenyl]allyloxy]-2-methylphenoxy]acetic Acid

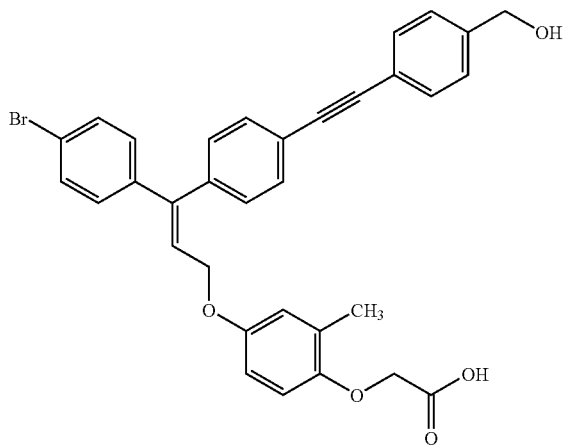

(4-Ethynylphenyl)methanol (200 mg, 1.51 mmol) and diisopropylamine (360 mg, 3.56 mmol) were added to a solution of methyl (Z)-[4-[3-(4-bromophenyl)-3-(4-iodophenyl)allyloxy]-2-methylphenoxy]acetate (445 mg, 0.75 mmol) in anhydrous tetrahydrofuran (15 mL). The solution was degassed and bis(triphenylphosphine)palladium(II) dichloride (30 mg, 0.042 mmol) and copper(I) iodide (15 mg, 0.078 mmol) were added. The reaction solution was degassed again and then stirred under inert atmosphere at ambient temperature over night. The reaction mixture was filtered through a paddle of silica gel; the paddle was thoroughly washed with ethyl acetate (4×20 mL) and the combined filtrates were concentrated in vacuo. The residue was purified by column chromatography (silica gel Fluka 60, dichloromethane/methanol 98:2) yielding methyl (E)-[4-[3-(4-bromophenyl)-3-[4-[4-(hydroxymethyl)phenylethynyl]phenyl]allyloxy]-2-methylphenoxy]acetate.

Yield: 350 mg (78%).

R$_F$ (SiO$_2$, chloroform/methanol 95:5): 0.40.

$^1$H NMR spectrum (300 MHz, CDCl$_3$, $\delta_H$): 7.57-7.53 (m, 4H); 7.42 (d, J=8.6 Hz, 2H); 7.36 (d, J=8.2 Hz, 2H); 7.18 (d, J=8.2 Hz, 2H); 7.12 (d, J=8.5 Hz, 2H); 6.67 (d, J=2.7 Hz, 1H); 6.62 (d, J=8.7 Hz, 1H); 6.57 (dd, J=8.9 and 2.8 Hz, 1H); 6.30 (t, J=6.6 Hz, 1H); 4.73 (s, 2H); 4.58 (s, 2H); 4.51 (d, J=6.6 Hz, 2H); 3.79 (s, 3H); 2.25 (s, 3H).

A solution of lithium hydroxide monohydrate (60 mg, 1.22 mmol) in distilled water (2 mL) was added to a solution of the above ester (350 mg, 0.59 mmol) in tetrahydrofuran (5 mL) and methanol (2 ml). The solution was stirred for 2 h and subsequently acidified with 2 M hydrochloric acid to pH~4. The solution was diluted with ethyl acetate (20 mL) and water (15 mL); the phases were separated and the aqueous phase was extracted with ethyl acetate (3×15 mL). The combined organic layers were washed with water (2×15 mL) and brine (2×15 mL), dried with anhydrous magnesium sulfate and evaporated in vacuo. The residue was purified by column chromatography (silica gel Fluka 60, dichloromethane/methanol/acetic acid 98:8:0.5) affording the oil, which was triturated with hexanes (2×5 mL) giving the title acid as yellow amorphous solid.

Yield: 110 mg (32%).

M.p.: 125-133° C. (amorphous).

R$_F$ (SiO$_2$, chloroform/methanol/acetic acid 98:2:0.5): 0.50.

$^1$H NMR spectrum (300 MHz, DMSO-d$_6$, $\delta_H$): 7.61 (d, J=8.2 Hz, 2H); 7.55-7.51 (m, 4H); 7.37 (d, J=8.2 Hz, 2H); 7.23 (d, J=8.1 Hz, 2H); 7.16 (d, J=8.5 Hz, 2H); 6.61 (dd, J=8.6 and 2.7 Hz, 1H); 6.37 (t, J=6.6 Hz, 1H); 4.58 (s, 2H); 4.53 (s, 2H); 4.48 (d, J=6.6 Hz, 2H); 2.13 (s, 3H).

Example 71

(E)-1-[4-[4-[1-(4-Bromophenyl)-3-[4-(carboxymethoxy)-3-methylphenoxy]propenyl]-phenylethynyl]benzyl]piperidine-4-carboxylic Acid

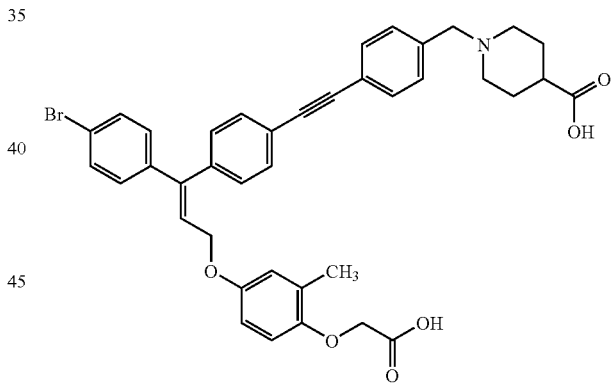

Ethyl 1-ethynylpiperidine-4-carboxylate (260 mg, 1.43 mmol) and diisopropylamine (340 mg, 3.36 mmol) were added to a solution of methyl (Z)-[4-[3-(4-bromophenyl)-3-(4-iodophenyl)allyloxy]-2-methylphenoxy]acetate (420 mg, 0.70 mmol) in anhydrous tetrahydrofuran (15 mL). The solution was degassed and bis(triphenylphosphine)palladium(II) dichloride (30 mg, 0.042 mmol) and copper(I) iodide (15 mg, 0.078 mmol) were added. The reaction solution was degassed again and then stirred under inert atmosphere at ambient temperature for 6 h. The reaction mixture was filtered through a paddle of silica gel; the paddle was thoroughly washed with ethyl acetate (4×20 mL) and the combined filtrates were concentrated in vacuo. The residue was purified by column chromatography (silica gel Fluka 60, dichloromethane/methanol 99:1) yielding ethyl (E)-1-[4-[4-[1-(4-Bromophenyl)-3-[4-(carboxymethoxy)-3-methylphenoxy]propenyl]phenylethynyl]benzyl]piperidine-4-carboxylate.

Yield: 440 mg (96%).

$R_F$ (SiO$_2$, chloroform/methanol 95:5): 0.85.

$^1$H NMR spectrum (300 MHz, CDCl$_3$, $\delta_H$): 7.48-7.42 (m, 4H); 7.16-7.11 (m, 4H); 6.68 (d, J=2.8 Hz, 1H); 6.62 (d, J=8.8 Hz, 1H); 6.57 (dd, J=8.8 and 2.8 Hz, 1H); 6.30 (t, J=6.6 Hz, 1H); 4.60 (s, 2H); 4.50 (d, J=6.6 Hz, 2H); 4.14 (q, J=7.1 Hz, 2H); 3.81 (s, 3H); 3.55 (s, 2H); 3.00-2.97 (m, 2H); 2.40-2.29 (m, 3H); 2.26 (s, 3H); 2.02-1.97 (m, 2H); 1.91-1.81 (m, 2H); 1.27 (t, J=7.1 Hz, 3H).

A solution of lithium hydroxide monohydrate (135 mg, 2.75 mmol) in distilled water (3 mL) was added to a solution of the above ester (440 mg, 0.63 mmol) in tetrahydrofuran (5 mL) and methanol (2 ml). The solution was stirred for 4 h and then acidified with 2 M hydrochloric acid to pH~6. The solution was diluted with ethyl acetate (20 mL) and 10% aqueous solution of ammonium chloride (15 mL); the phases were separated and the aqueous phase was extracted with ethyl acetate (3×15 mL). The combined organic layers were washed with 10% aqueous solution of ammonium chloride (2×15 mL) and brine (2×15 mL), dried with anhydrous magnesium sulfate and evaporated in vacuo. The residue was triturated with hexanes (2×7 mL) giving the title acid as yellow amorphous solid.

Yield: 120 mg (29%).

M.p.: 101-120° C. (amorphous).

$R_F$ (SiO$_2$, chloroform/methanol 80:20): 0.05.

$^1$H NMR spectrum (300 MHz, DMSO-d$_6$, $\delta_H$): 7.53 (d, J=8.5 Hz, 2H); 7.50 (d, J=8.1 Hz, 2H); 7.19-7.14 (m, 4H); 6.72-6.69 (m, 2H); 6.60 (dd, J=8.8 and 2.7 Hz, 1H); 6.36 (t, J=6.5 Hz, 1H); 4.58 (s, 2H); 4.46 (d, J=6.6 Hz, 2H); 3.53 (s, 2H); 2.85-2.82 (m, 2H); 2.30-2.19 (m, 3H); 2.14 (s, 3H); 1.86-1.81 (m, 2H); 1.63-1.51 (m, 2H).

Example 72

(Z)-[4-[3-(4-Fluorophenyl)-3-[4-[3-(morpholin-4-yl)propynyl]phenyl]allyloxy]-2-methylphenoxy]acetic Acid

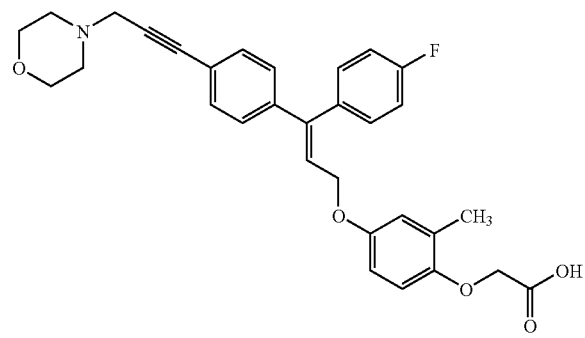

Sodium methoxide (10 mg, 0.185 mmol) was added to 1 M solution of lithium aluminum hydride in tetrahydrofuran (3.8 mL, 3.8 mmol) under nitrogen. The mixture was cooled to 0° C. and a solution of 3-(4-bromophenyl)prop-2-yn-1-ol (800 mg, 3.79 mmol) in tetrahydrofuran (5 mL) was added over 20 min. The reaction mixture was stirred at 0° C. for 4 h; dry ethyl acetate (1.2 mL, 11.8 mmol) was added and the whole mixture was stirred at ambient temperature for further 30 min. A degassed solution of 1-fluoro-4-iodobenzene (1 g, 4.51 mmol) in dry tetrahydrofuran (10 mL), anhydrous zinc chloride (310 mg, 2.27 mmol), tris(dibenzylideneacetone)dipalladium chloroform complex (79 mg, 0.076 mmol), and tri(2-furyl)phosphine (97 mg, 0.418 mmol) were added; the mixture was degassed and then heated at 60° C. over night under nitrogen. The suspension was cooled down to ambient temperature, anhydrous methanol (1.9 mL) was added and the mixture was stirred for additional 60 min. The resulting suspension was diluted with ether (20 mL) and saturated aqueous solution of ammonium chloride (1.1 mL) was added. The mixture was filtered through a paddle of silica gel and the paddle was thoroughly washed with ether (500 mL). The combined filtrates were evaporated in vacuo and the residue was separated by flash column chromatography (silica gel Fluka 60, hexanes/ethyl acetate 4:1-2:1) affording (E)-[3-(4-bromophenyl)-3-(4-fluorophenyl)prop-2-en-1-ol as oil.

Yield: 260 mg (22%).

$R_F$ (SiO$_2$, hexanes/ethyl acetate 2:1): 0.25.

$^1$H NMR spectrum (300 MHz, CDCl$_3$, $\delta_H$): 7.42 (d, J=8.6 Hz, 2H); 7.15-7.04 (m, 6H); 6.22 (t, J=6.8 Hz, 1H); 4.21 (d, J=6.7 Hz, 2H).

The above allyl alcohol (260 mg, 0.847 mmol), methyl (4-hydroxy-2-methylphenoxy)acetate (183 mg, 0.933 mmol) and triphenylphosphine (267 mg, 1.02 mmol) were dissolved in a mixture of anhydrous toluene (15 mL) and tetrahydrofuran (5 mL). The solution was cooled to 0° C., kept under nitrogen and a degassed solution of diisopropyl azodicarboxylate (0.2 mL, 1.01 mmol) in anhydrous tetrahydrofuran (4 mL) was added dropwise over 10 min. The reaction mixture was allowed to warm up to the ambient temperature with the bath and then was stirred for 18 h. The solvents were evaporated in vacuo and the residue was separated by flash column chromatography (silica gel Fluka 60, hexanes/ethyl acetate 9:1) affording methyl (E)-[4-[3-(4-bromophenyl)-3-(4-fluorophenyl)allyloxy]-2-methylphenoxy]acetate as yellow solid.

Yield: 278 mg (68%).

$R_F$ (SiO$_2$, hexanes/ethyl acetate 2:1): 0.50.

$^1$H NMR spectrum (300 MHz, CDCl$_3$, $\delta_H$): 7.39 (d, J=8.7 Hz, 2H); 7.16-7.03 (m, 6H); 6.65 (d, J=2.9 Hz, 1H); 6.60 (d, J=8.8 Hz, 1H); 6.54 (dd, J=8.9 and 2.9 Hz, 1H); 6.26 (t, J=6.7 Hz, 1H); 4.56 (s, 2H); 4.45 (d, J=6.7 Hz, 2H); 3.76 (s, 3H); 2.22 (s, 3H).

In atmosphere of nitrogen, the above bromo derivative (278 mg, 0.573 mmol) and N-propargylmorpholine (115 mg, 0.920 mmol) were dissolved in anhydrous tetrahydrofuran (8 mL). The solution was degassed; copper(I) iodide (7 mg, 0.037 mmol), bis(tri-t-butylphosphine)palladium (15 mg, 0.029 mmol) and 1,8-diazabicyclo[5.4.0]undec-7-ene (0.11 mL, 0.742 mmol) were subsequently added. The mixture was stirred under nitrogen at 60° C. for 18 h, cooled down and evaporated in vacuo. The residue was purified by flash column chromatography (silica gel Fluka 60, dichloromethane/methanol 98:2) yielding methyl (Z)-[4-[3-(4-fluorophenyl)-3-[4-[3-(morpholin-4-yl)propynyl]phenyl]allyloxy]-2-methylphenoxy]acetate as brownish oil.

Yield: 218 mg (72%).

$R_F$ (SiO$_2$, dichloromethane/methanol 95:5): 0.30.

$^1$H NMR spectrum (300 MHz, CDCl$_3$, $\delta_H$): 7.36 (d, J=8.5 Hz, 2H); 7.19-7.05 (m, 6H); 6.68 (d, J=2.9 Hz, 1H); 6.63 (d, J=8.8 Hz, 1H); 6.57 (dd, J=8.9 and 2.7 Hz, 1H); 6.32 (t, J=6.6 Hz, 1H); 4.58 (s, 2H); 4.49 (d, J=6.7 Hz, 2H); 3.79 (s, 3H); 3.78 (m, 4H (overlapped)); 3.51 (s, 2H); 2.64 (m, 4H); 2.25 (s, 3H).

To a solution of the above ester (218 mg, 0.412 mmol) in tetrahydrofuran/methanol mixture (5:1, 6 mL), a solution of lithium hydroxide monohydrate (52 mg, 1.24 mmol) in distilled water (1 mL) was added under cooling to 0° C. The solution was stirred for 1.5 h under cooling, acetic acid (0.071 mL, 1.24 mmol) was added and the resulting mixture was stirred for further 10 min. The solution was diluted with chloroform (40 mL) and water (30 mL); the phases were separated and the aqueous phase was extracted with chloroform (3×20 mL). The combined organic layers were washed with water (2×20 mL) and brine (2×20 mL), dried with anhydrous magnesium sulfate and evaporated in vacuo. The residue was triturated with hexanes (2×5 mL) yielding the title acid as white solid.

Yield: 120 mg (57%).
M.p.: 144-149° C.
$R_F$ (SiO$_2$, dichloromethane/methanol 90:10): 0.20.
$^1$H NMR spectrum (300 MHz, CDCl$_3$, $\delta_H$): 7.31 (d, J=8.4 Hz, 2H); 7.16-7.04 (m, 6H); 6.67 (d, J=2.8 Hz, 1H); 6.62 (d, J=8.8 Hz, 1H); 6.42 (dd, J=9.0 and 2.8 Hz, 1H); 6.30 (t, J=6.7 Hz, 1H); 4.54 (s, 2H); 4.43 (d, J=6.7 Hz, 2H); 3.82 (m, 4H); 3.63 (s, 2H); 2.83 (m, 4H); 2.24 (s, 3H).

Example 73

(E)-[2-M ethyl-4-[3-(4-methyl phenyl)-3-[4-[3-(morpholin-4-yl)propynyl]phenyl]allyloxy]-phenoxy] acetic Acid

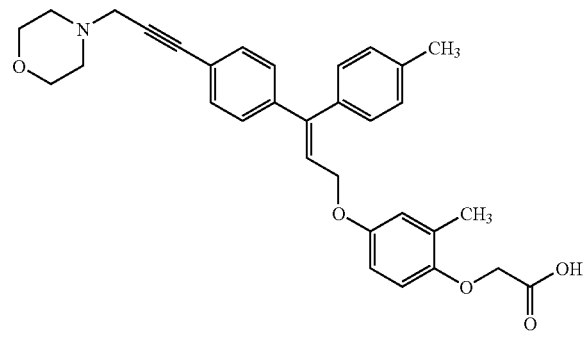

Sodium methoxide (11 mg, 0.204 mmol) was added to 1 M solution of lithium aluminum hydride in tetrahydrofuran (3.9 mL, 3.9 mmol) under nitrogen. The mixture was cooled to 0° C. and a solution of 3-(4-bromophenyl)prop-2-yn-1-ol (820 mg, 3.89 mmol) in tetrahydrofuran (5 mL) was added over 15 min. The reaction mixture was stirred at 0° C. for 3 h; dry ethyl acetate (1.2 mL, 12.1 mmol) was added and the whole mixture was stirred at ambient temperature for 30 min. A degassed solution of 1-iodo-4-methylbenzene (1.02 g, 4.68 mmol) in dry tetrahydrofuran (10 mL), anhydrous zinc chloride (318 mg, 2.33 mmol), tris(dibenzylideneacetone)dipalladium chloroform complex (81 mg, 0.078 mmol), and tri(2-furyl)phosphine (99 mg, 0.426 mmol) were added; the mixture was degassed and then heated at 60° C. over night under nitrogen. The suspension was cooled down to ambient temperature, anhydrous methanol (1.95 mL) was added and the resulting mixture was stirred for additional 60 min. The reaction was diluted with ether (20 mL) and saturated aqueous solution of ammonium chloride (1.15 mL) was added. The mixture was filtered through a paddle of silica gel and the paddle was thoroughly washed with ether (500 mL). The solvents were evaporated in vacuo and the residue was separated by flash column chromatography (silica gel Fluka 60, hexanes/ethyl acetate 4:1) affording (E)-[3-(4-bromophenyl)-3-(4-methylphenyl)prop-2-en-1-ol as yellow solid.

Yield: 192 mg (16%).
$R_F$ (SiO$_2$, hexanes/ethyl acetate 2:1): 0.35.
$^1$H NMR spectrum (300 MHz, CDCl$_3$, $\delta_H$): 7.39 (d, J=8.8 Hz, 2H); 7.17 (m, 2H); 7.11 (d, J=8.7 Hz, 2H); 7.01 (d, J=8.0 Hz, 2H); 6.18 (t, J=6.8 Hz, 1H); 4.21 (d, J=6.8 Hz, 2H); 2.37 (s, 3H).

The above allyl alcohol (192 mg, 0.633 mmol), methyl (4-hydroxy-2-methylphenoxy)acetate (137 mg, 0.698 mmol) and triphenylphosphine (199 mg, 0.759 mmol) were dissolved in a mixture of anhydrous toluene (15 mL) and tetrahydrofuran (5 mL). The solution was cooled to 0° C., kept under nitrogen and a degassed solution of diisopropyl azodicarboxylate (0.15 mL, 0.757 mmol) in anhydrous tetrahydrofuran (4 mL) was added dropwise over 10 min. The reaction mixture was allowed to warm up to the ambient temperature with the bath and then was stirred for 19 h. The solvents were evaporated in vacuo and the residue was separated by flash column chromatography (silica gel Fluka 60, hexanes/ethyl acetate 9:1) affording methyl (E)-[4-[3-(4-bromophenyl)-3-(4-methylphenyl)allyloxy]-2-methylphenoxy]-acetate as yellow oil.

Yield: 156 mg (51%).
$R_F$ (SiO$_2$, hexanes/ethyl acetate 2:1): 0.50.
$^1$H NMR spectrum (300 MHz, CDCl$_3$, $\delta_H$): 7.41 (d, J=8.5 Hz, 2H); 7.20 (d, J=7.8 Hz, 2H); 7.14 (d, J=8.6 Hz, 2H); 7.07 (d, J=8.1 Hz, 2H); 6.68 (d, J=2.8 Hz, 1H); 6.63 (d, J=8.7 Hz, 1H); 6.57 (dd, J=8.9 and 2.8 Hz, 1H); 6.25 (t, J=6.6 Hz, 1H); 4.58 (s, 2H); 4.53 (d, J=6.6 Hz, 2H); 3.79 (s, 3H); 2.40 (s, 3H); 2.25 (s, 3H).

In atmosphere of nitrogen, the above bromo derivate (156 mg, 0.324 mmol) and N-propargylmorpholine (65 mg, 0.520 mmol) were dissolved in anhydrous tetrahydrofuran (8 mL). The solution was degassed; copper(I) iodide (4 mg, 0.021 mmol), bis(tri-t-butylphosphine)palladium (8.5 mg, 0.017 mmol) and 1,8-diazabicyclo[5.4.0]undec-7-ene (0.063 mL, 0.421 mmol) were subsequently added. The mixture was stirred under nitrogen at 60° C. for 17 h, cooled down and evaporated in vacuo. The residue was purified by flash column chromatography (silica gel Fluka 60, dichloromethane/methanol 98:2) yielding methyl (E)-[2-methyl-4-[3-(4-methylphenyl)-3-[4-[3-(morpholin-4-yl)propynyl]phenyl]allyloxy]phenoxy]-acetate as brownish oil.

Yield: 157 mg (92%).
$R_F$ (SiO$_2$, dichloromethane/methanol 95:5): 0.35.
$^1$H NMR spectrum (300 MHz, CDCl$_3$, $\delta_H$): 7.35 (d, J=8.5 Hz, 2H); 7.20 (d, J=8.4 Hz, 4H); 7.07 (d, J=8.0 Hz, 2H); 6.68 (d, J=2.8 Hz, 1H); 6.63 (d, J=8.8 Hz, 1H); 6.57 (dd, J=8.9 and 2.8 Hz, 1H); 6.27 (t, J=6.6 Hz, 1H); 4.58 (s, 2H); 4.53 (d, J=6.6 Hz, 2H); 3.79 (s, 3H); 3.78 (m, 4H (overlapped)); 3.52 (s, 2H); 2.65 (m, 4H); 2.39 (s, 3H); 2.24 (s, 3H).

To a solution of the above ester (157 mg, 0.299 mmol) in tetrahydrofuran/methanol mixture (5:1, 6 mL), a solution of lithium hydroxide monohydrate (38 mg, 0.906 mmol) in distilled water (1 mL) was added under cooling to 0° C. The solution was stirred for 1.5 h under cooling, acetic acid (0.052 mL, 0.909 mmol) was added and the resulting mixture was stirred for further 10 min. The solution was diluted with chloroform (40 mL) and water (30 mL); the phases were separated and the aqueous phase was extracted with chloroform (3×20 mL). The combined organic layers were washed with water (2×20 mL) and brine (2×20 mL), dried with anhydrous magnesium sulfate and evaporated in vacuo. This afforded the title acid as yellow solid.

Yield: 77 mg (50%).
M.p.: 109-118° C.
$R_F$ (SiO$_2$, dichloromethane/methanol 90:10): 0.20.
$^1$H NMR spectrum (300 MHz, CDCl$_3$, $\delta_H$): 7.30 (d, J=8.2 Hz, ~2H (overlapped)); 7.17 (m, 4H); 7.06 (d, J=7.8 Hz, 2H); 6.67 (d, J=2.5 Hz, 1H); 6.62 (d, J=9.0 Hz, 1H); 6.45 (dd, J=8.4 and 2.7 Hz, 1H); 6.26 (t, J=6.5 Hz, 1H); 4.54 (s, 2H); 4.48 (d, J=6.6 Hz, 2H); 3.81 (m, ~4H); 3.62 (s, 2H); 2.81 (m, 4H); 2.38 (s, 3H); 2.24 (s, 3H).

Example 74

(Z)-[4-[3-(4-Chlorophenyl)-3-[4-[3-(morpholin-4-yl)propynyl]phenyl]allyloxy]-2-methylphenoxy]acetic Acid

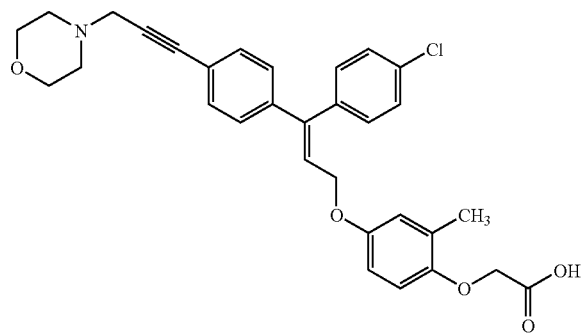

1 M Solution of lithium aluminum hydride in tetrahydrofuran (7.9 mL, 7.9 mmol) was added to sodium methoxide (21 mg, 0.396 mmol) under nitrogen. The mixture was cooled to 0° C. and a solution of 3-(4-bromophenyl)-prop-2-yn-1-ol (1.67 g, 7.91 mmol) in dry tetrahydrofuran (12 mL) was added dropwise. The reaction mixture was stirred at 0° C. for 3.5 h; dry ethyl acetate (2.4 mL, 15.8 mmol) was added and the whole mixture was stirred at ambient temperature for 30 min. A degassed solution of 1-chloro-4-iodobenzene (1.89 g, 7.91 mmol) in anhydrous tetrahydrofuran (12 mL), anhydrous zinc chloride (0.65 g, 4.77 mmol), tris(dibenzylideneacetone)dipalladium chloroform complex (0.165 g, 0.16 mmol) and tri-(2-furyl)phosphine (0.184 g, 0.791 mmol) were added; the mixture was degassed and stirred at 65° C. for 22 h under atmosphere of nitrogen. The suspension was cooled down; methanol (3.5 mL) was added and the mixture was stirred for additional 1 h. The mixture was diluted with ether (40 mL) and saturated aqueous solution of ammonium chloride (2 mL), was filtered through a pad of silica gel and the pad was thoroughly washed with ether (80 mL). the filtrate was evaporated in vacuo and the residue was purified by flash column chromatography (silica gel Fluka 60, dichloromethane/ethyl acetate 20:1) affording (E)-3-(4-bromophenyl)-3-(4-chlorophenyl)-prop-2-en-1-ol as yellow oil, which solidified in fridge.

Yield: 0.540 g (21%).

$R_F$ (SiO$_2$, ethyl acetate/hexane 20:1): 0.20.

$^1$H NMR spectrum (300 MHz, CDCl$_3$, $\delta_H$): 7.42 (d, J=8.7 Hz, 2H); 7.36 (d, J=8.7, 2H); 7.10 (d, J=8.7 Hz, 2H); 7.09 (d, J=8.7 Hz, 2H); 6.25 (t, J=6.8 Hz, 1H); 4.20 (d, J=6.8 Hz, 2H).

The above allyl alcohol (0.28 g, 0.865 mmol), methyl (4-hydroxy-2-methylphenoxy)acetate (0.187 g, 0.952 mmol) and triphenylphosphine (0.261 g, 0.995 mmol) were dissolved in a mixture of anhydrous toluene (3 mL) and tetrahydrofuran (1.5 mL). The mixture was cooled to 0° C., kept under nitrogen and a degassed solution of diisopropyl azodicarboxylate (0.196 mL, 0.995 mmol) in anhydrous tetrahydrofuran (1 mL) was added dropwise. The reaction mixture was allowed to warm up to ambient temperature and then was stirred over night. The solvents were evaporated in vacuo and the residue was submitted to flash column chromatography (silica gel Fluka 60, hexanes/ethyl acetate 6:1) affording (E)-[4-[3-(4-bromophenyl)-3-(4-chlorophenyl)allyloxy]-2-methylphenoxy]acetate as yellow oil.

Yield: 270 mg (62%).

$R_F$ (SiO$_2$, hexanes/ethyl acetate 6:1): 0.50.

$^1$H NMR spectrum (300 MHz, CDCl$_3$, $\delta_H$): 7.42 (d, J=8.7 Hz, 2H); 7.36 (d, J=8.7, 2H); 7.10 (d, J=8.7 Hz, 2H); 7.09 (d, J=8.7 Hz, 2H); 6.67 (d, J=2.8 Hz, 1H); 6.62 (d, J=8.8 Hz, 1H); 6.56 (dd, J=8.8 and 2.8 Hz, 1H); 6.30 (t, J=6.7 Hz, 1H); 4.58 (s, 2H); 4.47 (d, J=6.7 Hz, 2H); 3.79 (s, 3H); 2.25 (s, 3H).

To a degassed solution of the above ester (270 mg, 0.538 mmol), N-propargylmorpholine (101 mg, 0.807 mmol) and 1,8-diazabicyclo[5.4.0]undec-7-ene (0.322 mL, 2.15 mmol) in anhydrous tetrahydrofuran (5 mL), bis(tri-t-butylphosphine)palladium (15 mg, 0.03 mmol) and copper(I) iodide (8 mg, 0.04 mmol) were added. The reaction mixture was stirred at 50° C. for 20 h under nitrogen. The solvents were evaporated in vacuo and the residue was purified by flash column chromatography (silica gel Fluka 60, chloroform/methanol 100:0-98:2) yielding methyl (Z)-[4-[3-(4-chlorophenyl)-3-[4-[3-(morpholin-4-yl)propynyl]phenyl]-allyloxy]-2-methylphenoxy]acetate as yellow oil.

Yield: 200 mg (68%).

$R_F$ (SiO$_2$, chloroform/methanol 95:5): 0.30.

$^1$H NMR spectrum (300 MHz, CDCl$_3$, $\delta_H$): 7.37 (d, J=8.4 Hz, 2H); 7.36 (d, J=8.4 Hz, 2H); 7.18 (d, J=8.4 Hz, 2H); 7.13 (d, J=8.4 Hz, 2H); 6.67 (d, J=2.7 Hz, 1H); 6.63 (d, J=8.8 Hz, 1H); 6.57 (dd, J=8.8 and 2.8 Hz, 1H); 6.33 (t, J=6.7 Hz, 1H); 4.58 (s, 2H); 4.48 (d, J=6.7 Hz, 2H); 3.77 (m, 7H); 3.51 (s, 2H); 2.64 (m, 2H); 2.25 (s, 3H).

The above ester (200 mg, 0.37 mmol) was dissolved in a mixture of tetrahydrofuran (6 mL) and methanol (4 mL) and a solution of lithium hydroxide monohydrate (35 mg, 0.83 mmol) in distilled water (2 mL) was added. The mixture was stirred over night and then diluted with saturated aqueous solution of ammonium chloride (45 mL). The resulting mixture was extracted with ether (3×30 mL); the combined organic layers were dried with anhydrous magnesium sulfate and evaporated in vacuo. The residue was triturated with hexanes (2×10 mL) yielding the title acid as yellowish powder.

Yield: 120 mg (62%).

M.p.: 92-95° C.

$R_F$ (SiO$_2$, chloroform/methanol 4:1): 0.50.

$^1$H NMR spectrum (300 MHz, CDCl$_3$, $\delta_H$): 7.38 (d, J=4.7 Hz, 2H); 7.35 (d, J=4.8 Hz, 2H); 7.19 (d, J=8.3 Hz); 7.13 (d, J=8.3 Hz, 2H); 6.68-6.64 (m, 2H, overlapped); 6.56 (dd, J=8.8 and 2.7 Hz, 1H); 6.33 (t, J=6.7 Hz, 1H); 4.59 (s, 2H); 4.48 (d, J=6.6 Hz, 2H); 3.84 (t, J=4.4 Hz, 4H); 3.71 (s, 2H); 2.89 (t, J=4.4 Hz, 4H); 2.25 (s, 3H).

Example 75

Methyl (E)-[2-Methyl-4-[3-[4-[3-(morpholin-4-yl)propynyl]phenyl]-3-(4-trifluoromethylphenyl)allyloxy]phenoxy]acetate

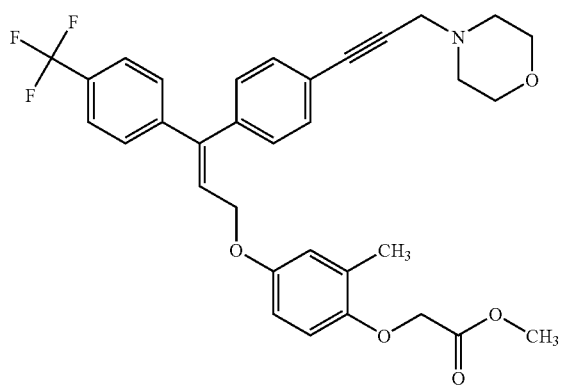

To a degassed solution of 1-bromo-4-trifluoromethylbenzene (17.7 g, 78.6 mmol) in tetrahydrofuran (140 mL) was added in the following order: copper(I) iodide (447 mg, 2.35 mmol), bis(triphenylphosphine)palladium(II) dichloride (1.65 g, 2.35 mmol), and 1,8-diazabicyclo[5.4.0]undec-7-ene (14.4 g, 94.3 mmol). The resulting mixture was degassed one more time, cooled in an ice bath and a solution of propargyl alcohol (5.29 g, 94.3 mmol) in tetrahydrofuran (5 mL) was added over period of 10 min. The reaction mixture was slowly heated up to 55° C. and then stirred at this temperature for 3 h and subsequently at ambient temperature overnight. The mixture was diluted with ether (200 mL), washed with 5% hydrochloric acid (60 mL), water (3×50 mL) and saturated aqueous solution of sodium hydrogen carbonate (30 mL). The organic solution was dried with anhydrous magnesium sulfate and evaporated in vacuo. The residue was purified by column chromatography (silica gel Fluka 60, dichloromethane) yielding 3-(4-trifluoromethylphenyl)prop-2-yn-1-ol.

Yield: 15.1 g (~100%).

$R_F$ (SiO$_2$, chloroform): 0.25.

Sodium methoxide (0.375 g, 6.95 mmol) was added to 1 M solution of lithium aluminum hydride in tetrahydrofuran (146 mL, 146 mmol) under atmosphere of argon. The mixture was cooled to 0° C. and a solution of the above alcohol (27.8 g, 139 mmol) in tetrahydrofuran (210 mL) was added over 70 min. The reaction was stirred at 0° C. for 3 h; dry dimethyl carbonate (14.5 g, 161 mmol) was added under cooling and then the whole mixture was stirred at ambient temperature for 15 min. A degassed solution of 1,4-diiodobenzene (50.5 g, 153 mmol) in dry tetrahydrofuran (120 mL), anhydrous zinc chloride (11.4 g, 83.3 mmol), tris(dibenzylideneacetone)dipalladium chloroform complex (2.88 g, 2.78 mmol), and tri(2-furyl)phosphine (3.55 g, 15.3 mmol) were added; the mixture was degassed and then heated at 65° C. for 15 h under argon. The suspension was cooled down; methanol (75 mL) was added and the mixture was stirred for additional 1 h. Saturated solution of ammonium chloride was added (40 mL), the reaction mixture was diluted with water (200 mL), acidified with 5% hydrochloric acid under stirring. Ether was added (1000 mL) and the mixture was filtered through a pad of silica gel and the pad was thoroughly washed with ether (3×100 mL). The combined filtrates were evaporated in vacuo and the residue was purified by column chromatography (silica gel Fluka 60, dichloromethane) and the obtained crude product (55 g) was crystallized from ethanol/toluene/n-heptane mixture. This afforded (Z)-3-(4-iodophenyl)-3-(4-trifluoromethylphenyl)prop-2-en-1-ol as yellow crystals.

Yield: 26.9 g (48%).

M.p.: 109-111° C.

$R_F$ (SiO$_2$, hexanes/ethyl acetate 3:1): 0.35.

$^1$H NMR spectrum (300 MHz, CDCl$_3$, δ$_H$): 7.72 (d, J=8.3 Hz, 2H); 7.55 (d, J=8.1 Hz, 2H); 7.34 (d, J=8.1 Hz, 2H); 6.90 (d, J=8.3 Hz, 2H); 6.31 (t, J=6.8 Hz, 1H); 4.24 (d, J=6.8 Hz, 2H).

The above allyl alcohol (11.88 g, 29.4 mmol), methyl (4-hydroxy-2-methylphenoxy)acetate (6.34 g, 32.3 mmol) and triphenylphosphine (9.25 g, 35.3 mmol) were dissolved in a mixture of anhydrous tetrahydrofuran (200 mL) and toluene (550 mL). The mixture was cooled to 0° C., kept under nitrogen and a degassed solution of diisopropyl azodicarboxylate (7.36 mL, 35.3 mmol) in anhydrous tetrahydrofuran (50 mL) was added dropwise during 70 min. The reaction mixture was allowed to warm up to ambient temperature with the bath and then stirred overnight. The solvents were evaporated in vacuo and the residue was submitted to column chromatography (silica gel Fluka 60, hexanes/ethyl acetate 85:15) affording methyl (Z)-[4-[3-(4-iodophenyl)-3-(4-trifluoromethylphenyl)allyloxy]-2-methylphenoxy]acetate as solidifying yellow oil.

Yield: 14.1 g (82%).

$R_F$ (SiO$_2$, hexanes/ethyl acetate 3:1): 0.55.

$^1$H NMR spectrum (300 MHz, CDCl$_3$, δ$_H$): 7.74 (d, J=8.4 Hz, 2H); 7.55 (d, J=8.1 Hz, 2H); 7.35 (d, J=8.1 Hz, 2H); 6.93 (d, J=8.4 Hz, 2H); 6.69-6.55 (m, 3H); 6.37 (t, J=6.6 Hz, 1H); 4.59 (s, 2H); 4.51 (d, J=6.6 Hz, 2H); 3.79 (s, 3H); 2.26 (s, 3H).

A solution of the above ester (13.9 g, 23.9 mmol), N-propargylmorpholine (5.98 g, 47.7 mmol) and N,N-diisopropylamine (11.35 g, 112 mmol) in tetrahydrofuran (250 mL) was cooled down and degassed; bis(triphenylphosphine)palladium(II) dichloride (0.84 g, 1.19 mmol) and copper(I) iodide (0.365 g, 1.9 mmol) were added. The reaction mixture was stirred at ambient temperature for 18 h. The mixture was evaporated in vacuo and the residue was purified by column chromatography (silica gel Fluka 60, hexanes/ethyl acetate/methanol 64:32:4) yielding the title compound as a white crystals.

Yield: 13.2 g (71%).

M.p.: 83-85° C.

$R_F$ (SiO$_2$, hexanes/ethyl acetate/methanol 64:32:4): 0.25.

$^1$H NMR spectrum (300 MHz, CDCl$_3$, δ$_H$): 7.54 (d, J=8.3 Hz, 2H); 7.48 (d, J=8.3 Hz, 2H); 7.35 (d, J=8.5 Hz, 2H); 7.14 (d, J=8.3 Hz, 2H); 6.68-6-55 (m, 3H); 6.37 (t, J=6.7 Hz, 1H); 4.59 (s, 2H); 4.53 (d, J=6.7 Hz, 2H); 3.80 (s, 3H); 3.77 (m, 4H); 3.54 (s, 2H); 2.66 (m, 4H); 2.25 (s, 3H).

Example 76

(Z)-[4-[3-(4-Chlorophenyl)-3-[4-[3-(morpholin-4-yl)propynyl]phenyl]allyloxy]-2-methylphenyl]-propionic Acid

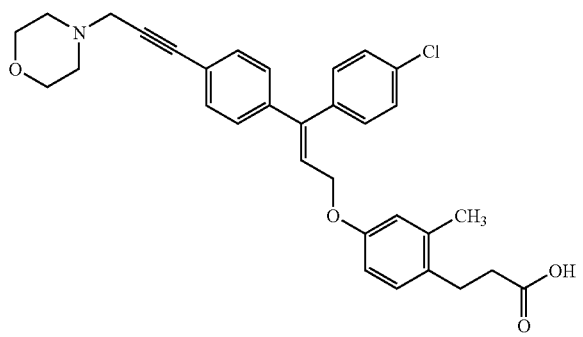

Ethyl 4-hydroxy-2-methylphenylpropionate (0.21 g, 1.0 mmol), (E)-[3-(4-bromophenyl)-3-(4-chlorophenyl)]allyl alcohol (0.26 g, 0.80 mmol) and triphenylphosphine (0.29 g, 1.1 mmol) were dissolved in a mixture of anhydrous toluene (5 mL) and tetrahydrofuran (5 mL). The mixture was cooled to 0° C., kept under nitrogen and diisopropyl azodicarboxylate (0.25 g, 1.17 mmol) was added dropwise. The reaction mixture was stirred at 0° C. for 3 h and then left to stand at ambient temperature for 1 week. The solvents were evaporated in vacuo and the residue was submitted to column chromatography (silica gel Fluka 60, benzene) affording ethyl (E)-[4-[3-(4-bromophenyl)-3-(4-chlorophenyl)allyloxy]-2-methyl phenyl]-propionate.

Yield: 0.28 g (68%).
$R_F$ (SiO$_2$, benzene): 0.30.
$^1$H NMR spectrum (300 MHz, CDCl$_3$, $\delta_H$): 7.42 (d, J=8.6 Hz, 2H); 7.37 (d, J=8.5 Hz, 2H); 7.12 (t, 4H); 7.01 (d, J=8.3 Hz, 1H); 6.64 (d, J=2.5 Hz, 1H); 6.61 (dd, J=8.3 and 2.5 Hz, 1H); 6.31 (t, J=6.6 Hz, 1H); 4.50 (d, J=6.6 Hz, 2H); 4.13 (q, J=7.1 Hz, 2H); 2.86 (t, J=8.4 Hz, 2H); 2.52 (t, J=8.4 Hz, 2H); 2.27 (s, 3H); 1.24 (t, J=7.1 Hz, 3H).

Under nitrogen atmosphere, 4-propargylmorpholine (550 mg, 4.4 mmol) bis(triphenylphosphine)palladium(II) dichloride (40 mg, 0.057 mmol) and copper(II) acetate (7 mg, 0.038 mmol) were added to a degassed solution of the above ester (280 mg, 0.55 mmol) in triethylamine (30 mL). The reaction mixture was refluxed for 8 h, diluted with benzene (100 mL), filtered and evaporated in vacuo. The residue was purified by column chromatography (silica gel Fluka 60, chloroform/methanol 9:1) yielding ethyl (Z)-[4-[3-(4-chlorophenyl)-3-[4-[3-(morpholin-4-yl)propynyl]phenyl]allyloxy]-2-methylphenyl]propionate.

Yield: 0.20 g (66%).
$R_F$ (SiO$_2$, chloroform/ethanol 5:1): 0.65.
$^1$H NMR spectrum (300 MHz, CDCl$_3$, $\delta_H$): 7.36 (t, 4H); 7.18 (d, J=8.4 Hz, 2H); 7.14 (d, J=8.4 Hz, 2H); 7.01 (d, J=8.3 Hz, 1H); 6.64 (d, J=2.5 Hz, 1H); 6.60 (dd, J=8.3 and 2.5 Hz, 1H); 6.34 (t, J=6.6 Hz, 1H); 4.51 (d, J=6.6 Hz, 2H); 4.12 (q, J=7.1 Hz, 2H); 3.77 (bt, 4H); 3.51 (s, 2H); 2.86 (t, J=7.4 Hz, 2H); 2.64 (bt, 4H); 2.52 (t, J=7.4 Hz, 2H) 2.27 (s, 3H); 1.24 (t, J=7.1 Hz, 3H).

The above ester (0.20 g, 0.358 mmol) was dissolved in ethanol (20 mL), a solution of lithium hydroxide monohydrate (0.06 g, 1.43 mmol) in water (2 mL) was added and the mixture was left to stand for 48 h. The solvents were evaporated in vacuo; the residue was diluted with water (25 mL) and extracted with ether (10 mL). The ethereal extract was discarded, the aqueous layer was acidified with acetic acid (0.5 mL) and the separated title compound was filtered off and dried in the air.

Yield: 0.15 g (79%).
$R_F$ (SiO$_2$, chloroform/methanol 3:1): 0.80.
$^1$H NMR spectrum (300 MHz, CDCl$_3$, $\delta_H$): 7.34 (t, 4H); 7.18 (d, J=8.4 Hz, 2H); 7.13 (d, J=8.4 Hz, 2H); 7.03 (d, J=8.4 Hz, 1H); 6.64 (d, J=2.4 Hz, 1H); 6.60 (dd, J=8.4 and 2.4 Hz, 1H); 6.34 (t, J=6.6 Hz, 1H); 4.51 (d, J=6.6 Hz, 2H); 3.78 (bt, 4H); 3.54 (s, 2H); 2.87 (t, J=7.7 Hz, 2H); 2.69 (bt, 4H); 2.57 (t, J=7.7 Hz, 2H) 2.27 (s, 3H).

Example 77

(Z)-[2-Methyl-4-[3-[4-[3-(morpholin-4-yl)propynyl]phenyl]-3-(4-trifluoromethylphenyl)allyloxy]-phenoxy]acetic Acid

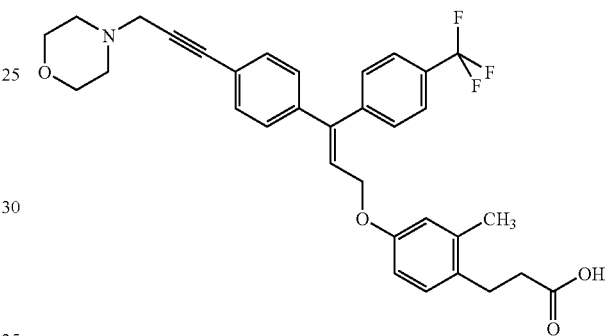

Sodium methoxide (23 mg, 0.43 mmol) was added to 1 M solution of lithium aluminum hydride in tetrahydrofuran (9 mL, 9.0 mmol). The mixture was cooled to 0° C. and a solution of 3-(4-bromophenyl)prop-2-yn-1-ol (1.9 g, 9.0 mmol) in tetrahydrofuran (15 mL) was slowly added. The reaction was stirred for at 0° C. for 3 h; ethyl acetate (2.7 mL, 9.0 mmol) was added and the mixture was stirred for 10 min without cooling. 4-Iodobenzotrifluoride (2.33 g, 8.6 mmol), anhydrous zinc chloride (0.74 g, 5.4 mmol), tris(dibenzylideneacetone)dipalladium chloroform complex (0.19 g, 0.18 mmol) and tri(2-furyl)phosphine (0.17 g, 0.73 mmol) were added, the mixture was evacuated and kept under nitrogen. The mixture was heated at 65° C. for 16 h. Methanol (4.5 mL) was added and the mixture was stirred for additional 1 h. The reaction mixture was diluted with ether (300 mL) and saturated aqueous solution of ammonium chloride (2.5 mL) was added. The mixture was filtered through a pad of silica gel, evaporated in vacuo and the residue was submitted to column chromatography (silica gel Fluka 60, hexanes/ethyl acetate 80:20) affording (E)-3-(4-bromophenyl)-3-(4-trifluoromethyl phenyl)-prop-2-en-1-ol.

Yield: 0.77 g (24%).
$R_F$ (SiO$_2$, hexanes/ethyl acetate 70:30): 0.25.
$^1$H NMR spectrum (300 MHz, CDCl$_3$, $\delta_H$): 7.65 (d, J=7.9 Hz, 2H); 7.43 (d, J=8.7 Hz, 2H); 7.28 (d, J=7.9 Hz, 2H); 7.08 (d, J=8.6 Hz, 2H); 6.30 (t, J=6.9 Hz, 1H); 4.19 (d, J=6.7 Hz, 2H).

The above allyl alcohol (0.77 g, 2.16 mmol), methyl (4-hydroxy-2-methylphenoxy)acetate (0.47 g, 2.37 mmol) and triphenylphosphine (0.68 g, 2.59 mmol) were dissolved in a mixture of anhydrous toluene (10 mL) and tetrahydrofuran (3 mL). The mixture was degassed, cooled to 0° C. and a degassed solution of diisopropyl azodicarboxylate (0.525 g, 2.60 mmol) in anhydrous tetrahydrofuran (3 mL) was added dropwise under nitrogen. The reaction mixture was stirred at ambient temperature over night. The solvents were evaporated in vacuo and the residue was submitted to column chromatography (silica gel Fluka 60, hexanes/ethyl acetate 95: 5-90:10) affording methyl (E)-[4-[3-(4-bromophenyl)-3-[4-trifluoromethyl phenyl]allyloxy]-2-methylphenoxy]acetate.

Yield: 0.84 g (73%).

$R_F$ (SiO$_2$, hexanes/ethyl acetate 80:20): 0.55.

$^1$H NMR spectrum (300 MHz, CDCl$_3$, $\delta_H$): 7.66 (d, J=8.0 Hz, 2H); 7.43 (d, J=8.5 Hz, 2H); 7.31 (d, J=7.9 Hz, 2H); 7.09 (d, J=8.5 Hz, 2H); 6.67 (d, J=2.7 Hz, 1H); 6.63 (d, J=8.8 Hz, 1H); 6.56 (dd, J=8.8 and 2.9 Hz, 1H); 6.37 (t, J=6.7 Hz, 1H); 4.58 (s, 2H); 4.46 (d, J=6.7 Hz, 2H); 3.79 (s, 3H); 2.25 (s, 3H).

Under nitrogen atmosphere, N-propargylmorpholine (160 mg, 1.28 mmol) and 1,8-diazabicyclo[5.4.0]undec-7-ene (480 mg, 1.73 mmol) were added to a degassed solution of the above compound (420 mg, 0.78 mmol) in tetrahydrofuran (10 mL). Bis(tri-tert-butylphosphine)palladium (20 mg, 0.04 mmol) and copper(I) iodide (10 mg, 0.05 mmol) were added; the reaction mixture was degassed again and then stirred at ambient temperature over night under inert atmosphere. The reaction mixture was filtered through a pad of silica gel; the pad was washed with ethyl acetate (4×15 mL) and the combined organic filtrates were evaporated in vacuo. The residue was purified by repeated column chromatography (silica gel Fluka 60, hexanes/ethyl acetate 1:1 and then dichloromethane/ethyl acetate/methanol 72:25:3) yielding methyl (Z)-[2-methyl-4-[3-[4-[3-(morpholin-4-yl)propynyl]phenyl]-3-(4-trifluoromethylphenyl)allyloxy]phenoxy]acetate.

Yield: 190 mg (42%).

$R_F$ (SiO$_2$, dichloromethane/ethyl acetate/methanol 20:10:1): 0.40.

$^1$H NMR spectrum (300 MHz, CDCl$_3$, $\delta_H$): 7.65 (d, J=8.0 Hz, 2H); 7.36 (d, J=8.0 Hz, 2H); 7.32 (d, J=8.0 Hz, 2H); 7.16 (d, J=8.2 Hz, 2H); 6.67 (d, J=2.4 Hz, 1H); 6.62 (d, J=8.8 Hz, 1H); 6.56 (dd, J=8.8 and 2.7 Hz, 1H); 6.39 (t, J=6.7 Hz, 1H); 4.58 (s, 2H); 4.47 (d, J=6.7 Hz, 2H); 3.78 (s, 3H, overlapped); 3.78-3.76 (m, 4H, overlapped); 3.51 (s, 2H); 2.65-2.62 (m, 4H); 2.25 (s, 3H).

A solution of the above ester (0.19 g, 0.33 mmol) in a mixture of tetrahydrofuran (5 mL) and methanol (2 mL) was cooled to 0° C. A solution of lithium hydroxide monohydrate (30 mg, 0.71 mmol) in distilled water (1.5 mL) was added and the mixture was stirred for 2 h. The reaction mixture was acidified with 2 M hydrochloric acid to pH~6 and then diluted with 10% aqueous solution of ammonium chloride (20 mL) and ethyl acetate (20 mL). The phases were separated, the aqueous phase was washed with ethyl acetate (4×15 mL); the combined organic extracts were washed with 10% aqueous solution of ammonium chloride (2×15 mL) and brine (2×15 mL), dried with anhydrous magnesium sulfate and concentrated in vacuo. The residue was triturated with hexanes (2×10 mL) yielding the title compound as amorphous white solid.

Yield: 0.160 g (86%).

$R_F$ (SiO$_2$, chloroform/methanol 90:10): 0.15.

M.p.: 96-100° C.

$^1$H NMR spectrum (300 MHz, CDCl$_3$, $\delta_H$): 7.64 (d, J=8.1 Hz, 2H); 7.33-7.28 (m, 4H); 7.13 (d, J=8.4 Hz, 2H); 6.65 (d, J=2.8 Hz, 1H); 6.62 (d, J=8.9 Hz, 1H); 6.45-6.36 (m, 2H); 4.53 (s, 2H); 4.41 (d, J=6.7 Hz, 2H); 3.84-3.81 (m, 4H); 3.66 (s, 2H); 2.85 (bs, 4H), 2.24 (s, 3H).

Example 78

(Z)-[4-[3-(Benzo[b]thiophen-2-yl)-3-[4-(4-(trifluoromethylphenyl)ethynyl]phenyl]allyloxy]-2-methylphenoxy]acetic Acid

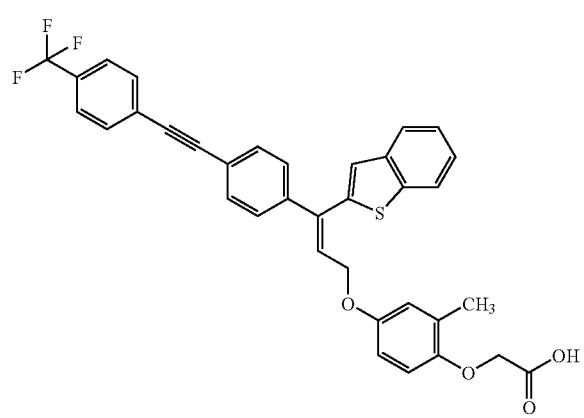

(Z)-3-(4-Bromophenyl)-3-iodoprop-2-en-1-ol (0.950 g, 2.8 mmol), carbon tetrabromide (0.913 g, 3 mmol) and triphenylphosphine (0.786 g, 3 mmol) were mixed in anhydrous dichloromethane (10 mL) and the mixture was stirred at 0° C. for 3 h and then at 20° C. overnight. Ether (50 mL) and hexanes (30 mL) were added and the mixture was filtrated through a paddle of silica to remove precipitated triphenylphosphine oxide. Solvents were removed by evaporation in vacuo and crude 1-bromo-4-((Z)-3-bromo-1-iodopropenyl)benzene was prepared in quantitative yield and was subsequently used without further purification.

Yield: 1.20 g (100%).

$R_F$ (SiO$_2$, hexanes/ethyl acetate 9:1) 0.90.

The above allyl bromide (0.787 g, 1.96 mmol), methyl (4-hydroxy-2-methylphenoxy)acetate (0.652 g, 2.00 mmol) and cesium carbonate (0.652 g, 2.00 mmol) were stirred at 20° C. overnight. The mixture was filtered and evaporated in vacuo. The residue was submitted to column chromatography (silica gel Fluka 60, hexanes/ethyl acetate 95:5) affording methyl (Z)-[4-[3-(4-bromophenyl)-3-iodoallyloxy]-2-methylphenoxy]acetate.

Yield: 0.722 g (71%).

$R_F$ (SiO$_2$, hexanes/ethyl acetate 9:1) 0.35

Methyl (Z)-[4-[3-(4-bromophenyl)-3-iodoallyloxy]-2-methylphenoxy]acetate (760 mg, 1.47 mmol) and (benzo[b]thiophen-2-yl)-tributyltin (0.72 g, 1.7 mmol) were dissolved in anhydrous N,N-dimethylformamide (20 mL) and the solution was degassed. 0.15 M solution of tri-t-butylphosphine in cyclohexane (1.2 mL, 0.18 mmol) and tris(dibenzylidenacetone)dipalladium chloroform complex (46 mg, 0.044 mmol) were added; the reaction solution was degassed again and then stirred under inert atmosphere at 50° C. for 2 h. The reaction mixture was diluted with ethyl acetate (50 mL) and extracted with 10% aqueous solution of potassium fluoride (50 mL), water (2×50 mL) and brine (2×30 mL). The organic layer was dried with anhydrous magnesium sulfate and evaporated in vacuo. The residue was purified by column chromatography (silica gel Fluka 60, hexanes/ethyl acetate 95:5-90:10) yielding methyl (Z)-[4-[3-(benzo[b]thiophen-2-yl)-3-(4-bromophenyl)allyloxy]-2-methylphenoxy]-acetate.

Yield: 530 mg (68%).

$R_F$ (hexanes/ethyl acetate 80:20): 0.45.

$^1$H NMR spectrum (300 MHz, CDCl$_3$, $\delta_H$): 7.84-7.77 (m, 2H); 7.45 (d, J=8.6 Hz, 2H); 7.39-7.35 (m, 2H); 7.27-7.22 (m, 2H); 6.73 (bs, 1H); 6.63-6.61 (m, 2H); 6.34 (t, J=6.3 Hz, 1H); 4.76 (d, J=6.3 Hz, 2H); 4.58 (s, 2H); 3.79 (s, 3H); 2.25 (s, 3H).

Under nitrogen atmosphere, 1-ethynyl-4-trifluoromethyl-benzene (135 mg, 0.79 mmol) and 1,8-diazabicyclo[5.4.0]undec-7-ene (100 mg, 0.66 mmol) were added to a degassed solution of the above compound (260 mg, 0.50 mmol) in tetrahydrofuran (10 mL). Bis(tri-tert-butylphosphine)palladium (15 mg, 0.03 mmol) and copper(I) iodide (10 mg, 0.05 mmol) were added; the reaction mixture was degassed again and then stirred at ambient temperature over night under inert atmosphere. The reaction mixture was filtered through a pad of silica gel; the pad was washed with ethyl acetate (4×15 mL) and the combined organic filtrates were evaporated in vacuo. The residue was purified by column chromatography (silica gel Fluka 60, hexanes/ethyl acetate 95:5) yielding methyl (Z)-[4-[3-(benzo[b]-thiophen-2-yl)-3-[4-[4-(trifluoromethylphenyl)ethynyl]phenyl]allyloxy]-2-methylphenoxy]-acetate.

Yield: 210 mg (71%).

$R_F$ (SiO$_2$, hexanes/ethyl acetate 80:20): 0.40.

$^1$H NMR spectrum (300 MHz, CDCl$_3$, $\delta_H$): 7.85-7.77 (m, 2H); 7.65-7.59 (m, 4H); 7.50 (d, J=8.4 Hz, 2H); 7.43-7.36 (m, 3H); 7.26-7.24 (m, 2H, overlapped); 6.74 (bs, 1H); 6.64-6.63 (m, 2H); 6.42 (t, J=6.2 Hz, 1H); 4.79 (d, J=6.2 Hz, 2H); 4.59 (s, 2H); 3.79 (s, 3H); 2.26 (s, 3H).

A solution of lithium hydroxide monohydrate (30 mg, 0.71 mmol) in distilled water (2 mL) was added to a solution of the above ester (210 mg, 0.34 mmol) in tetrahydrofuran (5 mL) and methanol (2 ml) cooled to 0° C. The solution was stirred for 2 h, acidified with 2 M hydrochloric acid to pH~6 and diluted with ethyl acetate (20 mL) and water (15 mL). The phases were separated and the aqueous phase was extracted with ethyl acetate (3×15 mL). The combined organic layers were washed with water (2×15 mL) and brine (2×15 mL), dried with anhydrous magnesium sulfate and evaporated in vacuo. The residue was triturated with hexanes (2×15 mL) yielding the title acid as amorphous off-white powder.

Yield: 155 mg (76%).

M.p.: 162-172° C. (amorphous).

$R_F$ (SiO$_2$, chloroform/methanol 90:10): 0.20.

$^1$H NMR spectrum (300 MHz, CDCl$_3$, $\delta_H$): 7.85-7.78 (m, 2H); 7.65-7.58 (m, 4H); 7.50 (d, J=8.4 Hz, 2H); 7.41-7.38 (m, 2H); 7.24 (s, 1H); 6.75 (bs, 1H); 6.66 (bs, 2H); 6.41 (t, J=6.2 Hz, 1H); 4.78 (d, J=6.2 Hz, 2H); 4.61 (s, 2H); 2.25 (s, 3H).

Example 79

(E)-[7-[3-[4-[3-(Morpholin-4-yl)propynyl]phenyl]-3-(4-trifluoromethylphenyl)allyloxy]-benzo[b]furan-4-yl]oxyacetic Acid

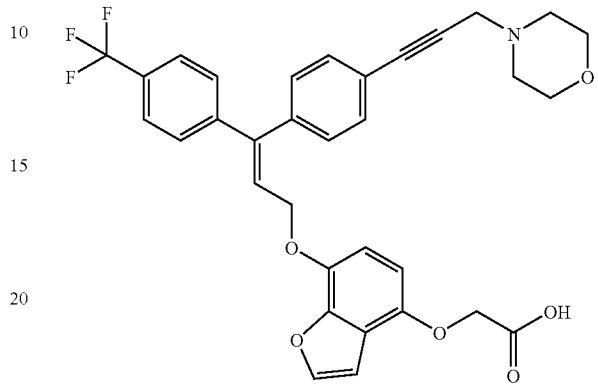

A mixture of 4-hydroxy-7-methoxybenzo[b]furan (2.0 g, 12.2 mmol; prepared according to Eur. J. Med. Chem. 1981, 16, 563), ethyl bromoacetate (2.2 g, 13.2 mmol), potassium carbonate (2.0 g, 14.5 mmol) and 2-butanone (50 mL) was refluxed for 10 h, then filtered and evaporated in vacuo. The residue was purified by column chromatography (silica gel Fluka 60, chloroform) affording ethyl (7-methoxybenzo[b]furan-4-yloxy)acetate.

Yield: 2.77 g (91%).

$R_F$ (SiO$_2$, benzene): 0.20.

$^1$H NMR spectrum (300 MHz, CDCl$_3$, $\delta_H$): 7.57 (d, J=1.8 Hz, 1H); 6.93 (d, J=1.8 Hz, 1H); 6.66 (d, J=8.4 Hz, 1H); 6.48 (d, J=8.4 Hz, 1H); 4.70 (s, 2H); 4.27 (q, J=7.1 Hz, 2H); 3.96 (s, 3H); 1.29 (t, J=7.1 Hz, 3H).

A solution of boron tribromide (5.50 g, 22 mmol) in dichloromethane (20 mL) was added dropwise to a solution of the above ester (2.77 g, 11.1 mmol) in dichloromethane (30 mL) at −40° C. and the mixture was stirred for 3 h without cooling while the temperature reached 0° C. Water (3 mL) was added to the mixture the organic layer was evaporated in vacuo. The obtained residue was purified by column chromatography (silica gel Fluka 60, chloroform) affording ethyl (7-hydroxybenzo[b]furan-4-yloxy)acetate.

Yield: 2.15 g (82%).

$R_F$ (SiO$_2$, ethyl acetate): 0.55.

$^1$H NMR spectrum (300 MHz, CDCl$_3$, $\delta_H$): 7.51 (d, J=1.8 Hz, 1H); 6.92 (d, J=1.8 Hz, 1H); 6.67 (d, J=8.7 Hz, 1H); 6.41 (d, J=8.7 Hz, 1H); 4.70 (s, 2H); 4.28 (q, J=7.1 Hz, 2H); 1.29 (t, J=7.1 Hz, 3H).

The above ester (0.83 g, 3.50 mmol), (Z)-3-(4-iodophenyl)-3-(4-trifluoromethylphenyl)prop-2-en-1-ol (1.35 g, 3.35 mmol) and triphenylphosphine (1.30 g, 5.00 mmol) were dissolved in a mixture of anhydrous toluene (30 mL) and tetrahydrofuran (3 mL). The mixture was cooled to 0° C., kept under nitrogen and diisopropyl azodicarboxylate (1.10 g, 5.50 mmol) was added dropwise. The reaction mixture was stirred at 0° C. for 3 h and then left to stand at ambient temperature for 3 days. The solvents were evaporated in vacuo and the residue was submitted to column chromatography (silica gel Fluka 60, benzene) affording ethyl (Z)-[7-

[3-(4-iodophenyl)-3-(4-trifluoromethyl phenyl)allyloxy]benzo[b]furan-4-yloxy]-acetate.

Yield: 1.70 g (79%).

$R_F$ (SiO$_2$, hexanes/ethyl acetate 5:1): 0.35.

$^1$H NMR spectrum (300 MHz, CDCl$_3$, $\delta_H$): 7.72 (d, J=8.4 Hz, 2H); 7.54 (m, 3H); 7.34 (d, J=8.4 Hz, 2H); 6.92 (m, 3H); 6.57 (d, J=8.4 Hz, 1H); 6.48 (t, J=6.6 Hz, 1H); 6.42 (d, J=8.4 Hz, 1H); 4.73 (d, J=6.6 Hz, 2H); 4.69 (s, 2H); 4.27 (q, J=7.1 Hz, 2H); 1.29 (t, J=7.1 Hz, 3H).

N-Propargylmorpholine (0.64 g, 5.1 mmol) was added under nitrogen atmosphere to a degassed solution of ethyl (Z)-[7-[3-(4-iodophenyl)-3-(4-trifluoromethylphenyl)allyloxy]-benzo[b]furan-4-yl]oxyacetate (0.68 g, 1.09 mmol) in a mixture of tetrahydrofuran (20 mL) and triethylamine (10 mL) The solution was cooled to 0° C., tetrakis(triphenylphosphine)palladium (0.17 g, 0.147 mmol) and copper(I) iodide (0.03 g, 0.16 mmol) were added. The reaction mixture was stirred at ambient temperature for 120 h, diluted with benzene (100 mL), decanted and evaporated in vacuo. The residue was purified by column chromatography (silica gel Fluka 60, benzene/ethyl acetate 1:0-0:1) yielding ethyl (E)-[7-[3-[4-[3-(morpholin-4-yl)propynyl]phenyl]-3-(4-trifluoromethylphenyl)allyloxy]benzo[b]furan-4-yl]oxyacetate.

Yield: 0.60 g (89%).

$R_F$ (SiO$_2$, chloroform/ethanol 5:1): 0.70.

$^1$H NMR spectrum (300 MHz, CDCl$_3$, $\delta_H$): 7.53 (m, 3H); 7.46 (d, J=8.2 Hz, 2H); 7.35 (d, J=8.2 Hz, 2H); 7.13 (d, J=8.2 Hz, 2H); 6.94 (d, J=2.1 Hz, 1H); 6.56 (d, J=8.7 Hz, 1H); 6.47 (t, J=6.6 Hz, 1H); 6.42 (d, J=8.7 Hz, 1H); 4.75 (d, J=6.6 Hz, 2H); 4.69 (s, 2H); 4.27 (q, J=7.1 Hz, 2H); 3.79 (m, 4H); 3.54 (s, 2H); 2.67 (m, 4H); 1.29 (t, J=7.1 Hz, 3H).

The above ester (0.60 g, 1.02 mmol) was dissolved in ethanol (20 mL), a solution of lithium hydroxide monohydrate (0.085 g, 2.02 mmol) in water (2 mL) was added and the mixture was left to stand for 48 h. The solvents were evaporated in vacuo; the residue was treated with water (30 mL) and extracted with ether (2×10 mL) discarding the extracts. The aqueous layer was acidified with acetic acid (1.0 mL) and extracted with dichloromethane (3×15 mL). The solvent was evaporated in vacuo and the residue was triturated with ether (2×15 mL) yielding the title compound as foam.

Yield: 0.35 g (61%).

$R_F$ (SiO$_2$, chloroform/ethanol 5:1): 0.25.

$^1$H NMR spectrum (300 MHz, CDCl$_3$, $\delta_H$): 7.53 (m, 3H); 7.42 (d, J=8.2 Hz, 2H); 7.33 (d, J=8.2 Hz, 2H); 7.07 (d, J=8.2 Hz, 2H); 6.95 (d, J=2.1 Hz, 1H); 6.49 (d+t, 2H); 6.38 (d, J=8.7 Hz, 1H); 4.69 (d, J=6.6 Hz, 2H); 4.65 (s, 2H); 3.85 (m, 4H); 3.77 (s, 2H); 2.97 (m, 4H).

Pharmacological Methods

In Vitro PPARδ Activation Activity

The PPAR transient transactivation assay is based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seeded in 96-well plates the day before transfection to give a confluency of 50-80% at transfection. A total of 0.8 µg DNA containing 0.64 µg pM1α/γLBD, 0.1 µg pCMVβGal, 0.08 µg pGL2(Gal4)$_5$ and 0.02 µg pADVANTAGE was transfected per well using FuGene transfection reagent according to the manufacturers instructions (Roche). Cells were allowed to express protein for 48 h followed by addition of compound.

Plasmids: Human PPAR-δ was obtained by PCR amplification using cDNA synthesized by reverse transcription of mRNA from human liver, adipose tissue and placenta respectively. Amplified cDNAs were cloned into pCR2.1 and sequenced. The ligand binding domain (LBD) of each PPAR isoform was generated by PCR (PPARδ: aa 128—C-terminus) and fused to the DNA binding domain (DBD) of the yeast transcription factor GAL4 by sub-cloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5×CGGAGTACTGTCCTCCG(AG)) (Webster et al. (1988), Nucleic Acids Res. 16, 8192) into the vector pGL2 promotor (Promega) generating the plasmid pGL2(GAL4)$_5$. pCMVβ-Gal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 µM. Cells were treated with compound for 24 h followed by luciferase assay. Each compound was tested in at least two separate experiments.

Luciferase assay: Medium including test compound was aspirated and 100 µl PBS incl. 1 mM Mg++ and Ca++ were added to each well. The luciferase assay was performed using the LucLite kit according to the manufacturer's instructions (Packard Instruments). Light emission was quantified by counting on a Packard LumiCounter. To measure β-galactosidase activity 25 µl supernatant from each transfection lysate was transferred to a new microplate. β-Galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as means±SD.

While the invention has been described and illustrated with reference to certain preferred embodiments thereof, those skilled in the art will appreciate that various changes, modifications, and substitutions can be made therein without departing from the spirit and scope of the present invention.

The invention claimed is:

1. (E)-[4-[3-(4-Fluorophenyl)-3-[4-[3-(morpholin-4-yl)propynyl]phenyl]allyloxy]-2-methyl-phenoxy]acetic acid or a pharmaceutically acceptable salt thereof.

2. The compound of claim 1, where the compound is (E)-[4-[3-(4-fluorophenyl)-3-[4-[3-(morpholin-4-yl)propynyl]phenyl]allyloxy]-2-methyl-phenoxy]acetic acid.

3. The compound of claim 1, where the compound is a pharmaceutically acceptable salt of (E)-[4-[3-(4-fluorophenyl)-3-[4-[3-(morpholin-4-yl)propynyl]phenyl]allyloxy]-2-methyl-phenoxy]acetic acid.

4. The compound of claim 3, where the pharmaceutically acceptable salt of (E)-[4-[3-(4-fluorophenyl)-3-[4-[3-(morpholin-4-yl)propynyl]phenyl]allyloxy]-2-methyl-phenoxy]acetic acid is selected from the group consisting of a sodium salt, a potassium salt, a magnesium salt, and a calcium salt.

5. The compound of claim 4, where the compound is a sodium salt of (E)-[4-[3-(4-fluorophenyl)-3-[4-[3-(morpholin-4-yl)propynyl]phenyl]allyloxy]-2-methyl-phenoxy]acetic acid.

6. (Z)-[4-[3-(4-Fluorophenyl)-3-[4-[3-(morpholin-4-yl)propynyl]phenyl]allyloxy]-2-methyl-phenoxy]acetic acid or a pharmaceutically acceptable salt thereof.

7. The compound of claim 6, where the compound is (Z)-[4-[3-(4-fluorophenyl)-3-[4-[3-(morpholin-4-yl)propynyl]phenyl]allyloxy]-2-methyl-phenoxy]acetic acid.

8. The compound of claim 6, where the compound is a pharmaceutically acceptable salt of (Z)-[4-[3-(4-fluorophenyl)-3-[4-[3-(morpholin-4-yl)propynyl]phenyl]allyloxy]-2-methyl-phenoxy]acetic acid.

9. The compound of claim 8, where the pharmaceutically acceptable salt of (Z)-[4-[3-(4-fluorophenyl)-3-[4-[3-(morpholin-4-yl)propynyl]phenyl]allyloxy]-2-methyl-phenoxy]acetic acid is selected from the group consisting of a sodium salt, a potassium salt, a magnesium salt, and a calcium salt.

10. The compound of claim 9, where the compound is a sodium salt of (Z)-[4-[3-(4-fluorophenyl)-3-[4-[3-(morpholin-4-yl)propynyl]phenyl]allyloxy]-2-methyl-phenoxy]acetic acid.

11. A pharmaceutical composition comprising a compound according to claim 1 and a pharmaceutically acceptable carrier or excipient.

12. A pharmaceutical composition comprising a compound according to claim 2 and a pharmaceutically acceptable carrier or excipient.

13. A pharmaceutical composition comprising a compound according to claim 3 and a pharmaceutically acceptable carrier or excipient.

14. A pharmaceutical composition comprising a compound according to claim 4 and a pharmaceutically acceptable carrier or excipient.

15. A pharmaceutical composition comprising a compound according to claim 5 and a pharmaceutically acceptable carrier or excipient.

16. A pharmaceutical composition comprising a compound according to claim 6 and a pharmaceutically acceptable carrier or excipient.

17. A pharmaceutical composition comprising a compound according to claim 7 and a pharmaceutically acceptable carrier or excipient.

18. A pharmaceutical composition comprising a compound according to claim 8 and a pharmaceutically acceptable carrier or excipient.

19. A pharmaceutical composition comprising a compound according to claim 9 and a pharmaceutically acceptable carrier or excipient.

20. A pharmaceutical composition comprising a compound according to claim 10 and a pharmaceutically acceptable carrier or excipient.

21. A compound of formula (I) or a pharmaceutically acceptable salt thereof:

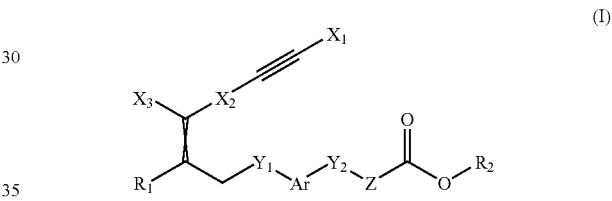

wherein ⫟ is a double bond, with either E or Z substitution;
$X_1$ is $C_{1-6}$-alkyl substituted with morpholino;
$X_2$ is phenylene;
$X_3$ is phenyl substituted with one or more halogens;
Ar is phenylene optionally substituted with methyl;
$Y_1$ is O;
$Y_2$ is O;
Z is $CH_2$;
$R_1$ is H; and
$R_2$ is H;
or a hydrate of any of the foregoing.

22. The compound of claim 21 wherein $X_1$ is morpholin-4-ylmethyl.

23. A pharmaceutical composition comprising a compound according to claim 21 and a pharmaceutically acceptable carrier or excipient.

24. A pharmaceutical composition comprising a compound according to claim 22 and a pharmaceutically acceptable carrier or excipient.

* * * * *